US007312234B2

(12) United States Patent  
Bridger et al.

(10) Patent No.: US 7,312,234 B2
(45) Date of Patent: Dec. 25, 2007

(54) CHEMOKINE RECEPTOR BINDING HETEROCYCLIC COMPOUNDS

(75) Inventors: Gary Bridger, Bellingham, WA (US); Renato Skerlj, Vancouver (CA); Al Kaller, Vancouver (CA); Curtis Harwig, Vancouver (CA); David Bogucki, Surrey (CA); Trevor R. Wilson, Langley (CA); Jason Crawford, British Columbia (CA); Ernest J. McEachern, White Rock (CA); Bem Atsma, Abbotsford (CA); Siqiao Nan, Richmond (CA); Yuanxi Zhou, Surrey (CA); Dominique Schols, Herent (BE); Christopher Dennis Smith, Toronto (CA); Maria Rosaria Di Fluri, Burnaby (CA)

(73) Assignee: AnorMED, Langley (CA)

( * ) Notice: Subject to any disclaimer, the term of this patent is extended or adjusted under 35 U.S.C. 154(b) by 122 days.

(21) Appl. No.: 10/914,663

(22) Filed: Aug. 9, 2004

(65) Prior Publication Data

US 2005/0026942 A1 Feb. 3, 2005

Related U.S. Application Data

(62) Division of application No. 09/957,654, filed on Sep. 17, 2001, now Pat. No. 6,835,731.

(60) Provisional application No. 60/233,087, filed on Sep. 15, 2000, provisional application No. 60/234,816, filed on Sep. 22, 2000.

(51) Int. Cl.
*A61K 31/4706* (2006.01)
*C07D 215/38* (2006.01)
*A61K 31/4709* (2006.01)
*C07D 239/32* (2006.01)
*C07D 237/14* (2006.01)

(52) U.S. Cl. ............. 514/314; 546/171; 546/175
(58) Field of Classification Search ............. 514/313, 514/314; 546/134, 135, 171, 175
See application file for complete search history.

(56) References Cited

U.S. PATENT DOCUMENTS

| 5,583,131 | A | 12/1996 | Bridger et al. | 514/183 |
|---|---|---|---|---|
| 5,698,546 | A | 12/1997 | Bridger et al. | 514/183 |
| 5,817,807 | A | 10/1998 | Bridger et al. | 540/474 |
| 6,001,826 | A | 12/1999 | Murrer et al. | 514/183 |
| 6,207,671 | B1 | 3/2001 | Schmidt et al. | 514/277 |
| 6,365,583 | B1 | 4/2002 | MacFarland et al. | 514/183 |
| 6,410,561 | B1 * | 6/2002 | Shinkai et al. | 514/313 |
| 6,506,770 | B1 | 1/2003 | Bridger et al. | 514/300 |

FOREIGN PATENT DOCUMENTS

| JP | 11-269146 | 10/1999 |
|---|---|---|
| WO | WO 99/38514 | 8/1999 |
| WO | WO 00/42852 | 7/2000 |
| WO | WO 00/51607 | 9/2000 |
| WO | WO 00/56729 | 9/2000 |

OTHER PUBLICATIONS

U.S. Appl. No. 60/172,153, filed Dec. 17, 1999, Bridger et al.
Abi-Younes et al. (2000). *Circ. Res.* 86:131-138.
Alkhatib et al. (1996). *Science* 272:1955-1958.
Arai et al. (2000). *Eur. J. Haematol.* 64:323-332.
Arenburg et al. (1997). *J. Leukocyte Biol.* 62:554-562.
Auiti et al. (1997). *J. Exp. Med.* 185:111-120.
Baggiolini, M. (1998). *Nature* 392:565-568.
Bajetto et al. (1999). *J. Neurochem*.73:2348-2357.
Berger et al. (1999). *Annu Rev. Immunol*.17:657-700.
Biard-Piechaczyk et al. (2000). *Virology* 268:329-344.
Blaak et al. (2000). *Proc. Natl. Acad. Sci.* 97:1269-1274.
Blanco et al. (2000). *Antimigrobial Agents and Chemother* 44:51-56.
Bleul et al. (1998). *J. Exp. Med.* 187:753-762.
Bleul et al. (1996). *Nature* 382:829-833.
Bradstock et al. (2000). *Leukemia* 14:882-888.
Bridger et al. (1999). "Bicyclam Derivatives as HIV Inhibitors" in *Advances in Antiviral Drug Design*. vol. 3., JAI press., pp. 161-229.
Bridger et al. (1999). *J. Med. Chem.* 42:3971-3981.
Burger et al. (1999). *Blood* 94:3658-3667.
Buttini et al. (1998). *Nature Med.* 4:441-446.
Carroll et al. (1997). *Science* 276:273-276.
Cocchi et al. (1995). *Science* 270: 1811-1815.
Connor, R.I., Ho, D.D. (1994). *J. Virol.* 68:4400-4408.
Database WPI AN 209951 XP 002188972.
Deng et al. (1996). *Nature* 381:661-666.
Donzella et al. (1998). *Nature Medicine* 4:72-77.
Dragic et al. (1996). *Nature* 381:667-673.
Egberink et al. (1999). *J. Virol.* 73:6346-6352.
Eitner et al. (1998). *Transplantation* 66:1551-1557.
Fedyk et al. (1999). *J. Leukocyte Biol.* 66:667-673.
Feng et al. (1996). *Science* 272:872-877.
Gonzalo et al. (2000). *J.Immunol.* 165:499-508.
Gupta et al. (1998). *J.Biol. Chem.* 7:4282-4287.
Herbein et al. (1998). *Nature* 395:189-194.
Hesselgesser et al. (1999). "Chemokines and Chemokine receptors in the Brain" in *Chemokines in Disease*, Humana Press, pp. 295-312.
Hesselgesser et al. (1997). *Curr. Biol.* 7:112-121.
Hesselgesser et al. (1998). *Curr. Biol.* 8:595-598.
Ishii et al. (1999). *J.Immunol.* 163:3612-3620.
Lataillade et al. (2000). *Blood* 95:756-768.
Liu et al. (1996). *Cell* 86:367-377.
Locati et al. (1999). *Annu. Rev. Med.* 50:425-40.
Maekawa et al. (2000). *Internal Medicine* 39:90-100.
Michael et al. (1997). *Nature Med.* 3:338-340.
Michael et al. (1998). *J. Virol.* 72:6040-6047.

(Continued)

*Primary Examiner*—James O. Wilson
*Assistant Examiner*—Tamthom N Truong
(74) *Attorney, Agent, or Firm*—Morrison & Foerster LLP

(57) ABSTRACT

Tertiary amines containing a multiplicity of heteroaromatic substituents are useful as chemokine receptor modulators.

6 Claims, No Drawings

OTHER PUBLICATIONS

Miedema et al. (1994). *Immune. Rev.* 140:35-72.
Moore et al. (1998). *J. Invest. Med.* 46:113-120.
Moore et al. (1998). *Trends Cardiovasc. Med.* 8:51-58.
Murdoch et al. (2000). *Blood* 95:3032-3043.
Nagasawa et al. (1996). *Nature* 382:635-638.
Nagase, et al. (2000). *J. Immunol* 164:5935-5943.
Nanki et al. (2000). *J. Immunol* 164:5010-5014.
Oberlin et al. (1996). *Nature* 382:833-835.
O'Brien et al. (1997). *Lancet* 349:1219.
Ohagen et al. (1999). *J. Virol.* 73(2):897-906.
Peled et al. (2000). *Blood* 95(11):3289-3296.
Peled et al. (1999). *Science* 283:845-848.
Ponath, P. (1998). *Exp. Opin. Invest. Drugs* 7(1):1-18.
Qing et al. (1999). *Immunity* 10:463-471.
Rana et al. (1997). *J. Virol.* 71:3219-3227.
Rizzuto et al. (1998). *Science* 280:1949-1953.
Salcedo et al. (1999). *Am. J. Pathol.* 154(4):1125-1135.
Samson et al. (1996). *Nature* 382:722-725.
Sanders et al. (2000). *J. Neuroscience Res.* 59:671-679.
Schols et al. (1997). *Antiviral Research* 35:147-156.
Schols et al. (1997). *J. Exp. Med.* 186(8):1383-1388.
Schuitemaker et al. (1992). *J. Virol.* 66:1354-1360.
Seghal et al. (1998). *J. Surg. Oncol.* 69:99-104.
Simmons et al. (1969). *J. Virol.* 70(12):8355-8360.
Simmons et al. (1988). *J. Virol.* 72(10):8453-8457.
Tachibana et al. (1998). *Nature* 393:591-594.
Tersmette et al. (1988). *J. Virol.* 62(6):2026-2032.
Theodorou et al. (1997). *Lancet* 349:1219-1220.
Viardot et al. (1998). *Ann. Hematol.* 77:193-197.
Volin et al (1998). *Biochem. Biophys Res. Commun.* 242:46-53.
Wyatt et al. (1998). *Science* 280:1884-1888.
Xia et al. (1999). *J. NeuroVirology* 5:32-41.
Yssel et al. (1998). *Clinical and Experimental Allergy* 28:104-109.
Zhang et al. (1997). *AIDS Res. Hum. Retroviruses* 13(16):1357-1366.
Zhang et al. (1998). *J. Virol.* 72:9307-9312.
Zhang et al. (1999). *J. Virol.* 73(4):3443-3448.
Zheng et al. (1999). *J. Virol.* 73(10):8256-8267.

* cited by examiner

CHEMOKINE RECEPTOR BINDING HETEROCYCLIC COMPOUNDS

CROSS-REFERENCE TO RELATED APPLICATIONS

This application is a divisional of application Ser. No. 09/957,654, filed 17 Sep. 2001, now U.S. Pat. No. 6,835,731, which claims priority under 35 U.S.C. § 119(e) to provisional application Ser. No. 60/233,087 filed 15 Sep. 2000 and to U.S. Ser. No. 60/234,816 filed 22 Sep. 2000. The contents of these applications are incorporated herein by reference.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrate protective effects against infection of target cells by a human immunodeficiency virus (HIV).

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs,* 7:1-18, 1998; Baggiolini, M., *Nature* 392:565-568 (1998); Locati, et at, *Annu. Rev. Med.* 50:425-440 (1999)). These chemotactic cytokines, or chemokines, constitute a family of proteins, approximately 8-10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR" while those of the α-chemokines are designated "CXCR".

Chemokines are considered to be principal mediators in the initiation and maintenance of inflammation (see *Chemokines in Disease* published by Humana Press (1999), Edited by C. Herbert; Murdoch, et al., *Blood* 95:3032-3043 (2000)). More specifically, chemokines have been found to play an important role in the regulation of endothelial cell function, including proliferation, migration and differentiation during angiogenesis and re-endothelialization after injury (Gupta, et al., *J. Biol. Chem.,* 7:4282-4287 (1998); Volin, et al., *Biochem. Biophys Res. Commun.* 242:46-53 (1998)). Two specific chemokines have been implicated in the etiology of infection by human immunodeficiency virus (HIV).

In most instances, HIV initially binds via its gp120 envelope protein to the CD4 receptor of the target cell. A conformational change appears to take place in gp120 which results in its subsequent binding to a chemokine receptor, such as CCR5 (Wyatt, et al., *Science,* 280:1884-1888 (1998); Rizzuto, et al., *Science,* 280:1949-1953 (1998); Berger, et al., *Annu. Rev. Immunol.* 17:657-700 (1999)). HIV-1 isolates arising subsequently in the infection bind to the CXCR4 chemokine receptor.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll, et al., *Science,* 276:273-276 (1997); Feng, et al., *Science* 272:872-877 (1996); Bleul, et al., *Nature* 382:829-833 (1996); Oberlin, et al., *Nature* 382:833-835 (1996); Cocchi, et al., *Science* 270:1811-1815 (1995); Dragic, et al., *Nature* 381:667-673 (1996); Deng, et al., *Nature* 381:661-666 (1996); Alkhatib, et al., *Science* 272:1955-1958 (1996). During the course of infection within a patient, it appears that a majority of HIV particles shift from the M-tropic to the more pathogenic T-tropic viral phenotype (Blaak, et al., *Proc. Natl. Acad. Sci.* 97:1269-1274 (2000); Miedema, et al., *Immune. Rev.,* 140:35 (1994); Simmonds, et al., *J. Virol.* 70:8355-8360 (1996); Tersmette, et al., *J. Virol.* 62:2026-2032 (1988); Connor, R. I., Ho, D. D. *J. Virol.* 68:4400-4408 (1994); Schuitemaker, et al., *J. Virol.* 66:1354-1360 (1992)). The M-tropic viral phenotype correlates with the virus's ability to enter the cell following binding of the CCR5 receptor, while the T-tropic viral phenotype correlates with viral entry into the cell following binding and membrane fusion with the CXCR4 receptor. Clinical observations suggest that patients who possess genetic mutations in CCR5 appear resistant, or less susceptible to HIV infection (Liu, et al., *Cell* 86:367-377 (1996); Samson, et al., *Nature* 382:722-725 (1996); Michael, et al., *Nature Med.* 3:338-340 (1997); Michael, et al., *J. Virol.* 72:6040-6047 (1998); Obrien, et al., *Lancet* 349:1219 (1997); Zhang, et al., *AIDS Res. Hum. Retroviruses* 13:1357-1366 (1997); Rana, et al., *J. Virol.* 71:3219-3227 (1997); Theodorou, et al., *Lancet* 349:1219-1220 (1997). Despite the number of chemokine receptors which have been reported to HIV mediate entry into cells, CCR5 and CXCR4 appear to be the only physiologically relevant coreceptors used by a wide variety of primary clinical HIV-1 strains (Zhang, et al., *J. Virol.* 72:9307-9312 (1998); Zhang, et al., *J. Virol.* 73:3443-3448 (1999); Simmonds, et al., *J. Virol.* 72:8453-8457 (1988)). Fusion and entry of T-tropic viruses that use CXCR4 are inhibited by the natural CXC-chemokine stromal cell-derived factor-1, whereas fusion and entry of M-tropic viruses that use CCR5 are inhibited by the natural CC-chemokines namely, Regulated on Activation Normal T-cell Expressed and Secreted (RANTES) and Macrophage Inflammatory proteins (MIP-1 alpha and beta).

In addition to serving as a co-factor for HIV entry, the direct interaction of virus-associated gp120 with CXCR4 has been recently suggested as a possible cause of CD8+ T-cell apoptosis and AIDS-related dementia via induction of neuronal cell apoptosis (Hesselgesser, et al., *Curr. Biol.* 8:595-598 (1998); Hesselgesser, et al., *Curr. Biol.* 7:112-121 (1997); Hesselgesser, et al., "Chemokines and Chemokine receptors in the Brain" in *Chemokines in Disease* published by Humana Press (1999), Edited by C. Herbert; Herbein, et al., *Nature* 395:189-194 (1998); Buttini, et al., *Nature Med.* 4:441-446 (1998); Ohagen, et al., *J. Virol.* 73:897-906 (1999); Biard-Piechaczyk, et al., *Virology* 268:329-344 (2000); Sanders, et al., *J. Neuroscience Res.* 59:671-679 (2000); Bajetto, et al., *J. Neurochem.* 73:2348-2357 (1999); Zheng, et al., *J. Virol.* 73:8256-8267 (1999)).

However, the binding of chemokine receptors to their natural ligands appears to serve a more evolutionary and central role than only as mediators of HIV infection. The binding of the natural ligand, pre-B-cell growth-stimulating factor/stromal cell derived factor (PBSF/SDF-1) to the CXCR4 chemokine receptor provides an important signaling mechanism: CXCR4 or SDF-1 knock-out mice exhibit cerebellar, cardiac and gastrointestinal tract abnormalities and die in utero (Zou, et al., *Nature,* 393:591-594 (1998); Tachibana, et al., *Nature,* 393:591-594 (1998); Nagasawa, et al., *Nature* 382:635-638 (1996)). CXCR4-deficient mice also display hematopoietic defects (Nagasawa, et al., *Nature* 382:635-638 (1996)); the migration of CXCR4 expressing leukocytes and hematopoietic progenitors to SDF-1 appears to be important for maintaining B-cell lineage and localization of CD34+ progenitor cells in bone marrow (Bleul, et al., *J. Exp. Med.* 187:753-762 (1998); Viardot, et al., *Ann. Hematol.* 77:195-197 (1998); Auiti, et al., *J. Exp. Med.* 185:111-120 (1997); Peled, et al., *Science* 283:845-848 (1999); Qing, et al., *Immunity* 10:463-471 (1999); Lataillade, et al., *Blood* 95:756-768 (1999); Ishii, et al., *J. Immunol.* 163:3612-3620 (1999); Maekawa, et al., *Internal Medicine* 39:90-100 (2000); Fedyk, et al., *J. Leukocyte Biol.* 66:667-673 (1999); Peled, et al., *Blood* 95:3289-3296 (2000)).

The signal provided by SDF-1 on binding to CXCR4 may also play an important role in tumor cell proliferation and regulation of angiogenesis associated with tumor growth (See *"Chemokines and Cancer"* published by Humana Press (1999); Edited by B. J. Rollins; Arenburg, et al., *J. Leukocyte Biol.* 62:554-562 (1997); Moore, et al., *J. Invest. Med.* 46:113-120 (1998); Moore, et al., *Trends cardiovasc. Med.* 8:51-58 (1998); Seghal, et al., *J. Surg. Oncol.* 69:99-104 (1998)); the known angiogenic growth factors VEG-F and bFGF, up-regulate levels of CXCR4 in endothelial cells, and SDF-1 can induce neovascularization in vivo (Salcedo, et al., *Am. J. Pathol.* 154:1125-1135 (1999)); Leukemia cells that express CXCR4 migrate and adhere to lymph nodes and bone marrow stromal cells that express SDF-1 (Burger, et al., *Blood* 94:3658-3667 (1999); Arai, et al., *Eur. J. Haematol.* 64:323-332 (2000); Bradstock, et al., *Leukemia* 14:882-888 (2000)).

The binding of SDF-1 to CXCR4 has also been implicated in the pathogenesis of atherosclerosis (Abi-Younes, et al., *Circ. Res.* 86:131-138 (2000)), renal allograft rejection (Eitner, et al., *Transplantation* 66:1551-1557 (1998)), asthma and allergic airway inflammation (Yssel, et al., *Clinical and Experimental Allergy* 28:104-109 (1998); *J. Immunol.* 164:5935-5943 (2000); Gonzalo, et al., *J. Immunol.* 165:499-508 (2000)), Alzheimer's disease (Xia, et al., *J. Neurovirology* 5:32-41 (1999)) and Arthritis (Nanki, et al., *J. Immunol.* 164:5010-5014 (2000)).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols, et al., *J. Exp. Med* 186:1383-1388 (1997); Schols, et al., *Antiviral Research* 35:147-156 (1997); Bridger, et al., *J. Med. Chem.* 42:3971-3981 (1999); Bridger, et al., "Bicyclam Derivatives as HIV Inhibitors" in *Advances in Antiviral Drug Design* Vol. 3:161-229; Published by JAI press (1999); Edited by E. De Clercq). Small molecules, such as bicyclams, appear to specifically bind to CXCR4 and not CCR5 (Donzella, et al., *Nature Medicine,* 4:72-77 (1998)). These experiments demonstrated interference with HIV entry and membrane fusion into the target cell in vitro. More recently, bicyclams were also shown to inhibit fusion and replication of Feline Immunodeficiency Virus that uses CXCR4 for entry (Egberink, et al., *J. Virol.* 73:6346-6352 (1999)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco, et al., *Antimicrobial Agents and Chemother.* 44:51-56 (2000)).

U.S. Pat. Nos. 5,583,131; 5,698,546; and 5,817,807, which are herein incorporated in their entirety by reference, disclose cyclic compounds that are active against HIV-1 and HIV-2 in in vitro tests. It was subsequently discovered and further disclosed in copending application U.S. Ser. No. 09/111,895 and U.S. Ser. No. 60/172,153 that these compounds exhibit anti-HIV activity by binding to the chemokine receptor CXCR4 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). We further disclosed that these novel compounds demonstrate protective effects against HIV infection of target cells by binding in vitro to the CCR5 receptor.

Additionally we have disclosed in U.S. Ser. No. 09/495,298 that these cyclic polyamine antiviral agents described in the above-mentioned patents have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, we disclosed in PCT International Application PCT/CA00/00321, a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

Herein, we disclose novel compounds that exhibit protective effects against HIV infection of target cells by binding to the chemokine receptors CXCR4 or CCR5, in a similar manner to the previously disclosed macrocyclic compounds.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

SUMMARY OF THE INVENTION

The present invention provides novel compounds that bind chemokine receptors and interfere with the binding of the natural ligand thereto. The compounds of the present invention are useful as agents demonstrating protective effects on target cells from HIV infection. Other embodiments of the present invention are compounds that act as antagonists or agonists of chemokine receptors, as well as other biological activities related to the ability of these compounds to inhibit the binding of chemokines to their receptors.

The compounds of the invention are of the formula

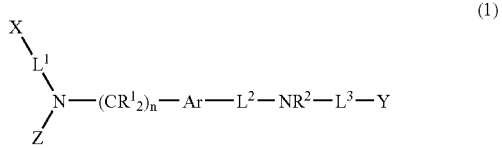

and the salts and prodrug forms thereof,
wherein:

X is a monocyclic (5-6 membered) or fused bicyclic (9-12 membered) unsubstituted or substituted ring system containing at least one heteroatom selected from N, O and S;

Z is H, or is a monocyclic (5-6 membered) or fused bicyclic (9-12 membered) unsubstituted or substituted ring system containing at least one heteroatom selected from N, O and S;

Ar is an optionally substituted aromatic or heteroaromatic ring;

each of $L^1$, $L^2$ and $L^3$ is independently a bond, CO, $SO_2$, or $CH_2$, wherein at least one of $L^2$ and $L^3$ must comprise CO or $SO_2$; and wherein $L^1$ can also be alkylene (2-5C) wherein one or two C may optionally be replaced by N and which alkylene may itself optionally be substituted by a bridge alkylene (3-4C); $L^2$ and $L^3$ also may be, independently, $SO_2NH$, CONH, $SO_2NHCH_2$ or $CONHCH_2$;

n is 0, 1 or 2;

each $R^1$ and $R^2$ is independently H or straight or branched chain or cyclic alkyl (1-6C) which may optionally be substituted, and wherein $R^2$ may be alkylene coupled to Y; and Y comprises at least one aromatic or heteroaromatic or other heterocyclic substituted or unsubstituted ring coupled directly to $L^3$.

The invention is directed to the compounds of formula I above, and to the use of these compounds in treating and in the preparation for medicaments for treating conditions which are affected by modulating the CXCR4 and/or CCR5 receptors.

MODES FOR CARRYING OUT THE INVENTION

The present invention is directed to compounds of Formula I which can act as agents that modulate chemokine receptor activity. Such chemokine receptors include but are not limited to CCR1, CCR2, CCR3, CCR4, CCR5, CCR6, CCR7, CCR8 and CXCR1, CXCR2, CXCR3, CXCR4 and CXCR5.

The present invention provides novel compounds of Formula I that demonstrate protective effects on target cells from HIV infection in a manner as to bind specifically to the chemokine receptor, and which affect the binding of a natural ligand or chemokine to a receptor such as CXCR4 and/or CCR5 of a target cell.

Compounds of Formula I are useful as agents which affect chemokine receptors, such as CCR1, CCR2, CCR3, CCR4, CCR5, CCR6, CCR7, CCR8 and CXCR1, CXCR2, CXCR3, CXCR4 and CXCR5 where such chemokine receptors have been correlated as being important mediators of many human inflammatory as well as immunoregulatory diseases. Thus, a compound that modulates the activity of such chemokine receptors would be useful for the treatment or prevention of such diseases.

The term "modulators" as used herein is intended to encompass antagonist, agonist, partial antagonist, and or partial agonist, inhibitors, and activators. In one preferred embodiment of the present invention, compounds of Formula I demonstrate protective effects against HIV infection by inhibiting the binding of HIV to a chemokine receptor such as CXCR4 and/or CCR5 of a target cell. The invention includes a method which comprises contacting the target cell with an amount of the compound which is effective at inhibiting the binding of the virus to the chemokine receptor.

Compounds that inhibit chemokine receptors may be used for the treatment of diseases associated with hematopoiesis, including but not limited to, controlling the side-effects of chemotherapy, enhancing the success of bone marrow transplantation, enhancing wound healing and burn treatment, as well as combating bacterial infections in leukemia.

Compounds that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria, vasculitis (e.g., necrotizing, cutaneous, and hypersensitivity vasculitis); eosinophilic myotis, eosiniphilic fascuitis; and cancers.

Compounds that activate or promote chemokine receptor function may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum*.

It will be understood that that compounds of Formula I may be used in combination with any other pharmaceutical composition where such combined therapy may be useful to modulate chemokine receptor activity and thereby prevent and treat inflammatory and immunoregulatory diseases.

It is also contemplated that the present invention may be used in combinations with one or more agents useful in the prevention or treatment of HIV. Examples of such agents include:

(1) nucleotide reverse transcriptase inhibitor such as zidovudine, didanosine, lamivudine, zalcitabine, abacavir, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, etc.; and (3) protease inhibitors such as saquinavir, ritonavir, indinavir, nelfinavir, amprenavir, palinavir, lasinavir, etc.

The scope of combinations of compounds of Formula I of this invention with HIV agents is not limited to (1), (2), and or (3), but includes in principle, any combination with any pharmaceutical composition useful for the treatment of HIV. Further, in such combinations the compounds of the present invention and other HIV agents may be administered separately or in conjunction. In addition, the administration of one element may be prior to, concurrent to, or subsequent to the administration of other agent(s).

The compounds of Formula I in the present invention may be administered by oral, parenteral (e.g., intramuscular, intraperitoneal, intravenous, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The compounds of Formula I are all active and used to treat animals, including mice, rats, horses, cattle, sheep, dogs, cats, and monkey. The compounds of the invention are also effective for use in humans.

The compounds of Formula I of the present invention may form hydrates or solvates. When the compounds of Formula I of the present invention exist as regioisomers, configurational isomers, conformers, diasteroisomeric forms and mixtures of diasteroisomeric forms thereof, it is possible to isolate individual isomers using known separation and purification methods, if desired. When the compound of Formula I of the present invention is racemate, it can be separated into the (S)-compound and (R)-compound by optical resolution. Individual optical isomers and a mixture thereof are included in the scope of the present invention.

This invention also relates to a pharmaceutical composition comprising a pharmaceutically acceptable carrier or diluent and an effective amount of compound of Formula I. A compound of Formula I may be administered alone or as an admixture with a pharmaceutically acceptable carrier (e.g., solid formulations such as tablets, capsules, granules, powders, etc.; liquid formulations such as syrups, injections, etc.) may be orally or non-orally administered. Examples of non-oral formulations include injections, drops, suppositories, pessaryies.

In the treatment or prevention of conditions which require chemokine receptor modulation an appropriate dosage level will generally be about 0.01 to 500 mg per kg patient body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

The present invention further provides novel compounds that bind chemokine receptors and interfere with the binding of the natural ligand thereto. The compounds of the present invention are useful as agents demonstrating protective effects on target cells from HIV infection. The compounds of the present invention are also useful as antagonists or agonists of chemokine receptors, as well as other biological activities related to the ability of these compounds to inhibit the binding of chemokines to their receptors.

The compounds of the invention may be used as the "pro-drug" forms, that is, protected forms of the compounds, which release the compound after administration to a patient. For example, the compound may carry a protective groups which is split off by hydrolysis in body fluids e.g., in the bloodstream, thus releasing active compound or is oxidized or reduced in body fluids to release the compound. A discussion of pro-drugs may be found in "Smith and Williams' Introduction to the Principles of Drug Design", H. J. Smith, Wright, Second Edition, London 1988.

Acid addition salts, which are pharmaceutically acceptable, such as salt with inorganic base, a salt with organic base, a salt with inorganic acid, a salt with organic acid, a salt with basic or acidic amino acid, etc. are also encompassed in the present invention. Examples of a salt with an inorganic base include a salt with alkali metal (e.g., sodium, potassium, etc.), alkaline earth metal (e.g., calcium, magnesium, etc.), aluminum, ammonium, etc. Examples of the salt with an organic base include a salt with trimethylamine, triethylamine, pyridine, picoline, ethanolamine, diethanolamine, triethanolamine, dicyclohexylamine, N,N'-dibenzylethylenediamine etc. Examples of the salt with an inorganic acid include a salt with hydrochloric acid, hydrobromic acid, nitric acid, sulfuric acid, phosphoric acid, etc. Examples of the salt with an organic acid include a salt with formic acid, oxalic acid, acetic acid, tartaric acid, methanesulfonic acid, benzenesulfonic acid, malic acid, methanesulfonic acid, benzenesulfonic acid, p-toluenesulfonic acid, etc. Examples of salts with basic amino acids include a salt with arginine, lysine, ornithine, etc. Examples of salts with the acidic amino acid include a salt with aspartic acid, glutamic acid, etc. Non-toxic in the present context has to be considered with reference to the prognosis for the infected patient without treatment.

Further Definition of the Compounds

X, Y and Z can be coupled to the remainder of the molecule through any ring position.

In one set of preferred embodiments of the present invention, $L^1$ is a chemical bond.

In other preferred embodiments, Z comprises an optionally substituted aromatic or heteroaromatic group. In other preferred embodiments, Y comprises an unsubstituted heteroaromatic ring.

In one preferred set of embodiments, X or Z is a fused bicyclic system of the formula

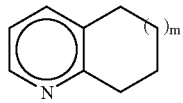
(A)

wherein m can be 0, 1 or 2.

In a another preferred cinbodlinent of X or Z comprises a group of the formula

(B)

which can be unsubstituted or substituted and wherein W is C, N, O or S. A panicularly preferred embodiment is

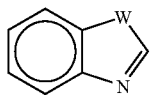
(C)

which may also be substituted or unsubstituted, but wherein W=NH is preferred.

Other preferred forms include compounds of the formula

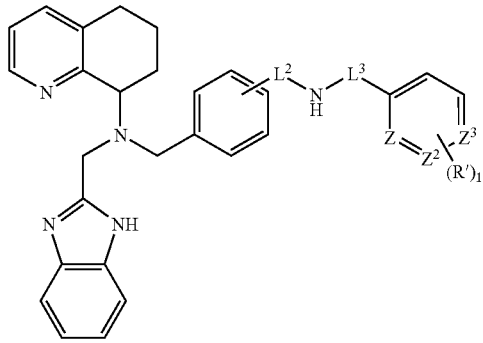
(D)

or of the formula:

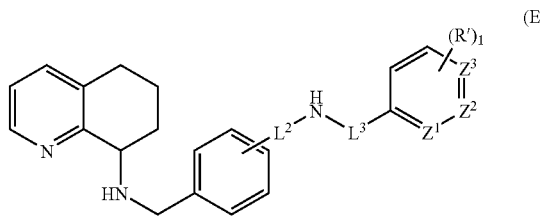
(E)

wherein l is 0-3, and R' is OH, MeO, SH SMe, CN, $CO_2Me$, F, Cl, Br, $NO_2$, $CH_3CO$, $NH_2$, $NHCH_3$, $N(CH_3)_2$, $CH_3CONH$, $CH_3SO_2NH$, $CONH_2$, $SO_2NH_2$, $CF_3$, or Me;

each of $Z^1$, $Z^2$ and $Z^3$ is independently CH, CR' or N, wherein only two of said $Z^1$, $Z^2$ and $Z^3$ can be N;

and $L^2$ and $L^3$ are as defined.

Still other preferred forms are compounds of the formula

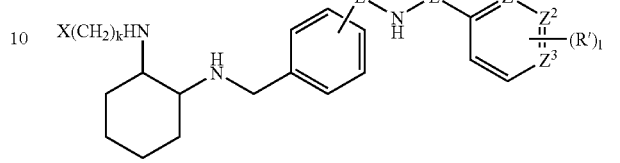
(F)

wherein l is 0-3, and R' is OH, MeO, SH SMe, CN, $CO_2Me$, F, Cl, Br, $NO_2$, $CH_3CO$, $NH_2$, $NHCH_3$, $N(CH_3)_2$, $CH_3CONH$, $CH_3SO_2NH$, $CONH_2$, $SO_2NH_2$, $CF_3$, or Me;

k is 0-2;

each of $Z^1$, $Z^2$ and $Z^3$ is independently CH, CR' or N, wherein only two of said $Z^1$, $Z^2$ and $Z^3$ can be N;

and X, $L^2$ and $L^3$ are as defined.

In Formula I, examples of the optionally substituted ring system, X or Z, are dihydroquinoline, tetrahydroquinoline, pyranopyridine, dihydropyranopyridine, thiapyranopyridine, dihydrothiapyranopyridine, dihydronaphthyridine, and tetrahydronaphthyridine. Oxides of nitrogen and sulfur-containing heterocycles are also encompassed in the present invention. In the above ring system, any ring nitrogen atom may be substituted with hydrogen, a substituted alkyl, alkenyl, cycloalkyl or aryl group, or may be the nitrogen atom of a carboxamide, carbamate or sulfonamide. A preferred embodiment is tetrahydroquinoline.

In Formula I, the "optional substituents" on X or Z may be halogen, nitro, cyano, carboxylic acid, an optionally substituted alkyl, alkenyl or cycloalkyl groups, an optionally substituted hydroxyl group, an optionally substituted thiol group, an optionally substituted amino or acyl group, an optionally substituted carboxylate, carbamate, carboxamide or sulfonamide group, an optionally substituted aromatic or heterocyclic group.

Examples of halogen include fluorine, chlorine, bromine, iodine, etc., with fluorine and chlorine preferred.

Examples of the optionally substituted alkyl include $C_{1-10}$ alkyl, including methyl, ethyl propyl etc., examples of the optionally substituted alkenyl groups include, $C_{2-10}$ alkenyl such as allyl, crotyl, 2-pentenyl, 3-hexenyl, etc., and examples of the optionally substituted cycloalkyl groups include $C_{3-10}$ cycloalkyl such as cyclopropyl, cyclobutyl, cyclopentyl, cyclohexyl, cycloheptyl, etc. In these cases, $C_{1-6}$ alkyl, alkenyl and cycloalkyl are preferred. The optional substituent may also be an optionally substituted aralkyl (e.g., phenyl$C_{1-4}$ alkyl) or heteroalkyl for example, phenylmethyl (benzyl), phenethyl, pyridinylmethy, pyridinylethyl etc. The heterocyclic group may be a 5 or 6 membered ring containing 1-4 heteroatoms.

Examples of the optionally substituted hydroxyl and thiol groups include an optionally substituted alkyl (e.g., $C_{1-10}$ alkyl) such as methyl, ethyl, propyl, isopropyl, butyl, isobutyl, sec-butyl, tert-butyl, pentyl etc., preferably ($C_{1-6}$) alkyl; an optionally substituted cycloalkyl (e.g., $C_{3-7}$ cycloalkyl, etc. such as cyclopropyl, cyclobutyl, cyclopentyl, cyclohexyl, cycloheptyl, etc.); an optionally substituted aralkyl (e.g., phenyl-$C_{1-4}$ alkyl, e.g., benzyl, phenethyl, etc.). Where there are two adjacent hydroxyl or thiol substituents, the heteroatoms may be connected via an alkyl group such as O(CH$_2$)$_n$O and S(CH$_2$)$_n$S (where n=1-5). Examples include methylenedioxy, ethylenedioxy etc. Oxides of thio-ether groups such as sulfoxides and sulfones are also encompassed.

Further examples of the optionally substituted hydroxyl group include an optionally substituted C$_{2-4}$ alkanoyl (e.g., acetyl, propionyl, butyryl, isobutyryl, etc.), C$_{1-4}$ alkylsulfonyl (e.g., methanesulfonyl, ethanesulfonyl, etc.) and an optionally substituted aromatic and heterocyclic carbonyl group including benzoyl, pyridinecarbonyl etc.

The substituents on the optionally substituted amino group may bind to each other to form a cyclic amino group (e.g., 5- to 6-membered cyclic amino, etc. such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g., fluorine, chlorine, bromine, iodine, etc.), nitro, cyano, hydroxy group, thiol group, amino group, carboxyl group, an optionally halogenated C$_{1-4}$ alkyl (e.g., trifluoromethyl, methyl, ethyl, etc.), an optionally halogenated C$_{1-4}$ alkoxy (e.g., methoxy, ethoxy, trifluoromethoxy, trifluoroethoxy, etc.), C$_{2-4}$ alkanoyl (e.g., acetyl, propionyl, etc.), C$_{1-4}$ alkylsulfonyl (e.g., methanesulfonyl, ethanesulfonyl, etc.) the number of preferred substituents are 1 to 3.

The amino group may also be substituted once or twice (to form a secondary or tertiary amine) with a group such as an optionally substituted alkyl group including C$_{1-10}$ alkyl (e.g., methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, C$_{1-6}$ alkyl, alkenyl and cycloalkyl are preferred. The amine group may also be optionally substituted with an aromatic or heterocyclic group, aralkyl (e.g., phenylC$_{1-4}$ alkyl) or heteroalkyl for example, phenyl, pyridine, phenylmethyl(benzyl), phenethyl, pyridinylmethyl, pyridinylethyl etc. The heterocyclic group may be a 5 or 6 membered ring containing 1-4 heteroatoms. The optional substituents of the "optionally substituted amino groups are the same as defined above for the "optionally substituted cyclic amino group."

The amino group may be substituted with an optionally substituted C$_{2-4}$ alkanoyl e.g., acetyl, propionyl, butyryl, isobutyryl etc., or a C$_{1-4}$ alkylsulfonyl (e.g., methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl etc. The heterocycles are as defined above.

Examples of the optionally substituted acyl group as the substituents on the fused ring system containing X include a carbonyl group or a sulfonyl group binding to hydrogen; an optionally substituted alkyl (e.g., C$_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower (C$_{1-6}$) alkyl, etc.; an optionally substituted cycloalkyl (e.g., C$_{3-7}$ cycloalkyl, etc., such as cyclopropyl, cyclobutyl, cyclopentyl, cyclohexyl, cycloheptyl, etc.); an optionally substituted alkenyl (e.g., C$_{2-10}$ alkenyl such as allyl, crotyl, 2-pentenyl, etc., preferably lower (C$_{2-6}$) alkenyl, etc.); an optionally substituted cycloalkenyl (e.g., C$_{3-7}$ cycloalkenyl, etc., such as 2-cyclopentenyl, 2-cyclohexenyl, 2-cyclopentenylmethyl, 2-cyclohexenylmethyl, etc.) an optionally substituted 5- to 6-membered monocyclic aromatic group (e.g., phenyl, pyridyl, etc.).

Examples of the optionally substituted carboxylate group (ester groups) include an optionally substituted alkyl (e.g., C$_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower (C$_{1-6}$) alkyl, etc.); an optionally substituted cycloalkyl (e.g., C$_{3-7}$ cycloalkyl, etc. such as cyclopropyl, cyclobutyl, cyclopentyl, cyclohexyl, cycloheptyl, etc.); an optionally substituted alkenyl (e.g., C$_{2-10}$ alkenyl such as allyl, crotyl, 2-pentenyl, 3-hexenyl, etc., preferably lower (C$_{2-6}$) alkenyl, etc.); an optionally substituted cycloalkenyl (e.g., C$_{3-7}$ cycloalkenyl, etc., such as 2-cyclohexenylmethyl, etc.); an optionally substituted aryl (e.g., phenyl, naphthyl, etc.) and C$_{1-4}$ aryl for example, benzyl, phenethyl etc. Groups such as methoxymethyl, methoxyethyl etc., are also encompassed.

Examples of the optionally substituted carboxamide and sulfonamide groups are identical in terms of the amine definition as the "optionally substituted amino group" defined above.

Examples of the optionally substituted aromatic or heterocyclic groups as optional substituents are phenyl, naphthyl, or a 5- or 6-membered heterocyclic ring containing 1-4 heteroatoms. The optional substituents are essentially identical to those listed above.

In the above examples the number of substituents is 1-4, preferably 1-2. The substituents on the optionally substituted groups are the same as the optionally substituted groups described above. Preferred substituents are halogen (fluorine, chlorine etc.), nitro, cyano, hydroxy group, thiol group, amino group, carboxyl group, carboxylate group, sulfonate group, sulfonamide group, carboxamide group, an optionally halogenated C$_{1-4}$ alkyl, an optionally halogenated C$_{1-4}$ alkoxy (e.g., trifluoromethoxy, etc.), C$_{2-4}$ alkanoyl (e.g., acetyl, propionyl, etc.) or aroyl, a C$_{1-4}$ alkylsulfonyl (e.g., methanesulfonyl, ethanesulfonyl, etc.), an optionally substituted aryl or heterocyclic group. The number of substituents on the said groups are preferably 1 to 3.

In the above Formulas, W may be CH (pyrrole), O (oxazole), S (thiazole), NH or NR' (imidazole) where R' is a C$_{1-6}$ alkyl group or acyl or sulfonyl group. Examples of fused ring systems that embody X or Z include but are not limited to indole, tetrahydroindole, benzimidazole, tetrahydrobenzimidazole, azabenzimidazole, benzoxazole, tetrahydrobenzoxazole, benzothiazole, tetrahydrobenzothiazole. Preferred ring systems are imidazole and benzimidazole.

In the above Formula I, Y is an optionally substituted heterocyclic group including a heteroaromatic group or aromatic group. Examples of the optionally substituted aromatic groups include benzene and naphthalene, or dihydronaphthalene and tetrahydronaphthalene. Examples of optionally substituted heterocyclic groups include 5 to 6-membered saturated, partially saturated, or aromatic heterocyclic rings containing 1 to 4 heteroatoms selected from nitrogen, oxygen and sulfur. The heterocycles may be pyridine, quinoline, isoquinoline, imidazole, benzimidazole, azabenzimidazole, benzotriazole, furan, benzofuran, thiazole, benzothiazole, oxazole, benzoxazole, pyrrole, indole, indoline, indazole, pyrrolidine, pyrrolidone, pyrroline, piperidine, piperazine, tetrahydroquinoline, tetrahydroisoquinoline, pyrazole, thiophene, isoxazole, isothiazole, triazole, tetrazole, oxadiazole, thiadiazole, morpholine, thiamorpholine, pyrazolidine, imidazolidine, imidazoline, tetrahydropyran, dihydropyran, benzopyran, dioxane, dithiane, tetrahydrofuran, tetrahydrothiophene, dihydrofuran, dihydrothiophene etc. Oxides of the nitrogen and sulfur containing heterocycles are also included in the present invention. The optional substituents for the fused or unfused aromatic or heterocyclic rings are identical to those described above.

When X or Z is of the formula A, B or C, optional substituents include additional ring systems such as cyclopentyl, cyclohexyl, cycloheptyl, tetrahydrofuran, tetrahydrothiophene(thiolane), tetrahydropyran, tetrahydrothiapyran(pentamethylene sulfide), phenyl, oxepine, thiepin, pyrollidine, piperidine, etc. Oxides of nitrogen and sulfur-containing heterocycles are also encompassed in the present invention. Other optional substituents are identical to the those described above.

The novel compounds of Formula I of the present invention may be formulated as pharmaceutical compositions that may be administered topically; percutaneously, including intravenously; orally; and by other standard routes of pharmaceutical administration to mammalian subjects as determined according to routine clinical practice.

Having now generally described the invention, the same will be more readily understood through reference to the following examples which are provided by way of illustration, and are not intended to be limiting of the present invention, unless specified.

EXPERIMENTAL

General Procedure A: Direct Reductive Amination with NaBH$_3$CN

To a stirred solution of the amine (1 equivalent) in anhydrous methanol (concentration ~0.1 M), at room temperature, was added the carbonyl compound (~1-2 equivalents) in one portion. Once the carbonyl had dissolved (~5 minutes), NaBH$_3$CN (~2-4 equiv.) was added in one portion and the resultant solution was stirred at room temperature. The solvent was removed under reduced pressure and CH$_2$Cl$_2$ (20 mL/mmol of amine) and brine or 1.0 M aqueous NaOH (10 mL/mmol amine) were added to the residue. The phases were separated and the aqueous phase was extracted with CH$_2$Cl$_2$ (3×10 mL/mmol amine). The combined organic phases were dried (Na$_2$SO$_4$) and concentrated. The crude material was purified chromatography.

General Procedure B: Direct Reductive Amination with NaBH(OAc)$_3$

To a stirred solution of the amine (I equivalent) in CH$_2$Cl$_2$ (concentration ~0.2 M), at room temperature, was added the carbonyl compound (~1-2 equivalents), glacial acetic acid (0-2 equivalents) and, NaBH(OAc)$_3$ (~1.5-3 equiv.) and the resultant solution was stirred at room temperature. The reaction mixture was poured into either saturated aqueous NaHCO$_3$ or 1.0 M aqueous NaOH (10 mL/mmol amine). The phases were separated and the aqueous phase was extracted with CH$_2$Cl$_2$ (3×10 mL/mmol amine). The combined organic phases were dried (Na$_2$SO$_4$) and concentrated. The crude material was purified chromatography.

General Procedure C: Deprotection of the 2-nitrobenzenesulfonyl group (nosyl)

To a stirred solution of the nosyl-protected amine (1 equivalent) in anhydrous CH$_3$CN (or DMF) (concentration ~0.05 M), at room temperature, was added thiophenol (4-8 equiv.) followed by powdered K$_2$CO$_3$ (8-12 equivalents). The resulting bright yellow solution was stirred at room temperature (or 50° C.) for 1-24 hours. The solvent was removed under reduced pressure and CH$_2$Cl$_2$ (10 mL/mmol amine) and water (2 mL/mmol amine) were added to the residue. The phases were separated and the aqueous phase was extracted with CH$_2$Cl$_2$ (3×5 mL). The combined organic phases were dried (Na$_2$SO$_4$) and concentrated. Purification of the crude material by chromatography provided the free base.

Alternative work-up: the reaction mixture was filtered and concentrated to provide a yellow oil which was purified by chromatography on basic alumina (eluant CH$_2$Cl$_2$ then 20:1 CH$_2$Cl$_2$—CH$_3$OH) and provided the free base as a colorless oil.

General Procedure D: Salt Formation Using Saturated HBr(g) in Acetic Acid

To a solution of the free base in glacial acetic acid (or dioxane) (2 mL) was added, a saturated solution of HBr(g) in acetic acid (or dioxane) (2 mL). A large volume of ether (25 mL) was then added to precipitate a solid, which was allowed to settle to the bottom of the flask and the supernatant solution was decanted. The solid was washed by decantation with ether (3×25 mL) and the remaining traces of solvent were removed under vacuum. For additional purification (where necessary), the solid can be dissolved in methanol and re-precipitated with a large volume of ether. Washing the solid with ether by decantation, followed by drying of the solid in vacuo (0.1 Torr) gave the desired compound.

General Procedure E: SEM-deprotection

To a stirred solution of the SEM-protected compound (1 equiv.) was added 6N HCl (30 mL/mmol), and the resultant solution was stirred at 50° C. for indicated time. The solution was diluted with water (50 mL/mmol), and it was neutralised with NaHCO$_3$ and extracted with EtOAc (3×100 mL/mmol). The combined organic phases were dried (Na$_2$SO$_4$) and concentrated. The crude material was purified by chromatography.

General Procedure F: EDCI Coupling

To a stirred solution of the amine (1 equiv.), acid (1.1 equiv.), 1-hydroxybenzotriazole (1.1 equiv.), 4-methyl morpholine (1.5 equiv.) in anhydrous DMF (~0.3 M), at room temperature under nitrogen atmosphere, was added EDCI (1.1 equiv.). The resultant solution was stirred at room temperature for the indicated time. DMF was removed under vacuum. The mixture was diluted with CH$_2$Cl$_2$ (100 mL/mmol), washed with NaHCO$_3$, dried (Na$_2$SO$_4$) and concentrated.

General Procedure G: Mesylation of Alcohols

To a stirred solution of the alcohol (1 equiv.), and Et$_3$N (1.2 equiv.), in anhydrous CH$_2$Cl$_2$ (~0.1 M), at 0° C. under nitrogen atmosphere, was added MsCl (1.1 equiv.) dropwise. The resultant solution was stirred at the indicated temperature for the indicated time. The mixture was diluted with CH$_2$Cl$_2$ (100 mL/mmol), washed with aqueous NH$_4$Cl, dried (Na$_2$SO$_4$) and concentrated.

General Procedure H: Substitution Reactions with Mesylates

To a stirred solution of the amine (1.5 equiv.), and Et$_3$N (1.0 equiv.), in anhydrous CH$_2$Cl$_2$ (~0.2 M), at 0° C. under nitrogen atmosphere, was added the mesylate (1.0 equiv.) solution dropwise. The resultant solution was stirred at room

EXAMPLE 1

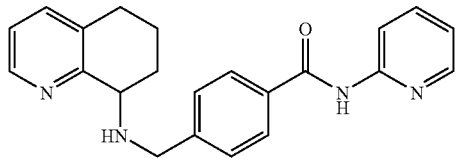

AMD9362: Preparation of N-Pyridin-2-yl-4-[(5,6,7,8-tetrahydro-quinolin-8-ylamino)-methyl]-benzamide 4-Chloromethyl-N-pyridinyl-2-yl-benzamide To a pre-cooled (ice bath) solution of 2-aminopyridine (304 mg, 3.22 mmol) and triethylamine (0.8 mL, 5.70 mmol) in anhydrous THF (5 mL) was added a solution of 4-chloromethylbenzoyl chloride (282 mg, 1.40 mmol) in THF (5 mL). The reaction mixture was allowed to stir at 0° C. for 3 hours under $N_2$ and then diluted with 300 mL ethyl acetate. The resulting organic solution was washed with sat. $NH_4Cl$, brine, dried over $Na_2SO_4$ and evaporated. The residue was purified by flash chromatography on silica gel, using 10% ethyl acetate in hexanes, to give the title compound (170 mg, 49%) as white solid. $^1H$ NMR (CDCl$_3$) δ 4.63 (s, 2H), 7.07 (dd, 1H, J=5.1, 7.2 Hz), 7.50 (d, 2H, J=8.1), 7.76 (ddd, 1H, J=1.5, 7.8, 8.1 Hz), 7.92 (d, 2H, J=8.4 Hz), 8.21 (d, 1H, J=4.5 Hz), 8.38 (d, 1H, J=8.4 Hz), 8.89 (br, s, 1H); ES-MS m/z 247.0 (M+H).

4-{[(2-Nitrobenzenesulfonyl)(5,6,7,8-tetrahydroquinolin-8-yl)-amino]-methyl}-N-pyridin-2-yl-benzamide 8-[N-(2-nitrobenzenesulfonyl)]amino-5,6,7,8-tetrahydroquinoline (230 mg, 0.69 mmol), 4-Chloromethyl-N-pyridinyl-2-yl-benzamide (170 mg, 0.69 mmol), and $K_2CO_3$ (285 mg, 2.06 mmol) were heated to reflux in $CH_3CN$ (3 mL) for 24 hours under $N_2$. The reaction mixture was diluted with 200 mL ethyl acetate, and washed with sat. $NaHCO_3$, then brine and dried over $Na_2SO_4$. Evaporation of the solvent and purification of the residue by flash chromatography on silica gel using 6% ethyl acetate in $CH_2Cl_2$ afforded the title compound (344 mg, 92%) as white foam. $^1H$ NMR (CDCl$_3$) δ 1.61-1.65 (m, 1H), 1.74-1.86 (m, 2H), 2.33-2.37 (m, 1H), 2.59-2.65 (m, 2H), 3.92 (d, 1H, J=16.2), 4.87 (d, 1H, J=16.5 Hz), 5.32 (dd, 1H, J=5.8, 11.3 Hz), 7.04-7.11 (m, 2H), 7.31-7.37 (m, 3H), 7.49-7.67 (m, 3H), 7.73-7.80 (m, 3H), 8.15 (d, 1H, J=7.8 Hz), 8.22 (d, 1H, J=4.2 Hz), 8.31 (d, 1H, J=4.2 Hz), 8.35 (d, 1H, J=8.4 Hz), 8.45 (br, s, 1H); ES-MS m/z 544.1 (M+H).

Using general procedure C: Reaction of 4-{[(2-Nitrobenzenesulfonyl)-(5,6,7,8-tetrahydro-quinolin-8-yl)-amino]-methyl}-N-pyridin-2-yl-benzamide (340 mg, 0.62 mmol), thiophenol (0.12 mL, 1.24 mmol) and $K_2CO_3$ (258 mg, 1.87 mmol) in DMF (3 mL) at room temperature under $N_2$ for 16 hours followed by purification of the crude material using radial chromatography on silica gel (2 mm plate, 3:3:94 $CH_3OH$—$NH_3$ $H_2O$—$CH_2Cl_2$), afforded AMD9362 (210 mg, 93%) as pale yellow oil. $^1H$ NMR (CDCl$_3$) δ 1.72-1.87 (m, 2H), 1.98-2.09 (m, 1H), 2.15-2.23 (m, 1H), 2.73-2.91 (m, 2H), 3.00 (br, s, 1H), 3.87 (dd, 1H, J=5.1, 7.5 Hz), 4.02 (d, 1H, J=13.8 Hz), 4.04 (d, 1H, J=13.8 Hz), 7.06-7.10 (m, 2H), 7.38 (d, 1H, J=7.5 Hz), 7.58 (d, 2H, J=8.1 Hz), 7.76 (ddd, 1H, J=1.8, 6.9, 8.7 Hz), 7.88 (d, 2H, J=8.4 Hz), 8.31 (d, 1H, J=4.2 Hz), 8.38-8.41 (m, 2H), 8.52 (br, s, 1H); $^{13}C$ NMR (CDCl$_3$) δ 20.04, 29.12, 29.22, 51.87, 58.09, 114.61, 120.20, 122.31, 127.78, 128.91, 132.87, 133.11, 137.32, 138.82, 146.04, 147.25, 148.26, 152.10, 157.63, 166.15; ES-MS m/z 359.2 (M+H); Anal. Calcd. for ($C_{22}H_{22}N_4O$).0.7($H_2O$): C, 71.21; H, 6.36; N, 15.10. Found: C, 71.16; H, 6.02; N, 14.79.

EXAMPLE: 2

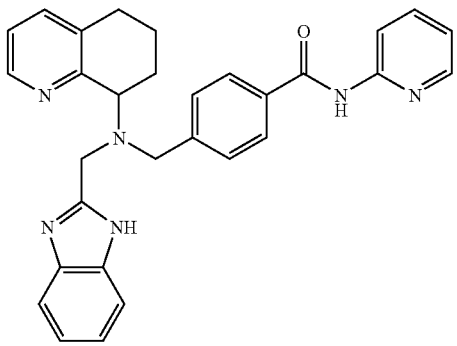

AMD9370: Preparation of 4-{[(1H-Benzimidazol-2-ylmethyl)(5,6,7,8-tetrahydro-quinolin-8-yl)amino]-methyl}-N-pyridin-2-yl-benzamide N-BOC-chloromethylbenzimidazole (115 mg, 0.43 mmol), N-Pyridin-2-yl-4-[(5,6,7,8-tetrahydro-quinolin-8-ylamino)methyl]-benzamide (AMD9362) (155 mg, 0.43 mmol), and $K_2CO_3$ (179 mg, 1.29 mmol) were heated to reflux in $CH_3CN$ (3 mL) for 24 hours under $N_2$. The reaction mixture was diluted with 200 mL ethyl acetate, and washed with sat. $NaHCO_3$, brine and dried over $Na_2SO_4$. Evaporation of the solvent and purification of the residue by flash chromatography on silica gel, followed by radial chromatography on silica gel (2 mm plate, 3:3:94 $CH_3OH$—$NH_3$ $H_2O$—$CH_2Cl_2$), afforded AMD9370 (100 mg, 47%) as white foam. $^1H$ NMR (CDCl$_3$) δ 1.68-1.75 (m, 1H), 1.97-2.08 (m, 2H), 2.26-2.32 (m, 1H), 2.71-2.84 (m, 1H), 2.86-2.91 (m, 1H), 3.84 (s, 2H), 3.95 (d, 1H, J=16.5 Hz), 4.08-4.14 (m, 1H), 4.22 (d, 1H, J=16.0 Hz), 7.03-7.07 (m, 1H), 7.16-7.22 (m, 3H), 7.45 (d, 1H, J=6.9 Hz), 7.52-7.61 (m, 3H), 7.65 (d, 1H, J=7.5 Hz), 7.73 (ddd, 1H, J=1.8, 7.2, 8.7 Hz), 7.80 (d, 2H, J=8.1 Hz), 8.27-8.29 (m, 1H), 8.33 (d 1H, J=8.4 Hz), 8.44 (br, s, 1H), 8.72-8.80 (m, 1H); $^{13}C$ NMR (CDCl$_3$) δ 21.72, 23.30, 29.56, 49.29, 54.16, 60.83, 111.39, 114.52, 120.17, 122.29, 122.81, 127.72, 129.28, 133.58, 135.17, 137.76, 138.77, 144.61, 147.38, 148.21, 152.00, 156.13, 157.54, 165.99; ES-MS m/z 489.2 (M+H); Anal. Calcd. for ($C_{30}H_{28}N_6O$).0.6($H_2O$).0.7($CHCl_3$): C, 63.25; H, 5.17; N, 14.42. Found: C, 63.56; H, 5.25; N, 14.31.

EXAMPLE: 3

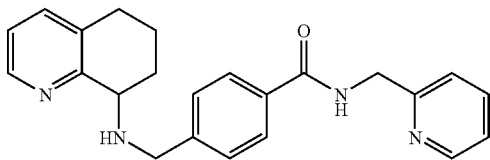

AMD9363: Preparation of N-Pyridin-2-ylmethyl-4-[(5,6,7,8-tetrahydro-quinolin-8-ylamino)-methyl]-benzamide 4-Chloromethyl-N-pyridinyl-2-ylmethyl-benzamide To a pre-cooled (ice bath) solution of 2-aminomethylpyridine (133 mg, 1.23 mmol) and triethylamine (0.35 mL, 2.50 mmol) in anhydrous THF (3 mL) was added the solution of 4-chloromethylbenzoyl chloride (240 mg, 1.23 mmol) in THF (3 mL). The reaction mixture was allowed to stir at 0° C. for 2 hours under $N_2$ and then diluted with 300 mL ethyl acetate. The resulting organic solution was washed with sat. $NH_4Cl$, then brine, dried over $Na_2SO_4$ and evaporated. The residue was purified by flash chromatography on silica gel, using 50% ethyl acetate in hexanes, to give the title compound (314 mg, 95%) as pale yellow oil. $^1H$ NMR ($CDCl_3$) δ 4.62 (s, 2H), 4.76 (d, 2H, J=4.5 Hz), 7.21-7.26 (m, 1H), 7.32 (d, 1H, J=7.8 Hz), 7.47 (d, 2H, J=8.4 Hz), 7.60 (br, s, 1H), 7.69 (ddd, 1H, J=1.8, 7.5, 7.8 Hz), 7.86 (d, 2H, J=8.4 Hz), 8.57 (d, 1H, J=4.8 Hz); ES-MS m/z 261.0 (M+H).

4-{[(2-Nitrobenzenesulfonyl)-(5,6,7,8-tetrahydro-quinolin-8-yl)-amino]-methyl}-N-pyridin-2-ylmethyl-benzamide 8-(2-nitrobenzenesulfonyl)amino-5,6,7,8-tetrahydro-quinoline (402 mg, 1.20 mmol), 4-Chloromethyl-N-pyridin-2-ylmethyl-benzamide (314 mg, 1.20 mmol), and $K_2CO_3$ (498 mg, 3.60 mmol) were heated to reflux in $CH_3CN$ (4 mL) for 24 hours under $N_2$. The reaction mixture was diluted with 200 mL ethyl acetate, and washed with sat. $NaHCO_3$, then brine and dried over $Na_2SO_4$. Evaporation of the solvent and purification of the residue by flash chromatography on silica gel, using 50% ethyl acetate in $CH_2Cl_2$, afforded the title compound (603 mg, 90%) as white foam. $^1H$ NMR ($CDCl_3$) δ 1.56-1.61 (m, 1H), 1.74-2.05 (m, 2H), 2.32-2.36 (m, 1H), 2.58-2.64 (m, 2H), 3.95 (d, 1H, J=16.2 Hz), 4.74 (d, 2H, J=4.5 Hz), 4.85 (d, 1H, J=15.9 Hz), 5.30 (dd, 1H, J=11.1, 17.4 Hz), 7.05 (dd, 1H, J=4.5, 7.5 Hz), 7.22-7.29 (m, 2H), 7.34 (dd, 2H, J=7.5, 7.8 Hz), 7.48-7.73 (m, 8H), 8.12-8.15 (m, 1H), 8.20-8.24 (m, 1H), 8.45-8.59 (m, 1H); ES-MS m/z 558.2 (M+H).

Using general procedure C: Reaction of 4-{[(2-Nitrobenzenesulfonyl)-(5,6,7,8-tetrahydro-quinolin-8-yl)-amino]-methyl}-N-pyridin-2-ylmethyl-benzamide (600 mg, 1.07 mmol), thiophenol (0.22 mL, 2.14 mmol) and $K_2CO_3$ (445 mg, 3.22 mmol) in DMF (5 mL) at room temperature under $N_2$ for 16 hours followed by purification of crude material using radial chromatography on silica gel (2 mm plate, 3:3:94 $CH_3OH$—$NH_3$ $H_2O$—$CH_2Cl_2$), afforded AMD9363 (390 mg, 93%). $^1H$ NMR ($CDCl_3$) δ 1.76-1.85 (m, 2H), 1.97-2.02 (m, 1H), 2.10-2.21 (m, 1H), 2.70-2.89 (m, 2H), 3.82-3.86 (m, 1H), 3.94 (d, 1H, J=13.5 Hz), 4.02 (d, 1H, J=13.8 Hz), 4.76 (d, 2H, J=4.8 Hz), 7.06 (dd, 1H, J=4.8, 7.5 Hz), 7.20-7.26 (m, 1H), 7.34 (dd, 2H, J=7.5, 15.6 Hz), 7.52 (d, 2H, J=8.1 Hz), 7.50-7.52 (m, 1H), 7.68 (ddd, 1H, J=1.5, 7.5, 7.8 Hz), 7.83 (d, 2H, J=8.1 Hz), 8.39 (d, 1H, J=3.9 Hz), 8.56 (d, 1H); $^{13}C$ NMR ($CDCl_3$) δ 20.02, 29.07, 29.21, 45.14, 51.86, 57.97, 122.26, 122.51, 122.75, 127.59, 128.65, 132.84, 133.21, 137.17, 137.28, 145.02, 147.21, 149.37, 156.78, 157.68, 167.69; ES-MS m/z 373.2 (M+H); Anal. Calcd. for ($C_{23}H_{24}N_4O$).0.5($H_2O$).0.3($CHCl_3$).0.2 ($C_4H_8O_2$): C, 66.56; H, 6.23; N, 12.88. Found: C, 66.20; H, 6.16; N, 12.88.

EXAMPLE: 4

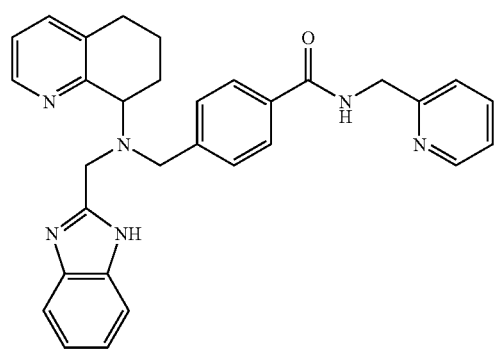

AMD9369: Preparation of 4-{[(1H-Benzimidazol-2-ylmethyl)-(5,6,7,8-tetrahydro-quinolin-8-yl)-amino]-methyl}-N-pyridin-2-ylmethyl-benzamide (hydrobromide salt)

N-BOC-chloromethyl benzimidazole (215 mg, 0.84 mmol), N-Pyridin-2-ylmethyl-4-[(5,6,7,8-tetrahydro-quinolin-8-ylamino)-methyl]-benzamide (AMD9363) (300 mg, 0.84 mmol), and $K_2CO_3$ (346 mg, 2.50 mmol) were heated to reflux in $CH_3CN$ (4 mL) for 24 hours under $N_2$. The reaction mixture was diluted with 200 mL ethyl acetate, and washed with sat. $NaHCO_3$, then brine, and dried over $Na_2SO_4$. Evaporation of the solvent and purification of the residue by flash chromatography on silica gel, followed by radial chromatography on silica gel (1 mm plate, 3:3:94 $CH_3OH$—$NH_3$ $H_2O$—$CH_2Cl_2$,), afforded the free base of the title compound (120 mg, 28%) as pale yellow oil.

Using general procedure D: the oil from above was converted to the corresponding hydrobromide salt to afford AMD9369. $^1H$ NMR ($D_2O$) δ 1.82-1.95 (m, 1H), 2.19-2.30 (m, 2H), 2.41-2.45 (m, 1H), 3.01-3.02 (m, 2H), 3.78 (d, 1H, J=12.6 Hz), 3.87 (d, 1H, J=12.6 Hz), 4.43 (d, 1H, J=16.5 Hz), 4.62 (d, 1H, J=16.2 Hz), 4.72 (s, 2H), 4.92-4.95 (m, 1H), 7.23 (d, 2H, J=8.4 Hz), 7.27-7.32 (m, 2H), 7.35 (d, 2H, J=8.4 Hz), 7.45-7.54 (m, 2H), 7.80 (d, 1H, J=8.1 Hz), 7.90-7.96 (m, 2H), 8.39 (d, 1H, J=8.1 Hz), 8.52-8.59 (m, 1H), 8.67 (dd, 1H, J=0.6, 5.7 Hz), 8.76 (d, 1H); $^{13}C$ NMR ($D_2O$) δ 20.43, 21.06, 27.86, 41.49, 50.28, 56.74, 63.48, 113.83, 126.15, 126.41, 127.31, 130.33, 130.51, 131.00, 139.78, 141.03, 141.34, 141.50, 147.59, 148.34, 150.62, 151.49, 153.11, 169.39; ES-MS m/z 503.14 (M+H); Anal. Calcd. for ($C_{31}H_{30}N_6O$).3.0(HBr).2.4($H_2O$): C, 47.22; H, 4.83; N, 10.66; Br, 30.40. Found: C, 47.35; H, 4.98; N, 10.37; Br, 30.35.

EXAMPLE: 5

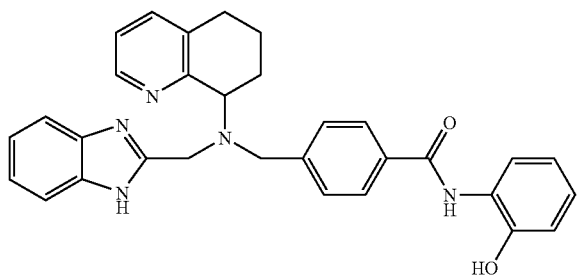

AMD9728: Preparation of [4-(1H-benzimidazol-2-ylmethyl)-(5,6,7,8-tetrahydroquinolin-8-yl)-aminomethyl]-N-(2-hydroxyphenyl)-benzamide (hydrobromide salt)

Preparation of 4-formyl-N-(2-hydroxyphenyl)-benzamide

A solution of 2-nitrophenol (1.55 g, 11.2 mmol) and methyl 4-chlorocarbonyl benzoate (2.44 g, 12.2 mmol) in THF (14 mL) and pyridine (2.8 mL) was stirred for 2 h at room temperature. The reaction was diluted with saturated sodium bicarbonate (30 mL) and EtOAc (20 mL), the phases separated and the aqueous phase extracted with EtOAc (2×15 mL). The combined organic extracts were dried ($Na_2SO_4$), filtered and concentrated under reduced pressure to afford terephthalic acid 1-methyl ester 4-(2-nitrophenyl) ester (3.15 g, 94%). $^1$H NMR ($CDCl_3$) δ 3.98 (s, 3H), 7.43 (d, 1H, J=7.8 Hz), 7.48 (t, 1H, J=7.8 Hz), 7.73 (t, 1H, J=7.8 Hz), 8.20 (m, 4H), 8.27 (m, 1H).

To a solution of terephthalic acid 1-methyl ester 4-(2-nitrophenyl)ester (3.13 g, 10.4 mmol) in glacial acetic acid (35 mL) was added iron powder (<5 μm mesh, 1.6 g, 28.0 mmol) and the mixture stirred at reflux for 1.5 h. The mixture was cooled, stirred at room temperature for 2 h and concentrated under reduced pressure. The residue was partitioned between saturated sodium bicarbonate (75 mL) and ethyl acetate (75 mL), the phases separated and the organic layer washed with saturated $NaHCO_3$ (50 mL). The organic extract was dried ($MgSO_4$), filtered, concentrated and purified by chromatography on silica gel (2% MeOH/$CH_2Cl_2$) to give (2-hydroxyphenyl)-terephthalamic acid methyl ester (1.31 g, 46%). $^1$H NMR ($CDCl_3$) δ 3.98 (s, 3H), 6.95 (t, 1H, J=7.8 Hz), 7.07 (d, 1H, J=7.8 Hz), 7.19 (t, 1H, J=7.8 Hz), 7.28 (d, 1H, J=7.8 Hz), 7.98 (d, 2H, J=8.4 Hz), 8.20 (m, 4H).

To a solution of (2-hydroxyphenyl)-terephthalamic acid methyl ester (1.31 g, 4.8 mmol) in THF (50 mL) at −78° C. was added a solution of DIBAL-H (27 mL, 1.0 M in THF). The reaction was allowed to warm to room temperature, stirred for 1 h and quenched with a saturated potassium sodium tartrate solution (15 mL). The biphasic mixture was stirred vigorously for 1 h, the phases separated and the organic layer dried ($MgSO_4$), filtered, concentrated and purified by column chromatography on silica gel (5% MeOH/$CH_2Cl_2$) to give 4-hydroxymethyl-N-(2-hydroxyphenyl)-benzamide (0.58 g, 50%). $^1$H NMR ($CDCl_3$) δ 1.83 (t, 1H (OH)), 4.82 (d, 2H, J=6.0 Hz), 6.93 (t, 1H, J=7.8 Hz), 7.08 (t, 1H, J=7.8 Hz), 7.19 (d, 2H, J=7.8 Hz), 7.53 (d, 2H, J=6.0 Hz), 7.92 (d, 2H, J=7.8 Hz), 8.07 (br, 1H), 8.62 (s, 1H).

4-Hydroxymethyl-N-(2-hydroxyphenyl)-benzamide from above (0.56 g, 2.3 mmol) was dissolved in $CH_2Cl_2$ (12 mL) and THF (12 mL), treated with activated $MnO_2$ (2.0 g, 23 mmol) and stirred at room temperature overnight. The mixture was filtered through celite, the cake washed with $CH_2Cl_2$ and the solvent from the eluent removed under reduced pressure. Purification of the crude by column chromatography on silica gel (5% MeOH/$CH_2Cl_2$) gave 4-formyl-N-(2-hydroxyphenyl)-benzamide (0.05 g, 10%). $^1$H NMR ($CDCl_3$) δ 6.95 (t, 1H, J=7.8 Hz), 7.05 (d, 1H, J=7.8 Hz), 7.16 (t, 1H, J=7.8 Hz), 7.42 (d, 1H, J=7.8 Hz), 8.04 (m, 5H), 8.33 (br, 1H).

Using General procedure A: To a solution of 4-formyl-N-(2-hydroxyphenyl)-benzamide (50 mg, 0.2 mmol) and (N-tert-butoxycarbonylbenzimidazol-2-ylmethyl)-(5,6,7,8-tetrahydroquinolin-8-yl)-amine (75 mg, 0.2 mmol) in MeOH (2 mL) was added $NaBH_3CN$ (25 mg, 0.4 mmol) and the mixture stirred at room temperature for 16 h. Purification of the crude material by radial chromatography on silica gel ($CH_2Cl_2$/MeOH/$NH_4OH$, 98:1:1) afforded the alkylated product (11 mg, 10%) as a colorless oil. $^1$H NMR ($CDCl_3$) δ 1.69 (m, 1H), 1.97 (m, 2H), 2.17 (m, 1H), 2.80 (m, 2H), 3.70 (s, 2H), 3.92 (d, 1H, J=16.8 Hz), 4.06 (m, 1H), 4.10 (d, 1H, J=17.1 Hz), 6.84 (t, 1H, J=6.0 Hz), 6.95 (d, 2H, J=6.0 Hz), 7.20 (m, 4H), 7.44 (m, 4H), 7.63 (br, 1H), 7.73 (d, 2H, J=7.2 Hz), 8.00 (d, 1H, J=6.0 Hz), 8.63 (d, 1H, J=3.5 Hz), 8.78 (s, 1H).

Using General procedure D: Conversion of the oil from above (11 mg) to the hydrobromide salt, followed by re-precipitation of the intermediate solid from methanol/ether, provided AMD9628 (15 mg) as a pale yellow solid. $^1$H NMR ($D_2O$) δ 1.87 (br m, 1H), 2.25 (m, 2H), 2.44 (br m, 1H), 3.05 (br m, 2H), 3.78 (d, 1H, J=12.6 Hz), 3.88 (d, 1H, J=12.6 Hz), 4.45 (d, 1H, J=16.2 Hz), 4.64 (d, 1H, J=16.2 Hz), 4.75 (m, 1H), 7.02 (d, 2H, J=7.8 Hz), 7.22 (d, 1H, J=7.8 Hz), 7.24 (d, 2H, J=11.4 Hz), 7.34 (d, 1H, J=7.8 Hz), 7.41 (d, 2H, J=7.8 Hz), 7.45 (d, 2H, J=9.0 Hz), 7.55 (dd, 2H, J=3.3, 6.3 Hz), 7.96 (t, 1H, J=8.4 Hz), 8.42 (d, 1H, J=8.1 Hz), 8.79 (d, 1H, J=5.4 Hz); $^{13}$C NMR ($D_2O$) δ 20.44, 21.04, 27.86, 50.32, 56.76, 63.57, 113.82 (2C), 116.90, 121.15, 124.08, 126.19, 126.38, 126.59, 126.81 (2C), 127.39 (2C), 128.62, 130.40 (2C), 130.47, 132.12, 139.76, 141.13 (2C), 148.34 (2C), 150.16, 150.76, 151.50. ES-MS m/z 504 (M+H). Anal. Calcd. for $C_{31}H_{29}N_5O_2 \cdot 2.2HBr \cdot 2.0H_2O$: C, 52.05; H, 4.96; N, 9.79; Br, 24.21. Found: C, 52.07; H, 5.01; N, 9.69; Br, 24.21.

EXAMPLE: 6

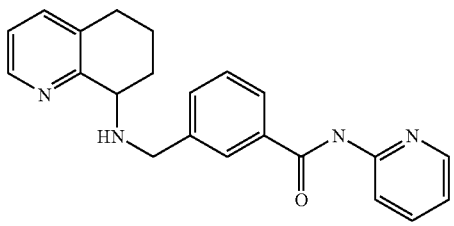

AMD9560: Preparation of N-Pyridinyl-2-yl-3-[(5,6,7,8-tetrahydro-quinolin-8-ylamino)-methyl]-benzamide (hydrobromide salt)

Preparation of 3-chloromethyl-N-pyridinyl-2-yl-benzamide

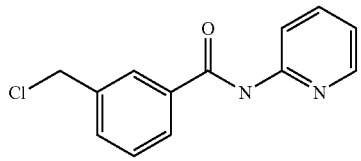

To a pre-cooled (ice bath) solution of 2-amino pyridine (2.0 g, 21.20 mmol) in anhydrous DMF (10 mL) was added the solution of 3-chloromethylbenzoyl chloride (1.51 ml, 10.60 mmol). The reaction mixture was allowed to stir at 0° C. for 1 hour and at 50° C. for 0.5 h under $N_2$. The reaction was concentrated in vacuo and the resultant white solid was filtered, washing with MeOH. The filtrate was concentrated in vacuo and the resultant crude product was purified by flash chromatograph on silica gel (Hexanes/EtOAc, 4:1) to give the title compound (402 mg, 15%) as a colorless oil. $^1$H NMR (CDCl$_3$) δ 4.63 (s, 2H), 7.63 (dd, 1H, J=5.1, 7.2 Hz), 7.49 (t, 1H, J=7.6 Hz), 7.59 (d, 1H, J=7.8 Hz), 7.76 (ddd, 1H, J=1.8, 9.0, 9.0 Hz), 7.78 (d, 1H, J=7.8 Hz), 7.96 (s, 1H), 8.22 (d, 1H, J=4.5 Hz), 8.39 (d, 1H, J=8.4 Hz), 8.96 (br s, 1H).

Preparation of 3-{[(2-Nitro-benzenesulfonyl)-(5,6,7,8-tetrahydro-quinolin-8-yl)-amino]-methyl}-N-pyridinyl-2-yl-benzamide

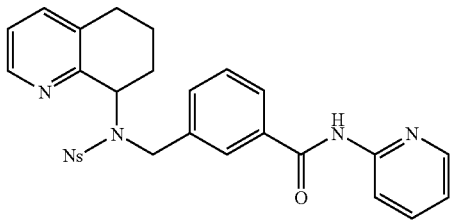

8-[N-(2-nitrobenzenesulfonyl)]amino-1,2,3,4-tetrahydroquinoline (248 mg, 0.74 mmol), 3-chloromethyl-N-pyridinyl-2-yl-benzamide (183 mg, 0.74 mmol), and K$_2$CO$_3$ (308 mg, 2.23 mmol) were heated to 80° C. in CH$_3$CN (2.5 mL) for 4 hours under N$_2$. The reaction mixture was concentrated in vacuo, diluted with ethyl acetate, and filtered through celite. Evaporation of the solvent and purification of the residue by flash chromatography on silica gel (EtOAc/CH$_2$Cl$_2$ 1:19) afforded the title compound (298 mg, 74%) as a yellow form. $^1$H NMR (CDCl$_3$) δ 1.21-1.29 (m, 2H), 1.90-2.05 (m, 1H), 2.40-2.45 (m, 1H), 2.68-2.75 (m, 2H), 4.06 (d, 1H, J=15.0 Hz), 4.79 (d, 1H, J=15.0 Hz), 5.37 (dd, 1H, J=4.5, 12.0 Hz), 6.91-7.09 (m, 2H), 7.35-7.37 (m, 2H), 7.49-7.54 (m, 5H), 7.61-7.74 (m, 2H), 8.12 (d, 1H, J=4.2 Hz), 8.31-8.34 (m, 3H), 8.42 (br s, 1H).

Using the nosyl deprotection procedure C: Reaction of 3-{[(2-nitro-benzenesulfonyl)-(5,6,7,8-tetrahydro-quinolin-8-yl)-amino]-methyl}-N-pyridinyl-2-yl-benzamide (298 mg, 0.55 mmol), thiophenol (0.17 mL, 1.65 mmol) and K$_2$CO$_3$ (379 mg, 2.75 mmol) in DMF (5.5 mL) at room temperature under N$_2$ for 1.5 hours followed by purification of crude material by chromatography on silica gel (CH$_3$OH/NH$_3$ H$_2$O/CH$_2$Cl$_2$ 1:1:48) afforded the desired amide (144 mg, 73%) as a white solid.

Using the HBr salt formation general procedure D: Conversion of the solid from above to the hydrobromide salt gave AMD9560 as a white powder. $^1$H NMR (D$_2$O) δ 2.00-2.04 (m, 2H), 2.31-2.46 (m, 2H), 2.92-3.15 (m, 2H), 4.55 (d, 1H, J=13.2 Hz), 4.66 (d, 1H, J=13.2 Hz), 4.86-4.90 (m, 1H), 7.65-7.73 (m, 3H), 7.76-7.81 (m, 2H), 7.86 (d, 1H, J=7.8 Hz), 8.05 (d, 1H, J=8.1 Hz), 8.14 (s, 1H), 8.19 (d, 1H, J=4.8 Hz), 8.43-8.49 (m, 2H), 8.63 (d, 1H, J=4.8 Hz); $^{13}$C NMR (D$_2$O) δ 17.21, 24.26, 27.02, 49.49, 55.03, 117.53, 121.88, 126.96, 129.82, 130.41, 130.51, 131.77, 132.95, 135.83, 137.86, 138.84, 143.71, 144.80, 145.75, 147.95, 148.09, 170.41. ES-MS m/z 359 (M+H). Anal. Calcd. for (C$_{22}$H$_{22}$N$_4$O).3.0(HBr).2.0(H$_2$O): C, 41.47; H, 4.59; N, 8.79; Br, 37.62 Found: C, 41.70; H, 4.60; N, 8.60, Br, 37.33.

EXAMPLE: 7

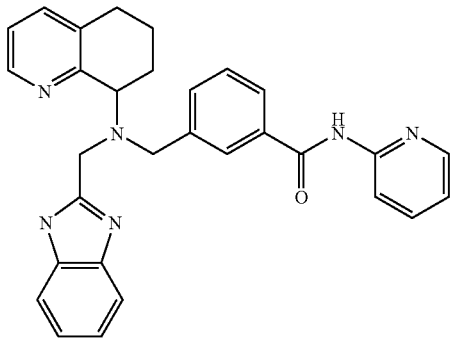

AMD9579: Preparation of N-pyridin-2-ylmethyl-3-[(5,6,7,8-tetrahydro-quinolin-8-ylamino)-methyl]-benzenesulfonamide (hydrobromide salt)

Preparation of pyridin-2-yl-3-({(5,6,7,8-tetrahydro-quinolin-8-yl)-[1-(2-trimethylsilanyl-ethoxymethyl)-1H-benzimidazol-2-ylmethyl]-amino}-methyl)-benzamide

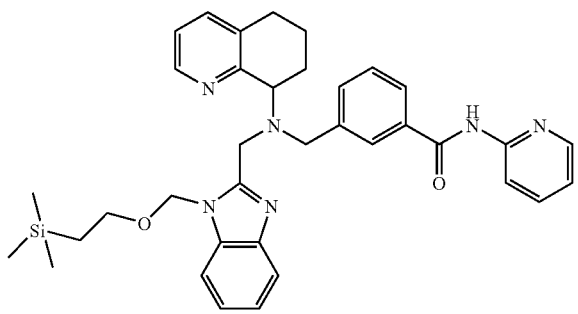

Using the reductive amination general procedure B: Reaction of N-pyridinyl-2-yl-3-[(5,6,7,8-tetrahydro-quinolin-8-ylamino)-methyl]-benzamide (AMD9560) (80 mg, 0.22 mmol), 1-(2-trimethylsilanyl-ethoxymethyl)-1H-benzoimidazole-2-carbaldehyde (62 mg, 0.22 mmol), NaBH(OAc)$_3$ (142 mg, 0.67 mmol), and AcOH (90 uL) for 1.5 h at room temperature followed by column chromatography on silica gel (CH$_2$Cl$_2$/MeOH/NH$_4$OH 98:1:1) gave the title compound (61 mg, 44%) as a white foam. $^1$H NMR (300 MHz, CDCl$_3$) δ 0.00 (s, 9H), 0.69 (2H, dd, J=8.4, 8.1 Hz), 1.24-1.25 (m, 1H), 2.03-2.14 (m, 2H), 2.25-2.29 (m, 1H), 2.65-2.88 (m, 2H), 3.21-3.34 (m, 2H), 3.79 (d, 1H, J=15.0 Hz), 3.90 (d, 1H, J=12.0 Hz), 4.09 (dd, 1H, J=9.0, 6.0 Hz), 4.25 (s, 2H), 5.73 (d, 1H, J=12.0 Hz), 6.16 (d, 1H, J=12.0 Hz), 7.03-7.10 (m, 2H), 7.16-7.20 (m, 2H), 7.30-7.34 (m, 3H), 7.45 (m, 1H, J=7.5 Hz), 7.64-7.69 (m, 2H), 7.74-7.80 (m, 1H), 8.25 (s, 1H), 8.39-8.41 (m, 2H), 8.71 (d, 1H, J=3.3 Hz), 8.98 (s, 1H).

Using the SEM deprotection general procedure E: Reaction of pyridin-2-yl-3-({(5,6,7,8-tetrahydro-quinolin-8-yl)-[1-(2-trimethylsilanyl-ethoxymethyl)-1H-benzimidazol-2-ylmethyl]-amino}-methyl)-benzamide (61 mg, 0.10 mmol) with 6N HCl (3.5 mL) at 50° C. for 3 h followed by column chromatography on silica gel (CH₂Cl₂/MeOH/NH₄OH 98:1: 1) gave desired product (46 mg, 96%) as a white foam.

Using the HBr salt formation general procedure D: Conversion of the foam from above to the hydrobromide salt gave AMD9579 as a white powder. $^1$H NMR (300 MHz, D₂O) δ 1.90-1.96 (m, 1H), 2.18-2.33 (m, 2H), 2.44-2.48 (m, 1H), 3.02-3.03 (m, 2H), 3.85 (d, 1H, J=12.9 Hz), 3.94 (d, 1H, J=12.9 Hz), 4.45 (d, 1H, J=16.5 Hz), 4.64 (d, 1H, J=16.2 Hz), 4.67-4.78 (m, 1H), 7.26-7.40 (m, 4H), 7.43-7.50 (m, 3H), 7.61 (s, 1H), 7.66 (d, 2H, J=8.1 Hz), 7.93 (dd, 1H, J=7.2, 5.7 Hz), 8.40 (d, 2H, J=7.8 Hz), 8.45 (d, 1H, J=6.0 Hz), 8.77 (d, 1H, J=5.4 Hz); $^{13}$C NMR (75.5 MHz, D₂O) δ 20.45, 21.05, 27.86, 50.20, 56.72, 63.37, 113.92, 117.32, 121.93, 126.19, 126.65, 127.02, 129.50, 129.65, 130.47, 130.85, 135.53, 137.80, 139.10, 139.81, 141.07, 147.13, 148.15, 148.35, 150.66, 151.62, 169.08. ES-MS m/z 489 (M+H). Anal. Calcd. for C₃₀H₂₈N₆O.2.7(HBr).3.4H₂O.0.2 (C₄H₁₀O): C, 47.24; H, 5.08; N, 10.73, Br, 27.55; Found: C, 47.26; H, 4.89; N, 10.51; Br, 27.41.

EXAMPLE: 8

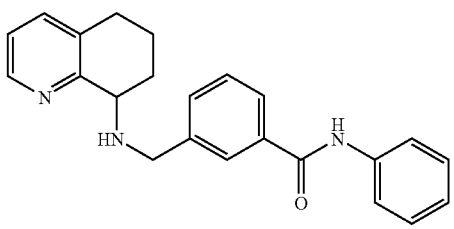

AMD9656: N-Phenyl-3-[(5,6,7,8-tetrahydro-quinolin-8-ylamino)-methyl]-benzamide (hydrobromide salt)

Preparation of 3-Chloromethyl-N-phenyl-benzamide

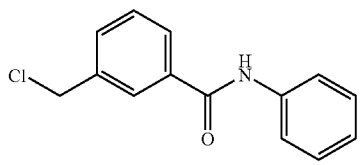

To a stirred solution of aniline (0.4 mL, 4.30 mmol) in anhydrous CH₂Cl₂ (10 mL) was added 3-chloromethylbenzoyl chloride (360 mg, 1.90 mmol). The reaction mixture was allowed to stir at room temperature overnight. The solvent was removed under reduced pressure. Purification of the residue on strong acid ion exchange resin column (elution with methanol) afforded the title compound (400 mg, 86%) as a white solid.

8-[N-(2-nitrobenzenesulfonyl)]amino-1,2,3,4-tetrahydroquinoline (332 mg, 1.00 mmol), 3-Chloromethyl-N-phenyl-benzamide (245 mg, 1.00 mmol), and K₂CO₃ (412 mg, 2.99 mmol) were heated to 85° C. in CH₃CN (10 mL) overnight under N₂. The reaction mixture was concentrated in vacuo, diluted with ethyl acetate, washed with H₂O, NaCl (aq), and dried (Na₂SO₄). Evaporation of the solvent and purification of the residue by flash chromatography on silica gel (3:7 EtOAc-Hexanes; 3:7 EtOAc-CH₂Cl₂) afforded the title compound (531 mg, 98%) as a yellow foam.

Using the nosyl deprotection general procedure C: Reaction of 3-{[(2-Nitro-benzenesulfonyl)-(5,6,7,8-tetrahydro-quinolin-8-yl)-amino]-methyl}-N-phenyl-benzamide (531 mg, 0.98 mmol), thiophenol (0.20 mL, 1.95 mmol) and K₂CO₃ (404 mg, 2.90 mmol) in DMF (5 mL) at room temperature under N₂ for 2 d followed by purification of the crude material by chromatography on silica gel (CH₃OH—NH₃ H₂O—CH₂Cl₂ 1:1:98) afforded the desired compound (200 mg, 57%) as a white foam.

Using General Procedure D: Conversion of the foam from above (200 mg, 0.56 mmol) to the hydrobromide salt using an acetic acid/HBr solution, followed by re-precipitation of the salt from diethyl ether gave AMD9656 as a white solid. $^1$H NMR (CD₃OD) δ 1.88-1.98 (m, 1H), 2.01-2.22 (m, 2H), 2.48-2.56 (m, 1H), 2.87-3.05 (m, 2H), 4.44 (d, 1H, J=12.9 Hz), 4.55 (d, 1H, J=12.9 Hz), 4.64 (dd, 1H, J=5.7, 9.3 Hz), 7.16 (dd, 1H, J=7.2, 7.2 Hz), 7.37 (dd, 2H, J=8.4, 8.4 Hz), 7.45 (dd, 1H, J=4.8, 7.8 Hz), 7.64 (dd, 1H, J=7.8, 7.8 Hz), 7.70 (d, 2H, J=8.1 Hz), 7.81 (dd, 2H, J=7.3, 7.3 Hz), 8.01 (d, 1H, J=7.8 Hz), 8.19 (s, 1H), 8.58 (d, 1H); $^{13}$C NMR (CD₃OD) δ 20.97, 26.66, 28.77, 50.22 (overlap with CD₃OD) 58.15, 122.65, 126.21, 129.98, 130.26, 131.01, 131.06, 133.68, 134.71, 136.67, 137.70, 140.10, 141.45, 147.82, 150.43, 168.35; ES-MS m/z 358.2 (M+H); Anal. Calcd. For (C₂₃H₂₃N₃O).1.7(HBr).1.0(H₂O): C, 53.85; H, 5.25; N, 8.19; Br, 26.48. Found: C, 53.64; H, 5.23; N. 7.92; Br, 26.77.

EXAMPLE: 9

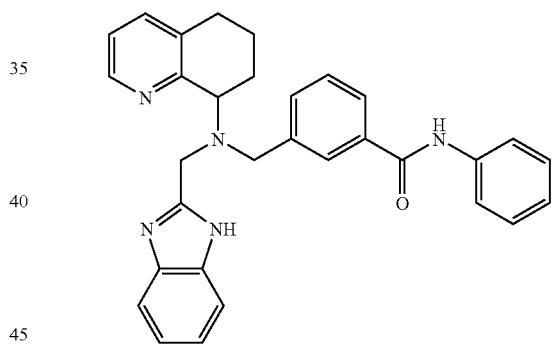

AMD9657: N-(3-{[(1H-enzimidazol-2-ylmethyl)-(5,6,7,8-tetrahydro-quinolin-8-yl)-amino]-methyl}-phenyl)-benzamide (hydrobromide salt)

Using general procedure B: Reaction of 1-(2-Trimethylsilanyl-ethoxymethyl)-1H-benzimidazole-2-carbaldehyde (62 mg, 0.22 mmol), N-Phenyl-3-[(5,6,7,8-tetrahydro-quinolin-8-ylamino)-methyl]-benzamide (80 mg, 0.22 mmol) and sodium triacetoxyborohydride (46 mg, 0.29 mmol) in CH₂Cl₂ (2 mL) at room temperature under N₂ for 40 min., followed by purification of the crude material by chromatography on silica gel (1:1:98 CH₃OH—NH₃ H₂O—CH₂Cl₂) afforded the title compound (127 mg, 92%) as a white foam.

Using general procedure E: Reaction of N-[3-({(5,6,7,8-Tetrahydro-quinolin-8-yl)-[1-(2-trimethylsilanyl-ethoxymethyl)-1H-benzoimidazol-2-ylmethyl]-amino}-methyl)-phenyl]-benzamide (127 mg, 0.20 mmol), 6 N HCl solution (3 ml) at 50° C. for 3 h, followed by purification of the crude material by chromatography on silica gel 1:1:98 $CH_3$OH—$NH_3$ $H_2O$—$CH_2Cl_2$) afforded the title compound (70 mg, 72%) as a white foam.

Using General Procedure D: Conversion of the foam from above (70 mg, 0.14 mmol) to the hydrobromide salt using an acetic acid/HBr solution, followed by re-precipitation of the salt from diethyl ether gave AMD9657 as a white solid. $^1$H NMR ($CD_3OD$) δ 1.87-2.01 (m, 1H), 2.24-2.37 (m, 2H), 2.47-2.51 (m, 1H), 3.05-3.10 (m, 2H), 3.88 (d, 1H, J=12.9 Hz), 3.94 (d, 1H, J=12.9 Hz), 4.29 (d, 1H, J=16.2 Hz), 4.63 (d, 1H, J=16.2 Hz), 4.76-4.82 (m, 1H), 7.14-7.20 (m, 2H), 7.39 (ddd, 2H, J=2.1, 5.4, 5.4 Hz), 7.45-7.54 (m, 4H), 7.65-7.69 (m, 2H), 7.77 (d, 2H, J=8.1 Hz), 7.93 (dd, 1H, J=6.0, 7.8 Hz), 8.04 (s, 1H), 8.38 (d, 1H, J=8.1 Hz), 8.95 (d, 1H, J=5.7 Hz); $^{13}$C NMR ($CD_3OD$) δ 21.97, 22.12, 29.27, 50.79, 57.90, 63.33, 115.14, 123.04, 126.22, 127.19, 127.93, 128.72, 130.07, 130.15, 130.63, 132.33, 134.87, 136.41, 138.10, 141.86, 142.03, 148.95, 152.29, 152.96; ES-MS m/z 488.3 (M+H); Anal. Calcd. For ($C_{31}H_{29}N_5O$).2.0(HBr).1.7 ($H_2O$): C, 54.75; H, 5.10; N, 10.30; Br, 23.50. Found: C, 54.81; H, 5.10; N, 10.21; Br, 23.41.

EXAMPLE: 10

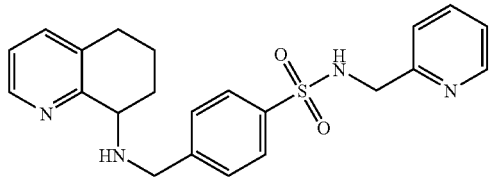

AMD9367: Preparation of N-Pyridin-2-ylmethyl-4-[(5,6,7,8-tetrahydro-quinolin-8-ylamino)-methyl]-benzenesulfonamide To a stirred solution of 4-bromomethyl-benzenesulfonyl chloride (500 mg, 1.85 mmol) and $Et_3N$ (269 uL, 1.85 mmol) in $CH_2Cl_2$ (10 mL), at −78° C., was added aminomethyl pyridine (190 uL, 1.85 mmol) in one portion. The resultant solution was stirred at −78° C. for 20 minutes. A second portion of $Et_3N$ (269 uL, 1.85 mmol) was added, followed by addition of 8-amino-5,6,7,8-tetrahydroquinoline (274 mg, 1.85 mmol). The solution was stirred for 18 h at room temperature. The mixture was diluted with $CH_2Cl_2$ (100 mL/mmol), filtered through celite, and concentrated. The crude material was purified by chromatography on silica gel ($CH_2Cl_2$/MeOH/$NH_4OH$ 48:1:1) to give AMD9367 (150 mg, 20%) as a white foam. $^1$H NMR (300 MHz, $CD_3COCD_3$) δ 1.69-1.98 (m, 2H), 2.00-2.05 (m, 1H), 2.11-2.18 (m, 1H), 2.71-2.85 (m, 3H), 3.82 (m, 1H), 3.96 (d, 2H, J=6.0 Hz), 4.23 (br s, 2H), 6.10 (br s, 1H), 7.05-7.15 (m, 3 H), 7.38 (d, 1H, J=7.8 Hz), 7.49 (d, 2H, J=9.0 Hz), 7.55-7.58 (m, 1H), 7.79 (d, 2H, J=9.0 Hz), 8.39 (d, 1H, J=4.8 Hz), 8.44 (d, 1H, J=4.5 Hz), $^{13}$C NMR (75.5 MHz, $CD_3COCD_3$) δ 20.05, 29.14, 29.20, 47.79, 51.70, 58.09, 122.39, 123.01, 127.68, 129.07, 132.90, 137.17, 137.40, 138.24, 146.62, 147.24, 149.38, 155.21, 157.54. ES-MS m/z 409 (M+H). Anal. Calcd. for $C_{22}H_{24}N_4O_2S$.0.2$H_2O$: C, 64.12; H, 5.97; N, 13.59. Found: C, 64.10; H, 5.91; N, 13.71.

EXAMPLE: 11

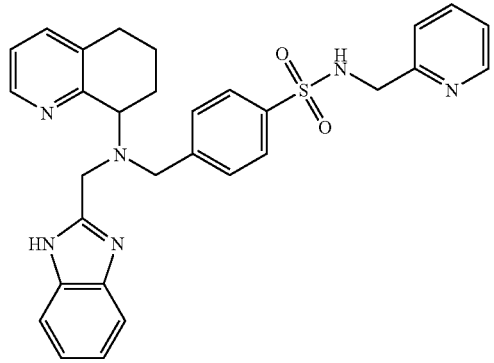

AMD9371: Preparation of 4-{[(1H-Benzimidazol-2-ylmethyl)-(5,6,7,8-tetrahydro-quinolin-8-yl)-amino]-methyl}-N-pyridin-2-ylmethyl-benzenesulfonamide Preparation of N-Pyridin-2-ylmethyl-4-({(5,6,7,8-tetrahydro-quinolin-8-yl)-[1-(2-trimethylsilanyl-ethoxymethyl)-1H-benzimidazol-2-ylmethyl]-amino}-methyl)-benzenesulfonamide Using general procedure B: Reaction of N-pyridin-2-ylmethyl-4-[(5,6,7,8-tetrahydro-quinolin-8-ylamino)-methyl]-benzenesulfonamide (97 mg, 0.24 mmol), 1-(2-trimethylsilanyl-ethoxymethyl)-1H-benzimidazole-2-carbaldehyde (72 mg, 0.26 mmol), and $NaBH(OAc)_3$ (151 mg, 0.71 mmol) for 1 h at room temperature followed by column chromatography on silica gel ($CH_2Cl_2$/MeOH/$NH_4OH$ 98:1:1) gave the title compound (63 mg, 50%) as a white foam. $^1$H NMR (300 MHz, $CDCl_3$) δ 0.00 (s, 9H), 0.77 (dd, 2H, J=7.5, 7.5 Hz), 1.73-1.74 (m, 1H), 1.95-2.06 (m, 2H), 2.20-2.25 (m, 1H), 2.66-2.86 (m, 2H), 3.29-3.35 (m, 2H), 3.78 (d, 1H, J=14.7 Hz), 3.98 (d, 1H, J=14.7 Hz), 4.05 (dd, 1H, J=9.3, 6.3 Hz), 4.13 (d, 2H, J=6.0 Hz), 4.18 (brs, 2H), 5.70 (d, 1H, J=12.0 Hz), 5.98 (d, 1H, J=12.0 Hz), 7.06-7.10 (m, 2H), 7.13-7.18 (m, 3H), 7.31-7.36 (m, 2H), 7.43 (d, 2H, J=8.1 Hz), 7.52-7.66 (m, 4H), 8.42 (d, 1H, J=4.8 Hz), 8.52 (d, 1H, J=4.5 Hz).

Using General Procedure E: Reaction of N-pyridin-2-ylmethyl-4-({(5,6,7,8-tetrahydro-quinolin-8-yl)-[1-(2-trimethylsilanyl-ethoxymethyl)-1H-benzoimidazol-2-ylmethyl]-amino}-methyl)-benzenesulfonamide (63 mg, 0.09 mmol), and 6N HCl (2.5 mL) for 3 h at 50° C. followed by column chromatography on silica gel ($CH_2Cl_2$/MeOH/$NH_4OH$ 48:1:1) gave AMD9371 (38 mg, 75%) as a white powder. $^1$H NMR (300 MHz, $CD_3OD$) δ 1.68-1.71 (m, 1H), 2.01-2.09 (m, 2H), 2.29 (br s, 1H), 2.73-2.89 (m, 2H), 3.68 (br s, 2H), 3.93 (br s, 1H), 4.00 (br s, 2H), 4.13-4.18 (m, 2H), 7.04-7.30 (m, 5H), 7.50-7.54 (m, 8H), 8.26 (br s, 1H), 8.60 (br s, 1H); $^{13}$C NMR (75.5 MHz, $CD_3OD$) δ 22.83, 24.68, 30.57, 51.69, 55.98, 63.36, 123.85, 124.14, 128.12, 130.93, 137.52, 138.92, 139.64, 140.66, 146.18, 148.46, 149.85, 155.92, 158.08, 158.74. ES-MS m/z 539 (M+H). Anal. Calcd. for $C_{30}H_{30}N_6O_2$ S: C, 66.89; H, 5.61; N, 15.60. Found: C, 66.65; H, 5.65; N, 15.60.

EXAMPLE: 12

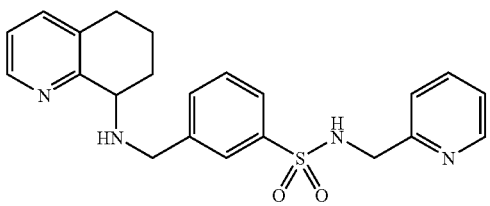

AMD9577: Preparation of N-Pyridin-2-ylmethyl-3-[(5,6,7,8-tetrahydro-quinolin-8-ylamino)-methyl]-benzenesulfonamide (hydrobromide salt)

Preparation of 3-[(Pyridin-2-ylmethyl)-sulfamoyl]-benzoic acid

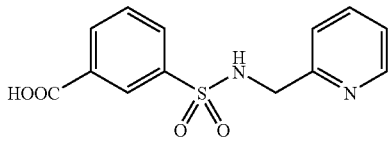

To a pre-cooled (ice bath) solution of 2-(aminomethyl)-pyridine (1.05 g, 9.7 mmol) in anhydrous $CH_2Cl_2$ (15 ml) was added 3-(Chlorosulfonyl)benzoic acid (714 mg, 3.23 mmol) under $N_2$ and the ice bath was removed after addition. Stirring was continued for 18 hours at room temperature, and the reaction mixture was diluted with 300 ml $CH_2Cl_2$, and filtered through celite. Evaporation of the solvent and purification of the residue by flash chromatography on silica gel, using 3:6:91 $CH_3COOH$-MeOH—$CH_2Cl_2$, gave the title compound (840 mg, 89%) as a pure white solid.

Purification of 3-Hydroxymethyl-N-pyridin-2-ylmethyl-benzenesulfonamide

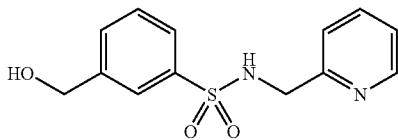

To solution of 3-[(Pyridin-2-ylmethyl)-sulfamoyl]-benzoic acid (840 mg, 2.87 mmol) in THF (5 ml) was added $BH_3$·THF (1M, 14.4 ml, 14.4 mmol) dropwise. After the addition, the reaction mixture was allowed to stir for 18 h at room temperature, and 5 N HCl (8 ml) was carefully added, resulting in the evolution of $H_2$. Upon heating to 70° C. for 2 h, a clear solution was obtained. Water (30 ml) was added, and the resulting solution was extracted with diethyl ether (3×20 ml). The aqueous phase was cooled to 0° C., neutralized with solid NaOH, and then solid $NaHCO_3$ and extracted with $CHCl_3$ (6×20 ml). The combined organic extracts were dried over $MgSO_4$, and concentrated under reduced pressure. The crude material was used without further purification in the next reaction.

Preparation of 3-Formyl-N-pyridin-2-ylmethyl-benzenesulfonamide

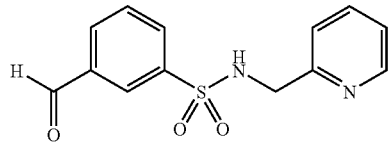

3-Hydroxymethyl-N-pyridin-2-ylmethyl-benzenesulfonamide (crude from previous step, 2.87 mmol) and $MnO_2$ (2.9 g, 28.7 mmol) in methanol (0.5 mL) and $CH_2Cl_2$ (15 mL) were reacted at 50° C. under $N_2$ overnight. The mixture was concentrated and purified by chromatography on silica gel (50% ethyl acetate and $CH_2Cl_2$) to afford the title compound (600 mg, 79% over two steps) as a white foam.

Using general procedure B: Reaction of 3-Formyl-N-pyridin-2-ylmethyl-benzenesulfonamide (317 mg, 1.21 mmol), 5,6,7,8-Tetrahydro-quinolin-8-ylamine (179 mg, 1.21 mmol), acetic acid (0.2 mL) and sodium triacetoxyborohydride (513 mg, 2.4 mmol) in THF (10 mL) at room temperature under $N_2$ for 40 min., followed by purification of the crude material by chromatography on silica gel (1:1:98 $CH_3OH$—$NH_3$ $H_2O$—$CH_2Cl_2$,), afforded the title compound (284 mg, 78%) as a white foam.

Using General Procedure: Conversion of the foam from above (30 mg, 0.073 mmol) to the hydrobromide salt using a solution of acetic acid/HBr, followed by re-precipitation of the salt from diethyl ether gave AMD9577 as a white solid. $^1H$ NMR ($D_2O$) δ 1.89-1.96 (m, 1H), 1.96-2.09 (m, 1H), 2.15-2.25 (m, 1H), 2.36-2.47 (m, 1H), 2.83-3.02 (m, 2H), 4.52 (s, 2H), 4.56 (s, 2H), 4.64-4.68 (m, 1H), 7.47-7.51 (m, 1H), 7.69 (t, 2H, J=7.8 Hz), 7.83-7.94 (m, 4H), 8.02 (s, 1H), 8.45-8.50 (m, 2H), 8.65 (d, 1H, J=6 Hz); $^{13}C$ NMR ($D_2O$) δ 17.86, 24.55, 27.11, 43.69, 48.86, 55.88, 126.33, 126.66, 128.55, 128.77, 131.27, 132.77, 135.88, 137.70, 139.03, 141.53, 143.94, 144.77, 147.69, 152.17; ES-MS m/z 409.2 (M+H); Anal. Calcd. for $(C_{22}H_{24}N_4O_2S)$·3.0(HBr)·0.4 $(H_2O)$·0.6$(C_4H_{10}O)$: C, 40.06; H, 4.49; N, 8.27; Br, 35.37; S, 4.73. Found: C, 39.80; H, 4.81; N, 8.35; Br, 35.65; S, 4.74.

EXAMPLE: 13

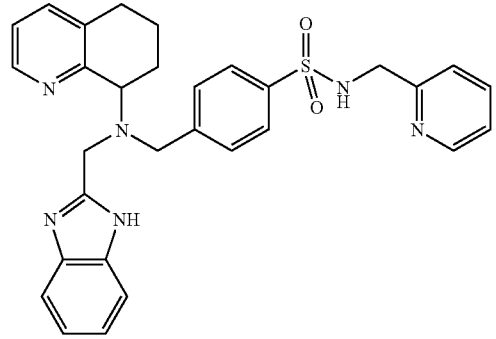

AMD9578: Preparation of 3-{[(1H-Benzimidazol-2-ylmethyl)-(5,6,7,8-tetrahydro-quinolin-8-yl)-amino]-methyl}-N-pyridin-2-ylmethyl-benzenesulfonamide (hydrobromide salt)

Using general procedure B: Reaction of 1-(2-Trimethylsilanyl-ethoxymethyl)-1H-benzimidazole-2-carbaldehyde (192 mg, 0.70 mmol), N-Pyridin-2-ylmethyl-3-[(5,6,7,8-tetrahydro-quinolin-8-ylamino)-methyl]-benzenesulfonamide (284 mg, 0.70 mmol), acetic acid (0.2 mL) and sodium triacetoxyborohydride (442 mg, 2.08 mmol) in THF (7 mL) at room temperature under N₂ for 40 min., followed by purification of the crude material by chromatography on silica gel (1:1:98 CH₃OH—NH₃H₂O—CH₂Cl₂,), afforded the title compound (177 mg, 38%) as a white foam.

Using general procedure E: Reaction of N-Pyridin-2-ylmethyl-3-({(5,6,7,8-tetrahydro-quinolin-8-yl)-[1-(2-trimethylsilanyl-ethoxymethyl)-1-N-benzimidazol-2-ylmethyl]-amino}-methyl)-benzenesulfonamide (177 mg, 0.26 mmol), 6 N HCl solution (3 ml) at 50° C. for 3 h, followed by purification of the crude material by chromatography on silica gel (2:2:98 CH₃OH—NH₃ H₂O—CH₂Cl₂,), afforded the title compound (104 mg, 73%) as a white foam.

Using General Procedure D: Conversion of the foam from above (104 mg, 0.19 mmol) to the hydrobromide salt using an acetic acid/HBr solution, followed by re-precipitation of the salt from diethyl ether gave AMD9578. $^1$H NMR (CD₃OD) δ 1.91-2.01 (m, 2H), 2.22-2.37 (m, 2H), 2.49-2.53 (m, 1H), 3.00-3.11 (m, 2H), 3.99 (d, 1H, J=12.9 Hz), 4.07 (d, 1H, J=13.2 Hz), 4.46 (d, 2H, J=4.2 Hz), 4.53 (d, 1H, J=16.5 Hz), 4.69 (d, 1H, J=16.5 Hz), 4.77-4.81 (m, 1H), 7.34 (dd, 1H, J=7.7, 7.7 Hz), 7.48 (d, 1H, J=8.1 Hz), 7.52-7.56 (m, 2H), 7.72-7.76 (m, 2H), 7.85 (d, 1H, J=7.8 Hz), 7.93-8.01 (m, 2H), 8.07 (s, 1H), 8.08 (d, 1H, J=9.0 Hz), 8.40 (d, 1H, J=7.8 Hz), 8.57 (ddd, 1H, J=1.5, 7.8, 7.8 Hz), 8.76 (d, 1H, J=6.0 Hz), 8.94 (d, 1H, J=5.1 Hz); $^{13}$C NMR (CD₃OD) δ 21.93, 29.27, 45.26, 50.48, 57.49, 62.41, 115.39, 127.31, 127.68, 128.05, 128.16, 128.24, 129.91, 130.99, 132.27, 136.64, 139.58, 140.94, 141.97, 142.15, 142.85, 148.53, 149.38, 151.97, 152.48, 155.26; ES-MS m/z 539.3 (M+H); Anal. Calcd. for (C₃₀H₃₀N₆O₂S).3.0(HBr).3.1(H₂O): C, 43.04; H, 4.72; N, 10.04; Br, 28.63; S, 3.83. Found: C, 43.15; H, 4.70; N, 10.03; Br, 28.56; S, 3.80.

EXAMPLE: 14

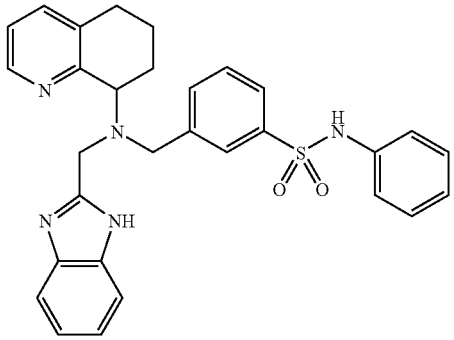

AMD9622: Preparation of 3-{[(1H-Benzoimidazol-2-ylmethyl)-(5,6,7,8-tetrahydro-quinolin-8-yl)-amino]-methyl}-N-phenyl-benzenesulfonamide (hydrobromide salt)

Preparation of 3-Phenylsulfamoyl-benzoic acid

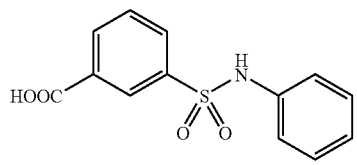

3-Chlorosulfonyl-benzoic acid (300 mg, 1.36 mmol), and aniline (0.30 mL, 3.29 mmol) were stirred at room temperature in anhydrous CH₂Cl₂ (10 mL) overnight under N₂. The reaction mixture was concentrated in vacuo. Purification of the residue on IR-120 ion exchange resin column (eluted with methanol) afforded the title compound (380 mg, 100%) as a white solid.

Preparation of 3-Hydroxymethyl-N-phenyl-benzenesulfonamide

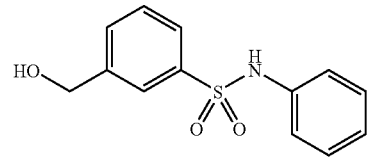

To solution of 3-Phenylsulfamoyl-benzoic acid (380 mg, 1.36 mmol) in THF (10 ml) was added BH₃.THF (1M, 5.4 ml, 5.4 mmol) dropwise. After the addition, the reaction mixture was allowed to stir for 3 d at room temperature. Methanol was added to the reaction and the mixture concentrated in vacuo (5×). This compound was used in the next step without further purification.

Preparation of 3-Formyl-N-phenyl-benzenesulfonamide

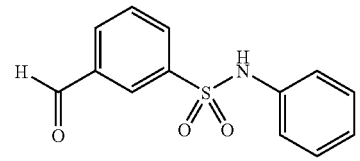

Reaction of 3-Hydroxymethyl-N-phenyl-benzenesulfonamide (crude from previous step, 1.36 mmol), MnO₂ (1.40 g, 13.60 mmol) in CH₂Cl₂ (10 mL) at 40° C. under N₂ overnight gave the title compound (293 mg, 82%) as a white solid.

Using general procedure B: Reaction of 2-[(5,6,7,8-Tetrahydro-quinolin-8-ylamino)-methyl]-benzoimidazole-1-carboxylic acid tert-butyl ester (172 mg, 0.46 mmol), 3-Formyl-N-phenyl-benzenesulfonamide (119 mg, 0.46 mmol) and sodium triacetoxyborohydride (116 mg, 0.55 mmol) in THF (4 mL) at room temperature under N₂ overnight, followed by purification of the crude material using chromatography on silica gel (2:1:97 CH₃OH—NH₃ H₂O—CH₂Cl₂,), afforded the title compound (93 mg, 33%) as a yellow foam.

Using General Procedure D: Boc deprotection of 2-{[(3-Phenylsulfamoyl-benzyl)-(5,6,7,8-tetrahydro-quinolin-8-yl)-amino]-methyl}-benzoimidazole-1-carboxylic acid tert-butyl ester from above (93 mg, 0.15 mmol) using an acetic acid/HBr solution, followed by re-precipitation of the salt from diethyl ether gave AMD9622 as a white solid. $^1$H NMR (CD₃OD) δ 1.76-1.85 (m, 1H), 2.15-2.25 (m, 2H), 2.35-2.39 (m, 1H), 2.96-3.05 (m, 2H), 3.85 (s, 2H), 4.38 (d, 1H, J=16.5 Hz), 4.60 (d, 1H, J=16.5 Hz), 4.59-4.61 (m, 1H), 6.90-6.93 (m, 1H), 7.00-7.10 (m, 4H), 7.22 (dd, 1H, J=7.6, 7.6 Hz), 7.34 (d, 1H, J=8.1 Hz), 7.51 (dd, 2H, J=3, 6.3 Hz), 7.69-7.72 (m, 3H), 7.79-7.83 (m, 2H), 8.21 (d, 1H, J=7.8 Hz), 8.85 (d 1H, J=4.8 Hz); $^{13}$C NMR (CD₃OD) δ 20.80, 21.30, 28.11, 49.24, 55.72, 61.29, 114.20, 121.15, 124.83, 125.61, 126.57, 126.74, 128.23, 129.26, 129.39, 131.49, 134.64, 137.95, 138.16, 140.09, 140.26, 141.43, 146.65, 151.71; ES-MS m/z 524.4 (M+H); Anal. Calcd. for (C₃₀H₂₉N₅O₂S).2.0(HBr). 1.2(H₂O): C, 50.96; H, 4.76; N, 9.90; Br, 22.60; S, 4.53. Found: C, 51.23; H, 4.96; N, 9.80; Br, 22.42; S, 4.45.

EXAMPLE: 15

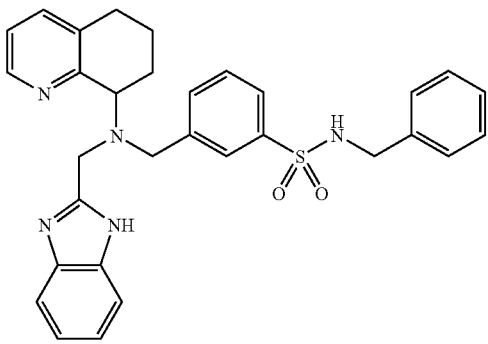

AMD9623: 3-{[(H-Benzimidazol-2-ylmethyl)-(5,6,7,8-tetrahydro-quinolin-8-yl)-amino]-methyl}-N-benzyl-benzenesulfonamide (hydrobromide salt)

Preparation of 3-Benzylsulfamoyl-benzoic acid

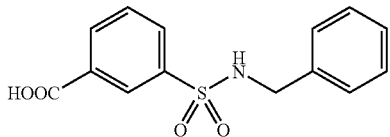

3-Chlorosulfonyl-benzoic acid (300 mg, 1.36 mmol), and benzylamine (0.60 mL, 5.49 mmol) were stirred at room temperature in anhydrous $CH_2Cl_2$ (10 mL) overnight under $N_2$. The reaction mixture was concentrated in vacuo. Purification of the residue on IR-120 ion exchange resin column (elution with methanol) afforded the title compound (395 mg, 100%) as a white solid.

Preparation of N-Benzyl-3-hydroxymethyl-benzenesulfonamide

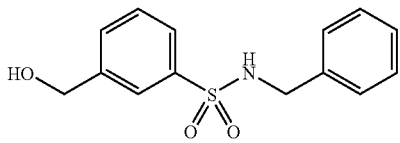

To solution of 3-Benzylsulfamoyl-benzoic acid (395 mg, 1.36 mmol) in THF (10 ml) was added $BH_3$.THF (1M, 5.4 ml, 5.4 mmol) dropwise. After addition, the reaction mixture was allowed to stir for 3 d at room temperature. Methanol was added to the reaction, and the mixture concentrated in vacuo (5×). This compound was used in the next step without further purification.

Preparation of N-Benzyl-3-formyl-benzenesulfonamide

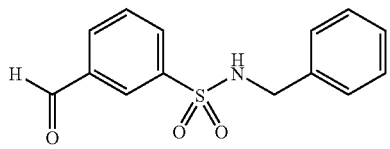

Reaction N-Benzyl-3-hydroxymethyl-benzenesulfonamide (crude from previous step, 1.36 mmol), $MnO_2$ (1.40 g, 13.60 mmol) in $CH_2Cl_2$ (10 mL) at 40° C. under $N_2$ overnight gave the title compound (317 mg, 85%) as a white solid.

Using general procedure B: Reaction 2-[(5,6,7,8-Tetrahydro-quinolin-8-ylamino)-methyl]-benzoimidazole-1-carboxylic acid tert-butyl ester (141 mg, 0.37 mmol), N-Benzyl-3-formyl-benzenesulfonamide (104 mg, 0.37 mmol) and sodium triacetoxyborohydride (95 mg, 0.45 mmol) in THF (4 mL) at room temperature under $N_2$ overnight, followed by purification of the crude material by chromatography on silica gel (1:1:98 $CH_3OH$—$NH_3$ $H_2O$—$CH_2Cl_2$) afforded the title compound (152 mg, 64%) as a yellow foam.

Using General Procedure D: Boc deprotection of 2-{[(3-Benzylsulfamoyl-benzyl)-(5,6,7,8-tetrahydro-quinolin-8-yl)-amino]-methyl}-benzimidazole-1-carboxylic acid tert-butyl ester (102 mg, 0.16 mmol) using an acetic acid/HBr solution, followed by re-precipitation of the salt from diethyl ether gave AMD9623 as a white solid. $^1H$ NMR ($CD_3OD$) δ 1.86-1.89 (m, 1H), 2.19-2.31 (m, 2H), 2.41-2.43 (m, 1H), 3.01-3.11 (m, 2H), 3.84 (d, 1H, J=12.9 Hz), 3.90 (d, 1H, J=12.9 Hz), 3.94 (s, 2H), 4.39 (d, 1H, J=16.2 Hz), 4.59-4.67 (m, 2H), 7.10 (b, 5H), 7.27 (dd, 1H, J=7.6, 7.6 Hz), 7.41 (d, 1H, J=7.8 Hz), 7.51 (dd, 2H, J=3, 6.3 Hz), 7.70-7.74 (m, 3H), 7.88 (dd, 2H, J=6.4, 6.4 Hz), 8.30 (d, 1H, J=7.8 Hz), 8.88 (d, 1H); $^{13}C$ NMR ($CD_3OD$) δ 20.39, 20.90, 27.81, 46.73, 50.11, 56.29, 62.83, 114.02, 125.94, 126.16, 126.69, 127.55, 127.95, 128.08, 128.78, 129.90, 134.45, 137.85, 139.81, 140.96, 148.22, 151.28; ES-MS m/z 538.4 (M+H); Anal. Calcd. for $(C_{31}H_{31}N_5O_2S).2.0(HBr).1.3(H_2O)$: C, 51.51; H, 4.96; N, 9.69; Br, 22.11; S, 4.43. Found: C, 51.60; H, 4.91; N, 9.63; Br, 22.07; S, 4.39.

EXAMPLE: 16

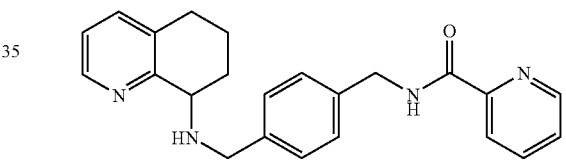

AMD 9397: Preparation of Pyridine-2-carboxylic acid 4-[(5,6,7,8-tetrahydro-quinolin-8-ylamino)-methyl]-benzylamide Preparation of Pyridine-2-carboxylic acid 4-hydroxymethyl-benzylamide Using General Procedure F: Reaction of (4-aminomethyl-phenyl)-methanol (200 mg, 1.46 mmol, 1-hydroxybenzotriazole (218 mg, 1.61 mmol), 4-methyl morpholine (241 uL, 2.19 mmol), and EDCI (309 mg, 1.61 mmol) for 2 h at room temperature gave the title compound (335 mg, 95%) as a yellow oil. $^1H$ NMR (300 MHz, $CDCl_3$) δ 4.67 (d, 2H, J=6.0 Hz), 4.69 (s, 2H), 7.36 (br s, 4H), 7.43-7.44 (m, 1H), 7.85-7.86 (m, 1H), 8.24 (d, 1H, J=9.0 Hz), 8.52 (br s, 1H), 8.52 (d, 1H, J=3.0 Hz). ES-MS m/z 243 (M+H).

Preparation of Methanesulfonic acid 4-{[(pyridine-2-carbonyl)-amino]-methyl}-benzyl ester Using General Procedure G: Reaction of pyridine-2-carboxylic acid 4-hydroxymethyl-benzylamide (200 mg, 0.83 mmol), $Et_3N$ (144 uL, 0.99 mmol), and MsCl (71 uL, 0.91 mmol) for 10 minutes at 0° C. gave the title compound (214 mg, 81%) as a white solid. $^1H$ NMR (300 MHz, $CDCl_3$) δ 2.92 (s, 3H), 4.69 (d, 2H, J=3.3 Hz), 5.23 (s, 2H), 7.41-7.47 (m, 5H), 7.85-7.87 (m, 1H), 8.24 (d, 1H, J=7.8 Hz), 8.50 (br s, 1H), 8.54 (d, 1H, J=3.9 Hz).

Preparation of Pyridine-2-carboxylic acid 4-[(5,6,7,8-tetrahydro-quinolin-8-ylamino)-methyl]-benzylamide Using General procedure H: Reaction of 8-amino-5,6,7,8-tetrahydroquinoline (148 mg, 1.00 mmol) with methanesulfonic acid 4-{[(pyridine-2-carbonyl)-amino]-methyl}-benzyl ester (214 mg, 0.67 mmol) for 3 h at room temperature followed by column chromatography on silica gel ($CH_2Cl_2$/MeOH/$NH_4OH$ 48:1:1) gave AMD9397 (81 mg, 33%) as a yellow oil. $^1$H NMR (300 MHz, $CDCl_3$) δ 1.72-1.83 (m, 2H), 2.00-2.06 (m, 1H), 2.16-2.20 (m, 1H), 2.75-2.83 (m, 2H), 3.82-3.84 (m, 1H), 3.88 (d, 1H, J=13.2 Hz), 3.98 (d, 1H, J=12.9 Hz), 4.65 (d, 2H, J=6.0 Hz), 7.05-7.06 (m, 1 H), 7.32-7.42 (m, 6H), 7.85 (ddd, 1H, J=7.8, 7.8, 1.8 Hz), 8.23 (d, 1H, J=7.8 Hz), 8.34 (br s, 1H), 8.37 (d, 1H, J=3.3 Hz), 8.52 (d, 1H, J=3.9 Hz). $^{13}$C NMR (75.5 MHz, $CDCl_3$) δ 20.05, 29.00, 29.24, 43.68, 51.85, 57.85, 122.19, 122.70, 126.56, 128.37 (2C), 129.01 (2C), 132.83, 137.07, 137.23, 137.73, 140.41, 147.20, 148.46, 150.23, 157.82, 164.57. ES-MS m/z 373 (M+H). Anal. Calcd. for $C_{23}H_{24}N_4O.0.3H_2O$: C, 73.11; H, 6.56; N, 14.83. Found: C, 72.98; H, 6.58; N, 14.63.

EXAMPLE: 17

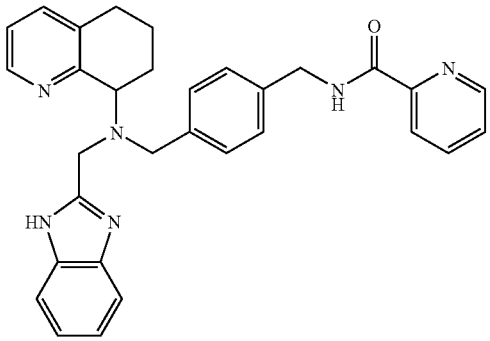

AMD9401: Preparation of Pyridine-2-carboxylic acid 4-{[(1H-benzimidazol-2-ylmethyl)-(5,6,7,8-tetrahydro-quinolin-8-yl)-amino]-methyl}-benzylamide Using General Procedure B:

Reaction of pyridine-2-carboxylic acid 4-[(5,6,7,8-tetrahydro-quinolin-8-ylamino)-methyl]-benzylamide (AMD9397) (40 mg, 0.11 mmol), 1H-benzoimidazole-2-carbaldehyde (16 mg, 0.11 mmol), and NaBH(OAc)$_3$ (68 mg, 0.32 mmol) for 2 h at 60° C. followed by column chromatography on silica gel ($CH_2Cl_2$/MeOH/$NH_4OH$ 198:1:1) gave AMD9401 (28 mg, 52%) as a white foam. $^1$H NMR (300 MHz, $CD_3OD$) δ 1.60-1.63 (m, 1H), 1.95-2.06 (m, 2H), 2.20-2.22 (m, 1H), 2.66-2.83 (m, 2H), 3.51 (d, 1H, J=13.2 Hz), 3.58 (d, 1H, J=13.2 Hz), 3.94 (d, 1H, J=15.3 Hz), 4.04-4.09 (m, 3H), 4.42 (br s, 2H), 7.09-7.15 (m, 4H), 7.20 (dd, 1H, J=7.8, 4.8 Hz), 7.20 (d, 1H, J=8.1 Hz), 7.28 (d, 2H, J=8.1 Hz), 7.41-7.47 (m, 2H), 7.48-7.52 (m, 2H), 7.91 (ddd, 1H, J=7.5, 7.5, 1.8 Hz), 8.06 (d, 1H, J=7.8 Hz), 8.55 (d, 1H, J=4.5 Hz), 8.60 (d, 1H, J=4.5 Hz); $^{13}$C NMR (75.5 MHz, $CD_3OD$) δ 22.84, 24.33, 30.62, 44.13, 51.41, 56.15, 63.13, 123.55, 124.03, 128.13, 128.61, 130.80, 137.39, 138.95, 139.14, 139.51, 139.67, 148.35, 150.17, 151.40, 156.31, 158.31, 166.94. ES-MS m/z 503 (M+H). Anal. Calcd. for $C_{31}H_{30}N_6O.0.8H_2O.0.3CH_2Cl_2$: C, 69.30; H, 5.98; N, 15.49. Found: C, 69.63; H, 6.14; N, 15.19.

EXAMPLE: 18

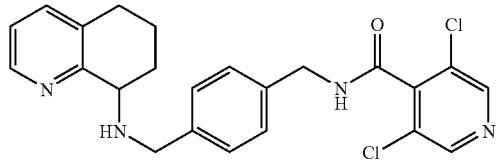

AMD9927: Preparation of 3,5-dichloro-N-{4-[(5,6,7,8-tetrahydro-quinolin-8-ylamino)-methyl]-benzyl}-isonicotinamide Preparation of 3,5-dichloro-N-(4-formyl-benzyl)-isonicotinamide To a partially dissolved solution of 3,5-dichloro-N-(4-hydroxymethyl-benzyl)-isonicotinamide (730 mg, 2.35 mmol) in $CH_2Cl_2$ (12 mL) and MeOH (1 mL) was added $MnO_2$ (2.43 g, 23.5 mmol) and the resultant suspension was stirred at 40° C. for 16 hours. The reaction mixture was cooled to room temperature and filtered through Celite. The cake was washed with $CH_2Cl_2$/MeOH (100:3) and the filtrate was concentrated under reduced pressure to afford a crude white solid (630 mg). Purification by column chromatography on silica gel ($CH_2Cl_2$/MeOH/$NH_4OH$, 100:1:1) afforded the desired aldehyde (480 mg, 66%) as a white solid. $^1$H NMR ($CDCl_3$) δ 4.78 (d, 2H, J=6.0 Hz), 6.19 (br s, 1H), 7.58 (d, 2H, J=9.0 Hz), 7.90 (d, 2H, J=9.0 Hz), 8.55 (s, 2H), 10.02 (s, 1H).

Using General Procedure B: A solution of the aldehyde from above (100 mg, 0.32 mmol) and 5,6,7,8-tetrahydro-quinolin-8-ylamine (56 mg, 0.38 mmol) in MeOH (2 mL) were stirred at room temperature overnight. NaBH$_4$ (24 mg, 0.65 mmol) was added and the resultant mixture stirred at room temperature for an additional 15 minutes. Purification of the crude brown foam (160 mg) by radial chromatography on silica gel (2 mm plate, 100% EtOAc) followed by radial chromatography on silica gel (1 mm plate, $CH_2Cl_2$/MeOH/$NH_4OH$, 100:2:1) afforded AMD9927 (70 mg, 50%) as a white foam. $^1$H NMR ($CDCl_3$) δ 1.61-1.78 (m, 2H), 1.92-2.18 (m, 2H), 2.65-2.90 (m, 3H), 3.73-3.81 (m, 2H), 3.89 (d, 1H, J=13.2 Hz), 4.55 (d, 2H, J=5.7 Hz), 6.97-7.06 (m, 2H), 7.25-7.28 (m, 2H), 7.31-7.36 (m, 3H), 8.30-8.32 (m, 1H), 8.38 (s, 2H); $^{13}$C NMR ($CDCl_3$) δ 20.05, 28.89, 29.18, 44.05, 51.66, 57.82, 122.27, 128.46, 128.97, 129.37, 132.84, 135.83, 137.31, 140.65, 142.70, 147.14, 147.93, 157.61, 162.36. ES-MS m/z 441.2 (M+H). Anal. Calcd. for $C_{23}H_{22}N_4Cl_2O.0.1H_2O$: C, 62.34; H, 5.05; N, 12.64; Cl, 16.00. Found: C, 62.38; H, 5.17; N, 12.48; Cl, 15.90.

EXAMPLE: 19

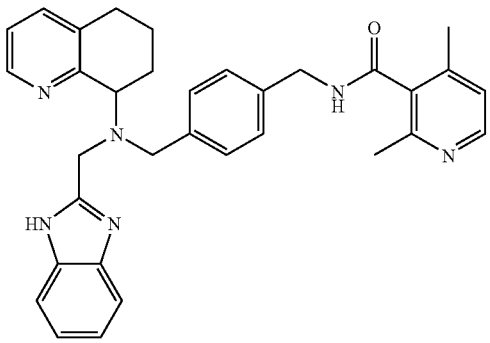

AMD9960: Preparation of N-(4-{[(1H-benzoimida-zol-2-ylmethyl)-(5,6,7,8-tetrahydro-quinolin-8-yl)-amino]-methyl}-benzyl)-2,4-dimethyl-nicotinamide (hydrobromide salt)

A solution of 2,4-dimethyl-nicotinic acid (54 mg, 0.35 mmol) in $SOCl_2$ (~2 mL, excess) was heated to 80° C. for 4 hours. The condenser was removed and the mixture was flushed with $N_2$ at 80° C. for ~5 minutes and then dried in vacuo for 10 minutes. The resulting syrup was dissolved in $CH_2Cl_2$ (2.4 mL) and added to a stirring mixture of (4-aminomethyl-benzyl)-(1H-benzoimidazol-2-ylmethyl)-(5,6,7,8-tetrahydro-quinolin-8-yl)-amine (187 mg, 0.47 mmol), $Et_3N$ (0.33 mL, 2.35 mmol) and a catalytic amount of DMAP. The reaction mixture was stirred overnight at room temperature. Purification of the crude yellow foam (240 mg) by radial chromatography on silica gel (2 mm plate, $CH_2Cl_2$/MeOH/$NH_4OH$, 100:2:1) followed by radial chromatography on silica gel (1 mm plate, EtOAc/MeOH/$NH_4OH$, 400:3:3) afforded the desired amide (61 mg, 33%) as a white foam.

Using General Procedure D: Conversion of the foam from above to the hydrobromide salt afforded AMD9960 as a white solid. $^1$H NMR ($D_2O$) δ 1.80-1.98 (m, 1H), 2.15-2.38 (m, 2H), 2.39-2.51 (m, 4H), 2.56 (s, 3H), 3.02-3.05 (m, 2H), 3.77 (d, 1H, J=12.6 Hz), 3.84 (d, 1H, J=12.6 Hz), 4.04 (s, 2H), 4.44 (d, 1H, J=16.5 Hz), 4.63 (d, 1H, J=16.5 Hz), 4.74-4.79 (m, 1H, overlap with HOD), 6.94 (d, 2H, J=8.1 Hz), 7.17 (d, 2H, J=8.1 Hz), 7.47-7.52 (m, 2H), 7.57-7.61 (m, 2H), 7.75 (d, 1H, J=6.3 Hz), 7.92 (dd, 1H, J=7.8, 5.7 Hz), 8.39 (d, 1H, J=7.8 Hz), 8.49 (d, 1H, J=6.3 Hz), 8.76 (dd, 1H, J=5.7, 0.9 Hz); $^{13}$C NMR ($D_2O$) δ 17.56, 19.96, 20.48, 20.92, 27.85, 43.03, 50.21, 56.67, 63.20, 113.86, 126.07, 126.66, 126.98, 127.69, 130.52, 135.29, 135.93, 137.22, 139.63, 140.81, 140.93, 148.21, 150.18, 150.93, 151.87, 157.45, 166.29. ES-MS m/z 531.3 (M+H). Anal. Calcd. for $C_{33}H_{33}N_6O.3.1HBr.1.8H_2O.0.4C_4H_{10}O$: C, 49.32; H, 5.23; N, 9.97; Br, 29.40. Found: C, 49.31; H, 5.25; N, 9.97; Br, 29.39.

EXAMPLE: 20

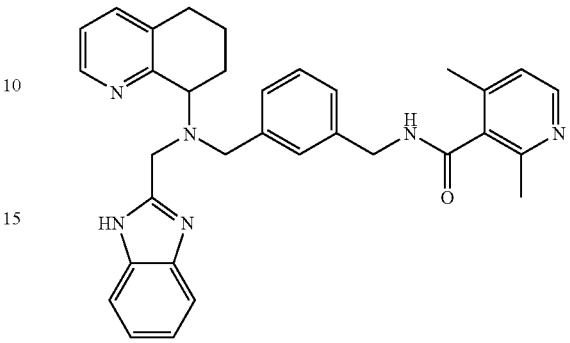

AMD9961: Preparation of N-(3-{[(1H-benzoimida-zol-2-ylmethyl)-(5,6,7,8-tetrahydro-quinolin-8-yl)-amino]-methyl}-benzyl)-2,4-dimethyl-nicotinamide (hydrobromide salt)

A solution of 2,4-dimethyl-nicotinic acid (56 mg, 0.37 mmol) in $SOCl_2$ (~3 mL, excess) was heated to 80° C. for 4 hours. The condenser was removed and the mixture was flushed with $N_2$ at 80° C. for ~5 minutes and then dried in vacuo for 10 minutes. The resulting syrup was dissolved in $CH_2Cl_2$ (2.0 mL) and added to a stirring mixture of (3-aminomethyl-benzyl)-(1H-benzoimidazol-2-ylmethyl)-(5,6,7,8-tetrahydro-quinolin-8-yl)-amine (147 mg, 0.37 mmol), $Et_3N$ (0.26 mL, 1.85 mmol) and a catalytic amount of DMAP. The reaction mixture was stirred overnight at room temperature. Purification of the crude yellow foam by column chromatography on silica gel ($CH_2Cl_2$/MeOH/$NH_4OH$, 100:1:1) followed by radial chromatography on silica gel (1 mm plate, EtOAc/MeOH/$NH_4OH$, 200:1:1) afforded the desired amide (85 mg, 43%) as a light yellow foam.

Using General Procedure D: Conversion of the foam from above to the hydrobromide salt afforded AMD9961 as a beige solid. $^1$H NMR ($D_2O$) δ 1.82-1.98 (m, 1H), 2.15-2.33 (m, 2H), 2.38 (s, 3H), 2.39-2.50 (m, 1H), 2.53 (s, 3H), 3.01-3.08 (m, 2H), 3.79 (d, 1H, J=12.9 Hz), 3.86 (d, 1H, J=12.6 Hz), 4.15 (s, 2H), 4.46 (d, 1H, J=16.5 Hz), 4.64 (d, 1H, J=16.5 Hz), 4.79 (m, 1H, overlap with HOD), 6.79 (d, 1H, J=7.8 Hz), 7.07-7.12 (m, 2H), 7.18 (d, 1H, J=7.8 Hz), 7.47-7.53 (m, 2H), 7.57-7.62 (m, 2H), 7.74 (d, 1H, J=6.0 Hz), 7.92 (dd, 1H, J=7.8, 5.7 Hz), 8.40 (d, 1H, J=7.2 Hz), 8.48 (d, 1H, J=6.0 Hz), 8.76 (dd, 1H, J=5.7, 1.2 Hz); $^{13}$C NMR ($D_2O$) δ17.52, 19.92, 20.49, 20.89, 27.87, 43.36, 50.14, 56.84, 62.98, 113.90, 126.10, 126.72, 127.01, 127.21, 129.39, 129.52, 129.64, 130.57, 135.27, 137.03, 137.43, 139.64, 140.78, 140.95, 148.24, 150.17, 150.88, 151.79, 157.50, 166.29. ES-MS m/z 531.3 (M+H). Anal. Calcd. for $C_{33}H_{33}N_6O.3.2HBr.1.4H_2O.0.5C_4H_{10}O$: C, 49.41; H, 5.21; N, 9.88; Br, 30.05. Found: C, 49.43; H, 5.25; N, 9.85; Br, 29.94.

EXAMPLE: 21

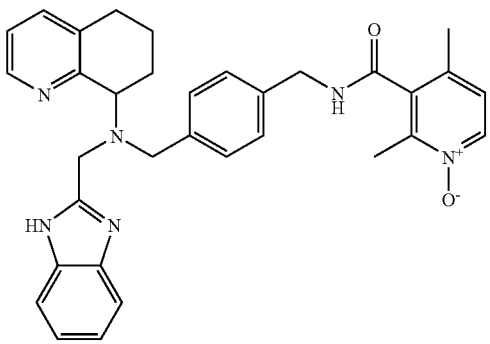

AMD11036: Preparation of N-(4-{[(1H-benzoimidazol-2-ylmethyl)-(5,6,7,8-tetrahydro-quinolin-8-yl)-amino]-methyl}-benzyl)-2,4-dimethyl-1-oxy-nicotinamide (hydrobromide salt)

Preparation of 2,4-dimethyl-1-oxy-nicotinic acid ethyl ester

To a solution of ethyl 2,4-dimethylpyridine-3-carboxylate (2.0 g, 11.2 mmol) in AcOH (28 mL) was added $H_2O_2$ (34-37%, 1.1 mL, 11.2 mmol) and the resultant mixture was heated to 70° C. for 3 hours. A second aliquot of $H_2O_2$ (34-37%, 1.1 mL, 11.2 mmol) was added and the mixture heated at 70° C. overnight. The reaction mixture was concentrated under reduced pressure and the resulting syrup was dissolved in $CH_2Cl_2$ (150 mL) and washed with saturated $NaHCO_3$ (2×25 mL). The aqueous layer was extracted with $CH_2Cl_2$ (2×100 mL) and the combined organic extracts were dried ($MgSO_4$), filtered and concentrated under reduced pressure to afford the desired N-oxide (2.07 g, 95%). $^1$H NMR ($CDCl_3$) δ 1.41 (t, 3H, J=7.2 Hz), 2.30 (s, 3H), 2.49 (s, 3H), 4.44 (q, 2H, J=7.2 Hz), 6.99 (d, 1H, J=6.6 Hz), 8.19 (d, 1H, J=6.6 Hz).

To a solution of the N-oxide from above (2.06 g, 10.55 mmol) in EtOH (25 mL) was added a solution of NaOH (844 mg, 21.1 mmol) in $H_2O$ (5 mL). The resultant mixture was stirred at 40° C. for 3 days. The solution was concentrated under reduced pressure. Saturated $NaHCO_3$ (10 mL) was added and the aqueous layer was extracted with $CH_2Cl_2$ (2×100 mL). The aqueous phase was acidified with 10% HCl and concentrated in vacuo. The resultant solid was partially dissolved in $CH_2Cl_2$/MeOH (10:1), filtered and concentrated. The N-oxide acid (1.40 g) was used without further purification in the next reaction.

Using General Procedure F: A solution of the acid from above (46 mg, 0.28 mmol), (4-aminomethyl-benzyl)-(1H-benzoimidazol-2-ylmethyl)(5,6,7,8-tetrahydro-quinolin-8-yl)-amine (100 mg, 0.25 mmol), HOBT (37 mg, 0.28 mmol) and 4-methylmorpholine (40 μL, 0.38 mmol) in DMF (0.8 mL) was flushed with $N_2$. EDCI (53 mg, 0.28 mmol) was added and the mixture was stirred at room temperature overnight. Purification of the yellow syrup (140 mg) by radial chromatography on silica gel (EtOAc/MeOH/$NH_4OH$, 100:4:1) afforded the desired amide (75 mg, 55%) as a yellow foam.

Using General Procedure D: Conversion of the foam from above to the hydrobromide salt afforded AMD11036 as a pale yellow solid. $^1$H NMR ($D_2O$) δ 1.80-1.98 (m, 1H), 2.13-2.28 (m, 5H), 2.34 (s, 3H), 2.36-2.48 (m, 1H), 2.97-3.07 (m, 2H), 3.72 (d, 1H, J=12.3 Hz), 3.81 (d, 1H, J=12.3 Hz), 4.01 (s, 2H), 4.43 (d, 1H, J=16.5 Hz), 4.61 (d, 1H, J=16.8 Hz), 4.72-4.79 (m, 1H, overlap with HOD), 6.91 (d, 2H, J=8.1 Hz), 7.14 (d, 2H, J=8.1 Hz), 7.39-7.46 (m, 3H), 7.54-7.58 (m, 2H), 7.91 (dd, 1H, J=7.8, 6.0 Hz), 8.29 (d, 1H, J=6.9 Hz), 8.38 (d, 1H, J=8.1 Hz), 8.75 (d, 1H, J=5.7 Hz); $^{13}$C NMR ($D_2O$) δ 14.97, 18.51, 20.49, 20.92, 27.86, 42.94, 50.21, 56.65, 63.16, 113.84, 126.08, 126.63, 126.90, 127.64, 130.50, 135.53, 135.82, 137.28, 139.63, 139.74, 140.92, 143.06, 146.82, 148.23, 150.90, 151.87, 167.37. ES-MS m/z 547.4 (M+H). Anal. Calcd. for $C_{33}H_{34}N_6O_2$·3.0HBr·2.1$H_2O$·0.3$C_4H_{10}O$: C, 48.36; H, 5.24; N, 9.89; Br, 28.22. Found: C, 48.17; H, 5.41; N, 9.98; Br, 28.48.

EXAMPLE: 22

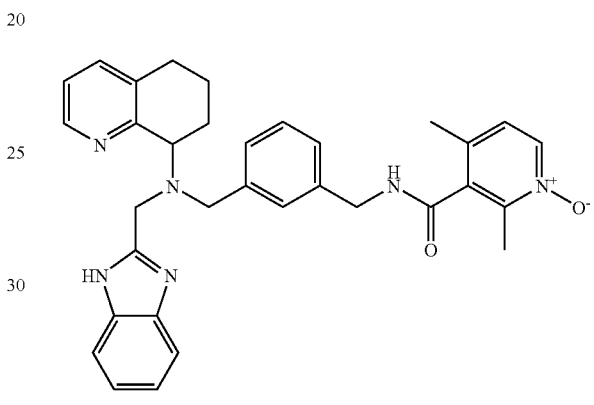

AMD11037: Preparation of N-(3-{[(1H-benzoimidazol-2-ylmethyl)-(5,6,7,8-tetrahydro-quinolin-8-yl)-amino]-methyl}-benzyl)-2,4-dimethyl-1-oxy-nicotinamide (hydrobromide salt)

Using General Procedure F: A solution of 2,4-dimethyl-1-oxy-nicotinic acid (46 mg, 0.28 mmol), (3-aminomethyl-benzyl)-(1H-benzoimidazol-2-ylmethyl)-(5,6,7,8-tetrahydro-quinolin-8-yl)-amine (100 mg, 0.25 mmol), HOBT (37 mg, 0.28 mmol) and 4-methylmorpholine (40 μL, 0.38 mmol) in DMF (0.8 mL) was flushed with $N_2$. EDCI (53 mg, 0.28 mmol) was added and the mixture was stirred at room temperature for 3 days. Purification of the yellow syrup (130 mg) by column chromatography on silica gel ($CH_2Cl_2$MeOH/$NH_4OH$, 100:5:1) followed by radial chromatography on silica gel (1 mm plate, $CH_2Cl_2$/MeOH/$NH_4OH$, 100:5:1) afforded the desired amide (81 mg, 59%) as a white foam.

Using General Procedure D: Conversion of the foam from above to the hydrobromide salt afforded AMD11037 as a white solid. $^1$H NMR ($D_2O$) δ 1.80-1.98 (m, 1H), 2.13-2.35 (m, 8H), 2.36-2.51 (m, 1H), 2.99-3.07 (m, 2H), 3.77 (d, 1H, J=12.6 Hz), 3.84 (d, 1H, J=12.9 Hz), 4.12 (s, 2H), 4.45 (d, 1H, J=16.5 Hz), 4.63 (d, 1H, J=16.5 Hz), 4.79 (m, 1H, overlap with HOD), 6.77 (d, 1H, J=7.5 Hz), 7.05-7.10 (m, 2H), 7.16 (d, 1H, J=7.8 Hz), 7.36 (d, 1H, J=6.9 Hz), 7.47-7.51 (m, 2H), 7.56-7.60 (m, 2H), 7.91 (dd, 1H, J=8.1, 6.0 Hz), 8.26 (d, 1H, J=6.9 Hz), 8.39 (d, 1H, J=7.8 Hz), 8.74 (d, 1H, J=4.5 Hz); $^{13}$C NMR ($D_2O$) δ 14.87, 18.35, 20.48, 20.87, 27.85, 43.25, 50.13, 56.80, 62.95, 113.87, 126.10, 126.72, 126.80, 127.21, 129.29, 129.48, 129.57, 130.54, 135.38, 136.97, 137.53, 139.61, 139.67, 140.94, 142.35, 146.65, 148.24, 150.88, 151.78, 167.58. ES-MS m/z 547.4 (M+H). Anal. Calcd. for $C_{33}H_{34}N_6O_2 \cdot 2.9HBr \cdot 2.2H_2O \cdot 0.2C_4H_{10}O$: C, 48.57; H, 5.22; N, 10.06; Br, 27.73. Found: C, 48.65; H, 5.46; N, 10.26; Br, 27.60.

EXAMPLE: 23

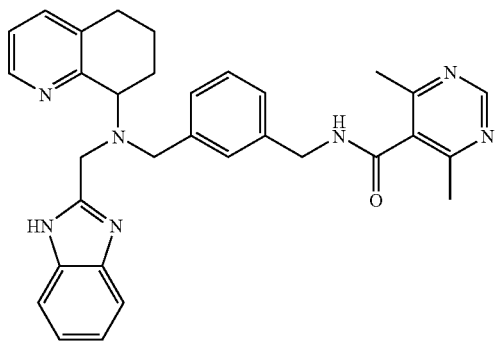

AMD11084: Preparation of 4,6-dimethyl-pyrimidine-5-carboxylic acid 3-{[(1H-benzoimidazol-2-ylmethyl)-(5,6,7,8-tetrahydro-quinolin-8-yl)-amino]-methyl}-benzylamide Preparation of 4,6-dimethyl-pyrimidine-5-carboxylic acid ethyl ester A solution of ethyl diacetoacetate (8.04 g, 46.7 mmol) and $Cs_2CO_3$ (15.93 g, 48.9 mmol) in $CH_3CN$ (82 mL) was cooled to 0° C. Methyl trifluoromethane sulfonate (5.3 mL, 46.8 mmol) was added dropwise and once addition was complete the ice bath was removed and the mixture stirred at room temperature for 3 hours. The mixture was filtered and the salts washed with $Et_2O$ (2×20 mL). $Et_2O$ (30 mL) was added to the filtrate and the mixture filtered and the salts washed with $Et_2O$ (2×40 mL). The combined filtrate was concentrated to half volume, cooled to 0° C. in an ice bath, washed with cold 2N NaOH (pH 11). The organic layer was dried ($MgSO_4$), filtered and concentrated under reduced pressure to a yellow slurry. $CH_2Cl_2$ (100 mL) was added and the mixture placed in the fridge overnight. The resultant mixture was filtered and the solid washed with cold $CH_2Cl_2$. The filtrant was concentrated under reduced pressure to afford a yellow liquid (9.6 g) that was used without further purification in the next reaction.

A solution of the ethyl ester from above (3.19 g, 17.13 mmol), sodium ethoxide (21 wt % solution in EtOH, 6.4 mL, 17.14 mmol) and formamidine acetate (1.78 g, 17.09 mmol) in EtOH (30 mL) was heated to reflux for 4 hours. The mixture was cooled to room temperature, filtered and the filtrate concentrated under reduced pressure. $CH_2Cl_2$ (200 mL) and $H_2O$ (15 mL) were added, the phases were separated and the aqueous layer was extracted with $CH_2Cl_2$ (2×50 mL). The combined organic extracts were dried ($MgSO_4$), filtered and concentrated under reduced pressure. Purification of the crude orange syrup by column chromatography on silica gel (Hexanes/EtOAc, 6:1) afforded the desired pyrimidine (2.23 g, 30% over 2 steps) as a yellow syrup. $^1$H NMR (CDCl$_3$) δ 1.41 (t, 3H, J=7.2 Hz), 2.55 (s, 6H), 4.44 (q, 2H, J=7.2 Hz), 8.96 (s, 1H).

To a solution of 4,6-dimethyl-pyrimidine-5-carboxylic acid ethyl ester (2.65 g, 14.7 mmol) in EtOH (20 mL) was added a solution of NaOH (991 mg, 24.8 mmol) in $H_2O$ (10 mL) and the mixture was stirred at 40° C. for 2 hours. The mixture was concentrated under reduced pressure, $H_2O$ (5 mL) was added and the mixture cooled to 0° C. in an ice bath. Concentrated HCl (1.3 mL) was added dropwise with continual stirring. The resulting precipitate was filtered, washed with ice water (2×3 mL) and air dried with suction for 20 minutes to afford a white solid (600 mg) which was used without further purification in the next reaction.

Using General Procedure F: A solution of 4,6-dimethyl-pyrimidine-5-carboxylic acid from above (prepared as described in patent application PCT/US00/11632) (42 mg, 0.28 mmol), (3-aminomethyl-benzyl)-(1H-benzoimidazol-2-ylmethyl)-(5,6,7,8-tetrahydro-quinolin-8-yl)-amine (100 mg, 0.25 mmol), HOBT (38 mg, 0.28 mmol) and 4-methylmorpholine (40 μL, 0.38 mmol) in DMF (0.8 mL) was flushed with $N_2$. EDCI (54 mg, 0.28 mmol) was added and the mixture was stirred at room temperature overnight. Purification of the colorless syrup (150 mg) by column chromatography on silica gel ($CH_2Cl_2$/MeOH/NH$_4$OH, 100:2:1) followed by radial chromatography on silica gel (1 mm plate, $CH_2Cl_2$/MeOH/NH4OH, 100:2:1) afforded AMD11084 (80 mg, 60%) as a white foam. $^1$H NMR (CDCl$_3$) δ 1.64-1.77 (m, 1H), 1.91-2.08 (m, 2H), 2.18-2.34 (m, 1H), 2.37 (s, 6H), 2.69-2.91 (m, 2H), 3.73 (s, 2H), 3.80 (d, 1H, J=16.5 Hz), 4.00 (d, 1H, J=16.5 Hz), 4.07-4.13 (m, 1H), 4.69 (d, 2H, J=5.7 Hz), 6.53 (t, 1H, J=5.7 Hz), 6.96-7.10 (m, 3H), 7.16-7.22 (m, 2H), 7.29-7.31 (m, 2H), 7.40-7.45 (m, 3H), 8.64 (d, 1H, J=3.6 Hz), 8.81 (s, 1H); $^{13}$C NMR (CDCl$_3$) δ 21.71, 22.28, 24.38, 29.55, 44.29, 49.22, 55.11, 61.90, 111.12, 118.82, 121.68, 122.78, 127.32, 128.67, 129.09, 129.24, 130.48, 135.22, 137.66, 137.83, 140.30, 147.22, 156.42, 157.60, 157.91, 163.43, 166.96. ES-MS m/z 532.4 (M+H). Anal. Calcd. for $C_{32}H_{33}N_7O \cdot 0.4CH_2Cl_2$: C, 68.80; H, 6.02; N, 17.33. Found: C, 68.56; H, 6.09; N, 17.34.

EXAMPLE: 24

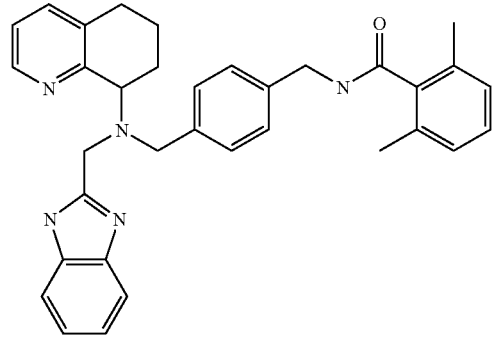

AMD9794: Preparation of N-(4-{[(1H-benzimidazol-2-ylmethyl)-(5,6,7,8-tetrahydro-quinolin-8-yl)-amino]-methyl}-benzyl)-2,6-dimethyl-benzamide Using the EDCI coupling general procedure F: Reaction of (4-aminomethyl-benzyl)-1H-benzimidazol-2-ylmethyl)-(5,6,7,8-tetrahydro-quinolin-8-yl)-amine (120 mg, 0.30 mmol), 2,6-dimethylbenzoic acid (50 mg, 0.33 mmol), 1-hydroxybenzotriazole (45 mg, 0.33 mmol), 4-methyl morpholine (49 uL, 0.45 mmol), and EDCI (63 mg, 0.33 mmol) for 4 h at room temperature followed by column chromatography on silica gel (EtOAc/MeOH/NH$_4$OH 199:1:1) gave the desired product (120 mg, 77%) as a white foam.

Using the HBr salt formation general procedure D: Conversion of the foam from above to the hydrobromide salt gave AMD9794 as a white powder. $^1$H NMR (300 MHz, D$_2$O) δ 1.90-1.94 (m, 1H), 2.15 (s, 6H), 2.18-2.26 (m, 2H), 2.41 (br s, 2H), 3.00-3.05 (m, 2H), 3.66 (d, 1H, J=12.3 Hz), 3.77 (d, 1H, J=12.6 Hz), 4.01-4.07 (m, 2H), 4.41 (d, 1H, J=16.5 Hz), 4.50 (d, 1H, J=16.8 Hz), 4.72-4.75 (m, 1H), 6.92 (d, 2H, J=7.5 Hz), 7.09-7.14 (m, 4H), 7.23-7.28 (m, 3H), 7.52 (dd, 1H, J=5.7, 3.3 Hz), 7.91-7.96 (m, 1H), 8.40 (d, 1H, J=7.8 Hz), 8.76 (d, 1H, J=5.4 Hz); $^{13}$C NMR (75.5 MHz, D$_2$O) δ 18.68 (2C), 20.47, 20.94, 27.85, 42.75, 50.20, 56.63, 63.17, 113.79, 126.11, 126.48, 127.87, 129.83, 130.45, 134.60, 135.61, 136.34, 137.74, 139.63, 140.90, 148.25, 150.83, 151.89, 173.13. ES-MS m/z 530 (M+H). Anal. Calcd. C$_{34}$H$_{35}$N$_5$O.0.1C$_4$H$_{10}$O.1.5H$_2$O.2.1HBr: C, 56.29; H, 5.64; N, 9.54; Br, 22.86; Found: C, 56.47; H, 5.62; N, 9.52; Br, 22.68.

EXAMPLE: 25

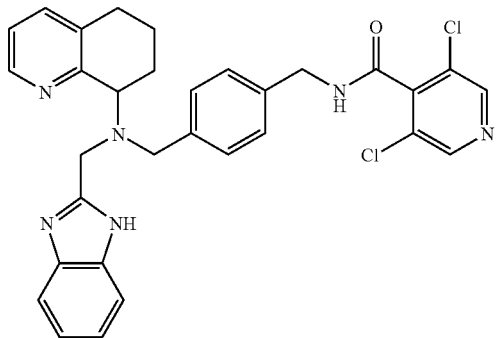

AMD9842: N-(4-{[(1H-Benzimidazol-2-ylmethyl)-(5,6,7,8-tetrahydro-quinolin-8-yl)-amino]-methyl}-benzyl)-3,5-dichloro-isonicotinamide Using the EDCI coupling general procedure F: Reaction of (4-aminomethyl-benzyl)-1H-benzimidazol-2-ylmethyl)-(5,6,7,8-tetrahydro-quinolin-8-yl)-amine (105 mg, 0.26 mmol), 3,5-dichloroisonicotinic acid (50 mg, 0.26 mmol), 1-hydroxybenzotriazole (36 mg, 0.26 mmol), 4-methyl morpholine (100 uL, 0.89 mmol), and EDCI (51 mg, 0.26 mmol) for 2 d at room temperature followed by column chromatography on silica gel (1:1:98 MeOH—NH$_4$OH—CH$_2$Cl$_2$) gave AMD9842 (42 mg, 28%) as a white foam. $^1$H NMR (CDCl$_3$) δ 1.68-1.74 (m, 1H), 1.94-2.05 (m, 2H), 2.16-2.25 (m, 1H), 2.69-2.75 (m, 1H), 2.81-2.88 (m, 1H), 3.70 (s, 2H), 3.78-3.83 (m, 1H), 4.03-4.09 (m, 2H), 5.54 (dd, 2H, J=4.5, 4.5 Hz), 7.02-7.12 (m, 3H), 7.17-7.21 (m, 3H), 7.34 (d, 2H, J=8.1 Hz), 7.44 (d, 2H, J=7.5 Hz), 7.50 (d, 1H, J=7.8 Hz), 8.31-8.35 (m, 2H), 8.68 (d, 1H, J=3.9 Hz); $^{13}$C NMR (CDCl$_3$) δ 21.76, 23.87, 29.59, 44.13, 48.78, 54.26, 61.05, 111.30, 118.84, 121.62, 122.06, 122.74, 128.61, 129.43, 133.96, 135.16, 136.24, 137.72, 139.41, 142.90, 144.35, 147.31, 147.72, 156.69, 157.64, 162.39; ES-MS m/z 571.6 (M+H); Anal. Calcd. For (C$_{31}$H$_{28}$N$_6$Cl$_2$O).0.5(CH$_2$Cl$_2$).0.5 (H$_2$O): C, 60.73; H, 4.85; N, 13.49; Cl, 17.07. Found C, 60.60; H, 4.96; N, 13.13; Cl, 17.46.

EXAMPLE: 26

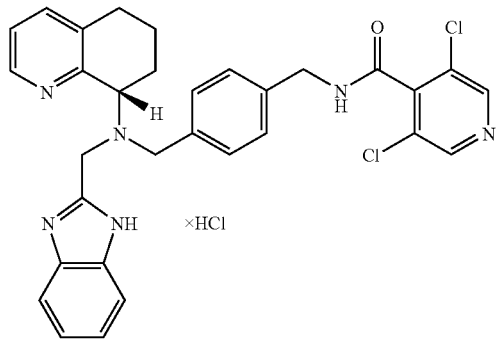

AMD11034: Preparation of N-(3,5-dichloroisonicotinamide)-N'-(1H-benzimidazol-2-ylmethyl)-N'-(S)-5,6,7,8-tetrahydro-quinolin-8-yl-1,4-benzene-dimethanamine (hydrochloride salt)

Preparation of 3,5-dichloro-N-(4-formyl-benzyl)-isonicotinamide

To a stirred, cooled (0° C.) solution of 4-cyanobenzaldehyde (3.47 g, 26.5 mmol) in anhydrous THF (150 mL) was added LAH (6.0 g, 160 mmol) portionwise. The slurry was stirred under N$_2$ at 60° C. for 24 h. After cooling to room temperature the reaction was slowly quenched with distilled water (6 mL), then 15% (w/v) NaOH (6 mL) followed by more distilled water (18 mL). The mixture was stirred for 20 min, diluted with diethyl ether (200 mL) and the white fluffy precipitate was removed by filtration. The filtrate was dried (MgSO$_4$) and concentrated in vacuo. The resultant amino alcohol (2.78 g) was used without further purification in the next reaction.

To a solution of the amine from above (1.75 g, 12.8 mmol) in DMF (13 mL) was added 3,5-dichloroisonicotinic acid (2.04 g, 10.6 mmol), 1-ethyl-3-(3-dimethylamino-propyl) carbodiimide hydrochloride (4.03 g, 21.0 mmol), 1-hydroxy-benzotriazole (2.84 g, 21.0 mmol), 4-methylmorpholine (7.9 mL, 71.8 mmol). The reaction mixture was stirred at 50° C., under N$_2$, for 65 h, then concentrated in vacuo. The residue was partitioned between chloroform (100 mL) and saturated NH$_4$Cl solution (100 mL). The aqueous layer was extracted with chloroform (2×100 mL) and the combined organic extracts were dried (MgSO$_4$), and concentrated in vacuo. The resultant crude orange oil (6.84 g) was purified by flash chromatography on a silica gel column (5 cm id., 140 g silica gel, eluted with 5% MeOH/CH$_2$Cl$_2$) to afford the desired alcohol (1.33 g, 30% over two steps).

The alcohol from above (1.33 g, 4.3 mmol) was taken up in 10% MeOH/CH$_2$Cl$_2$ (50 mL), treated with MnO$_2$ (5.9 g, 68 mmol), and refluxed under N$_2$ for 32 h. The slurry was cooled, filtered, and concentrated in vacuo to give the pure title compound (1.20 g, 91%). $^1$H NMR (CDCl$_3$) δ 4.79 (d, 2H, J=6.1 Hz) 6.13 (s br, 1H), 7.59 (d, 2H, J=8.3 Hz), 7.90 (d, 2H, J=8.3 Hz), 8.56 (s, 2H), 10.03 (s, 1H).

Using General Procedure B: 3,5-Dichloro-N-(4-formyl-benzyl)-isonicotinamide from above (1.28 g, 4.1 mmol) was reacted with S-(5,6,7,8-tetrahydro-quinolin-8-yl)-amine (0.80 g, 5.4 mmol) and NaBH(OAc)$_3$ (2.65 g, 12.5 mmol) in dichloromethane (80 mL). Flash chromatography (5 cm id, 80 g silica gel, eluted with 5% MeOH/CH$_2$Cl$_2$) provided the pure 2° amine as a pale yellow foamy solid (1.74 g, 95%).

To a solution of the amine from above (1.74 g, 3.9 mmol) in acetonitrile (40 mL) and chloroform (10 mL) was added diisopropylethylamine (1 mL, 5.8 mmol), 1-boc-2-chloromethylbenzimidazole (1.35 g, 5.0 mmol), and potassium iodide (66 mg, 0.40 mmol). The mixture was stirred under an N₂ atmosphere at 60° C. for 16 h, cooled to room temperature and concentrated in vacuo. The residue was partitioned between dichloromethane (100 mL) and brine (100 mL). The separated organic layer was dried (MgSO₄), concentrated to a brown oil (3.5 g) and purified by flash chromatography (5 cm id, 100 g silica gel, eluted with $CH_2Cl_2$ to remove unreacted chloride then 5% MeOH/$CH_2Cl_2$ to remove desired product) to give the pure desired boc-protected amine as a pale yellow foamy solid (2.36 g, 89%).

The amine from above (2.32 g, 3.45 mmol) was dissolved in glacial acetic acid (10 mL) and HCl gas was bubbled through the stirred solution for 10 min. The solution was allowed to stir at room temperature for an additional 30 min, then it was diluted with glacial acetic acid (10 mL) and slowly dropped into diethyl ether (500 mL) with vigorous stirring. The resultant slurry was suction filtered through a glass fritted funnel and the filter cake was washed with diethyl ether (100 mL) and dried in a vacuum oven at 40° C. for 65 h to give AMDI 1034 as a white solid (2.05 g, 88%). ¹H NMR (D₂O) δ 1.81-1.95 (m, 1H), 2.19-2.36 (m, 2H), 2.41-2.49 (m, 1H), 2.97-3.11 (m, 2H), 3.77-3.84 (m, 2H), 4.10 (s, 2H), 4.43 (d, 1H, J=16.3 Hz), 4.60 (d, 1H, J=16.3 Hz), 4.68-4.78 (m, 1H), 6.95 (d, 2H, J=7.8 Hz), 7.14 (d, 2H, J=7.8 Hz), 7.42-7.46 (m, 2H), 7.56-7.59 (m, 2H), 7.90 (t, 1H, J=5.7 Hz), 8.37 (d, 1H, J=7.8 Hz), 8.58 (s, 2H), 8.72 (d, 1H, J=5.7 Hz); ¹³C NMR (D₂O) δ 20.48, 20.87, 27.83, 42.74, 50.26, 56.61, 63.18, 113.85 (2 carbons), 126.02, 126.60 (2 carbons), 127.46 (2 carbons), 129.12, 130.35 (2 carbons), 130.64, 135.74, 137.15, 139.60, 140.86, 147.79 (2 carbons), 148.12, 150.98, 151.91. ES-MS m/z 571 (M+H). Anal. Calcd. for $C_{31}H_{28}N_6Cl_2O$·2.0HCl·1.8H₂O: C, 55.01; H, 5.00; N, 12.42; Cl, 20.95. Found: C, 55.11; H, 4.90; N, 12.36; Cl, 20.86.

The enantiomeric purity of AMD11034 was determined to be 100% by chiral HPLC using the following conditions: Instrument: Hewlett Packard 1100 HPLC (VWD2); Column: Chiralpak AD, 0.46 cm×25 cm; Mobile Phases: A: 90:10 hexanes/isopropanol with 0.1% DEA, B: isopropanol; Isocratic: 97% A, 3% B; Total Run Time: 25 min; Flow Rate: 2.0 mL/min; Temperature: 5° C.; Detector: UV@254 nm; Injection volume: 10 μL.

Retention time of the S enantiomer=13.0 min.
Retention time of the R enantiomer=15.5 min.

EXAMPLE: 27

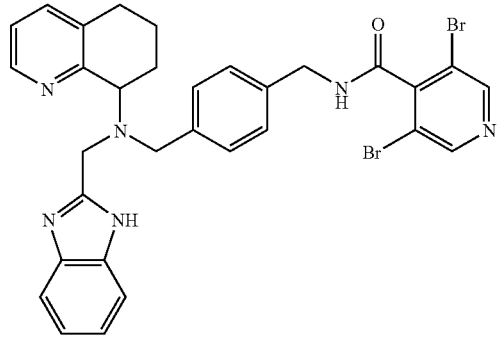

AMD9853: N-(4-{[(1H-Benzimidazol-2-ylmethyl)-(5,6,7,8-tetrahydro-quinolin-8-yl)-amino]-methyl}-benzyl)-3,5-dibromo-isonicotinamide (hydrobromide salt)

Reaction of 3,5-dibromoisonicotinic acid (73 mg, 0.26 mmol), thionyl chloride (2 mL) at reflux for 1 h, followed by reaction of the corresponding acyl chloride, (4-aminomethyl-benzyl)-1H-benzimidazol-2-ylmethyl)-(5,6,7,8-tetrahydro-quinolin-8-yl)-amine (103 mg, 0.26 mmol), Et₃N (0.50 mL, 3.46 mmol), and catalytical amount of DMAP for 3 h at room temperature gave the crude prodcuct as yellow oil. The crude material was purified by column chromatography on silica gel ($CH_2Cl_2$-MeOH—NH₄OH 98:1:1) to give the title compound (67 mg, 39%) as a white foam.

Using General Procedure D: Conversion of the foam from above (67 mg, 0.10 mmol) to the hydrobromide salt using an acetic acid/HBr solution, followed by re-precipitation of the salt from diethyl ether gave AMD9853 as a white solid.¹H NMR (CD₃OD) δ 1.96 (br s, 1H), 2.25-2.37 (m, 2H), 2.45 (br s, 1H), 3.06 (br s, 2H), 3.80-3.85 (m, 2H), 4.18 (br s, 2H), 4.47 (d, 1H, J=16.2 Hz), 4.68 (d, 1H, J=16.2 Hz), 4.77-4.82 (m, 1H), 7.13 (d, 2H, J=7.5 Hz), 7.45 (d, 2H, J=7.8 Hz), 7.55-7.58 (m, 2H), 7.76-7.79 (m, 2H), 7.93-7.97 (m, 1H), 8.40 (d, 1H, J=7.8 Hz), 8.70 (s, 2H), 8.94 (d, 1H, J=5.4 Hz); ¹³C NMR (CD₃OD) δ 21.97, 29.24, 43.94, 50.85, 57.71, 62.75, 115.28, 119.66, 127.21, 128.02, 129.16, 131.94, 132.28, 136.55, 139.46, 141.64, 141.89, 148.53, 149.24, 151.84, 152.19, 152.93, 166.75; ES-MS m/z 661.3 (M+H); Anal. Calcd. For $(C_{31}H_{28}Br_2N_6O)$·2.1(HBr)·1.3(H₂O): C, 43.61; H, 3.86; N, 9.84; Br, 38.37. Found C, 43.69; H, 3.80; N, 9.70; Br, 38.22.

EXAMPLE: 28

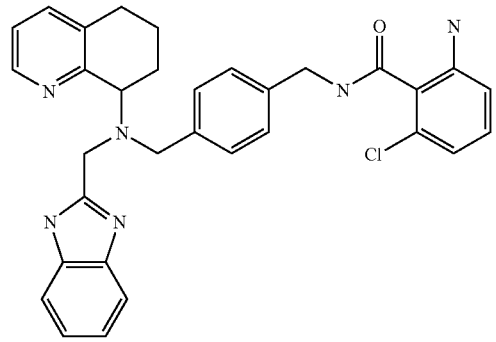

AMD9862: preparation of 2-amino-N-(4-{[(1H-benzimidazol-2-ylmethyl)-(5,6,7,8-tetrahydro-quinolin-8-yl)-amino]-methyl}-benzyl)-6-chloro-benzamide Using the EDCI coupling general procedure F: Reaction of (4-aminomethyl-benzyl)-1H-benzimidazol-2-ylmethyl)-(5,6,7,8-tetrahydro-quinolin-8-yl)-amine (100 mg, 0.25 mmol), 2-chloro-6-aminobenzoic acid (43 mg, 0.25 mmol), 1-hydroxybenzotriazole (34 mg, 0.25 mmol), 4-methyl morpholine (38 uL, 0.35 mmol), and EDCI (48 mg, 0.25 mmol) for 4 h at room temperature followed by column chromatography on silica gel (EtOAc/MeOH/NH₄OH 199:1:1) gave AMD9862 (90 mg, 65%) as a white foam. ¹H NMR (300 MHz, CD₃OD) δ 1.66-1.69 (m, 1H), 2.01-2.09 (m, 2H), 2.25 (br s, 1H), 2.78-2.89 (m, 2H), 3.55-3.65 (m, 2H), 3.97 (d, 1H, J=15.3 Hz), 4.08-4.13 (m, 2H), 4.37 (s, 2H), 6.85 (d, 2H, J=7.8 Hz), 7.22-7.29 (m, 3H), 7.36 (d, 2H, J=8.1 Hz), 7.43-7.47 (m, 1H), 7.50 (d, 2H, J=8.1 Hz), 7.62-7.65 (m, 2H), 7.75 (d, 1H, J=7.8 Hz), 8.79-8.81 (m, 1H); ¹³C NMR (75.5 MHz, CD₃OD) δ 22.83, 24.34, 30.62, 44.55, 51.36, 56.17, 63.17, 115.72, 119.07, 123.04, 123.51, 124.05, 128.92, 130.79, 132.13, 132.70, 137.39, 138.62, 139.54, 139.63, 148.36, 148.76, 156.41, 158.27, 169.43. ES-MS m/z 551 (M+H). Anal. Calcd. $C_{32}H_{31}ClN_6O$·0.8H₂O: C, 67.97; H, 5.81; N, 14.86; Cl, 6.27; Found: C, 68.07; H, 5.87; N, 14.87; Cl, 6.42.

EXAMPLE: 29

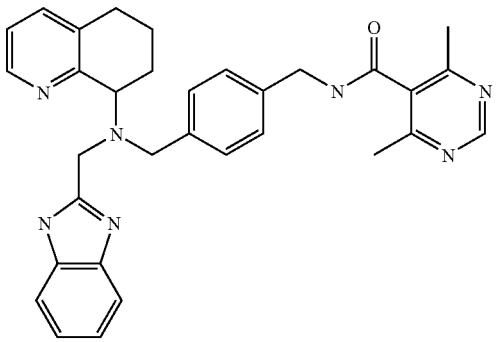

AMD11028: Preparation of 4,6-dimethyl-pyrimidine-5-carboxylic acid 4-{[(1H-benzimidazol-2-ylmethyl)-(5,6,7,8-tetrahydro-quinolin-8-yl)-amino]-methyl}-benzylamide Using the EDCI coupling general procedure F: Reaction of (4-aminomethyl-benzyl)-1H-benzimidazol-2-ylmethyl)-(5,6,7,8-tetrahydro-quinolin-8-yl)-amine (100 mg, 0.25 mmol), 4,6-dimethyl-pyrimidine-5-carboxylic acid (42 mg, 0.28 mmol), 1-hydroxybenzotriazole (38 mg, 0.28 mmol), 4-methyl morpholine (39 uL, 0.35 mmol), and EDCI (54 mg, 0.28 mmol) for 24 h at room temperature followed by column chromatography on silica gel (EtOAc/MeOH/NH$_4$OH 98:1:1) gave AMD11028 (101 mg, 76%) as a white foam. $^1$H NMR (300 MHz, CDCl$_3$) δ 1.71-1.98 (m, 1H), 2.02-2.05 (m, 2H), 2.24-2.35 (m, 1H), 2.41 (s, 6H), 2.70-2.86 (m, 2H), 3.70 (s, 2H), 3.84 (d, 1H, J=16.5 Hz), 4.03-4.11 (m, 2H), 4.47-4.50 (m, 2H), 6.54-6.57 (m, 1H), 7.07 (br s 2H), 7.14 (d, 2H, J=7.8 Hz), 7.17-7.27 (m, 1H), 7.35 (d, 2H, J=7.8 Hz), 7.43-7.46 (m, 3H), 8.68 (d, 1H, J=3.0 Hz), 8.83 (s, 1H); $^{13}$C NMR (75.5 MHz, CDCl$_3$) δ 21.74, 22.36, 23.99, 29.59, 44.18, 48.97, 54.36, 61.36, 111.30, 118.85, 121.85, 122.77, 128.48, 129.67, 130.48, 135.22, 136.42, 137.79, 139.51, 147.28, 156.48, 157.60, 157.93, 163.47, 167.01. ES-MS m/z 532 (M+H). Anal. Calcd. C$_{32}$H$_{33}$N$_7$O.1.6H$_2$O: C, 68.58; H, 6.51; N, 17.49; Found: C, 68.64; H, 6.44; N, 17.64.

EXAMPLE: 30

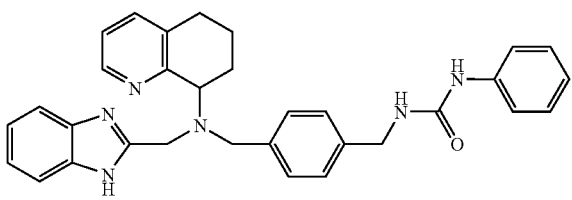

AMD 9593: Preparation of 1-(4-{[(1H-Benzimidazol-2-ylmethyl)-(5,6,7,8-tetrahydro-quinolin-8-yl)-amino]-methyl}-benzyl)-3-phenyl-urea (hydrobromide salt)

To a cold (0° C.) solution of (4-aminomethyl-benzyl)-(1H-benzimidazol-2-ylmethyl)-(5,6,7,8-tetrahydro-quinolin-8-yl)-amine (0.136 g, 0.34 mmol) in CH$_2$Cl$_2$ (3.5 mL) was added phenyl isocyanate (41 µL, 0.38 mmol) and the resultant solution was stirred for 50 minutes. The cooling bath was removed and the mixture was concentrated under reduced pressure. Purification of the crude material by column chromatography on silica gel (25:1:1 CH$_2$Cl$_2$—CH$_3$OH—NH$_4$OH) provided the free base of the title compound (0.127 g, 72%) as a white solid.

Using General Procedure D: Conversion of the free base (127 mg) to the hydrobromide salt, followed by re-precipitation of the intermediate solid from methanol/ether, gave AMD9593 (139 mg) as a white solid. $^1$H NMR (D$_2$O) δ 1.79-1.93 (m, 1H), 2.16-2.28 (m, 2H), 2.35-2.42 (m, 1H), 3.00 (br s, 2H), 3.65 (d, 1H, J=12.3 Hz), 3.73 (d, 1H, J=12.3 Hz), 3.79 (s, 2H) 4.38 (d, 1H, J=16.5 Hz), 4.62(d, 1H, J=16.5 Hz), 4.66-4.71 (m, 1H), 6.84 (d, 2H, J=7.8 Hz), 7.05 (d, 2H, J=7.8 Hz), 7.09-7.14 (m, 1H), 7.25 (d, 2H, J=7.8 Hz), 7.32-7.40 (m, 4H), 7.50 (br s, 2H), 7.87 (dd, 2H, J=6.6, 6.9 Hz), 8.34 (d, 1H, J=7.8 Hz), 8.69 (d, 1H, J=5.4 Hz); $^{13}$C NMR (D$_2$O) δ 20.44, 20.80, 27.79, 42.77, 50.25, 56.49, 63.07, 113.68, 121.31, 124.32, 126.00, 126.56, 127.33, 129.70, 130.22, 130.45, 135.09, 138.56, 139.51, 140.81, 148.14, 150.91, 151.74, 158.00; ES-MS m/z 517 (M+H). Anal. Calcd. for C$_{32}$H$_{32}$N$_6$O.2.3 HBr.1.4 H$_2$O: C, 52.80; H, 5.14; N, 11.54; Br, 25.25. Found: C, 52.76; H, 5.19; N, 11.30; Br, 25.30.

EXAMPLE: 31

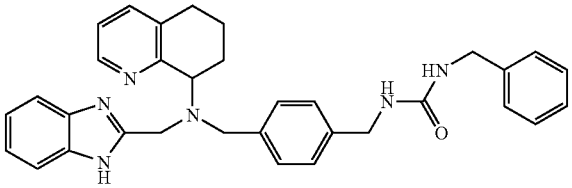

AMD9594: Preparation of 1-(4-{[(1H-Benzimidazol-2-ylmethyl)-(5,6,7,8-tetrahydro-quinolin-8-yl)-amino]-methyl}-benzyl)-3-benzyl-urea (hydrobromide salt)

To a cold (0° C.) solution of (4-aminomethyl-benzyl)-(1H-benzimidazol-2-ylmethyl)-(5,6,7,8-tetrahydro-quinolin-8-yl)-amine (0.130 g, 0.33 mmol) in CH$_2$Cl$_2$ (3.5 mL) was added benzyl isocyanate (45 µL, 0.36 mmol) and the resultant solution was stirred for 100 minutes. The cooling bath was removed and the mixture was concentrated under reduced pressure. Purification of the crude material by column chromatography on silica gel (25:1:1 CH$_2$Cl$_2$—CH$_3$OH—NH$_4$OH) followed by radial chromatography on silica gel (1 mm plate, 25:1:1 CH$_2$Cl$_2$—CH$_3$OH—NH$_4$OH) provided the free base of the title compound (0.047 g, 28%) as a white solid.

Using General Procedure D: Conversion of the free base (47 mg) to the hydrobromide salt, followed by re-precipitation of the intermediate solid from methanol/ether, gave AMD9594 (49 mg) as a white solid. $^1$H NMR (D$_2$O) δ 1.79-1.96 (m, 1H), 2.18-2.30 (m, 2H), 2.38 (br s, 1H), 3.00 (br s, 2H), 3.66-3.75 (m, 4H), 4.25 (s, 2H), 4.40 (d, 1H, J=16.5 Hz), 4.57 (d, 1H, J=16.5 Hz), 4.68-4.73 (m, 1H), 6.76 (d, 2H, J=7.5 Hz), 7.03 (d, 2H, J=7.5 Hz), 7.24-7.51 (m, 9H), 7.87 (dd, 1H, J=7.2, 6.3 Hz), 8.34 (d, 1H, J=7.8 Hz), 8.67 (d, 1H, J=5.4 Hz); $^{13}$C NMR (D$_2$O) δ 20.45, 20.78, 27.98, 42.92, 43.78, 50.24, 56.48, 63.01, 113.75, 125.98, 126.58, 127.00, 127.26, 127.62, 129.13, 130.15, 130.48, 135.02, 139.50, 139.70, 139.90, 140.80, 148.11, 150.93, 151.76, 160.44; ES-MS m/z 531 (M+H). Anal. Calcd. for C$_{33}$H$_{34}$N$_6$O.2.5 HBr.3.0 H$_2$O: C, 50.36; H, 5.44; N, 10.68; Br, 25.38. Found: C, 50.19; H, 5.26; N, 10.41; Br, 25.56.

EXAMPLE: 32

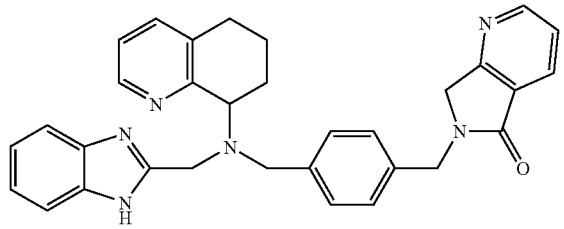

AMD 9547: Preparation of 6-(4-{[(1H-Benzimidazol-2-ylmethyl)-(5,6,7,8-tetrahydro-quinolin-8-yl)-amino]-methyl}-benzyl)-6,7-dihydro-pyrrolo[3,4-b]pyridin-5-one (hydrobromide salt)

Preparation of 3-carboethoxy-2-nyridinecarboxaldehyde

To a stirred solution of ethyl 2-methylnicotinate (1.657 g, 10.0 mmol) in 1,4-dioxane (10 mL) and water (1 mL) was added selenium dioxide (1.568 g, 14.1 mmol) and the resultant mixture was heated to reflux overnight. The reaction mixture was cooled to room temperature and concentrated under reduced pressure. The residue was purified by column chromatography on silica gel (3:1 hexanes/ethyl acetate) and provided the title compound (0.90 g, 50%) as a yellow oil. $^1$H NMR (CDCl$_3$) δ 1.41 (t, 3H, J=7.5 Hz), 4.45 (q, 2H; J=7.5 Hz), 7.56 (dd, 1H, J=6.0, 6.0 Hz), 8.11 (dd, 1H, J=6.0, 1.0 Hz), 8.87 (dd, 1H, J=6.0, 1.0 Hz), 10.34 (s, 1H).

Using General Procedure B: Reaction of 3-carboethoxy-2-pyridinecarboxaldehyde (0.210 g, 1.17 mmol) and (4-aminomethyl-benzyl)-(1H-benzimidazol-2-ylmethyl)-(5,6,7,8-tetrahydro-quinolin-8-yl)-amine (0.472 g, 1.18 mmol) with NaBH(OAc)$_3$ (0.507 g, 2.39 mmol) in CH$_2$Cl$_2$ (12 mL) for 75 minutes followed by purification of the crude material by column chromatography on silica gel (40:1:1 CH$_2$Cl$_2$—CH$_3$OH—NH$_4$OH) and subsequently by radial chromatography on silica gel (2 mm plate, 100:1:1 CH$_2$Cl$_2$—CH$_3$OH—NH$_4$OH) provided the free base of the title compound (0.396 g, 65%) as a white solid.

Using General Procedure D: Conversion of the free base (56 mg) to the hydrobromide salt, followed by re-precipitation of the intermediate solid from methanol/ether, gave AMD9547 (61 mg) as a white solid. $^1$H NMR (D$_2$O) δ 1.81-1.95 (m, 1H), 2.19-2.32 (m, 2H), 2.40-2.46 (m, 1H), 3.03 (br s, 2H), 3.70 (d, 1H, J=12.6 Hz), 3.80 (d, 1H, J=12.6 Hz) 4.14 (d, 2H, J=3.3 Hz) 4.31 (s, 2H), 4.44 (d, 1H, J=16.8 Hz), 4.62 (d, 1H, J=16.8 Hz), 4.73-4.80 (m, 1H, overlaps with HOD), 6.92-6.98 (m, 4H), 7.16 (d, 2H, J=8.1 Hz), 7.39 (dd, 2H, J=3.0, 6.0 Hz), 7.77 (dd, 1H, J=5.4, 7.8 Hz), 7.92 (dd, 1H, J=5.4, 7.8 Hz), 8.32 (d, 1H, J=7.8 Hz), 8.39 (d, 1H, J=7.8 Hz), 8.76 (d, 1H, J=5.7 Hz), 8.82 (d, 1H, J=5.1 Hz); $^{13}$C NMR (D$_2$O) δ 20.44, 20.97, 27.85, 45.99, 50.42, 51.23, 56.73, 63.50, 113.41, 125.30, 126.10, 127.59, 128.66, 130.23, 130.68, 135.30, 135.83, 136.11, 139.65, 141.02, 148.28, 150.66, 150.84, 152.02, 160.43, 167.55; ES-MS m/z 515 (M+H). Anal. Calcd. for C$_{32}$H$_{30}$N$_6$O.3.1 HBr.2.8 H$_2$O: C, 47.11; H, 4.78; N, 10.30; Br, 30.36. Found: C, 46.98; H, 4.60; N, 10.07; Br, 30.65.

EXAMPLE: 33

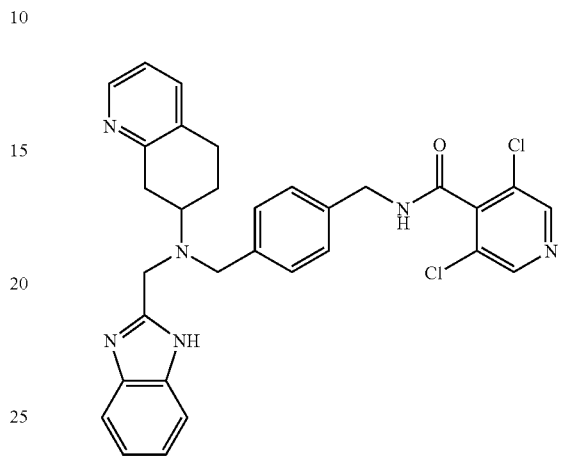

AMD9933: N-(4-{[(1H-Benzimidazol-2-ylmethyl)-(5,6,7,8-tetrahydro-quinolin-7-yl)-amino]-methyl}-benzyl)-3,5-dichloro-isonicotinamide Preparation of {4-[(5,6,7,8-Tetrahydro-quinolin-7-ylamino)-methyl]-benzyl}-carbamic acid tert-butyl ester

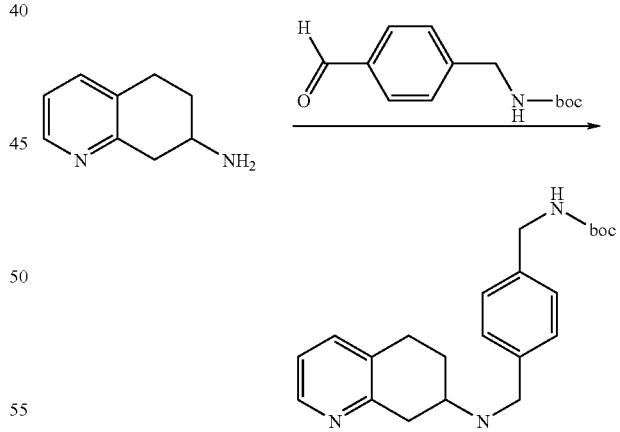

Using general procedure B: Reaction of (4-Formyl-benzyl)-carbamic acid tert-butyl ester (356 mg, 1.51 mmol), 5,6,7,8-Tetrahydro-quinolin-7-ylamine (224 mg, 1.51 mmol) in anhydrous MeOH (5 mL) at room temperature overnight under N$_2$ and 2 min of stirring after addition of sodium borohydride (115 mg, 3.00 mmol), followed by purification of crude material using chromatography on silica gel (2:2:96 CH$_3$OH—NH$_3$ H$_2$O—CH$_2$Cl$_2$) afforded the title compound (556 mg, 100%) as a white foam.

Preparation of 2-{[[4-(tert-Butoxycarbonylamino-methyl)-benzyl]-(5,6,7,8-tetrahydro-quinolin-7-yl)-amino]-methyl}-benzimidazole-1-carboxylic acid tert-butyl ester

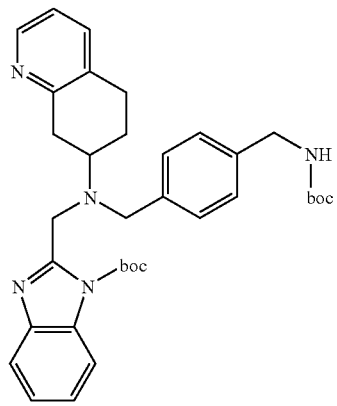

{4-[(5,6,7,8-Tetrahydro-quinolin-7-ylamino)-methyl]-benzyl}-carbamic acid tert-butyl ester (88 mg, 0.24 mmol), 2-Chloromethyl-benzimidazole-1-carboxylic acid tert-butyl ester (80 mg, 0.30 mmol), DIPEA (0.10 mL, 0.54 mmol), and KI (19 mg, 0.11 mmol) were heated to 80° C. in $CH_3CN$ (1.5 mL) for 2 h under $N_2$, then it was stirred at room temperature overnight. The reaction mixture was concentrated in vacuo, diluted with ethyl acetate, washed with $NH_4Cl$ (aq), NaCl (aq), and dried ($MgSO_4$). Evaporation of the solvent and purification of the residue by flash chromatography on silica gel (1:1:98 $CH_3OH$—$NH_3$ $H_2O$—$CH_2Cl_2$) afforded the title compound (80 mg, 56%) as a white foam.

Preparation of (4-Aminomethyl-benzyl)-(1H-benzimidazol-2-ylmethyl)(5,6,7,8-tetrahydro-quinolin-7-yl)-amine

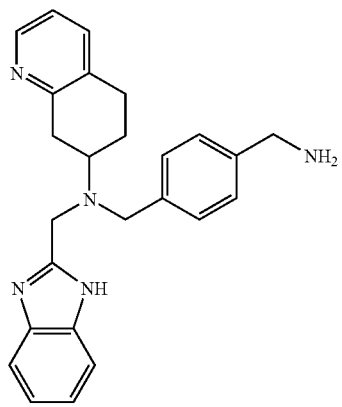

To a stirred solution of 2-{[[4-(tert-Butoxycarbony-lamino-methyl)-benzyl]-(5,6,7,8-tetrahydro-quinolin-7-yl)-amino]-methyl}-benzimidazole-1-carboxylic acid tert-butyl ester (120 mg, 0.20 mmol) in anhydrous $CH_2Cl_2$ (1 mL) was added TFA (1 mL). The resultant solution was stirred at room temperature overnight. The mixture was concentrated in vacuo, dissolved with MeOH, and added $NaHCO_3$. The mixture was stirred for 20 min, diluted with $CH_2Cl_2$, filtered through celite. The crude product was purified by flash chromatography on silica gel (2:2:96 $CH_3OH$—$NH_3$ $H_2O$—$CH_2Cl_2$) afforded the title compound (71 mg, 89%) as a white foam.

Using the EDCI coupling general procedure F: Reaction of (4-Aminomethyl-benzyl)-(1H-benzimidazol-2-ylmethyl)-(5,6,7,8-tetrahydro-quinolin-7-yl)-amine (71 mg, 0.18 mmol), 3,5-dichloroisonicotinic acid (75%, 48 mg, 0.18 mmol), 1-hydroxybenzotriazole (25 mg, 0.18 mmol), 4-methyl morpholine (60 uL, 0.53 mmol), and EDCI (34 mg, 0.18 mmol) for 2 d at 50° C. followed by column chromatography on silica gel (1:1:98 MeOH—$NH_4OH$—$CH_2Cl_2$) gave AMD9933 (29 mg, 28%) as a white powder. $^1$H NMR ($CDCl_3$) δ 1.72 (br s, 1H), 2.18-2.24 (m, 1H), 2.74-2.92 (m, 2H), 3.02-3.19 (m, 3H), 3.70 (d, 1H, J=13.5 Hz), 3.83 (d, 1H, J=13.5 Hz), 3.94-4.05 (m, 2H), 4.57 (d, 2H, J=5.4 Hz), 6.47 (br s, 1H), 7.00-7.08 (m, 3H), 7.21-7.36 (m, 6H), 7.56-7.59 (m, 1H), 8.31 (d, 1H, J=3.3 Hz), 8.48 (s, 2H), 9.59 (s, 1H); $^{13}$C NMR ($CDCl_3$) δ 24.73, 28.40, 35.98, 43.92, 49.16, 55.11, 57.07, 110.99, 119.39, 121.76, 122.20, 122.85, 128.55, 129.41, 131.78, 133.85, 136.51, 136.95, 139.03, 142.88, 143.55, 147.26, 147.91, 154.08, 156.03, 162.48; ES-MS m/z 571.2 (M+H); Anal. Calcd. For $(C_{31}H_{28}N_6Cl_2O).0.1(CH_2Cl_2).0.3(H_2O)$: C, 63.81; H, 4.96; N, 14.36; Cl, 13.32. Found: C, 63.85; H, 5.02; N, 14.24; Cl, 13.47.

EXAMPLE: 34

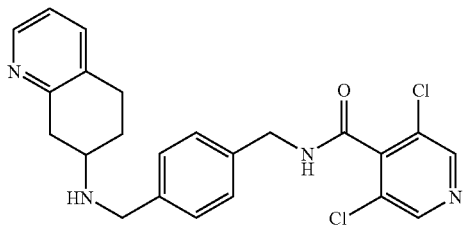

AMD9958: 3,5-Dichloro-N-{4-[(5,6,7,8-tetrahydro-quinolin-7-ylamino)-methyl]-benzyl}-isonicotinamide Preparation of (4-{[(2-Nitro-benzenesulfonyl)-(5,6,7,8-tetrahydro-quinolin-7-yl)-amino]-methyl}-benzyl)-carbamic acid tert-butyl ester

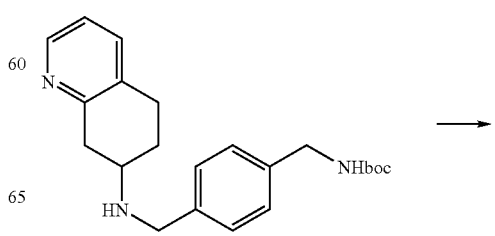

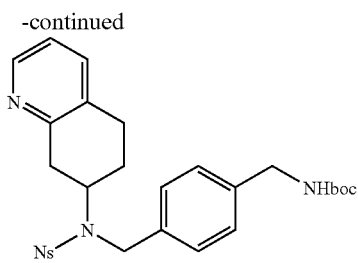

Reaction of {4-[(5,6,7,8-Tetrahydro-quinolin-7-ylamino)-methyl]-benzyl}-carbamic acid tert-butyl ester (98 mg, 0.27 mmol), NsCl (67 mg, 0.29 mmol), DIPEA (0.10 mL, 0.54 mmol) in anhydrous $CH_2Cl_2$ for 3 h at room temperature followed by column chromatography on silica gel (1:1:98 MeOH—$NH_4OH$—$CH_2Cl_2$) gave the title compound (70 mg, 47%) as a yellow foam.

Preparation of N-(4-Aminomethyl-benzyl)-2-nitro-N-(5,6,7,8-tetrahydro-quinolin-7-yl)-benzene-sulfonamide

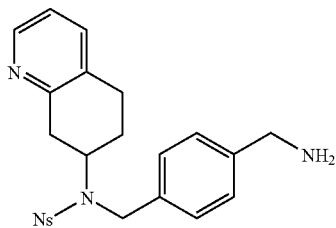

To a stirred solution of (4-{[(2-Nitro-benzenesulfonyl)-(5,6,7,8-tetrahydro-quinolin-7-yl)-amino]-methyl}-benzyl)-carbamic acid tert-butyl ester (160 mg, 0.29 mmol) in anhydrous $CH_2Cl_2$ (2 mL) was added TFA (2 mL). The resultant solution was stirred at room temperature overnight. The mixture was concentrated in vacuo, dissolved with MeOH, and added $NaHCO_3$. The mixture was stirred for 20 min, diluted with $CH_2Cl_2$, filtered through celite. The crude product was purified by flash chromatography on silica gel (1:1:98 $CH_3OH$—$NH_3$ $H_2O$—$CH_2Cl_2$) afforded the title compound (75 mg, 57%) as a white foam.

Preparation of 3,5-Dichloro-N-(4-{[(2-nitro-benzenesulfonyl)-(5,6,7,8-tetrahydro-quinolin-7-yl)-amino]-methyl}-benzyl)-isonicotinamide

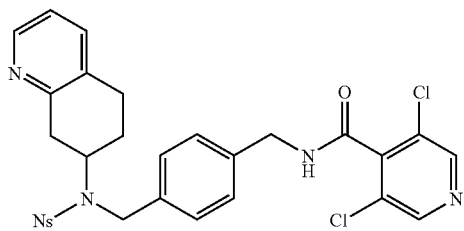

Using the EDCI coupling general procedure F: Reaction of N-(4-Aminomethyl-benzyl)-2-nitro-N-(5,6,7,8-tetrahydro-quinolin-7-yl)-benzenesulfonamide (75 mg, 0.17 mmol), 3,5-dichloroisonicotinic acid (75%, 55 mg, 0.22 mmol), 1-hydroxybenzotriazole (23 mg, 0.17 mmol), 4-methyl morpholine (100 uL, 0.89 mmol), and EDCI (32 mg, 0.17 mmol) for two days at 50° C. followed by column chromatography on silica gel (1:1:98 MeOH—$NH_4OH$—$CH_2Cl_2$) gave the title compound (42 mg, 40%) as a yellow foam.

Using the nosyl deprotection general procedure C: Reaction of 3,5-Dichloro-N-(4-{[(2-nitro-benzenesulfonyl)-(5,6,7,8-tetrahydro-quinolin-7-yl)-amino]-methyl}-benzyl)-isonicotinamide (42 mg, 0.07 mmol), thiophenol (0.10 mL, 0.97 mmol) and $K_2CO_3$ (269 mg, 1.95 mmol) in DMF (2 mL) at room temperature under $N_2$ for 4 h followed by purification of crude material by chromatography on silica gel (2:2:96 $CH_3OH$—$NH_3$ $H_2O$—$CH_2Cl_2$) afforded AMD9958 (15 mg, 51%) as a white foam. $^1H$ NMR ($CDCl_3$) δ 1.57-1.70 (m, 2H), 2.01-2.06 (m, 1H), 2.60-2.89 (m, 3H), 3.00-3.13 (m, 2H), 3.83 (s, 2H), 4.66 (d, 2H, J=5.7 Hz), 7.00 (dd, 2H, J=4.8, 7.5 Hz), 7.30-7.37 (m, 5H), 8.23 (d, 1H, J=3.9 Hz), 8.46 (s, 2H); $^{13}C$ NMR ($CDCl_3$) δ 26.48, 28.80, 39.42, 43.70, 50.69, 52.39, 121.16, 127.68, 128.27, 128.55, 129.02, 131.47, 135.75, 136.46, 140.19, 142.35, 146.79, 147.65, 155.51, 162.04; ES-MS m/z 441.5 (M+H); Anal. Calcd. For ($C_{23}H_{22}N_4Cl_2O$).0.5($CH_4O$): C, 61.71; H, 5.29; N, 12.25. Found: C, 61.71; H, 5.24; N, 12.24.

EXAMPLE: 35

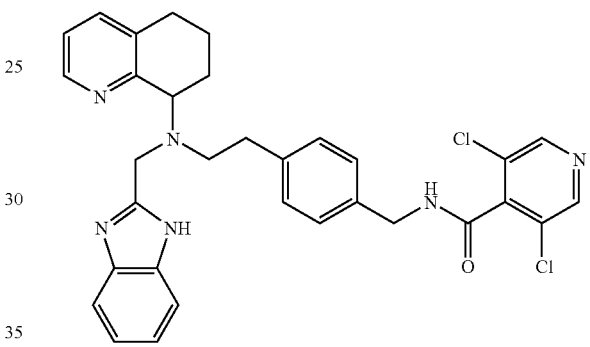

AMD11072: N-(4-{2-[(1H-Benzimidazol-2-ylmethyl)-(5,6,7,8-tetrahydro-quinolin-8-yl)-amino]-ethyl}-benzyl)-3,5-dichloro-isonicotinamide Preparation of 2-(4-Aminomethyl-phenyl)ethanol

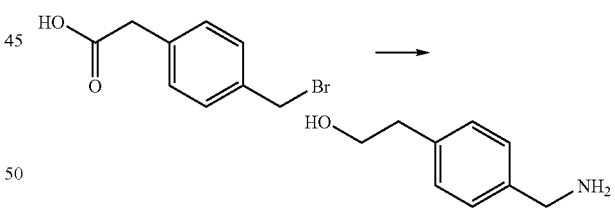

To a stirred solution of $NH_3$/EtOH (170 mL) was added (4-Bromomethyl-phenyl)-acetic acid (1.61 g, 7.01 mmol). The resultant solution was stirred at room temperature for 2 h. The mixture was concentrated in vacuo, and redissolved with anhydrous THF (10 mL). To the solution, $BH_3.Me_2S$ was added, and the mixture was stirred for 1 h at 70° C., and at room temperature for 2 d. The reaction was concentrated in vacuo, 6 N HCl (10 mL) was added, and the mixture was stirred at 70° C. for 1 h. Water (20 mL) was added, and it was neutralized with 1 N NaOH to pH~7. The solution was concentrated to dryness under high vacuum, washed with MeOH/$CH_2Cl_2$, and filtered. The crude product was purified by flash chromatography on silica gel (5:3:92 $CH_3OH$—$NH_3$ $H_2O$—$CH_2Cl_2$) to afford the title compound (820 mg, 77%) as a white foam.

Preparation of 3,5-Dichloro-N-[4-(2-hydroxy-ethyl)-benzyl]-isonicotinamide

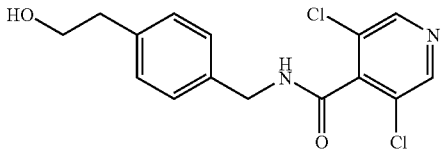

Using the EDCI coupling general procedure F: Reaction of 2-(4-Aminomethyl-phenyl)-ethanol (306 mg, 2.03 mmol), 3,5-dichloroisonicotinic acid (385 mg, 2.03 mmol), 1-hydroxybenzotriazole (301 mg, 2.22 mmol), 4-methyl morpholine (0.50 mL, 4.45 mmol), and EDCI (426 mg, 2.22 mmol) in anhydrous DMF (5 mL) overnight at room temperature and overnight at 40° C. followed by column chromatography on silica gel (2:2:96 MeOH—NH$_4$OH—CH$_2$Cl$_2$) gave the title compound (291 mg, 44%) as a white foam.

Preparation of 3,5-Dichloro-N-[4-(2-oxo-ethyl)-benzyl]-isonicotinamide

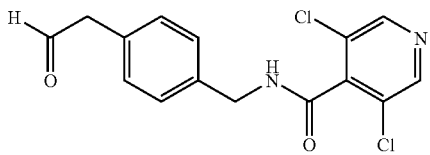

To a stirred solution of 3,5-Dichloro-N-[4-(2-hydroxy-ethyl)-benzyl]-isonicotinamide (105 mg, 0.32 mmol) in anhydrous CH$_2$Cl$_2$ (2.4 mL) was added Dess-Martin periodinane (206 mg, 0.48 mmol). The resultant solution was stirred at room temperature for 1 h. The mixture was diluted with 100 mL CH$_2$Cl$_2$, filtered through celite, and concentrated in vacuo. The crude product (74 mg, 71%) was used in the next step without further purification.

Preparation of 2-{[[2-(4-{[(3,5-Dichloro-pyridine-4-carbonyl)-amino]-methyl}-phenyl)-ethyl]-(5,6,7,8-tetrahydro-quinolin-8-yl)-amino]-methyl}-benzimidazole-1-carboxylic acid tert-butyl ester

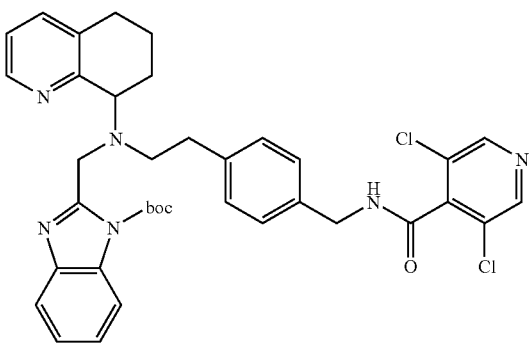

Using the reductive amination general procedure B: Reaction of 2-[(5,6,7,8-Tetrahydro-quinolin-8-ylamino)-methyl]-benzimidazole-1-carboxylic acid tert-butyl ester (74 mg, 0.20 mmol), 3,5-Dichloro-N-[4-(2-oxo-ethyl)-benzyl]-isonicotinamide (53 mg, 0.16 mmol), and NaBH(OAC)$_3$ (44 mg, 0.20 mmol) overnight at room temperature followed by column chromatography on silica gel (CH$_2$Cl$_2$-MeOH—NH$_4$OH 98:1:1) gave the tilte compound (99 mg, 88%) as a white foam.

To a stirred solution of 2-{[[2-(4-{[(3,5-Dichloro-pyridine-4-carbonyl)-amino]-methyl}-phenyl)-ethyl]-(5,6,7,8-tetrahydro-quinolin-8-yl)-amino]-methyl}-benzimidazole-1-carboxylic acid tert-butyl ester (99 mg, 0.14 mmol) in anhydrous CH$_2$Cl$_2$ (1 mL) was added TFA (1 mL). The resultant solution was stirred at room temperature overnight. The mixture was concentrated in vacuo, dissolved with MeOH, and added NaHCO$_3$. The mixture was stirred for 20 min, diluted with CH$_2$Cl$_2$, filtered through celite. The crude product was purified by flash chromatography on silica gel (2:2:96 CH$_3$OH—NH$_3$ H$_2$O—CH$_2$Cl$_2$) to afford AMD11072 (50 mg, 59%) as a light yellow foam. $^1$H NMR (CDCl$_3$) δ 1.67-1.73 (m, 1H), 1.84-1.95 (m, 1H), 2.01-2.05 (m, 1H), 2.17-2.24 (m, 1H), 2.65-3.02 (m, 6H), 3.99-4.14 (m, 3H), 4.61 (d, 2H, J=5.7 Hz), 6.13 (br s, 1H), 6.99 (d, 2H, J=7.8 Hz), 7.06-7.17 (m, 5H), 7.38-7.44 (m, 2H), 7.61 (d, 1H, J=8.1 Hz), 8.52 (br s, 3H); $^{13}$C NMR (CDCl$_3$) δ 21.79, 24.64, 29.51, 35.64, 43.87, 49.72, 52.89, 62.70, 114.04, 118.22, 121.99, 122.67, 127.78, 128.29, 129.43, 134.98, 135.34, 137.87, 139.86, 142.94, 146.89, 147.84, 156.88, 157.54, 162.54; ES-MS m/z 585.5 (M+H); Anal. Calcd. For (C$_{32}$H$_{30}$N$_6$Cl$_2$N$_6$O).0.3(CH$_2$Cl$_2$).0.3(H$_2$O): C, 62.94; H, 5.10; N, 13.63; Cl, 14.95. Found: C, 63.17; H, 5.14; N, 13.68; Cl, 14.64.

EXAMPLE: 36

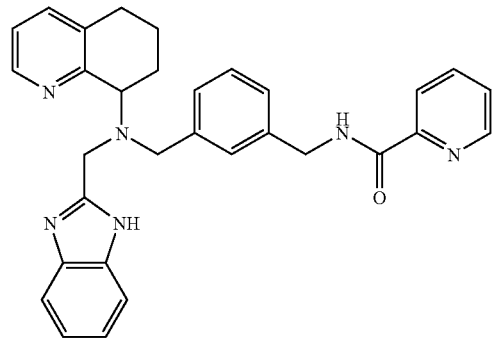

AMD9702: Pyridine-2-carboxylic acid 3-{[(1H-benzimidazol-2-ylmethyl)-(5,6,7,8-tetrahydro-quinolin-8-yl)-amino]-methyl}-benzylamide (hydrobromide salt)

Using the EDCI coupling general procedure F: Reaction of (3-aminomethyl-benzyl)-1H-benzimidazol-2-ylmethyl)-(5,6,7,8-tetrahydro-quinolin-8-yl)-amine (133 mg, 0.33 mmol), picolinic acid (40 mg, 0.33 mmol), 1-hydroxybenzotriazole (45 mg, 0.33 mmol), DIPEA (100 uL, 0.57 mmol), and EDCI (64 mg, 0.33 mmol) in anhydrous DMF (3 mL) for 3 d at room temperature followed by purification of the crude material by chromatography on silica gel (2:2:96 CH$_3$OH—NH$_3$ H$_2$O—CH$_2$Cl$_2$) afforded the title compound (158 mg, 94%) as a white foam.

Using General Procedure D: Conversion of the foam from above (158 mg, 0.31 mmol) to the hydrobromide salt using an acetic acid/HBr solution, followed by re-precipitation of the salt from diethyl ether gave AMD9702 as a white solid. $^1$H NMR (D$_2$O) δ 1.75-1.89 (m, 1H), 2.14-2.25 (m, 2H), 2.36 (b, 1H), 2.97-3.04 (m, 2H), 3.67-3.75 (m, 2H), 4.18 (s, 2H), 4.37 (d, 1H, J=16.2 Hz), 4.55 (d, 1H, J=16.2 Hz), 4.67-4.72 (m, 1H), 6.73 (d, 1H, J=7.2 Hz), 6.94-7.08 (m, 3H), 7.36-7.39 (m, 2H), 7.47-7.50 (m, 2H), 7.82-7.90 (m, 2H), 8.16 (d, 1H, J=7.8 Hz), 8.29-8.34 (m, 2H), 8.65 (d, 1H, J=5.7 Hz), 8.73 (d, 1H); $^{13}$C NMR (D$_2$O) δ 18.36, 18.74, 25.75, 41.20, 48.00, 54.57, 60.66, 111.72, 122.17, 123.99, 124.53, 125.21, 126.79, 127.13, 127.31, 128.32, 134.67, 135.79, 137.49, 138.72, 141.85, 143.48, 144.06, 146.11, 148.69, 149.54, 161.17; ES-MS m/z 503.3 (M+H); Anal. Calcd. For (C$_{31}$H$_{29}$N$_5$O).2.7(HBr).0.2(H$_2$O).0.2(C$_4$H$_{10}$O): C, 49.83; H, 5.01; N, 10.96; Br, 28.15. Found: C, 49.75; H, 4.77; N, 10.89; Br, 28.30.

EXAMPLE: 37

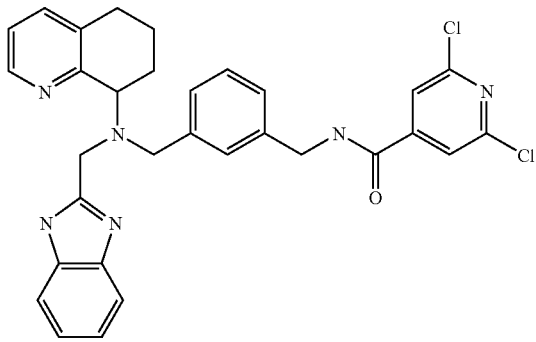

AMD9788: Preparation of: N-(3-{[(1H-benzimidazol-2-ylmethyl)-(5,6,7,8-tetrahydro-quinolin-8-yl)-amino]-methyl}-benzyl)-2,6-dichloro-isonicotinamide Using the EDCI coupling general procedure F: Reaction of (3-aminomethyl-benzyl)-1H-benzimidazol-2-ylmethyl)-(5,6,7,8-tetrahydro-quinolin-8-yl)-amine (94 mg, 0.24 mmol), 2,6-dichloroisonicotinic acid (50 mg, 0.26 mmol), 1-hydroxybenzotriazole (35 mg, 0.26 mmol), 4-methyl morpholine (40 uL, 0.36 mmol), and EDCI (50 mg, 0.26 mmol) for 24 h at room temperature followed by column chromatography on silica gel (EtOAc/MeOH/NH$_4$OH 199:1:1) gave AMD9788 (87 mg, 59%) as a white foam. $^1$H NMR (300 MHz, CDCl$_3$) δ 1.74-1.83 (m, 1H), 1.98-2.06 (m, 2H), 2.27-2.28 (m, 1H), 2.72-2.84 (m, 2H), 3.74 (s, 2H), 3.88 (d, 1H, J=18.0 Hz), 4.08 (d, 1H, J=18.0 Hz), 4.13-4.16 (m, 1H), 4.43 (dd, 1H, J=15.0, 3.0 Hz), 4.56 (dd, 1H, J=15.0, 6.0 Hz), 7.03-7.37 (m, 10H), 7.44 (s, 1H), 7.65 (s, 2H), 8.60-8.62 (m, 1H); $^{13}$C NMR (75.5 MHz, CDCl$_3$) δ 14.85, 21.94, 24.35, 37.14, 44.78, 49.25, 54.67, 61.32, 112.37, 118.95, 121.89, 122.34, 123.01, 127.43, 128.45, 128.97, 129.19, 135.48, 138.08, 138.14, 140.43, 147.42, 147.69, 151.66, 156.54, 157.73, 163.68. ES-MS m/z 573 (M+H). Anal. Calcd. C$_{31}$H$_{28}$N$_6$Cl$_2$O.1.0CH$_2$Cl$_2$.0.4H$_2$O: C, 57.92; H, 4.68; N, 12.66; Cl, 21.37; Found: C, 58.08; H, 4.60; N, 12.63; Cl, 21.20.

EXAMPLE: 38

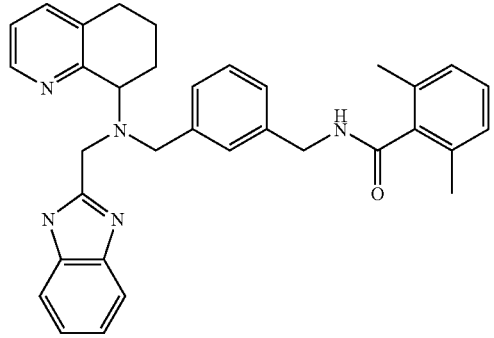

AMD9795: Preparation of N-(3-{[(1H-benzimidazol-2-ylmethyl)-(5,6,7,8-tetrahydro-quinolin-8-yl)-amino]-methyl}-benzyl)-2,6-dimethyl-benzamide Using the EDCI coupling general procedure F: Reaction of (3-aminomethyl-benzyl)-1H-benzimidazol-2-ylmethyl)-(5,6,7,8-tetrahydro-quinolin-8-yl)-amine (120 mg, 0.30 mmol), 2,6-dimethylbenzoic acid (50 mg, 0.33 mmol), 1-hydroxybenzotriazole (45 mg, 0.33 mmol), 4-methyl morpholine (49 uL, 0.45 mmol), and EDCI (63 mg, 0.33 mmol) for 4 h at room temperature followed by column chromatography on silica gel (EtOAc/MeOH/NH$_4$OH 199:1:1) gave the desired product (89 mg, 56%) as a white foam.

Using the HBr salt formation general procedure D: Conversion of the foam from above to the hydrobromide salt gave AMD9795 as a white powder. $^1$H NMR (300 MHz, D$_2$O) δ 1.92-2.09 (m, 1H), 2.13 (s, 6H), 2.20-2.33 (m, 2H), 2.46-2.49 (m, 1H), 3.02-3.08 (m, 2H), 3.77-3.88 (m, 2H), 4.14 (s, 2H), 4.47 (d, 1H, J=16.5 Hz), 4.66 (d, 1H, J=16.2 Hz), 4.76-4.81 (m, 1H), 6.92 (d, 1H, J=7.5 Hz), 7.09-7.12 (m, 4H), 7.16-7.19 (m, 1H), 7.24-7.29 (m, 1H), 7.42-7.50 (m, 2H), 7.58-7.63 (m, 2H), 7.94 (dd, 1H, J=7.5, 6.0 Hz), 8.42 (d, 1H, J=7.8 Hz), 8.75 (d, 1H, J=5.4 Hz); $^{13}$C NMR (75.5 MHz, D$_2$O) δ 18.55 (2C), 20.47, 20.85, 27.84, 43.00, 50.16, 56.80, 62.94, 113.83, 126.11, 126.76, 127.37, 127.84, 129.17, 129.38, 129.79, 130.55, 134.59, 136.85, 138.12, 139.58, 140.96, 148.24, 150.92, 151.81. ES-MS m/z 530 (M+H). Anal. Calcd. C$_{34}$H$_{35}$N$_5$O.2.2HBr.1.2H$_2$O: C, 55.99; H, 5.47; N, 9.60; Br, 24.10; Found: C, 55.80; H, 5.50; N, 9.53; Br, 24.26.

EXAMPLE: 39

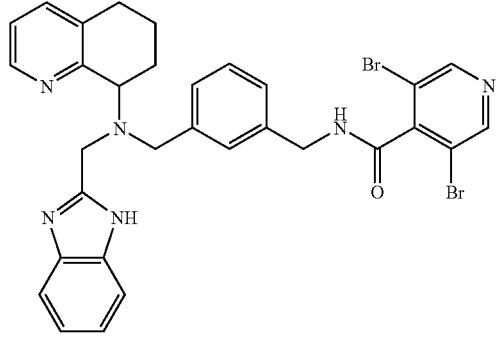

AMD9836: N-(3-{[(1H-Benzimidazol-2-ylmethyl)-(5,6,7,8-tetrahydro-quinolin-8-yl)-amino]-methyl}-benzyl)-3,5-dibromo-isonicotinamide (hydrobromide salt)

Reaction of 3,5-dibromoisonicotinic acid (73 mg, 0.26 mmol), oxalyl chloride (1 mL) at reflux for 1 h, followed by reaction of the corresponding acyl chloride, (3-aminomethyl-benzyl)-1H-benzimidazol-2-ylmethyl)-(5,6,7,8-tetrahydro-quinolin-8-yl)-amine (103 mg, 0.26 mmol), DIPEA (0.30 mL, 1.70 mmol), and catalytical amount of DMAP for 3 h at room temperature gave the crude prodcuct as yellow oil. The crude material was purified by column chromatography on silica gel (EtOAc-MeOH-NH$_4$OH 199:1:1) to give the title compound (60 mg, 35%) as a white foam.

Using General Procedure D: Conversion of the foam from above (60 mg, 0.09 mmol) to hydromide salt using an acetic acid/HBr solution, followed by re-precipitation of the salt from diethyl ether gave AMD9836 as a white foam. $^1$H NMR (CD$_3$OD) δ 1.88-1.93 (m, 1H), 2.22-2.35 (m, 2H), 2.44-2.48 (m, 1H), 3.05-3.09 (m, 2H), 3.80-3.89 (m, 2H), 4.40-4.46 (m, 3H), 4.64 (d, 1H, J=16.5 Hz), 4.72-4.77 (m, 1H), 6.99-7.07 (m, 2H), 7.28 (d, 1H, J=6.9 Hz), 7.55 (dd, 2H, J=3.3, 6.3 Hz), 7.65 (s, 1H), 7.73-7.77 (m, 2H), 7.94 (dd, 1H, J=6.0, 7.8 Hz), 8.40 (d, 1H, J=7.8 Hz), 8.67 (s, 2H), 8.93 (d, 1H, J=5.7 Hz); $^{13}$C NMR (CD$_3$OD) δ 25.22, 25.31, 32.59, 47.62, 54.07, 61.33, 66.00, 118.63, 122.98, 130.57, 131.39, 132.35, 133.36, 133.90, 134.59, 135.71, 141.05, 143.19, 145.09, 145.38, 151.80, 152.66, 155.26, 155.55, 156.18; ES-MS m/z 661.3 (M+H); Anal. Calcd. For (C$_{31}$H$_{28}$Br$_2$N$_6$O).0.4(C$_2$H$_4$O$_2$).0.7(H$_2$O).2.1(HBr): C, 44.06; H, 3.85; N, 9.69; Br, 37.79. Found: C, 44.22; H, 3.87; N, 9.75; Br, 37.77.

EXAMPLE: 40

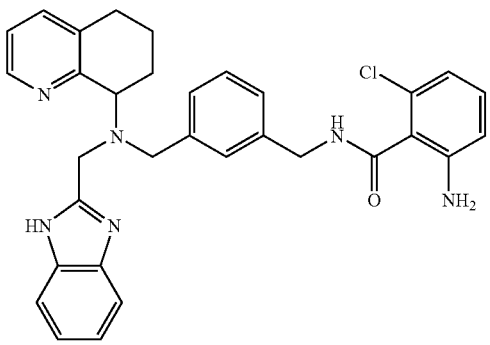

AMD9874: Preparation of 2-amino-N-(3-{[(1H-benzimidazol-2-ylmethyl)-(5,6,7,8-tetrahydro-quinolin-8-yl)-amino]-methyl}-benzyl)-6-chloro-benzamide Using the EDCI coupling general procedure F: Reaction of (3-aminomethyl-benzyl)-1H-benzimidazol-2-ylmethyl)-(5,6,7,8-tetrahydro-quinolin-8-yl)-amine (100 mg, 0.25 mmol), 2-chloro-6-aminobenzoic acid (43 mg, 0.25 mmol), 1-hydroxybenzotriazole (34 mg, 0.25 mmol), 4-methyl morpholine (38 uL, 0.35 mmol), and EDCI (48 mg, 0.25 mmol) for 4 h at room temperature followed by column chromatography on silica gel (EtOAc/MeOH/NH$_4$OH 199:1:1) gave AMD9874 (108 mg, 79%) as a white foam. $^1$H NMR (300 MHz, CD$_3$OD) δ 1.58-1.75 (m, 1H), 2.01-2.12 (m, 2H), 2.18-2.67 (m 1H), 2.73-2.94 (m, 2H), 3.56 (d, 1H, J=12.9 Hz), 3.64 (d, 1H, J=13.2 Hz), 3.97-4.15 (m, 3H), 4.20 (s, 2H), 6.64-6.69 (m, 2H), 7.03-7.08 (m, 3H), 7.13 (dd, 2H, J=6.0, 3.3 Hz), 7.20-7.28 (m, 2H), 7.37 (br s, 1H), 7.42-7.45 (m, 2H), 7.57 (d, 1H, J=7.8 Hz), 8.58 (d, 1H, J=5.4 Hz); $^{13}$C NMR (75.5 MHz, CD$_3$OD) δ 22.81, 24.38, 30.60, 44.81, 51.53, 56.52, 63.34, 115.78, 115.95, 119.12, 123.06, 123.65, 124.07, 127.93, 129.57, 129.86, 130.05, 132.16, 132.75, 137.41, 139.49, 139.62, 140.88, 148.34, 148.85, 156.26, 158.17, 169.44. ES-MS m/z 551 (M+H). Anal. Calcd. C$_{32}$H$_{31}$ClN$_6$O.0.8H$_2$O.0.7(C$_4$H$_8$O$_2$): C, 66.65; H, 6.14; N, 13.40; Cl, 5.65; Found: C, 66.62; H, 6.05; N, 13.28; Cl, 5.76.

EXAMPLE: 41

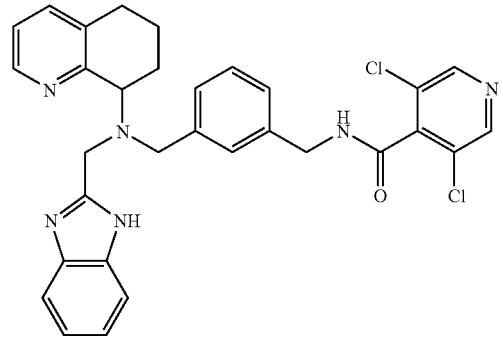

AMD9843: N-(3-{[(1H-Benzimidazol-2-ylmethyl)-(5,6,7,8-tetrahydro-quinolin-8-yl)-amino]-methyl}-benzyl)-3,5-dichloro-isonicotinamide Using the EDCI coupling general procedure F: Reaction of (3-aminomethyl-benzyl)-1H-benzimidazol-2-ylmethyl)-(5,6,7,8-tetrahydro-quinolin-8-yl)-amine (105 mg, 0.26 mmol), 3,5-dichloroisonicotinic acid (50 mg, 0.26 mmol), 1-hydroxybenzotriazole (36 mg, 0.26 mmol), 4-methyl morpholine (100 uL, 0.89 mmol), and EDCI (51 mg, 0.26 mmol) for 2 d at room temperature followed by column chromatography on silica gel (1:1:98 MeOH—NH$_4$OH—CH$_2$Cl$_2$) gave AMD9843 (62 mg, 41%) as a white foam. $^1$H NMR (CDCl$_3$) δ 1.65-1.77 (m, 1H), 1.91-2.07 (m, 2H), 2.23-2.28 (m, 1H), 2.70-2.91 (m, 1H), 3.71 (s, 2H), 3.81 (d, 1H, J=16.5 Hz), 4.01 (d, 1H, J=16.5 Hz), 4.05-4.10 (m, 1H), 4.53 (d, 2H, J=5.7 Hz), 7.02-7.04 (m, 3H), 7.12-7.21 (m, 3H), 7.29-7.35 (m, 2H), 7.42-7.45 (m, 3H), 7.50 (d, 1H, J=7.8 Hz), 8.29 (s, 2H), 8.65-8.67 (m, 1H); $^{13}$C NMR (CDCl$_3$) δ 21.72, 24.12, 29.56, 44.23, 49.04, 54.87, 61.48, 121.93, 122.80, 127.50, 128.54, 129.06, 129.13, 129.40, 135.27, 137.46, 137.92, 140.10, 142.89, 147.17, 147.73, 156.27, 157.48, 162.47; ES-MS m/z 571.6 (M+H); Anal. Calcd. For (C$_{31}$H$_{28}$N$_6$Cl$_2$O).0.2(CH$_2$Cl$_2$).0.7(H$_2$O): C, 62.34; H, 5.00; N, 13.98; Cl, 14.16. Found C, 62.28; H, 4.98; N, 13.58; Cl, 14.20.

EXAMPLE: 42

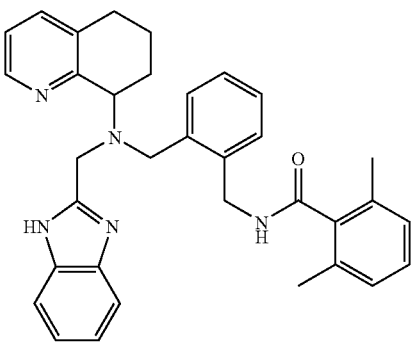

AMD9849: Preparation of N-(2-{[(1H-benzimidazol-2-ylmethyl)-(5,6,7,8-tetrahydro-quinolin-8-yl)-amino]-methyl}-benzyl)-2,6-dimethyl-benzamide Using the EDCI coupling general procedure F: Reaction of (2-aminomethyl-benzyl)-1H-benzimidazol-2-ylmethyl)-(5,6,7,8-tetrahydro-quinolin-8-yl)-amine (70 mg, 0.18 mmol), 2,6-dimethylbenzoic acid (29 mg, 0.19 mmol), 1-hydroxybenzotriazole (26 mg, 0.19 mmol), 4-methyl morpholine (27 uL, 0.25 mmol), and EDCI (37 mg, 0.19 mmol) for 18 h at room temperature followed by column chromatography on silica gel (EtOAc/MeOH/NH$_4$OH 199:1:1) gave the desired product (34 mg, 37%) as a white foam.

Using the HBr salt formation general procedure D: Conversion of the foam from above to the hydrobromide salt gave AMD9849 as a white powder. $^1$H NMR (300 MHz, D$_2$O) δ 1.94-1.98 (m, 1H), 2.08 (s, 6H), 2.23-2.28 (m, 1H), 2.40-2.48 (m, 2H), 3.06 (br s, 2H), 3.94 (d, 1H, J=12.9 Hz), 4.17 (d, 1H, J=12.9 Hz), 4.44-4.51 (m, 2H), 4.58-4.66 (m, 2H), 4.81-4.87 (m, 1H), 6.87-6.92 (m, 1H), 6.97-7.01 (m, 1H), 7.04-7.08 (m, 3H), 7.21-7.26 (m, 1H), 7.34 (d, 1H, J=7.5 Hz), 7.53-7.57 (m, 2H), 7.60-7.65 (m, 2H), 7.91 (dd, 1H, J=7.8, 6.0 Hz), 8.41 (d, 1H, J=7.8 Hz), 8.73 (d, 1H, J=5.7 Hz); $^{13}$C NMR (75.5 MHz, D$_2$O) δ 18.57 (2C), 20.46, 20.73, 27.93, 43.93, 49.60, 53.83, 62.04, 113.94, 126.19, 126.82, 127.76, 128.30, 129.24, 129.31, 129.75, 130.59, 131.89, 133.93, 134.50, 136.01, 136.34, 139.87, 141.06, 148.29, 150.67, 151.32, 173.34. ES-MS m/z 530 (M+H). Anal. Calcd. C$_{34}$H$_{35}$N$_5$O.2.1HBr.1.4H$_2$O: C, 56.34; H, 5.55; N, 9.66; Br, 23.15; Found: C, 56.48; H, 5.73; N, 9.30; Br, 23.18.

EXAMPLE: 43

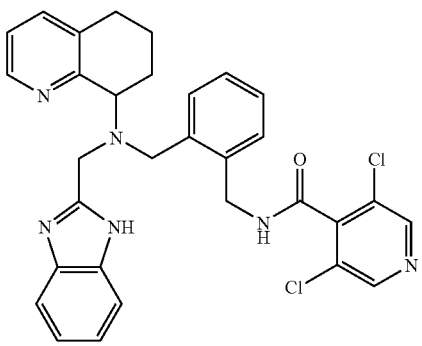

AMD9981: N-(2-{[(1H-Benzimidazol-2-ylmethyl)-(5,6,7,8-tetrahydro-quinolin-8-yl)-amino]-methyl}-benzyl)-3,5-dichloro-isonicotinamide Using the EDCI coupling general procedure F: Reaction of 2-aminomethyl-benzyl)-1H-benzimidazol-2-ylmethyl)-(5,6,7,8-tetrahydro-quinolin-8-yl)-amine (70 mg, 0.18 mmol), 3,5-dichloroisonicotinic acid (75%, 67 mg, 0.26 mmol), 1-hydroxybenzotriazole (24 mg, 0.18 mmol), 4-methyl morpholine (100 uL, 0.89 mmol), and EDCI (37 mg, 0.19 mmol) for 2 d at room temperature followed by column chromatography on silica gel (1:1:98 MeOH—NH$_4$OH—CH$_2$Cl$_2$) gave AMD9981 (40 mg, 40%) as a white foam. $^1$H NMR (CDCl$_3$) δ 1.53-1.77 (m, 2H), 2.02-2.08 (m, 1H), 2.35-2.39 (m, 1H), 2.68-2.88 (m, 2H), 3.56-3.85 (m, 5H), 4.20 (d, 1H, J=12.6 Hz), 5.01 (dd, 1H, J=9.6, 13.2 Hz), 6.75-6.79 (m, 1H), 7.18-7.33 (m, 8H), 7.47 (br s, 1H), 7.66 (d, 2H, J=7.5 Hz), 8.32 (s, 2H), 9.81 (m, 1H); $^{13}$C NMR (CDCl$_3$) δ 20.86, 21.16, 28.87, 40.32, 49.16, 55.17, 58.51, 110.68, 119.37, 122.04, 122.38, 123.07, 127.85, 128.82, 129.15, 130.47, 132.07, 134.95, 135.39, 138.01, 138.23, 143.38, 145.30, 147.33, 153.38, 157.32, 162.39; ES-MS m/z 571.2 (M+H); Anal. Calcd. For (C$_{31}$H$_{28}$N$_6$Cl$_2$O).0.2 (CH$_2$Cl$_2$): C, 63.68; H, 4.86; N, 14.28; Cl, 14.46. Found C, 64.00; H, 4.87; N, 14.10; Cl, 14.36.

EXAMPLE: 44

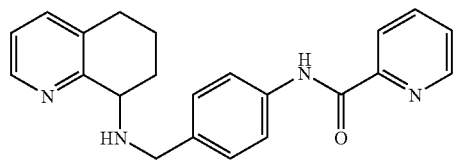

AMD9409: Preparation of pyridine-2-carboxylic acid {4-[(5,6,7,8-tetrahydro-quinolin-8-ylamino)-methyl]-phenyl}-amide Preparation of Pyridine-2-carboxylic acid (4-Hydroxymethyl-phenyl)-amide Using General Procedure F: Reaction of (4-Amino-phenyl)-methanol (200 mg, 1.63 mmol), picolinic acid (217 mg, 1.79 mmol), 1-hydroxybenzotriazole (242 mg, 1.79 mmol), 4-methyl morpholine (269 uL, 2.45 mmol) and EDCI (343 mg, 1.79 mmol) for 24 h at room temperature, gave the title compound (342 mg, 92%) as a red solid. $^1$H NMR (300 MHz, CDCl$_3$) δ 4.70 (d, 2H, J=3.9 Hz), 7.41 (d, 2H, J=8.4 Hz), 7.50 (ddd, 1H, J=7.5, 4.8, 1.3 Hz), 7.79 (d, 2H, J=8.4 Hz), 7.92 (ddd, 1H, J=7.5, 7.5, 4.5 Hz), 8.31 (d, 1H, J=6.0 Hz), 10.06 (br s, 1H).

Preparation of Pyridine-2-carboxylic acid (4-Chloromethyl-phenyl)-amide

Reaction of Pyridine-2-carboxylic acid (4-hydroxymethyl-phenyl)amide (342 mg, 1.50 mmol), Et$_3$N (262 uL, 1.80 mmol), and methanesulfonylchloride (128 uL, 1.65 mmol) for 2 h at reflux gave the title compound (352 mg, 95%) as a red solid. $^1$H NMR (300 MHz, CDCl$_3$) δ 4.61 (s, 2H), 7.45 (d, 2H, J=8.4 Hz), 7.50 (ddd, 1H, J=7.5, 4.8, 0.9 Hz), 7.80 (d, 2H, J=8.7 Hz), 7.92 (ddd, 1H, J=7.8, 7.8, 1.6 Hz), 8.63 (d, 1H, J=6.0 Hz), 10.08 (br s, 1H).

Preparation of pyridine-2-carboxylic acid {4-[(5,6,7,8-tetrahydro-quinolin-8-ylamino)-methyl]-phenyl}-amide General Procedure for substitution Reactions with Chlorides (1)

To a stirred solution of the amine (~1.5 equiv.), and Hunig base (1.0 equiv.), in anhydrous MeCN (~0.2M), at room temperature under nitrogen atmosphere, was added the chloride (1.0 equiv.) solution dropwise. The resultant solution was stirred at indicated temperature (~80° C.) for indicated time. The mixture was diluted with $CH_2Cl_2$ (100 mL/mmol), filtered through celite and concentrated. The crude material was purified by chromatography.

Using the above procedure I: Reaction of 8-amino-5,6,7,8-tetrahydroquinoline (181 mg, 1.22 mmol), N,N-diisopropylethylamine (142 uL, 0.81 mmol) and pyridine-2-carboxylic acid (4-chloromethyl-phenyl)-amide (200 mg, 0.81 mmol) for 3 h at 80° C. followed by column chromatography on silica gel ($CH_2Cl_2$/MeOH/$NH_4OH$ 198:1:1) gave AMD9409 (106 mg, 36%) as a yellow oil. $^1$H NMR (300 MHz, $CDCl_3$) δ 1.75-1.85 (m, 2H), 2.00-2.04 (m, 1H), 2.16-2.20 (m, 1H), 2.73-2.81 (m, 3H), 3.82-3.86 (m, 1H), 3.87 (d, 1H, J=12.0 Hz), 3.98 (d, 1H, J=15.0 Hz), 7.03 (dd, 1H, J=7.4, 4.7 Hz), 7.34 (d, 1H, J=7.5 Hz), 7.41-7.46 (m, 3H), 7.43 (d, 2H, J=8.4 Hz), 7.87 (ddd, 1H, J=7.8, 7.8, 1.7 Hz), 8.27 (d, 1H, J=7.8 Hz), 8.37 (d, 1H, J=7.8 Hz), 8.58 (d, 1H, J=3.3 Hz), 10.00 (br s, 1H); $^{13}$C NMR (75.5 MHz, $CDCl_3$) δ 20.09, 29.08, 29.28, 51.86, 57.98, 120.06 (2C), 122.20, 122.75, 126.79, 129.37 (2C), 132.85, 136.85, 137.25, 138.05, 147.23, 148.34, 150.25, 157.90, 162.28. ES-MS m/z 359 (M+H). Anal. Calcd. for $C_{22}H_{22}N_4O.0.2H_2O$: C, 72.99; H, 6.24; N, 15.48. Found: C, 72.98; H, 6.20; N, 15.48.

EXAMPLE: 45

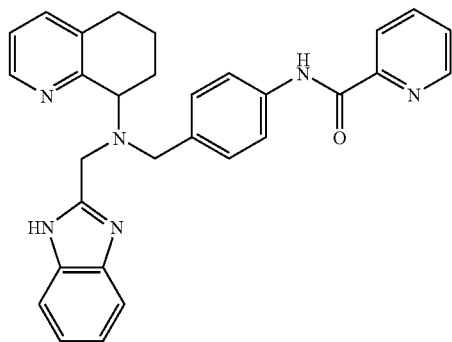

AMD9413: Preparation of pyridine-2-carboxylic acid (4-{[(1H-benzoimidazol-2-ylmethyl)-(5,6,7,8-tetrahydro-quinolin-8-yl)-amino]-methyl}-phenyl)-amide Using general procedure B: Reaction of pyridine-2-carboxylic acid {4-[(5,6,7,8-tetrahydro-quinolin-8-ylamino)-methyl]-phenyl}-amide (AMD9409) (67 mg, 0.19 mmol), 1H-benzoimidazole-2-carbaldehyde (30 mg, 0.21 mmol), and $NaBH(OAc)_3$ (119 mg, 0.50 mmol) for 0.5 h at 60° C. followed by purification of the crude product by column chromatography on silica gel ($CH_2Cl_2$/MeOH/$NH_4OH$ 198:1:1) gave AMD9413 (48 mg, 53%) as a white foam. $^1$H NMR (300 MHz, $CDCl_3$) δ 1.62-1.75 (m, 1H), 1.96-2.07 (m, 2H), 2.23-2.30 (m, 1H), 2.68-2.91 (m, 2H), 3.74 (br s, 2H), 3.98 (d, 1H, J=16.8 Hz), 4.09 (m, 1H), 4.19 (d, 1H, J=16.5 Hz), 7.16-7.20 (m, 3H), 7.41-7.46 (m, 4H), 7.53 (d, 1H, J=6.0 Hz), 7.64-7.67 (m, 3H), 7.87 (ddd, 1H, J=7.5, 7.5, 1.5 Hz), 8.26 (d, 1H, J=7.8 Hz), 8.58 (d, 1H, J=3.9 Hz), 8.70 (d, 1H, J=3.3 Hz), 9.94 (br s, 1H); $^{13}$C NMR (75.5 MHz, $CDCl_3$) δ 21.39, 23.41, 29.22, 48.54, 53.54, 60.11, 119.57, 121.50, 122.25, 122.36, 126.37, 129.28, 134.71, 135.33, 136.73, 137.21, 137.62, 146.93, 147.93, 149.80, 157.47, 161.84. ES-MS m/z 489 (M+H). Anal. Calcd. for $C_{30}H_{28}N_6O.0.5H_2O.0.3CHCl_3$: C, 68.23; H, 5.54; N, 15.76. Found: C, 68.06; H, 5.54; N, 15.46.

EXAMPLE: 46

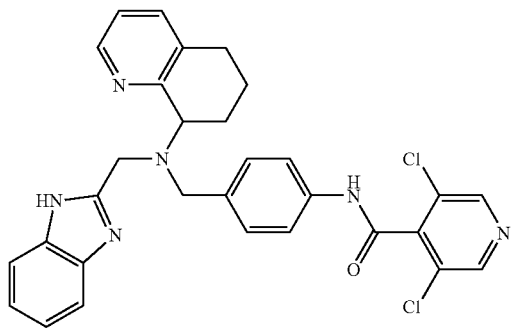

AMD9982: Preparation of N-(4-{[(1H-benzoimidazol-2-ylmethyl)-(5,6,7,8-tetrahydro-quinolin-8-yl)-amino]-methyl}-phenyl)-3,5-dichloro-isonicotinamide Preparation of 3,5-dichloro-N-(4-hydroxymethyl-phenyl)-isonicotinamide

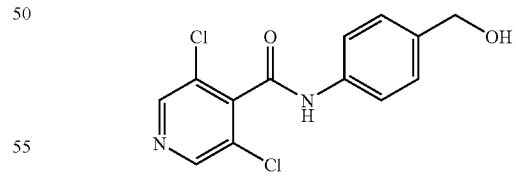

A suspension of 3,5-dichloroisonicotinic acid (128 mg, 0.667 mmol) in thionyl chloride (2 mL) was heated at reflux for 2 h, then concentrated. To the residue was added 4-aminobenzyl alcohol (123 mg, 0.999 mmol) and THF (2.2 mL), and the mixture was stirred at room temperature for 19 h. The mixture was filtered, and the filtrate was concentrated to give a yellow foam (125 mg, 63%). $^1$H NMR ($CD_3OD$) δ 4.60 (s, 2H), 7.38 (d, 2H, J=8.7 Hz), 7.63 (d, 2H, J=8.4 Hz), 8.66 (s, 2H).

Preparation of 3,5-Dichloro-N-(4-formyl-phenyl)-isonicotinamide

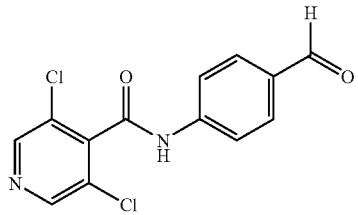

A solution of 3,5-dichloro-N-(4-hydroxymethyl-phenyl)-isonicotinamide (125 mg, 0.421 mmol) in CH$_2$Cl$_2$ (4.2 mL) was heated at reflux with a suspension of 85% MnO$_2$ (430 mg, 4.20 mmol) for 3 h. The mixture was filtered, and the filtrate was concentrated to give a brown solid (84 mg, 68%). $^1$H NMR (CDCl$_3$) δ 7.78 (s, 1H), 7.83 (d, 2H, J=8.7 Hz), 7.94 (d, 2H, J=8.4 Hz), 8.61 (s, 2H), 9.98 (s, 1H).

Using General Procedure B: To a stirred solution of (1H-benzoimidazol-2-ylmethyl)-(5,6,7,8-tetrahydro-quinolin-8-yl)-amine (76 mg, 0.27 mmol), 3,5-dichloro-N-(4-formyl-phenyl)-isonicotinamide (81 mg, 0.27 mmol), and AcOH (0.016 mL, 0.28 mmol) in THF (3 mL) was added NaBH(OAc)$_3$ (175 mg, 0.826 mmol) and the mixture was stirred at room temperature for 17.5 h. The crude material was dissolved in saturated HBr/AcOH (2 mL) and stirred at room temperature for 15 minutes. The solution was made basic with 10 N NaOH(aq) and extracted with CH$_2$Cl$_2$ (3×15 mL). The combined organic extracts were dried (MgSO$_4$) and concentrated in vacuo. Purification of the crude material by column chromatography on silica gel (400:5:1-200:5:1 CH$_2$Cl$_2$/MeOH/NH$_4$OH) afforded AMD9982 as a yellow foam (69 mg, 42%). $^1$H NMR (CDCl$_3$) δ 1.68 (m, 1H), 1.98 (m, 2H), 2.17 (m, 1H), 2.69-2.91 (m, 2H), 3.63 (d, 1H, J=17 Hz), 3.67 (d, 1H, J=17 Hz), 3.87 (d, 1H, J=17 Hz), 4.03 (m, 1H), 4.09 (d, 1H, J=17 Hz), 7.19 (m, 3H), 7.29 (d, 2H, J=8.4 Hz), 7.49 (m, 5H), 8.30 (s, 2H), 8.69 (d, 1H, J=3 Hz), 10.29 (s, 1H); $^{13}$C NMR (CDCl$_3$) δ 21.31, 24.10, 29.15, 48.10, 53.17, 60.55, 111.13, 118.26, 120.20, 121.50, 121.81, 122.40, 128.94, 129.13, 134.84, 136.13, 136.61, 137.42, 142.42, 146.79, 147.39, 156.23, 157.24, 160.31. ES-MS m/z 557 (M+H) ($^{35}$Cl), 559 (M+H) ($^{37}$Cl). Anal. Calcd. for C$_{30}$H$_{26}$N$_6$Cl$_2$O.0.2H$_2$O.0.4CH$_2$Cl$_2$: C, 61.36; H, 4.61; N, 14.12; Cl, 16.68. Found: C, 61.22; H, 4.62; N, 13.86; Cl, 16.80.

EXAMPLE: 47

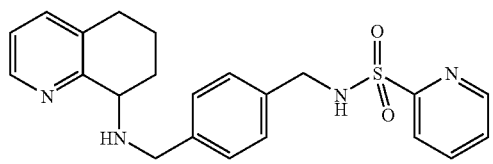

AMD9426: Preparation of Pyridine-2-sulfonic acid 4-[(5,6,7,8-tetrahydro-quinolin-8-ylamino)-methyl]-benzylamide

Preparation of Pyridine-2-sulfonic acid 4-hydroxymethyl-benzylamide

General Procedure for the Reaction of Amines with Sulfonyl Chlorides J

To a stirred solution of the amine (1.1 equiv.), and Hunig base (1.0 equiv.), in anhydrous CH$_2$Cl$_2$ (~0.2 M), at room temperature under nitrogen atmosphere, was added the sulfonyl chloride (1.0 equiv.) solution dropwise. The resultant solution was stirred at room temperature for indicated time. The mixture was diluted with CH$_2$Cl$_2$ (100 mL/mmol), washed with aqueous NaHCO$_3$, dried (Na$_2$SO$_4$) and concentrated. The crude material was purified by chromatography.

Using the above procedure J: Reaction of (4-aminomethyl-phenyl)-methanol (255 mg, 1.86 mmol, N,N-diisopropylethylamine (294 uL, 1.69 mmol), and pyridine-2-sulfonyl chloride (300 mg, 1.69 mmol) for 10 minutes at room temperature gave the title compound (400 mg, 85%) white solid. $^1$H NMR (300 MHz, CDCl$_3$) δ 4.26 (br s, 2H), 4.66 (br s, 2H), 5.28 (br s, 1H), 7.23-7.30 (m, 4H), 7.49-7.51 (m, 1H), 7.90-7.92 (m, 1H), 7.99 (d, 1H, J=4.8 Hz), 8.68 (d, 1H, J=4.5 Hz).

Preparation of Pyridine-2-sulfonic acid 4-chloromethyl-benzylamide

Reaction of pyridine-2-sulfonic acid 4-hydroxymethyl-benzylamide (140 mg, 0.50 mmol), Et$_3$N (88 uL, 0.60 mmol), and MsCl (47 uL, 0.60 mmol) for 2 h at reflux followed by column chromatography on silica gel (CH$_2$Cl$_2$/MeOH 99:1) gave the title compound (67 mg, 45%) as a white solid. $^1$H NMR (300 MHz, CDCl$_3$) δ 4.28 (d, 2H, J=6.0 Hz), 4.54 (s, 2H), 5.17 (br s, 1H), 7.23-7.49 (m, 4H), 7.47-7.52 (m, 1H), 7.88 (ddd, 1H, J=7.5, 7.5, 1.7 Hz), 7.97 (d, 2H, J=7.5 Hz), 8.69 (d, 1H, J=4.8 Hz). ES-MS m/z 319 (M+Na).

Preparation of Pyridine-2-sulfonic acid 4-[(5,6,7,8-tetrahydro-quinolin-8-ylamino)-methyl]-benzylamide Reaction of 8-amino-5,6,7,8-tetrahydroquinoline (200 mg, 1.35 mmol), N,N-diisopropylethylamine (157 uL, 0.90 mmol) and pyridine-2-sulfonic acid 4-chloromethyl-benzylamide (266 mg, 0.90 mmol) for 3 h at 50° C. followed by column chromatography on silica gel (CH$_2$Cl$_2$/MeOH/NH$_4$OH 98:1:1) gave AMD9426 (150 mg, 41%) as a yellow oil. $^1$H NMR (300 MHz, CDCl$_3$) δ 1.68-1.79 (m, 2H), 1.97-2.03 (m, 1H), 2.12-2.20 (m, 1H), 2.69-2.84 (m, 3H), 3.77-3.81 (m, 2H), 3.92 (d, 1H, J=12.0 Hz), 4.20 (br s, 2H), 7.05 (dd, 1H, J=7.5, 4.8 Hz), 7.15 (d, 2H, J=7.8 Hz), 7.25 (d, 2H, J=7.8 Hz), 7.36 (d, 1H, J=7.5 Hz), 7.39-7.44 (m, 1H), 7.82 (ddd, 1H, J=7.8, 7.8, 1.5 Hz), 7.92 (d, 1H, J=7.8 Hz), 8.36 (d, 1H, J=3.9 Hz), 8.59 (d, 1H, J=4.2 Hz); $^{13}$C NMR (75.5 MHz, CDCl$_3$) δ 20.09, 28.94, 29.23, 47.80, 51.75, 57.87, 122.25, 122.63, 126.94, 128.45 (2C), 128.88 (2C), 132.88, 135.25, 137.30, 138.35, 147.68, 147.15, 150.34, 157.75, 157.95. ES-MS m/z 409 (M+H). Anal. Calcd. for C$_{22}$H$_{24}$N$_4$O$_2$S.0.2H$_2$O.0.3CH$_2$Cl$_2$: C, 61.21; H, 5.76; N, 12.80; S, 7.33; O, 0.804. Found: C, 60.82; H, 5.73; N, 12.42; S, 7.30; O, 8.14.

EXAMPLE: 48

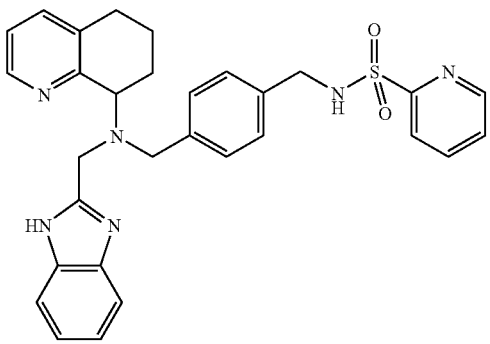

AMD9429: Preparation of Pyridine-2-sulfonic acid 4-{[(1H-benzoimidazol-2-ylmethyl)-(5,6,7,8-tetrahydro-quinolin-8-yl)-amino]-methyl}-benzylamide (hydrobromide salt)

Preparation of Pyridine-2-sulfonic acid 4-({(5,6,7,8-tetrahydro-quinolin-8-yl)-[1-(2-trime thylsilanyl-ethoxymethyl)-1H-benzoimidazol-2-ylmethyl]-amino}-methyl)-benzylamide Using general procedure B: Reaction of pyridine-2-sulfonic acid 4-[(5,6,7,8-tetrahydro-quinolin-8-ylamino)-methyl]-benzylamide (AMD9426) (150 mg, 0.37 mmol), 1-(2-trimethylsilanyl-ethoxymethyl)-1H-benzoimidazole-2-carbaldehyde (102 mg, 0.37 mmol), and NaBH(OAc)$_3$ (233 mg, 1.10 mmol) for 1 h at room temperature followed by column chromatography on silica gel (CH$_2$Cl$_2$/MeOH/NH$_4$OH 198:1:1) gave the title compound (101 mg, 41%) as a yellow foam. $^1$H NMR (300 MHz, CD$_3$OD) δ 0.00 (s, 9H), 0.75 (dd, 2H, J=8.1, 8.1 Hz), 1.58-1.75 (m, 2H), 2.22 (br s, 2H), 2.66-2.85 (m, 2H), 3.25 (dd, 2H, J=8.1, 8.1 Hz), 3.66 (d, 1H, J=14.1 Hz), 3.78 (d, 1H, J=14.1 Hz), 4.02 (d, 1H, J=6.0 Hz), 4.06-4.16 (m, 1H) 4.20 (brs, 2H), 4.81 (br s, 1H), 5.68 (d, 1H, J=12.0 Hz), 5.91 (d, 1H, J=12.0 Hz), 6.92 (d, 2H, J=7.8 Hz), 7.06 (dd, 1H, J=7.5, 4.8 Hz), 7.17-7.23 (m 4H), 7.30-7.35 (m, 2H), 7.45 (ddd, 1H, J=7.5, 4.5, 1.1 Hz), 7.61-7.64 (m, 1H), 7.87 (ddd, 1H, J=7.8, 7.8,1.7 Hz), 7.98 (d, 1H, J=7.8 Hz), 8.55 (d, 1H, J=3.6 Hz), 8.68 (d, 1H, J=3.9 Hz).ES-MS m/z 669 (M+H).

Preparation of Pyridine-2-sulfonic acid 4-{[(1H-benzoimidazol-2-ylmethyl)-(5,6,7,8-tetrahydro-quinolin-8-yl)-amino]-methyl}-benzylamide Using General Procedure E: Reaction of pyridine-2-sulfonic acid 4-({(5,6,7,8-tetrahydro-quinolin-8-yl)-[1-(2-trimethylsilanyl-ethoxymethyl)-1H-benzoimidazol-2-ylmethyl]-amino}-methyl)-benzylamide (100 mg, 0.15 mmol); and 6N HCl (3.9 mL) for 3 h at 50° C. followed by column chromatography on silica gel (CH$_2$Cl$_2$/MeOH/NH$_4$OH: 94:3:3) gave the title compound (68 mg, 85%) as a white foam.

Using general procedure D: the oil from above was converted to the corresponding hydrobromide salt to give AMD9429 as a white solid. $^1$H NMR (300 MHz, CD$_3$OD) δ 1.92-2.02 (m, 1H), 2 22-2.41 (m, 3H), 3.04-3.05 (m, 2H), 3.68 (br s, 4H), 4.42 (d, 1H, J=16.2 Hz), 4.64 (d, 1H, J=16.5 Hz), 4.77 (dd, 1H, J=10.2, 6.3 Hz), 6.93 (d, 2H, J=8.4 Hz), 7.33 (d, 2H, J=8.1 Hz), 7.53 (dd, 2H, J=6.3, 3.3 Hz), 7.60 (ddd, 1H, J=7.5, 4.8, 1.2 Hz), 7.73 (dd, 2H, J=6.3, 3.2 Hz), 7.91-7.97 (m, 2H), 8.01-8.07 (m, 1H), 8.39 (d, 1H, J=7.8 Hz), 8.65-8.67 (m, 1H), 8.92 (d, 1H, J=5.7 Hz); $^{13}$C NMR (75.5 MHz, CD$_3$OD) δ 15.86, 21.94, 29.21, 47.78, 57.69, 62.82, 67.31, 115.22 (2C), 123.70, 127.23, 128.03 (2C), 128.65, 129.10 (2C), 131.80 (2C), 132.24, 136.53, 139.56, 140.73, 141.58, 141.92, 149.29, 151.08 (2C), 152.21, 152.92, 159.36. ES-MS m/z 539 (M+H). Anal. Calcd. for C$_{30}$H$_{30}$N$_6$O$_2$S.2.2HBr.1.9H$_2$O: C, 47.99; H, 4.83; N, 11.19; O, 8.31; Br, 23.41; S, 4.27. Found: C, 43.35; H, 4.92; N, 11.13; O, 8.35; Br, 23.27; S, 4.22.

EXAMPLE: 49

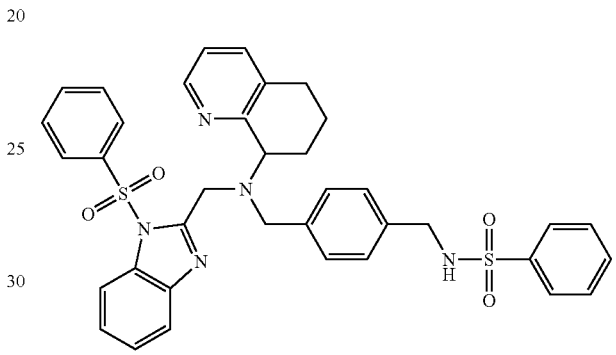

AMD9830: Preparation of N-(4-{[(1-benzenesulfonyl-1H-benzimidazol-2-ylmethyl)-(5,6,7,8-tetrahydro-quinolin-8-yl)-amino]-methyl}-benzyl)-benzenesulfonamide A solution of N'-(1H-benzimidazol-2-ylmethyl)-N'-(5,6,7,8-tetrahydro-8-quinolinyl)-1,4-benzenedimethanamine (302 mg, 0.760 mmol), benzenesulfonyl chloride (0.12 mL, 0.94 mmol), and Et$_3$N (0.15 mL, 1.1 mmol) in CH$_2$Cl$_2$ (7.5 mL) was heated at reflux for 17 h, then concentrated in vacuo. The residue was partitioned between saturated NaHCO$_3$(aq) (15 mL) and EtOAc (20 mL). The aqueous phase was extracted with EtOAc (20 mL), and the combined organic phases were dried (MgSO$_4$), filtered and concentrated in vacuo. Purification of the crude material by column chromatography on silica gel (400:5:1 CH$_2$Cl$_2$/MeOH/NH$_4$OH) afforded AMD9830 (229 mg, 71%) as a yellow foam. $^1$H NMR (CDCl$_3$) δ 1.64-2.03 (m, 3H), 2.37 (m, 1H), 2.66-2.84 (m, 2H), 3.76-3.89 (m, 4H), 4.06 (m, 1H), 4.41 (dd, 1H, J=9.6, 6.0 Hz), 4.66 (d, 1H, J=15 Hz), 4.79 (d, 1H, J=15 Hz), 6.76 (d, 2H, J=8.1 Hz), 7.07 (m, 1H), 7.18 (d, 2H, J=8.1 Hz, 7.27 (m, 2H), 7.41 (m, 3H), 7.55 (m, 5H), 7.84 (m, 3H), 7.96 (m, 2H), 8.48 (m, 1H); $^{13}$C NMR (CDCl$_3$) δ 20.15, 27.15, 27.55, 45.30, 51.78, 53.32, 61.49, 111.81, 118.60, 119.84, 122.59, 123.06, 125.43, 125.60, 127.06, 127.47, 127.76, 131.01, 131.24, 131.92, 132.55, 132.69, 134.81, 136.75, 138.13, 139.21, 140.14, 145.11, 151.74, 156.99. ES-MS m/z 678 (M+H). Anal. Calcd. for C$_{37}$H$_{35}$N$_5$S$_2$O$_4$.0.5H$_2$O: C, 64.70; H, 5.28; N, 10.20. Found: C, 64.65; H, 5.11; N, 10.08.

EXAMPLE: 50

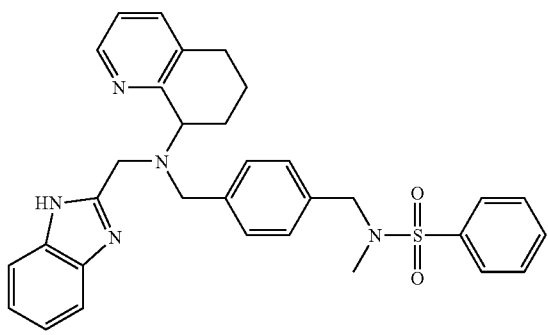

AMD9831: Preparation of N-(4-{[(1H-benzimidazol-2-ylmethyl)-(5,6,7,8-tetrahydro-quinolin-8-yl)-amino]-methyl}-benzyl)-N-methyl-benzenesulfonamide Preparation of 4-methylaminomethyl-benzoic acid methyl ester

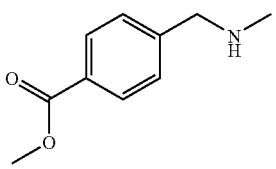

A mixture of methyl (4-bromomethyl)benzoate (600 mg, 2.62 mmol), methylamine (2.0 M/MeOH, 6.5 mL, 13 mmol), potassium iodide (cat.), and N,N-diisopropylethylamine (0.46 mL, 2.64 mmol) was warmed to 40° C. in $CH_3CN$ (13 mL) in a sealed vessel for 17 h, then concentrated in vacuo. The residue was partitioned between saturated $NaHCO_3$(aq) (20 mL) and $CH_2Cl_2$ (20 mL), and the aqueous phase was extracted with $CH_2Cl_2$ (20 mL). The combined organic phases were dried ($MgSO_4$), filtered and concentrated in vacuo. Purification of the crude material by column chromatography on silica gel (20% EtOAc/hexanes then 100:5:1 $CH_2Cl_2$/MeOH/$NH_4OH$) gave a colourless oil (262 mg, 56%). $^1H$ NMR ($CDCl_3$) δ 2.46 (s, 3H), 3.81 (s, 2H), 3.91 (s, 3H), 7.39 (d, 2H, J=8.1 Hz), 8.00 (d, 2H, J=8.1 Hz).

N-(4-Hydroxymethyl-benzyl)-N-methyl-benzenesulfonamide

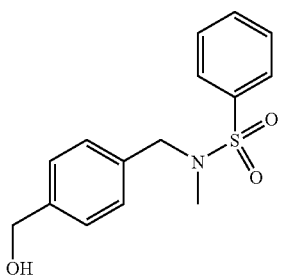

A solution of 4-methylaminomethyl-benzoic acid methyl ester (262 mg, 1.46 mmol), benzenesulfonyl chloride (0.22 mL, 1.7 mmol), and $Et_3N$ (0.29 mL, 2.1 mmol) in $CH_2Cl_2$ (15 mL) was heated at reflux for 15 h, then concentrated in vacuo. The residue was partitioned between saturated $NaHCO_3$(aq) (20 mL) and EtOAc (20 mL), and the aqueous phase was extracted with EtOAc (20 mL). The combined organic phases were washed with saturated $NaHCO_3$(aq) (15 mL) and brine (10 mL), then dried ($MgSO_4$), filtered and concentrated in vacuo to give tan crystals (672 mg).

To a solution of the crude ester from above (672 mg) in THF (2.9 mL) was added diisobutylaluminum hydride (1.0 M/THF, 8.8 mL, 8.8 mmol) at 0° C. and the solution was stirred at room temperature for 30 minutes. To the solution was added MeOH (4 mL) and the solution was acidified (pH 2) with 10% HCl(aq). The mixture was made basic with 1 N NaOH(aq) and extracted with EtOAc (2×20 mL). The combined organic extracts were dried ($MgSO_4$), filtered and concentrated in vacuo. Purification of the crude material by column chromatography on silica gel (40% EtOAc/hexanes) gave colourless crystals (258 mg, 61%). $^1H$ NMR ($CDCl_3$) δ 1.66 (t, 1H, J=6.0 Hz), 2.60 (s, 3H), 4.15 (s, 2H), 4.70 (d, 2H, J=6.0 Hz), 7.33 (m, 4H), 7.54-7.66 (m, 3H), 7.85 (m, 2H).

N-(4-Formyl-benzyl)-N-methyl-benzenesulfonamide

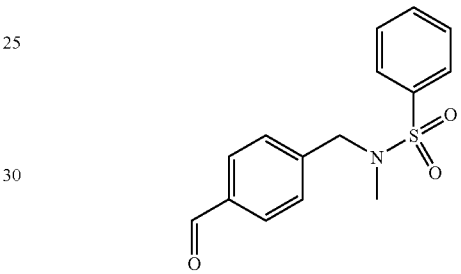

A solution of N-(4-hydroxymethyl-benzyl)-N-methylbenzenesulfonamide (258 mg, 0.885 mmol) in $CH_2Cl_2$ (9 mL) was stirred at room temperature with a suspension of 85% $MnO_2$ (900 mg, 8.8 mmol) for 63 h. The mixture was filtered through Celite and the solvent from the filtrate removed under reduced pressure to give a colourless solid (193 mg, 75%). $^1H$ NMR ($CDCl_3$) δ 2.65 (s, 3H), 4.24 (s, 2H), 7.50 (d, 2H, J=8.1 Hz), 7.56-7.68 (m, 3H), 7.87 (m, 4H), 10.02 (s, 1H).

Using General Procedure B: To a stirred solution of (1-tert-butoxycarbonyl-1H-Benzimidazol-2-ylmethyl)-(5,6,7,8-tetrahydro-quinolin-8-yl)-amine (130 mg, 0.343 mmol), N-(4-formyl-benzyl)-N-methyl-benzenesulfonamide (109 mg, 0.377 mmol) and AcOH (0.020 mL, 0.35 mmol) in THF (3.5 mL) was added $NaBH(OAc)_3$ (218 mg, 1.03 mmol) and the mixture was stirred at room temperature for 20 h. Purification of the crude material by column chromatography on silica gel (40% EtOAc/hexanes) afforded a colourless oil (41 mg).

A solution of the oil from above (41 mg, 0.063 mmol) in 3:1 TFA/$CH_2Cl_2$ (4 mL) was stirred at room temperature for 1 h, then concentrated in vacuo. The residue was partitioned between $CH_2Cl_2$ (10 mL) and 1 N NaOH(aq) (15 mL), and the aqueous phase was extracted with $CH_2Cl_2$ (2×10 mL). The combined organic extracts were dried ($MgSO_4$), filtered and concentrated in vacuo to give AMD9831 (33 mg, 16%) as a colourless foam. $^1H$ NMR ($CDCl_3$) δ 1.69 (m, 1H), 2.02 (m, 2H), 2.26 (m, 1H), 2.51 (s, 3H), 2.69-2.91 (m, 2H), 3.73 (s, 2H), 3.95 (d, 1H, J=17 Hz), 4.05 (s, 2H), 4.09 (m, 1H), 4.18 (d, 1H, J=17 Hz), 7.17 (m, 5H), 7.37 (d, 2H, J=8.1 Hz), 7.43 (d, 1H, J=6.6 Hz), 7.49-7.61 (m, 5H), 7.80 (m, 2H), 8.69 (m, 1H); $^{13}C$ NMR ($CDCl_3$) δ 21.77, 23.84, 29.61, 34.71, 49.05, 54.15, 60.81, 121.87, 122.69, 127.79, 128.68, 129.25, 129.48, 133.00, 134.85, 135.14, 137.66, 137.86, 139.57, 147.33, 156.54, 157.75. ES-MS m/z 552 (M+H). Anal. Calcd. for $C_{32}H_{33}N_5SO_2 \cdot 0.2H_2O \cdot 0.4C_4H_8O_2$: C, 68.34; H, 6.25; N, 11.86. Found: C, 68.31; H, 6.33; N, 11.86.

EXAMPLE: 51

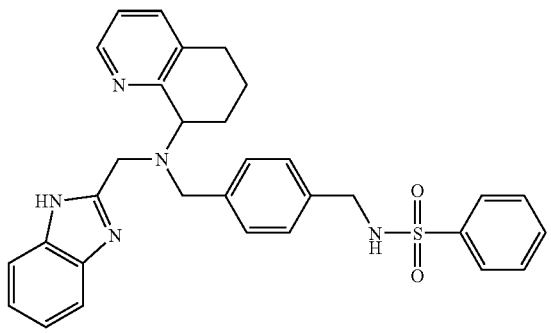

AMD9845: Preparation of N-(4-{[(1H-benzimidazol-2-ylmethyl)-(5,6,7,8-tetrahydro-quinolin-8-yl)-amino]-methyl}-benzyl)-benzenesulfonamide A solution of N-(4-{[(1-benzenesulfonyl-1H-benzimidazol-2-ylmethyl)-(5,6,7,8-tetrahydro-quinolin-8-yl)-amino]-methyl}-benzyl)-benzenesulfonamide (AMD9830) (161 mg, 0.234 mmol) in saturated HBr/AcOH (3 mL) was stirred at room temperature for 3.5 h, then diethyl ether (20 mL) was added to give a colourless precipitate. The supernatant was decanted, and the residue was partitioned between $CH_2Cl_2$ (10 mL) and saturated $NaHCO_3$(aq) (15 mL). The basic aqueous phase was extracted with $CH_2Cl_2$ (10 mL), and the combined organic phases were dried ($MgSO_4$), filtered and concentrated in vacuo. Purification of the crude material by column chromatography on silica gel (500:5:1 $CH_2Cl_2$/MeOH/$NH_4OH$) gave AMD9845 (59 mg, 44%) as a yellow foam. $^1$H NMR (CDCl$_3$) δ 1.68 (m, 1H), 1.99 (m, 2H), 2.24 (m, 1H), 2.67-2.91 (m, 2H), 3.68 (s, 2H), 3.86 (d, 1H, J=17 Hz), 4.05 (m, 3H), 4.14 (d, 1H, J=17 Hz), 4.87 (m, 1H), 7.01 (d, 2H, J=7.8 Hz), 7.18 (m, 3H), 7.28 (m, 2H), 7.37-7.60 (m, 6H), 7.80 (m, 2H), 8.68 (m, 1H); $^{13}$C NMR (CDCl$_3$) δ 22.08, 24.18, 29.90, 47.66, 49.21, 54.47, 61.26, 122.30, 123.03, 127.75, 128.54, 129.65, 129.73, 133.29, 135.47, 135.74, 138.01, 139.87, 140.65, 147.63, 156.87, 158.03. ES-MS m/z 538 (M+H). Anal. Calcd. for $C_{31}H_{31}N_5SO_2 \cdot 0.46CH_2Cl_2$: C, 65.52; H, 5.58; N, 12.14. Found: C, 65.56; H, 5.60; N, 12.09.

EXAMPLE: 52

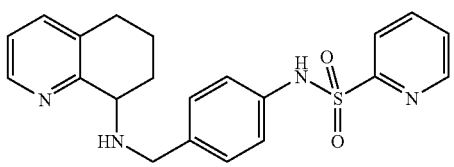

AMD9436: Preparation of Pyridine-2-sulfonic acid {4-[(5,6,7,8-tetrahydro-quinolin-8-ylamino)-methyl]-phenyl}-amide (hydrobromide salt)

Preparation of Pyridine-2-sulfonic acid (4-hydroxymethyl-phenyl)-amide

Reaction of (4-Amino-phenyl)-methanol (249 mg, 2.03 mmol), N,N-diisopropylethylamine (294 uL, 1.69 mmol), and pyridine-2-sulfonyl chloride (300 mg, 1.69 mmol) for 1 h at room temperature followed by column chromatography on silica gel ($CH_2Cl_2$/MeOH 194:3) gave the title compound (210 mg, 47%) as a red solid. $^1$H NMR (300 MHz, CDCl$_3$) δ 4.60 (d, 2H, J=6.0 Hz), 7.07 (br s, 1H), 7.15 (d, 2H, J=8.4 Hz), 7.23 (d, 2H, J=8.7 Hz), 7.44-7.48 (m, 1H), 7.83 (ddd, 1H, J=7.5, 7.5, 1.8 Hz), 7.89 (d, 1H, J=7.8 Hz), 8.72 (d, 1H, J=4.5 Hz).

Preparation of Pyridine-2-sulfonic acid (4-formyl-phenyl)-amide

To a stirred solution of pyridine-2-sulfonic acid (4-hydroxymethyl-phenyl)-amide (200 mg, 0.76 mmol), and pyridine (612 uL) in anhydrous $CH_2Cl_2$ (3 mL) was added Dess-Martin periodiane (450 mg, 1.06 mmol). The resultant solution was stirred at room temperature for 1 h. The mixture was diluted with 100 mL $CH_2Cl_2$, filtered through celite, and concentrated. The crude material was purified by recrystallisation from cold $CH_2Cl_2$ to give the title compound (120 mg, 60%) as a yellow powder. $^1$H NMR (300 MHz, CDCl$_3$) δ 7.34 (d, 2H, J=8.4 Hz), 7.49-7.50 (m, 1H), 7.74 (br s, 1H), 7.75 (d, 2H, J=8.4 Hz), 7.89-7.70 (m, 1H), 8.03 (d, 1H, J=8.1 Hz), 8.70 (d, 1H, J=4.2 Hz), 9.87 (s, 1H).

Preparation of Pyridine-2-sulfonic acid {4-[(5,6,7,8-tetrahydro-quinolin-8-ylamino)-methyl]-phenyl}-amide Using General Procedure B: Reaction of 5,6,7,8-tetrahydro-quinolin-8-ylamine (68 mg, 0.46 mmol), pyridine-2-sulfonic acid (4-formyl-phenyl)-amide (120 mg, 0.46 mmol), and NaBH(OAc)$_3$ (291 mg, 1.37 mmol) for 1 h at room temperature followed by purification of the crude product by column chromatography on silica gel ($CH_2Cl_2$/MeOH/NH$_4$OH 98:1:1) gave the title compound (121 mg, 67%) as a white foam.

Using general procedure D: the oil from above was converted to the corresponding hydrobromide salt to give AMD9436 as a white solid. $^1$H NMR (300 MHz, CD$_3$OD) δ 1.86-2.00 (m, 2H), 2.11-2.15 (m, 1H), 2.43-2.49 (m, 1H), 2.88-2.90 (m, 2H), 4.20 (d, 1H, J=13.2 Hz), 4.32 (d, 1H, J=12.9 Hz), 4.40(dd, 1H, J=9.6, 4.8 Hz), 7.29 (d, 2H, J=8.4 Hz), 7.35 (dd, 1H, J=7.8, 4.8 Hz), 7.42 (d, 2H, J=8.7 Hz), 7.53-7.59 (m, 1H), 7.67 (d, 1H, J=7.5 Hz), 7.95-7.99 (m, 2H), 8.50 (d, 1H, J=4.5 Hz), 8.62 (d, 1H, J=3.9 Hz); $^{13}$C NMR (75.5 MHz, CD$_3$OD) δ 20.34, 26.35, 28.67, 57.32, 122.43 (2C), 124.35, 126.69, 128.64, 128.89, 132.57 (2C), 137.67, 140.17, 140.73, 143.04, 146.85, 149.31, 151.52, 158.47. ES-MS m/z 395 (M+H). Anal. Calcd. for $C_{21}H_{22}N_4O_2S \cdot 2.0HBr \cdot 1.5H_2O$: C, 43.24; H, 4.67; N, 9.60; 0, 9.60; S, 5.50; Br, 27.40. Found: C, 42.89; H, 4.77; N, 9.63; 0, 9.33; S, 5.42; Br, 27.50.

EXAMPLE: 53

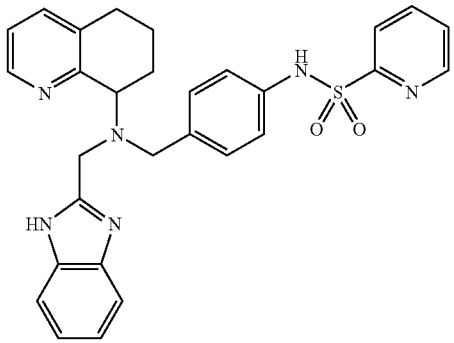

AMD9444: Preparation of Pyridine-2-sulfonic acid (4-{[(1H-benzoimidazol-2-ylmethyl)-(5,6,7,8-tetrahydro-quinolin-8-yl)-amino]-methyl}-phenyl)-amide Using general procedure B: Reaction of pyridine-2-sulfonic acid [4-({(5,6,7,8-tetrahydro-quinolin-8-yl)-[1-(2-trimthylsilanyl-ethoxymethyl)-1H-benzimidazol-2-ylmethyl]-amino}-methyl)-phenyl]-amide (AMD9436) (82 mg, 0.21 mmol), 1-(2-trimethylsilanyl-ethoxymethyl)-1H-benzoimidazole-2-carbaldehyde (57 mg, 0.21 mmol), and NaBH(OAc)₃ (132 mg, 0.62 mmol) for 1 h at room temperature followed by purification of the crude material by column chromatography on silica gel (CH₂Cl₂/MeOH/NH₄OH 198:1:1) gave Pyridine-2-sulfonic acid [4-({(5,6,7,8-tetrahydro-quinolin-8-yl)-[1-(2-trimethylsilanyl-ethoxymethyl)-1H-benzoimidazol-2-ylmethyl]-amino}-methyl)-phenyl]-amide (72 mg, 41%) as a yellow foam.

Using General Procedure E: Reaction of the above compound (72 mg, 0.11 mmol) with 6N HCl (2.0 mL) for 3 h at 50° C. followed by column chromatography on silica gel (CH₂Cl₂/MeOH/NH₄OH 194:3:3) gave the title compound (41 mg, 71%) as a white foam.

Using general procedure D: the oil from above was converted to the corresponding hydrobromide salt to give AMD9444 as a white solid. ¹H NMR (300 MHz, CD₃OD) δ 1.88-1.90 (m, 1H), 2.18-2.24 (m, 2H), 2.35-2.36 (m, 1H), 3.00-3.01 (m, 2H), 3.70 (d, 1H, J=12.9 Hz), 3.76 (d, 1H, J=12.9 Hz), 4.38 (d, 1H, J=16.2 Hz), 4.59 (d, 1H, J=16.2 Hz), 4.64-4.73 (m, 1H), 6.87 (d, 2H, J=8.4 Hz), 7.30 (d, 2H, J=8.4 Hz), 7.51-7.56 (m, 3H), 7.72 (dd, 2H, J=6.0, 3.0 Hz), 7.84-7.91 (m, 2H), 7.92-7.98 (m, 1H), 8.33 (d, 1H, J=7.8 Hz), 8.59 (d, 1H, J=4.5 Hz), 8.86 (d, 1H, J=4.5 Hz); ¹³C NMR (75.5 MHz, CD₃OD) δ 15.84, 21.90, 29.17, 50.61, 57.21, 62.46, 115.19 (2C), 121.77 (2C), 124.09, 127.11, 128.09 (2C), 128.77, 132.28 (2C), 133.15, 139.16, 140.07, 141.57, 141.81, 149.10, 151.46, 152.87. ES-MS m/z 525 (M+H). Anal. Calcd. for $C_{29}H_{28}N_6O_2$S.2.2HBr.1.5H₂O.0.3C₄H₁₀O: C, 48.24; H, 4.85; N, 11.18; O, 8.09; Br, 23.38; S, 4.26. Found: C, 48.44; H, 4.85; N, 11.18; O, 8.22; Br, 23.08; S, 4.34.

EXAMPLE: 54

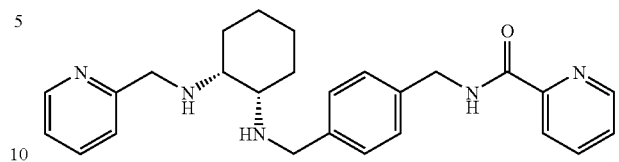

AMD9541: Preparation of Pyridine-2-carboxylic acid-4-{[cis-2-[(N-pyridin-2-ylmethyl)amino]cyclohexyl]aminomethyl}-benzylamide (hydrobromide salt)

Preparation of pyridine-2-carboxylic acid-4-hydroxymethyl-benzylamide

Using General Procedure F: To a stirred solution of 4-aminomethylbenzyl alcohol (203 mg, 1.48 mmol) in DMF (3 mL) was added picolinic acid (198 mg, 1.61 mmol), 1-hydroxybenzotriazole (213 mg, 1.58 mmol), N,N-diisopropylethylamine (0.39 mL, 2.24 mmol) and 1-(3-dimethylaminopropyl)-3-ethyl carbodiimide HCl (EDC) (315 mg, 1.64 mmol) and the mixture stirred overnight at room temperature. Standard work-up afforded the title compound (340 mg, 95%) as a yellow oil. ¹H NMR (300 MHz, CDCl₃) δ 4.67 (d, 2H, J=6.0 Hz), 4.69 (s, 2H), 7.36 (br s, 4H), 7.43-7.44 (m, 1H), 7.85-7.86 (m, 1H), 8.24 (d, 1H, J=9.0 Hz), 8.52 (br s, 1H), 8.52 (d, 1H, J=3.0 Hz). ES-MS m/z 243 (M+H).

Preparation of pyridine-2-carboxylic acid-4-formyl-benzylamide

To a stirred solution of pyridine-2-carboxylic acid-4-hydroxymethyl-benzylamide (360 mg, 1.48 mmol) in anhydrous CH₂Cl₂ (10 mL) was added Dess-Martin periodiane (690 mg, 1.63 mmol) and the reaction stirred at room temperature for 1 h. The mixture was diluted with diethyl ether (25 mL), ethyl acetate (25 mL), saturated aqueous sodium bicarbonate (15 mL) and saturated aqueous sodium thiosulfate (15 mL) and stirred for 30 minutes. The phases were separated and the aqueous phase washed with ethyl acetate (1×15 mL). The combined organic layers were washed with brine (1×20 mL), dried (Na₂SO₄), filtered and concentrated under reduced pressure. Purification of the crude oil by column chromatography on silica gel (CH₂Cl₂) gave the desired aldehyde as a pale yellow oil (300 mg, 85%). ¹H NMR (300 MHz, CDCl₃) δ 4.76 (d, 2H, J=6.0 Hz), 7.42-7.44 (m, 1H), 7.53 (d, 2H, J=6.0 Hz), 7.87 (d, 2H, J=6.0 Hz), 7.85-7.88 (m, 1H), 8.24 (d, 1H, J=6.0 Hz), 8.55 (br s, 1H), 8.57 (d, 1H, J=3.0 Hz), 10.00 (s, 1H).

Using General Procedure B: To a solution of cis-1-[N-(t-butoxycarbonyl)]-cyclohexane-1,2-diamine (0.79 g, 3.69 mmol) and 2-pyridinecarboxaldehyde (0.35 mL, 3.68 mmol) in CH₂Cl₂ (20 mL) was added NaBH(OAc)₃ (0.036 g, 0.57 mmol) and the mixture stirred at room temperature overnight. The resultant crude oil was used without further purification in the next step. ¹H NMR (CDCl₃) δ 1.35-1.51 (m, 4H), 1.44 (s, 9H), 1.54-1.64 (m, 3H), 2.01-2.04 (m, 2H), 2.75-2.79 (m, 1H), 3.66-3.70 (m, 1H), 3.87 (d, 1H, J=15 Hz), 3.96 (d, 1H, J=15 Hz), 5.42 (br s, 1H, NH), 7.16 (dd, 1H, J=9, 6 Hz), 7.30 (d, 1H, J=9 Hz), 7.61 (td, 1H, J=9, 3 Hz), 8.56 (d, 1H, J=3 Hz).

To a solution of the oil from above and N,N-diisopropylethylamine (0.96 mL, 5.52 mmol) in $CH_2Cl_2$ (10 mL) was added benzylchloroformate (0.64 mL, 4.48 mmol) and the mixture stirred at room temperature for 3 hours. The reaction was diluted with $CH_2Cl_2$ (15 mL) and brine (25 mL) and the phases separated. The aqueous phase was washed with $CH_2Cl_2$ (2×20 mL) and the combined organic extracts were dried ($Na_2SO_4$), filtered and concentrated under reduced pressure. Purification of the crude product by flash chromatography on silica gel ($CH_2Cl_2$/MeOH, 97:3) afforded the di-protected diamine (1.44 g, 89% over 2 steps) as an orange oil.

Removal of the Boc protecting group: The oil from above (1.44 g, 3.28 mmol) was dissolved in $CH_2Cl_2$ (2 mL) and treated with trifluoroacetic acid (2 mL) and the mixture stirred overnight. The usual work-up afforded an orange oil (1.17 g) which was use without further purification in the next reaction.

Using General Procedure B: To a solution of the oil from above (187 mg) and pyridine-2-carboxylic acid-4-formylbenzylamide (127 mg, 0.53 mmol) in $CH_2Cl_2$ (6 mL) was added $NaBH(OAc)_3$ (170 mg, 0.80 mmol) and the mixture stirred at room temperature overnight. Purification of the crude material by flash chromatography on silica gel ($CH_2Cl_2$/MeOH, 96:4 followed by 90:10) afforded the desired protected amine (150 mg, 50% over 2 steps) as a pale yellow foam.

Removal of Cbz Group: To a solution of the foam from above (150 mg, 0.27 mmol) in MeOH (5 mL) was added palladium on activated carbon (10%, 34 mg) and the mixture was hydrogenated (1 atmosphere) at room overnight. The reaction mixture was filtered through celite and the cake was washed with methanol. The combined filtrates were evaporated under reduced pressure and the resultant clear oil was purified by radial chromatography on silica gel (1 mm plate, 100:2:1 $CH_2Cl_2$/MeOH/$NH_4OH$) to afford the free amine (45 mg, 39%) as a clear oil.

Using General Procedure D: The free base from above (33 mg, 0.077 mmol) was converted to the hydrobromide salt to provide AMD9541 (70 mg) as a white solid. $^1H$ NMR ($D_2O$) δ 1.39-1.56 (m, 4H), 1.62-1.75 (m, 2H), 1.92-1.97 (m, 2H), 3.27-3.31 (m, 1H), 3.42-3.46 (m, 1H), 3.90 (d, 1H, J=17.4 Hz), 4.20 (d, 1H, J=13.5 Hz), 4.33 (d, 1H, J=13.5 Hz), 4.41 (d, 1H, J=17.4 Hz), 4.59 (s, 2H), 7.35 (d, 2H, J=8.1 Hz), 7.42 (d, 2H, J=8.1 Hz), 7.85-7.90 (m, 2H), 8.11-8.13 (br m, 1H), 8.40-8.47 (m, 2H), 8.56-8.63 (m, 2H), 8.82-8.87 (br m, 1H); $^{13}C$ NMR ($D_2O$) δ 19.63, 23.45, 24.83, 27.17, 44.41, 48.33, 49.12, 54.52, 58.88, 125.63, 126.66, 126.85, 129.15 (2 carbons), 130.42, 131.33 (2 carbons), 139.69, 141.47, 144.55, 145.00, 147.16, 147.45 (2 carbons), 155.72, 162.53. ES-MS m/z430 (M+H).

EXAMPLE: 55

Inhibition of Chemokine Induced Ca Flux Measured on a FLIPR (Molecular Devices)

Reagents:

Loading dye: Fluo-3, AM (Molecular Probes F-1241) is dissolved in anhydrous DMSO and stored frozen in aliquots. To increase the solubility of the dye in the loading medium, 10% (w/v) pluronic acid (Molecular Probes F-127) is added to the Fluo-3 stock solution immediately before use.

Flux buffer:

HBSS+20 mM Hepes buffer+0.2% BSA, pH 7.4. HBSS 10× [(w/o phenol red and sodium bicarbonate (Gibco 14 065-049)]; Hepes buffer 1M (Gibco 15 630-056), BSA (Sigma A3675). The flux buffer is vacuum-filtered and stored refrigerated for a maximum of 5 days. Before use in the experiment, the buffer is warmed at 37° C. in a waterbath.

Antagonists:

The test compounds were diluted in flux buffer at the desired concentration and added to 4 wells of a black microplate (4 parallel measurements per compound). The following control wells were used: 100% response control (no inhibition), flux buffer was added; 100% inhibition control: chemokine was added at 5-times the concentration required to induce a Ca flux.

Preparation of the Agonist (Chemokine) Plate

The chemokines are diluted in flux buffer to concentrations that are 4-fold higher than the desired concentrations required for stimulation of the cells (i.e. 2.5 nM for SDF-1α and 0.6 nM for RANTES). The chemokines were added to untreated 96-well Sero well compound plates (International Medical, Sterilin code 611F96). In the negative control well's (baseline monitoring), flux buffer is added instead of chemokine. As a positive control to check for dye loading efficiency, 20 μM digitonin (final concentration) was also included. The agonist plate was incubated in the FLIPR (37° C.) for 15-30 min.

Cell Loading Protocol for Measuring Inhibition of SDF-1α Induced Ca Flux in SUP-T1 Cells.

SUP-T1 cells were centrifuged at room temperature (RT) and re-suspended in loading medium (RPMI-1640 containing 2% FBS and 4 μM Fluo3, AM). The cells were incubate at room temperature for 45 min. then washed twice in flux buffer then incubated in flux buffer at room teperature for 10 min. The cells were centrifuged and re-suspended in flux buffer at a density of $3 \times 10^6$ cells per mL. A 100 μL aliquot of the cell suspension ($3 \times 10^5$ cells) was added to each well of a black microplate (Costar 3603), which already contains 50 μL of a solution of the test compound (at concentrations that are 3-fold higher than the desired final compound concentrations). The microplate is then gently centrifuged at room temperature. Homogeneous spreading of the cells on the bottom of the microplate wells was then confirmed with a microscope and the microplate was incubated in the FLIPR (37° C.) for 10 min. prior to testing.

Fluorescence Measurements as a Function of Time on the FLIPR

The FLIPR settings (camera exposure time and laser power) are adjusted to obtain initial fluorescence values between 8,000 and 10,000 units. After monitoring a 20 second-baseline, the agonist (chemokine) (50 μL) is added by automatic pipettor with black pipette tips. Fluorescence is measured simultaneously in all wells of the microplate every 2 seconds (first 2 min) and thereafter every 6 seconds (additional 2 min). The average ca-flux measured in each set of 4 identical wells (one test compound) was calculated by the FLIPR software.

The compounds of the current invention are tested for inhibition of SDF-1α induced Ca flux in SUP-T1 cells using the method described above. The exemplified compounds exhibit inhibition. The following compounds inhibited SDF-1α induced Ca flux greater than 20% at 20 μg/mL:

Example numbers: 2, 4, 11, 17, 45, 48.

EXAMPLE 56

Assay for Inhibition of HIV-1 (NL4.3) Replication in MT-4 Cells.

Inhibition of HIV-1 NL4.3 (or III$_B$, CXCR4 using) replication assays were performed as previously described (Bridger et al. J. Med. Chem. 1999, 42, 3971-3981; De Clercq et al. Proc. Natl. Acad. Sci, 1992, 89, 5286-5290; De Clercq et al. Antimicrob. Agents Chemother. 1994, 38, 668-674; Bridger et al. J. Med. Chem. 1995, 38, 366-378; Schols et al. J. Exp. Med., 1997, 186, 1383-1388). Anti-HIV activity and cytotoxicity measurements were carried out in parallel. They were based on the viability of MT-4 cells that had been infected with HIV in the presence of various concentrations of the test compounds. After the MT-4 cells were allowed to proliferate for 5 days, the number of viable cells was quantified by a tetrazolium-based calorimetric 3-(4,5-dimethylthiazol-2-yl)-2,5-diphenyltetrazolium bromide (MTT) procedure in 96-well microtrays. In all of these assays, viral input (viral multiplicity of infection, MOI) was 0.01, or 100 times the 50% cell culture infective dose (CCID$_{50}$). The EC$_{50}$ was defined as the concentration required to protect 50% of the virus-infected cells against viral cytopathicity.

When compounds of the current invention are tested for inhibition of HIV-1 NL4.3 or III$_B$ replication in MT-4 cells, all show inhibition. The following compounds exhibited EC$_{50}$'s of less than 20 µg/mL:

Examples numbers: 2, 4, 11, 17, 45, 48, 53.

EXAMPLE 57

Assay for Inhibition of HIV-1 (BaL) Replication in PBMC's.

When compounds of the current invention are tested for inhibition of HIV-1 BaL (CCR5 using) replication in PHA-stimulated PBMC's (peripheral blood mononuclear cells) using viral p24 antigen expression (De Clercq et al. Antimicrob. Agents Chemother. 1994, 38, 668-674; Schols et al. J. Exp. Med., 1997, 186, 1383-1388), all show inhibition. The following compounds exhibited EC$_{50}$'s of less than 20 µg/mL:

Example numbers: 2, 4, 11, 16, 17, 48, 53.

Also prepared according to the above methods are the following compounds:

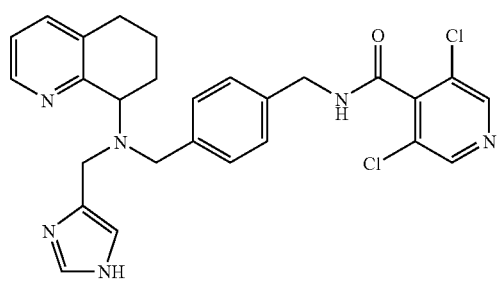

3,5-Dichloro-N-(4-{[(1H-imidazol-4-ylmethyl)-(5,6,7,8-tetrahydro-quinolin-8-yl)-amino]-methyl}-benzyl)-isonicotinamide

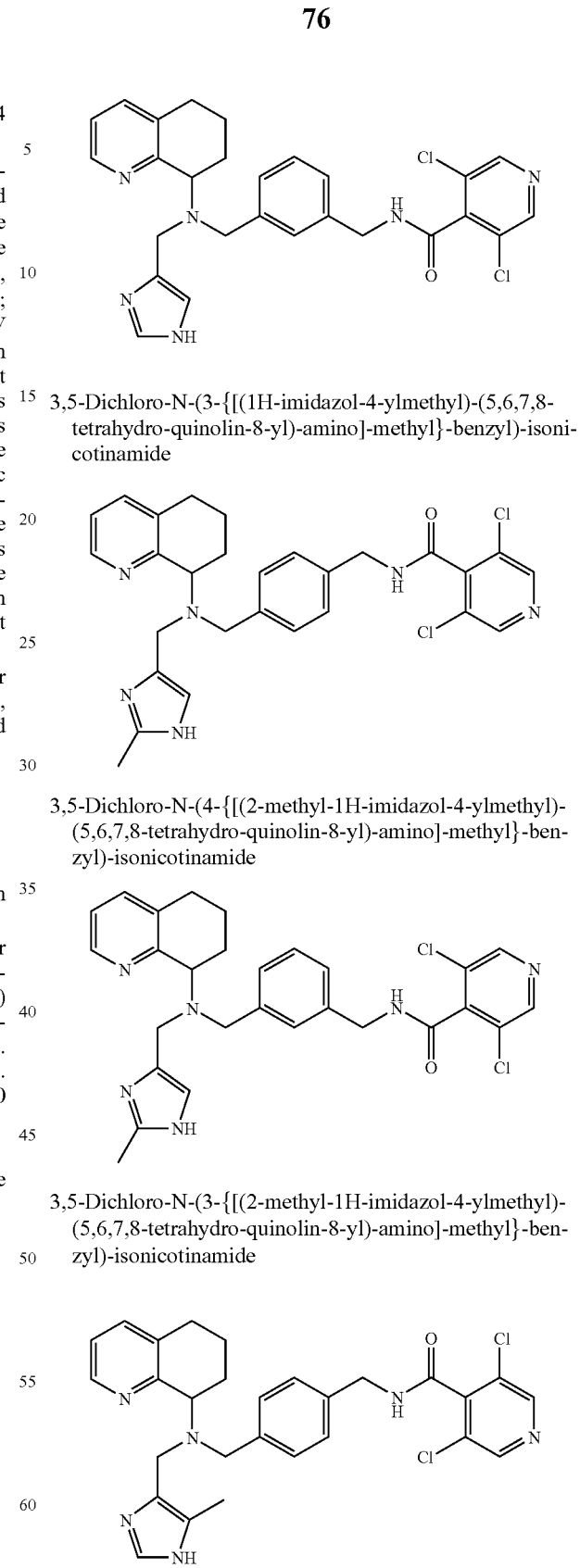

3,5-Dichloro-N-(3-{[(1H-imidazol-4-ylmethyl)-(5,6,7,8-tetrahydro-quinolin-8-yl)-amino]-methyl}-benzyl)-isonicotinamide 3,5-Dichloro-N-(4-{[(2-methyl-1H-imidazol-4-ylmethyl)-(5,6,7,8-tetrahydro-quinolin-8-yl)-amino]-methyl}-benzyl)-isonicotinamide 3,5-Dichloro-N-(3-{[(2-methyl-1H-imidazol-4-ylmethyl)-(5,6,7,8-tetrahydro-quinolin-8-yl)-amino]-methyl}-benzyl)-isonicotinamide 3,5-Dichloro-N-(4-{[(5-methyl-1H-imidazol-4-ylmethyl)-(5,6,7,8-tetrahydro-quinolin-8-yl)-amino]-methyl}-benzyl)-isonicotinamide

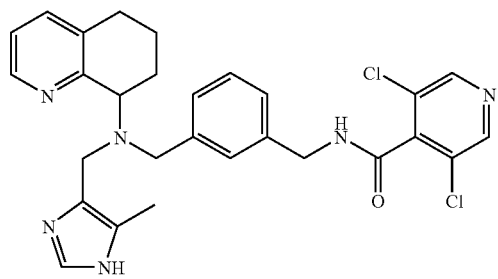

3,5-Dichloro-N-(3-({[(5-methyl-1H-imidazol-4-ylmethyl)-(5,6,7,8-tetrahydro-quinolin-8-yl)-amino]-methyl})-benzyl)-isonicotinamide

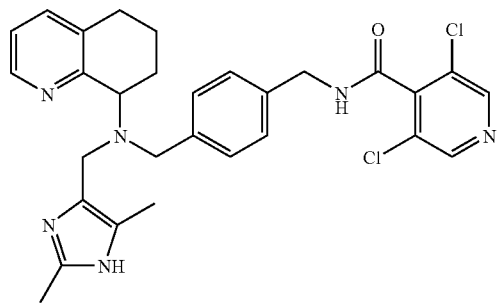

3,5-Dichloro-N-(4-{[(2,5-dimethyl-1H-imidazol-4-ylmethyl)-(5,6,7,8-tetrahydro-quinolin-8-yl)-amino]-methyl})-benzyl)-isonicotinamide

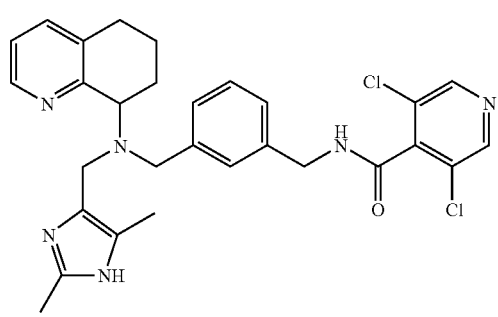

3,5-Dichloro-N-(3-({[(2,5-dimethyl-1H-imidazol-4-ylmethyl)-(5,6,7,8-tetrahydro-quinolin-8-yl)-amino]-methyl})-benzyl)-isonicotinamide

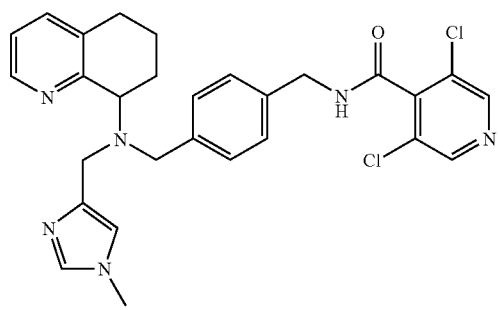

3,5-Dichloro-N-(4-{[(1-methyl-1H-imidazol-4-ylmethyl)-(5,6,7,8-tetrahydro-quinolin-8-yl)-amino]-methyl})-benzyl)-isonicotinamide

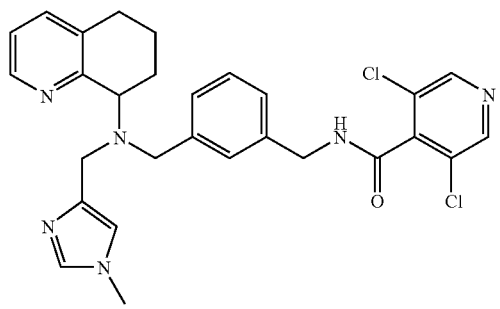

3,5-Dichloro-N-(3-{[(1-methyl-1H-imidazol-4-ylmethyl)-(5,6,7,8-tetrahydro-quinolin-8-yl)-amino]-methyl}-benzyl)-isonicotinamide

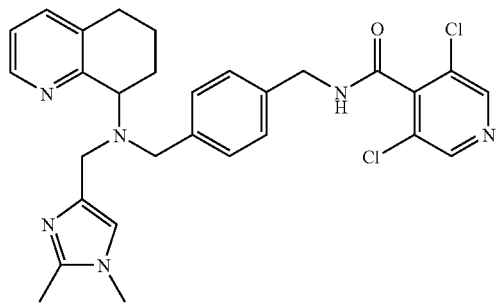

3,5-Dichloro-N-(4-{[(1,2-dimethyl-1H-imidazol-4-ylmethyl)-(5,6,7,8-tetrahydro-quinolin-8-yl)-amino]-methyl}-benzyl)-isonicotinamide

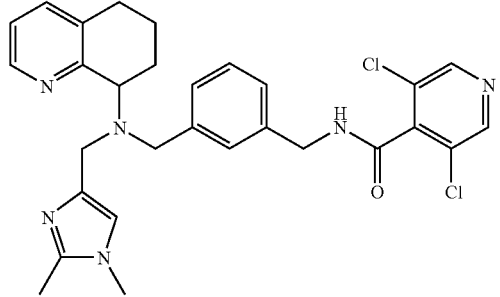

3,5-Dichloro-N-(3-{[(1,2-dimethyl-1H-imidazol-4-ylmethyl)-(5,6,7,8-tetrahydro-quinolin-8-yl)-amino]-methyl}-benzyl)-isonicotinamide

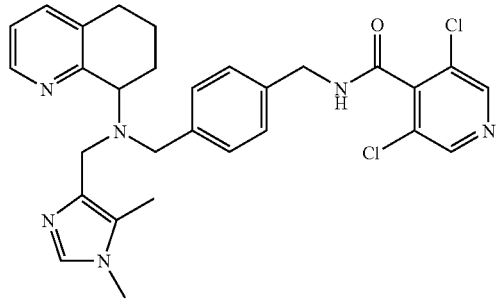

3,5-Dichloro-N-(4-{[(1,5-dimethyl-1H-imidazol-4-ylmethyl)-(5,6,7,8-tetrahydro-quinolin-8-yl)-amino]-methyl}-benzyl)-isonicotinamide

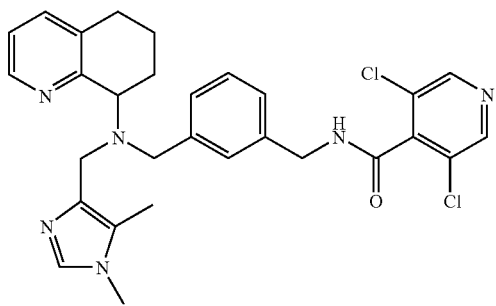

3,5-Dichloro-N-(3-{[(1,5-dimethyl-1H-imidazol-4-ylmethyl)-(5,6,7,8-tetrahydro-quinolin-8-yl)-amino]-methyl}-benzyl)-isonicotinamide

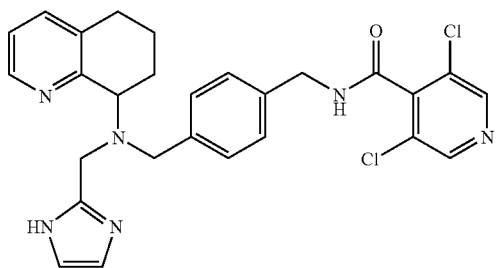

3,5-Dichloro-N-(4-{[(1H-imidazol-2-ylmethyl)-(5,6,7,8-tetrahydro-quinolin-8-yl)-amino]-methyl}-benzyl)-isonicotinamide

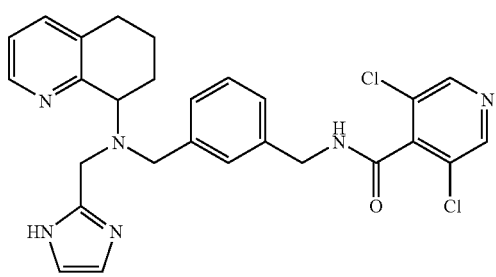

3,5-Dichloro-N-(3-{[(1H-imidazol-2-ylmethyl)-(5,6,7,8-tetrahydro-quinolin-8-yl)-amino]-methyl}-benzyl)-isonicotinamide

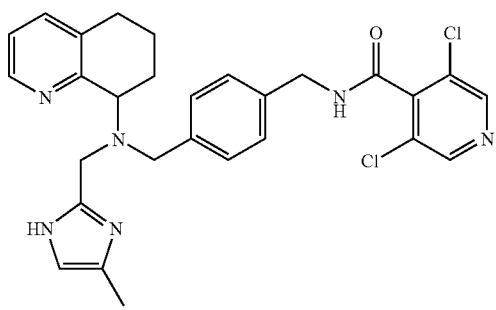

3,5-Dichloro-N-(4-{[(4-methyl-1H-imidazol-2-ylmethyl)-(5,6,7,8-tetrahydro-quinolin-8-yl)-amino]-methyl}-benzyl)-isonicotinamide

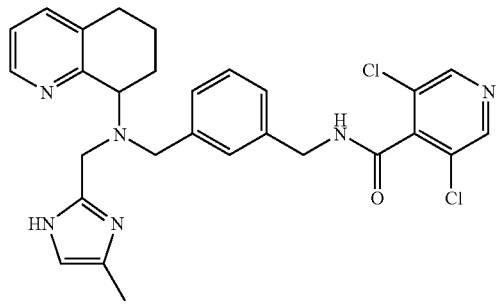

3,5-Dichloro-N-(3-{[(4-methyl-1H-imidazol-2-ylmethyl)-(5,6,7,8-tetrahydro-quinolin-8-yl)-amino]-methyl}-benzyl)-isonicotinamide

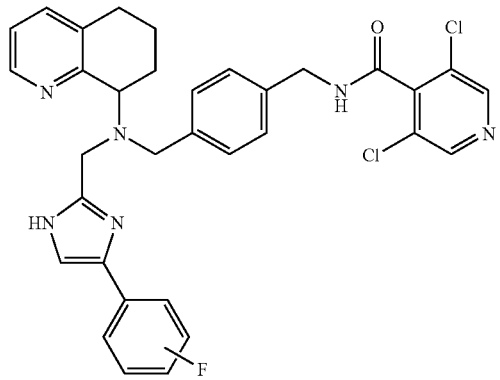

3,5-Dichloro-N-(4-{[[4-(2-fluoro-phenyl)-1H-imidazol-2-ylmethyl]-(5,6,7,8-tetrahydro-quinolin-8-yl)-amino]-methyl}-benzyl)-isonicotinamide
3,5-Dichloro-N-(4-{[[4-(3-fluoro-phenyl)-1H-imidazol-2-ylmethyl]-(5,6,7,8-tetrahydro-quinolin-8-yl)-amino]-methyl}-benzyl)-isonicotinamide
3,5-Dichloro-N-(4-{[[4-(4-fluoro-phenyl)-1H-imidazol-2-ylmethyl]-(5,6,7,8-tetrahydro-quinolin-8-yl)-amino]-methyl}-benzyl)-isonicotinamide

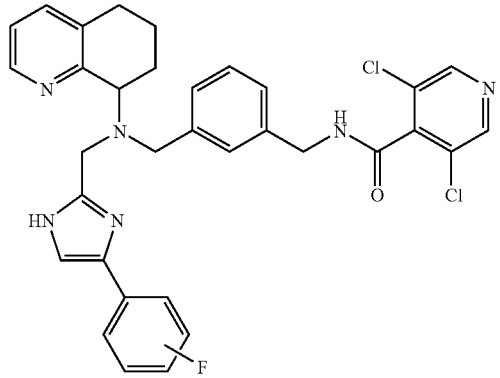

3,5-Dichloro-N-(3-{[[4-(2-fluoro-phenyl)-1H-imidazol-2-ylmethyl]-(5,6,7,8-tetrahydro-quinolin-8-yl)-amino]-methyl}-benzyl)-isonicotinamide
3,5-Dichloro-N-(3-{[[4-(3-fluoro-phenyl)-1H-imidazol-2-ylmethyl]-(5,6,7,8-tetrahydro-quinolin-8-yl)-amino]-methyl}-benzyl)-isonicotinamide
3,5-Dichloro-N-(3-{[[4-(4-fluoro-phenyl)-1H-imidazol-2-ylmethyl]-(5,6,7,8-tetrahydro-quinolin-8-yl)-amino]-methyl}-benzyl)-isonicotinamide

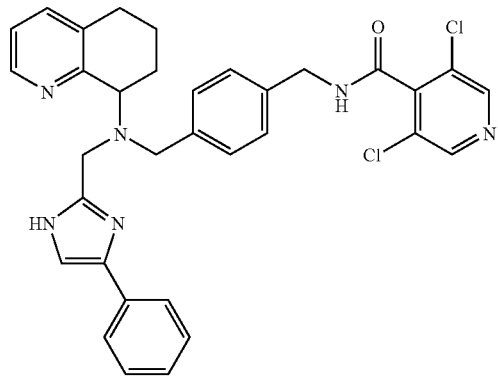

3,5-Dichloro-N-(4-{[(4-phenyl-1H-imidazol-2-ylmethyl)-(5,6,7,8-tetrahydro-quinolin-8-yl)-amino]-methyl}-benzyl)-isonicotinamide

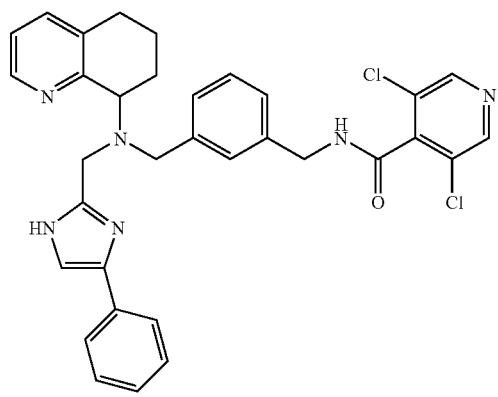

3,5-Dichloro-N-(3-{[(4-phenyl-1H-imidazol-2-ylmethyl)-(5,6,7,8-tetrahydro-quinolin-8-yl)-amino]-methyl}-benzyl)-isonicotinamide

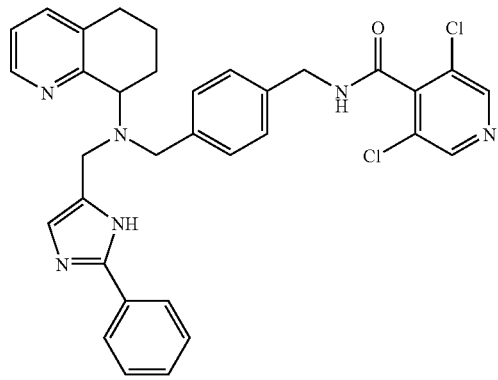

3,5-Dichloro-N-(4-{[(2-phenyl-3H-imidazol-4-ylmethyl)-(5,6,7,8-tetrahydro-quinolin-8-yl)-amino]-methyl}-benzyl)-isonicotinamide

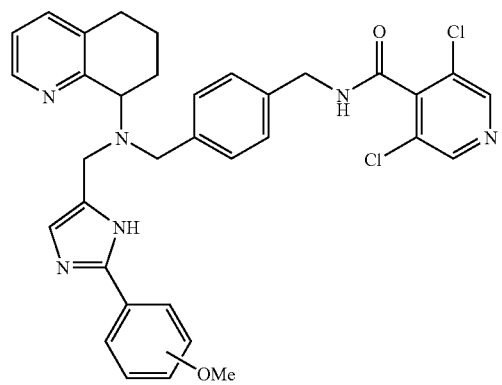

3,5-Dichloro-N-(4-{[[2-(2-methoxy-phenyl)-3H-imidazol-4-ylmethyl]-(5,6,7,8-tetrahydro-quinolin-8-yl)-amino]-methyl}-benzyl)-isonicotinamide 3,5-Dichloro-N-(4-{[[2-(3-methoxy-phenyl)-3H-imidazol-4-ylmethyl]-(5,6,7,8-tetrahydro-quinolin-8-yl)-amino]-methyl}-benzyl)-isonicotinamide 3,5-Dichloro-N-(4-{[[2-(4-methoxy-phenyl)-3H-imidazol-4-ylmethyl]-(5,6,7,8-tetrahydro-quinolin-8-yl)-amino]-methyl}-benzyl)-isonicotinamide

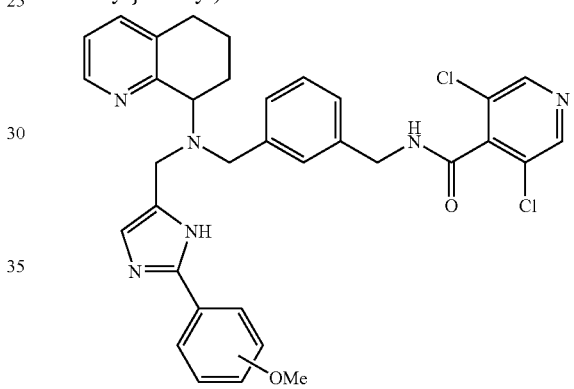

3,5-Dichloro-N-(3-{[[2-(2-methoxy-phenyl)-3H-imidazol-4-ylmethyl]-(5,6,7,8-tetrahydro-quinolin-8-yl)-amino]-methyl}-benzyl)-isonicotinamide 3,5-Dichloro-N-(3-{[[2-(3-methoxy-phenyl)3H-imidazol-4-ylmethyl]-(5,6,7,8-tetrahydro-quinolin-8-yl)-amino]-methyl}-benzyl)-isonicotinamide 3,5-Dichloro-N-(3-{[[2-(4-methoxy-phenyl)-3H-imidazol-4-ylmethyl]-(5,6,7,8-tetrahydro-quinolin-8-yl)-amino]-methyl}-benzyl)-isonicotinamide

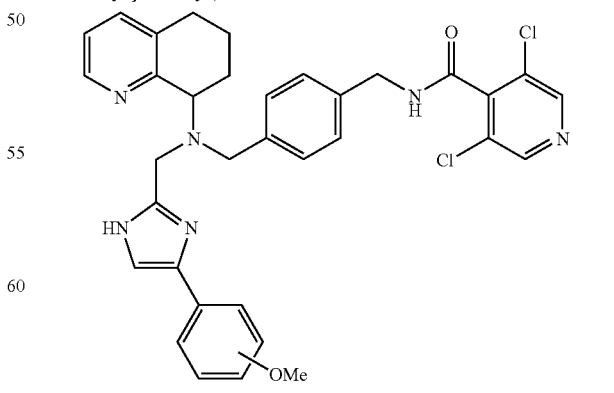

3,5-Dichloro-N-(4-{[[4-(2-methoxy-phenyl)-1H-imidazol-2-ylmethyl]-(5,6,7,8-tetrahydro-quinolin-8-yl)-amino]-methyl}-benzyl)-isonicotinamide 3,5-Dichloro-N-(4-{[[4-(3-methoxy-phenyl)-1H-imidazol-2-ylmethyl]-(5,6,7,8-tetrahydro-quinolin-8-yl)-amino]-methyl}-benzyl)-isonicotinamide 3,5-Dichloro-N-(4-{[[4-(4-methoxy-phenyl)-1H-imidazol-2-ylmethyl](5,6,7,8-tetrahydro-quinolin-8-yl)-amino]-methyl}-benzyl)-isonicotinamide

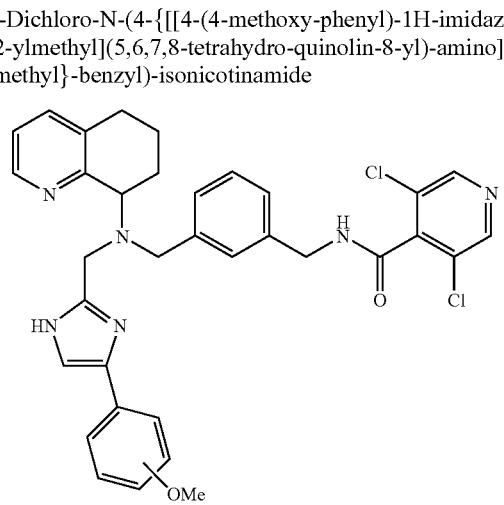

3,5-Dichloro-N-(3-{[[4-(2-methoxy-phenyl)-1H-imidazol-2-ylmethyl]-(5,6,7,8-tetrahydro-quinolin-8-yl)-amino]-methyl}-benzyl)-isonicotinamide 3,5-Dichloro-N-(3-{[[4-(3-methoxy-phenyl)-1H-imidazol-2-ylmethyl]-(5,6,7,8-tetrahydro-quinolin-8-yl)-amino]-methyl}-benzyl)-isonicotinamide 3,5-Dichloro-N-(3-{[[4-(4-methoxy-phenyl)-1H-imidazol-2-ylmethyl]-(5,6,7,8-tetrahydro-quinolin-8-yl)-amino]-methyl}-benzyl)-isonicotinamide

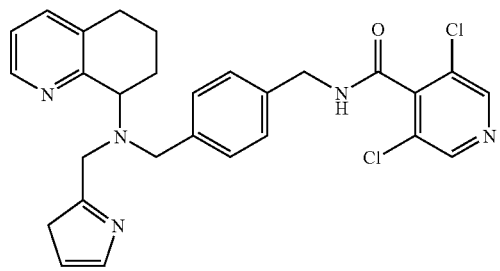

3,5-Dichloro-N-(4-{[(3H-pyrrol-2-ylmethyl)-(5,6,7,8-tetrahydro-quinolin-8-yl)-amino]-methyl}-benzyl)-isonicotinamide

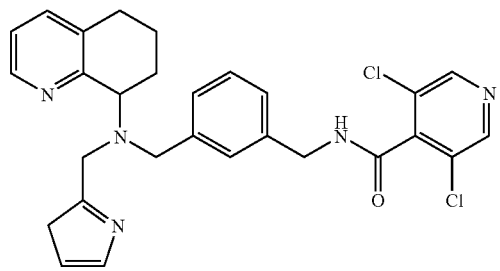

3,5-Dichloro-N-(3-{[(3H-pyrrol-2-ylmethyl)-(5,6,7,8-tetrahydro-quinolin-8-yl)-amino]-methyl}-benzyl)-isonicotinamide

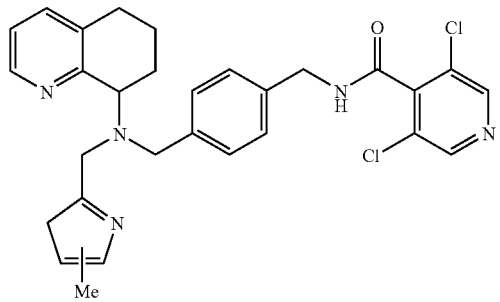

3,5-Dichloro-N-(4-{[(5-methyl-3H-pyrrol-2-ylmethyl)-(5,6,7,8-tetrahydro-quinolin-8-yl)-amino]-methyl}-benzyl)-isonicotinamide 3,5-Dichloro-N-(4-{[(4-methyl-3H-pyrrol-2-ylmethyl)-(5,6,7,8-tetrahydro-quinolin-8-yl)-amino]-methyl}-benzyl)-isonicotinamide

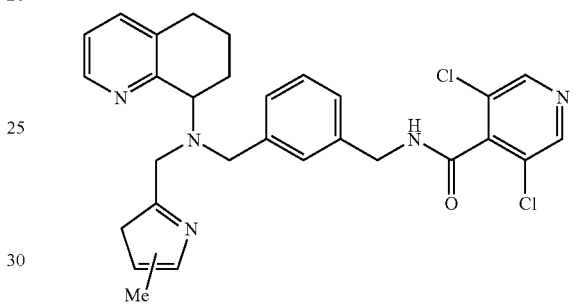

3,5-Dichloro-N-(3-{[(5-methyl-3H-pyrrol-2-ylmethyl)-(5,6,7,8-tetrahydro-quinolin-8-yl)-amino]-methyl}-benzyl)-isonicotinamide 3,5-Dichloro-N-(3-{[(4-methyl-3H-pyrrol-2-ylmethyl)-(5,6,7,8-tetrahydro-quinolin-8-yl)-amino]-methyl}-benzyl)-isonicotinamide

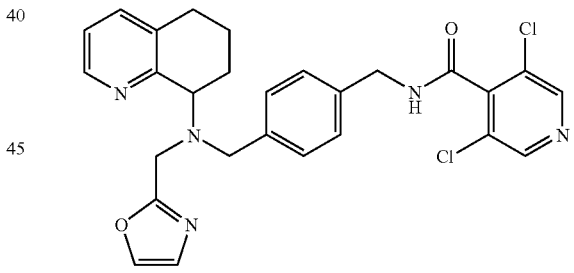

3,5-Dichloro-N-(4-{[oxazol-2-ylmethyl-(5,6,7,8-tetrahydro-quinolin-8-yl)-amino]-methyl}-benzyl)-isonicotinamide

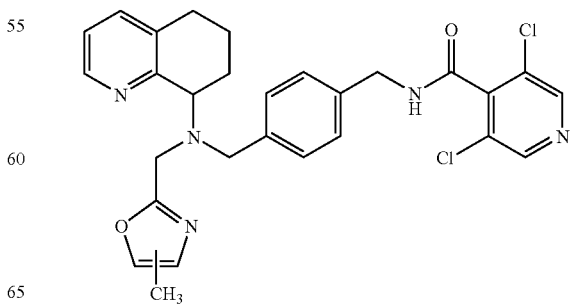

3,5-Dichloro-N-(4-{[(4-methyl-oxazol-2-ylmethyl)-(5,6,7,8-tetrahydro-quinolin-8-yl)-amino]-methyl}-benzyl)-isonicotinamide 3,5-Dichloro-N-(4-{[(5-methyl-oxazol-2-ylmethyl)-(5,6,7,8-tetrahydro-quinolin-8-yl)-amino]-methyl}-benzyl)-isonicotinamide

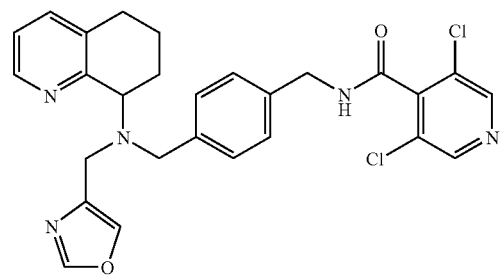

3,5-Dichloro-N-(4-{[oxazol-4-ylmethyl-(5,6,7,8-tetrahydro-quinolin-8-yl)-amino]-methyl}-benzyl)-isonicotinamide

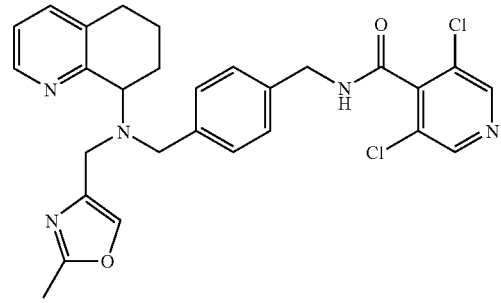

3,5-Dichloro-N-(4-{[(2-methyl-oxazol-4-ylmethyl)-(5,6,7,8-tetrahydro-quinolin-8-yl)-amino]-methyl}-benzyl)-isonicotinamide

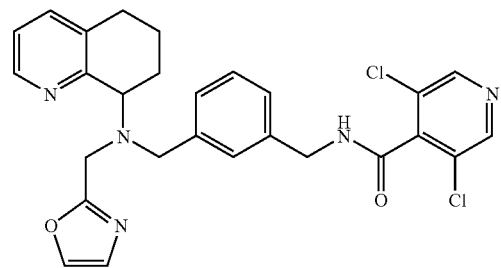

3,5-Dichloro-N-(3-{[oxazol-2-ylmethyl-(5,6,7,8-tetrahydro-quinolin-8-yl)-amino]-methyl}-benzyl)-isonicotinamide

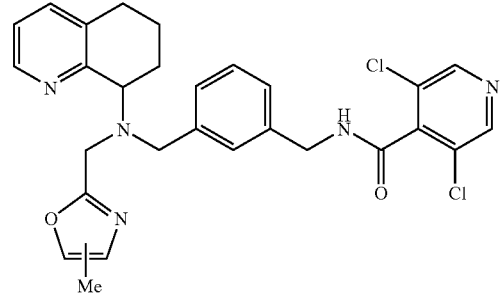

3,5-Dichloro-N-(3-{[(4-methyl-oxazol-2-ylmethyl)-(5,6,7,8-tetrahydro-quinolin-8-yl)-amino]-methyl}-benzyl)-isonicotinamide 3,5-Dichloro-N-(3-{[(5-methyl-oxazol-2-ylmethyl)-(5,6,7,8-tetrahydro-quinolin-8-yl)-amino]-methyl}-benzyl)-isonicotinamide

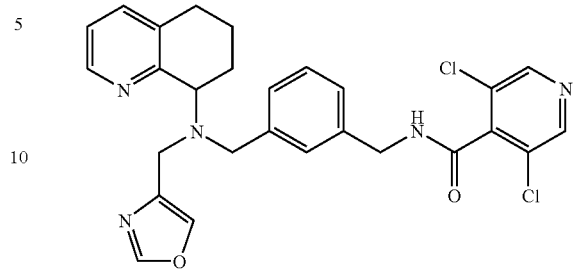

3,5-Dichloro-N-(3-{[oxazol-4-ylmethyl-(5,6,7,8-tetrahydro-quinolin-8-yl)-amino]-methyl}-benzyl)-isonicotinamide

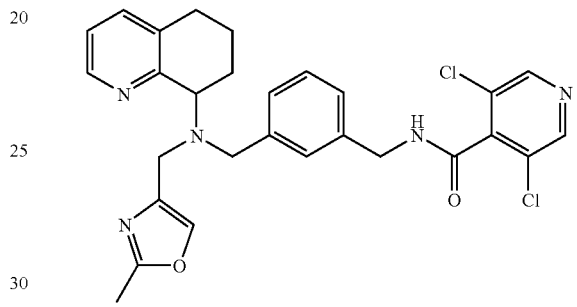

3,5-Dichloro-N-(3-{[(2-methyl-oxazol-4-ylmethyl)-(5,6,7,8-tetrahydro-quinolin-8-yl)-amino]-methyl}-benzyl)-isonicotinamide

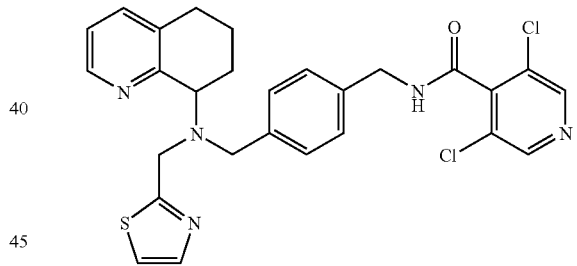

3,5-Dichloro-N-(4-{[(5,6,7,8-tetrahydro-quinolin-8-yl)-thiazol-2-ylmethyl-amino]-methyl}-benzyl)-isonicotinamide

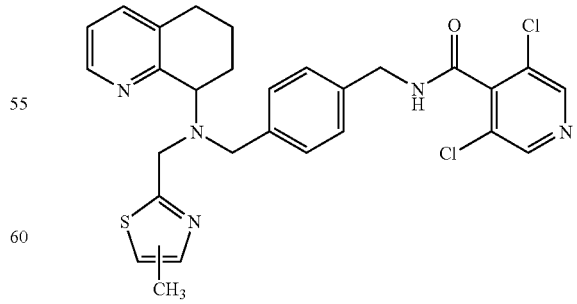

3,5-Dichloro-N-(4-{[(4-methyl-thiazol-2-ylmethyl)-(5,6,7,8-tetrahydro-quinolin-8-yl)-amino]-methyl}-benzyl)-isonicotinamide

87

3,5-Dichloro-N-(4-{[(5-methyl-thiazol-2-ylmethyl)-(5,6,7,8-tetrahydro-quinolin-8-yl)-amino]-methyl}-benzyl)-isonicotinamide

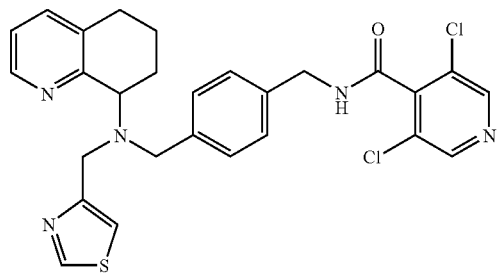

3,5-Dichloro-N-(4-{[(5,6,7,8-tetrahydro-quinolin-8-yl)-thiazol-4-ylmethyl-amino]-methyl}-benzyl)-isonicotinamide

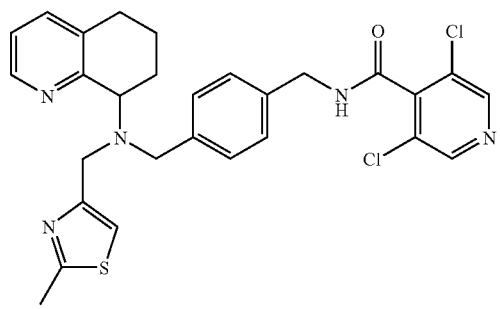

3,5-Dichloro-N-(4-{[(2-methyl-thiazol-4-ylmethyl)-(5,6,7,8-tetrahydro-quinolin-8-yl)-amino]-methyl}-benzyl)-isonicotinamide

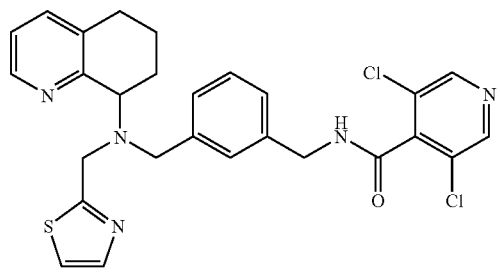

3,5-Dichloro-N-(3-{[(5,6,7,8-tetrahydro-quinolin-8-yl)-thiazol-2-ylmethyl-amino]-methyl}-benzyl)-isonicotinamide

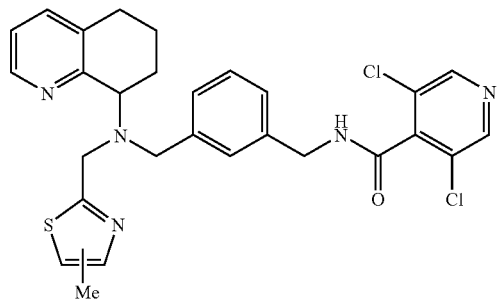

3,5-Dichloro-N-(3-{[(4-methyl-thiazol-2-ylmethyl)-(5,6,7,8-tetrahydro-quinolin-8-yl)-amino]-methyl}-benzyl)-isonicotinamide

88

3,5-Dichloro-N-(3-{[(5-methyl-thiazol-2-ylmethyl)-(5,6,7,8-tetrahydro-quinolin-8-yl)-amino]-methyl}-benzyl)-isonicotinamide

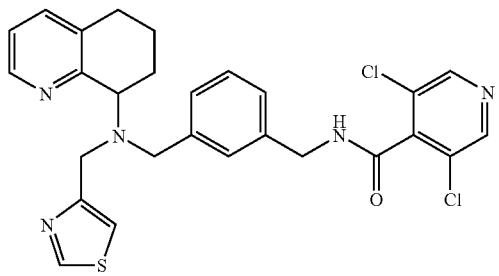

3,5-Dichloro-N-(3-{[(5,6,7,8-tetrahydro-quinolin-8-yl)-thiazol-4-ylmethyl-amino]-methyl}-benzyl)-isonicotinamide

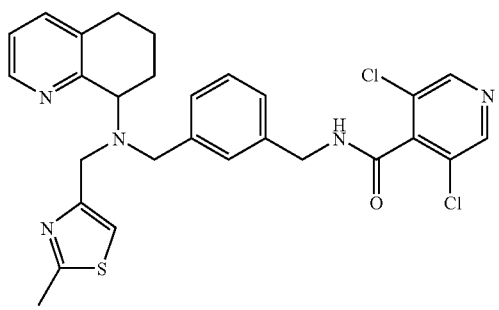

3,5-Dichloro-N-(3-{[(2-methyl-thiazol-4-ylmethyl)-(5,6,7,8-tetrahydro-quinolin-8-yl)-amino]-methyl}-benzyl)-isonicotinamide

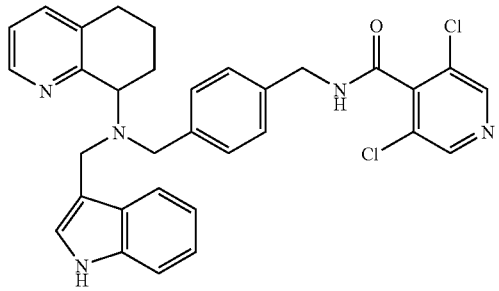

3,5-Dichloro-N-(4-{[(1H-indol-3-ylmethyl)-(5,6,7,8-tetrahydro-quinolin-8-yl)-amino]-methyl}-benzyl)-isonicotinamide

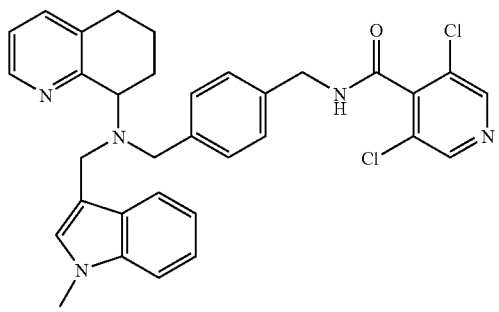

3,5-Dichloro-N-(4-{[(1-methyl-1H-indol-3-ylmethyl)-(5,6,7,8-tetrahydro-quinolin-8-yl)-amino]-methyl}-benzyl)-isonicotinamide

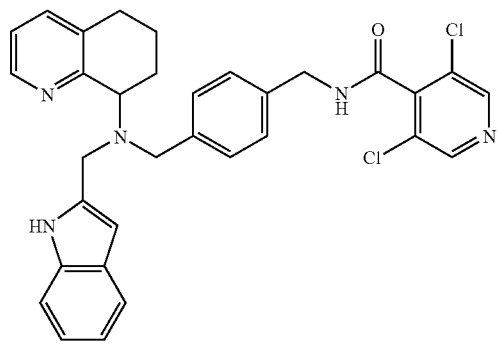

3,5-Dichloro-N-(4-{[(1H-indol-2-ylmethyl)-(5,6,7,8-tet-rahydro-quinolin-8-yl)-amino]-methyl}-benzyl)-isonico-tinamide

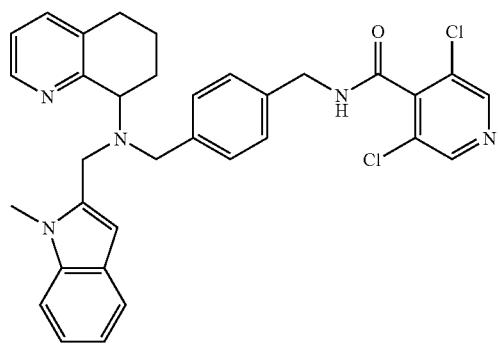

3,5-Dichloro-N-(4-{[(1-methyl-1H-indol-2-ylmethyl)-(5,6,7,8-tetrahydro-quinolin-8-yl)-amino]-methyl}-benzyl)-isonicotinamide

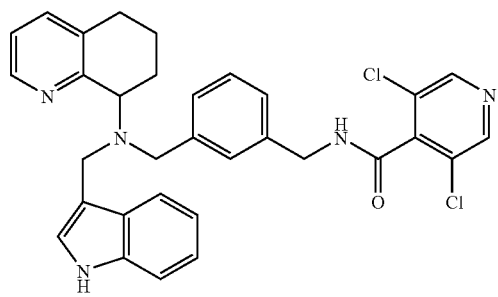

3,5-Dichloro-N-(3-{[(1H-indol-3-ylmethyl)-(5,6,7,8-tet-rahydro-quinolin-8-yl)amino]-methyl}-benzyl)-isonicoti-namide

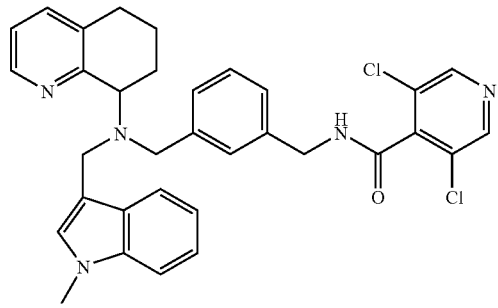

3,5-Dichloro-N-(3-{[(1-methyl-1H-indol-3-ylmethyl)-(5,6,7,8-tetrahydro-quinolin-8-yl)-amino]-methyl}-benzyl)-isonicotinamide

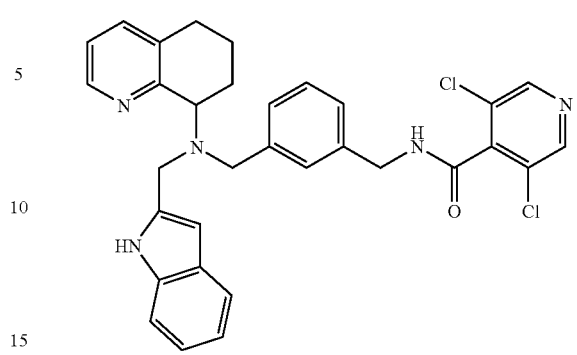

3,5-Dichloro-N-(3-{[(1H-indol-2-ylmethyl)-(5,6,7,8-tet-rahydro-quinolin-8-yl)-amino]-methyl}-benzyl)-isonico-tinamide

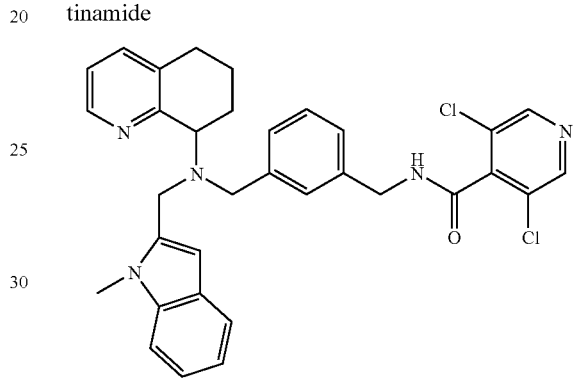

3,5-Dichloro-N-(3-{[(1-methyl-1H-indol-2-ylmethyl)-(5,6,7,8-tetrahydro-quinolin-8-yl)-amino]-methyl}-benzyl)-isonicotinamide

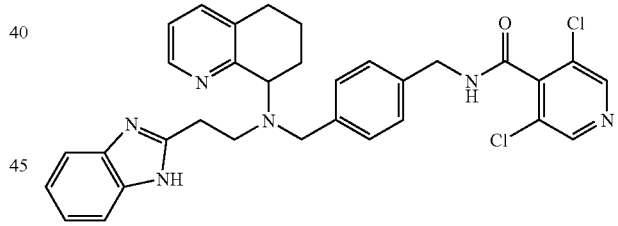

N-(4-{[[2-(1H-Benzoimidazol-2-yl)-ethyl]-(5,6,7,8-tetrahy-dro-quinolin-8-yl)-amino]-methyl}-benzyl)-3,5-dichloro-isonicotinamide

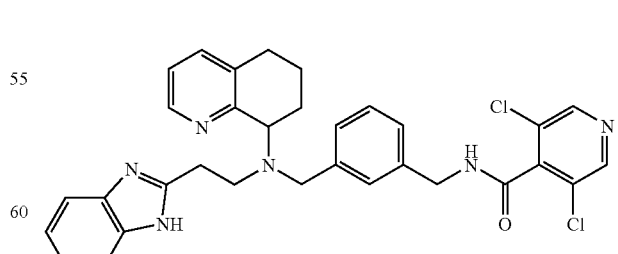

N-(3-{[[2-(1H-Benzoimidazol-2-yl)-ethyl]-(5,6,7,8-tetrahy-dro-quinolin-8-yl)-amino]-methyl}-benzyl)-3,5-dichloro-isonicotinamide

91

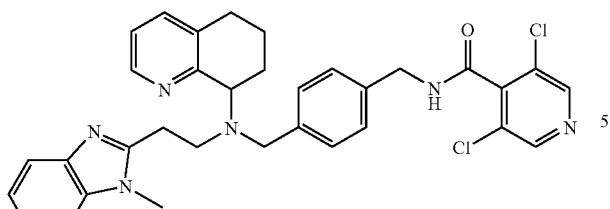

3,5-Dichloro-N-(4-{[[2-(1-methyl-1H-benzoimidazol-2-yl)-ethyl]-(5,6,7,8-tetrahydro-quinolin-8-yl)-amino]-methyl}-benzyl)-isonicotinamide

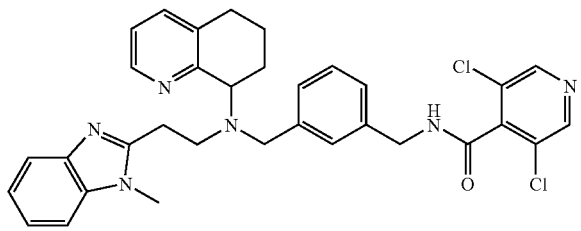

3,5-Dichloro-N-(3-{[[2-(1-methyl-1H-benzoimidazol-2-yl)-ethyl]-(5,6,7,8-tetrahydro-quinolin-8-yl)-amino]-methyl}-benzyl)-isonicotinamide

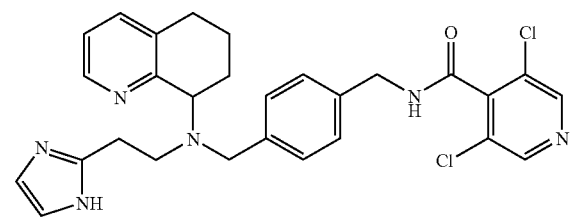

3,5-Dichloro-N-(4-{[[2-(1H-imidazol-2-yl)-ethyl]-(5,6,7,8-tetrahydro-quinolin-8-yl)-amino]-methyl}-benzyl)-isonicotinamide

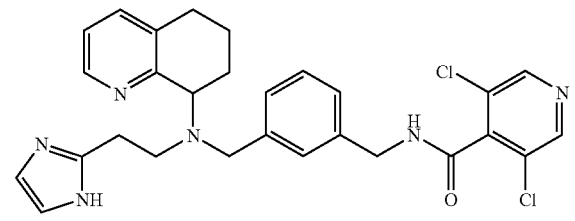

3,5-Dichloro-N-(3-{[[2-(1H-imidazol-2-yl)-ethyl]-(5,6,7,8-tetrahydro-quinolin-8-yl)-amino]-methyl}-benzyl)-isonicotinamide

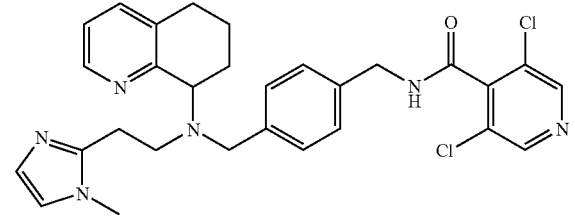

3,5-Dichloro-N-(4-{[[2-(1-methyl-1H-imidazol-2-yl)-ethyl]-(5,6,7,8-tetrahydro-quinolin-8-yl)-amino]-methyl}-benzyl)-isonicotinamide

92

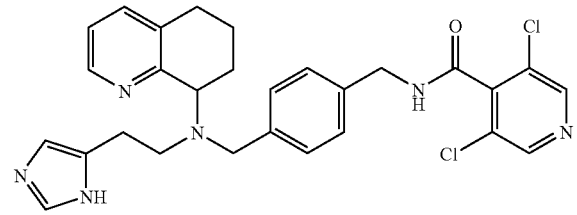

3,5-Dichloro-N-(3-{[[2-(1-methyl-1H-imidazol-2-yl)-ethyl]-(5,6,7,8-tetrahydro-quinolin-8-yl)-amino]-methyl}-benzyl)-isonicotinamide

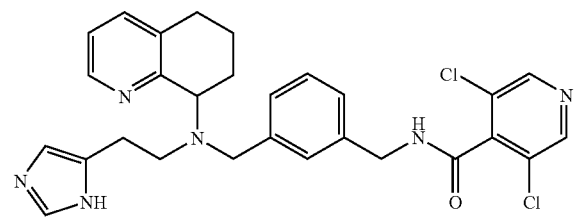

3,5-Dichloro-N-(4-{[[2-(3H-imidazol-4-yl)-ethyl]-(5,6,7,8-tetrahydro-quinolin-8-yl)-amino]-methyl}-benzyl)-isonicotinamide

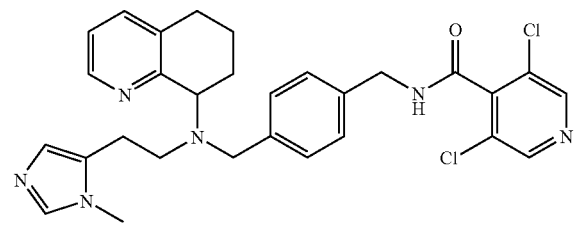

3,5-Dichloro-N-(3-{[[2-(3H-imidazol-4-yl)-ethyl]-(5,6,7,8-tetrahydro-quinolin-8-yl)-amino]-methyl}-benzyl)-isonicotinamide

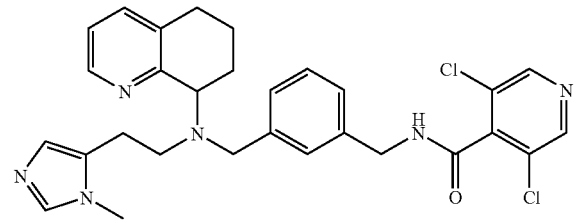

3,5-Dichloro-N-(4-{[[2-(3-methyl-3H-imidazol-4-yl)-ethyl]-(5,6,7,8-tetrahydro-quinolin-8-yl)-amino]-methyl}-benzyl)-isonicotinamide 3,5-Dichloro-N-(3-{[[2-(3-methyl-3H-imidazol-4-yl)-ethyl]-(5,6,7,8-tetrahydro-quinolin-8-yl)-amino]-methyl}-benzyl)-isonicotinamide

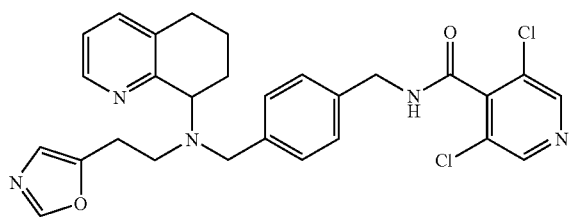

3,5-Dichloro-N-(4-{[(2-oxazol-5-yl-ethyl)-(5,6,7,8-tetrahydro-quinolin-8-yl)-amino]-methyl}-benzyl)-isonicotinamide

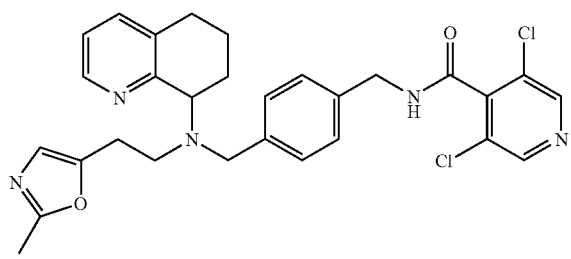

3,5-Dichloro-N-(4-{[[2-(2-methyl-oxazol-5-yl)-ethyl]-(5,6,7,8-tetrahydro-quinolin-8-yl)-amino]-methyl}-benzyl)-isonicotinamide

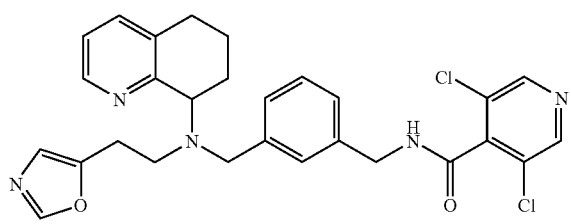

3,5-Dichloro-N-(3-{[(2-oxazol-5-yl-ethyl)-(5,6,7,8-tetrahydro-quinolin-8-yl)-amino]-methyl}-benzyl)-isonicotinamide

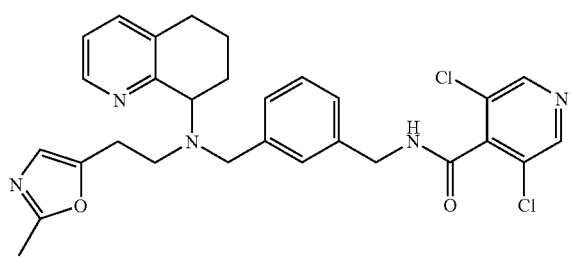

3,5-Dichloro-N-(3-{[[2-(2-methyl-oxazol-5-yl)-ethyl]-(5,6,7,8-tetrahydro-quinolin-8-yl)-amino]-methyl}-benzyl)-isonicotinamide

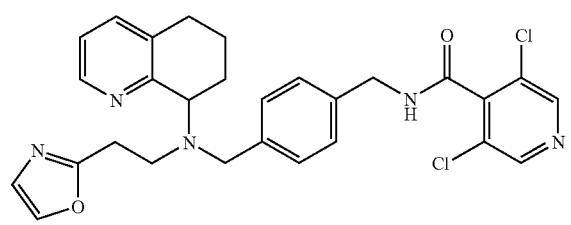

3,5-Dichloro-N-(4-{[(2-oxazol-2-yl-ethyl)-(5,6,7,8-tetrahydro-quinolin-8-yl)-amino]-methyl}-benzyl)-isonicotinamide

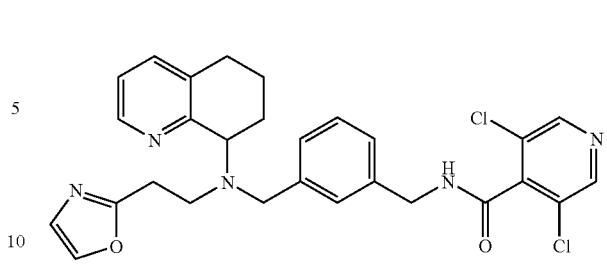

3,5-Dichloro-N-(3-{[(2-oxazol-2-yl-ethyl)-(5,6,7,8-tetrahydro-quinolin-8-yl)-amino]-methyl}-benzyl)-isonicotinamide

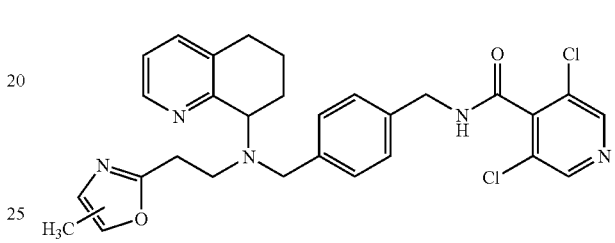

3,5-Dichloro-N-(4-{[[2-(4-methyl-oxazol-2-yl)-ethyl]-(5,6,7,8-tetrahydro-quinolin-8-yl)-amino]-methyl}-benzyl)-isonicotinamide
3,5-Dichloro-N-(4-{[[2-(5-methyl-oxazol-2-yl)-ethyl]-(5,6,7,8-tetrahydro-quinolin-8-yl)-amino]-methyl}-benzyl)-isonicotinamide

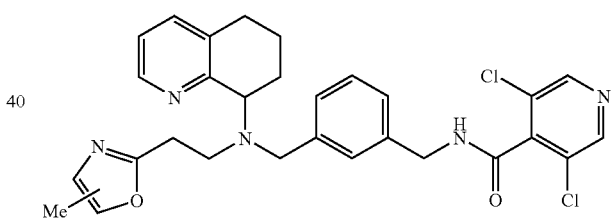

3,5-Dichloro-N-(3-{[[2-(4-methyl-oxazol-2-yl)-ethyl]-(5,6,7,8-tetrahydro-quinolin-8-yl)-amino]-methyl}-benzyl)-isonicotinamide
3,5-Dichloro-N-(3-{[[2-(5-methyl-oxazol-2-yl)-ethyl]-(5,6,7,8-tetrahydro-quinolin-8-yl)-amino]-methyl}-benzyl)-isonicotinamide

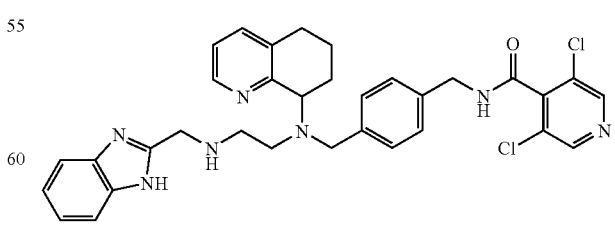

N-(4-({[{2-[(1H-Benzoimidazol-2-ylmethyl)-amino]-ethyl}-(5,6,7,8-tetrahydro-quinolin-8-yl)-amino]-methyl}-benzyl)-3,5-dichloro-isonicotinamide

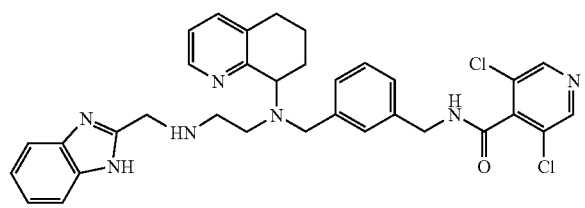

N-(3-{[{2-[(1H-Benzoimidazol-2-ylmethyl)-amino]-ethyl}-(5,6,7,8-tetrahydro-quinolin-8-yl)-amino]-methyl})-benzyl)-3,5-dichloro-isonicotinamide

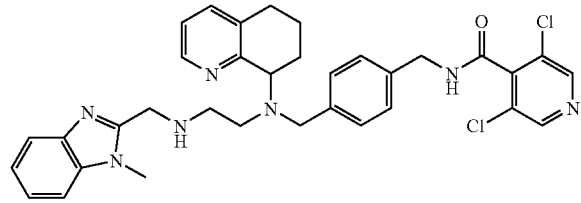

3,5-Dichloro-N-(4-{[{2-[(1-methyl-1H-benzoimidazol-2-ylmethyl)-amino]-ethyl}-(5,6,7,8-tetrahydro-quinolin-8-yl)-amino]-methyl}-benzyl)-isonicotinamide

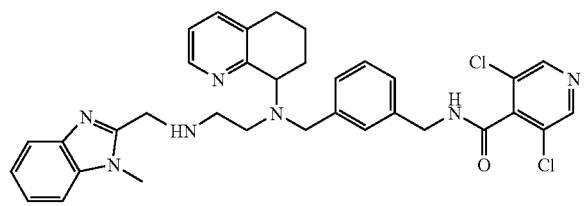

3,5-Dichloro-N-(3-{[{2-[(1-methyl-1H-benzoimidazol-2-ylmethyl)-amino]-ethyl}-(5,6,7,8-tetrahydro-quinolin-8-yl)-amino]-methyl}-benzyl)-isonicotinamide

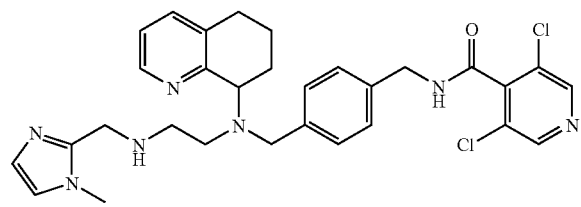

3,5-Dichloro-N-(4-{[{2-[(1-methyl-1H-imidazol-2-ylm-ethyl)-amino]-ethyl}-(5,6,7,8-tetrahydro-quinolin-8-yl)-amino]-methyl}-benzyl)-isonicotinamide

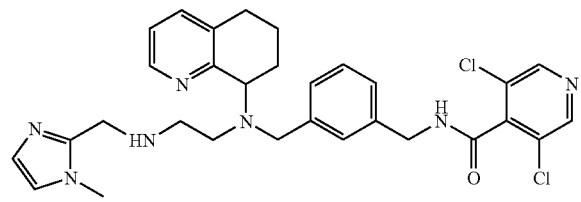

3,5-Dichloro-N-(3-{[{2-[(1-methyl-1H-imidazol-2-ylm-ethyl)-amino]-ethyl}-(5,6,7,8-tetrahydro-quinolin-8-yl)-amino]-methyl}-benzyl)-isonicotinamide

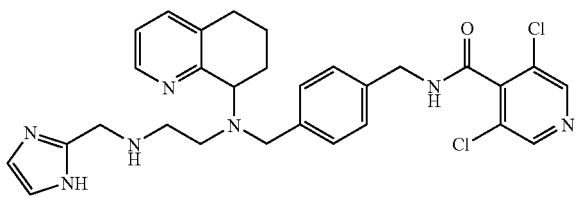

3,5-Dichloro-N-(4-{[{2-[(1H-imidazol-2-ylmethyl)-amino]-ethyl}-(5,6,7,8-tetrahydro-quinolin-8-yl)-amino]-methyl}-benzyl)-isonicotinamide

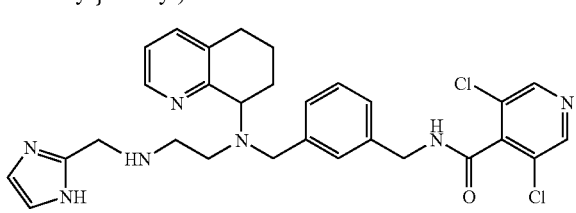

3,5-Dichloro-N-(3-{[{2-[(1H-imidazol-2-ylmethyl)-amino]-ethyl}-(5,6,7,8-tetrahydro-quinolin-8-yl)-amino]-methyl}-benzyl)-isonicotinamide

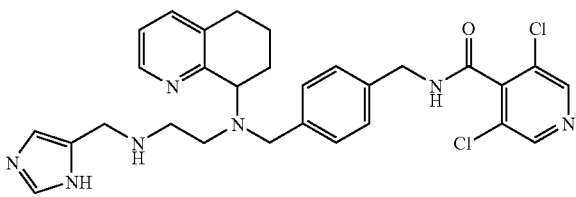

3,5-Dichloro-N-(4-{[{2-[(3H-imidazol-4-ylmethyl)-amino]-ethyl}-(5,6,7,8-tetrahydro-quinolin-8-yl)-amino]-methyl}-benzyl)-isonicotinamide

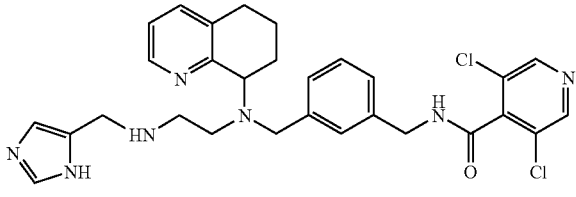

3,5-Dichloro-N-(3-{[{2-[(3H-imidazol-4-ylmethyl)-amino]-ethyl}-(5,6,7,8-tetrahydro-quinolin-8-yl)-amino]-methyl}-benzyl)-isonicotinamide

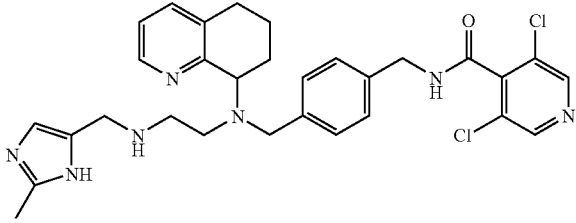

3,5-Dichloro-N-(4-{[{2-[(2-methyl-3H-imidazol-4-ylm-ethyl)-amino]-ethyl}-(5,6,7,8-tetrahydro-quinolin-8-yl)-amino]-methyl}-benzyl)-isonicotinamide

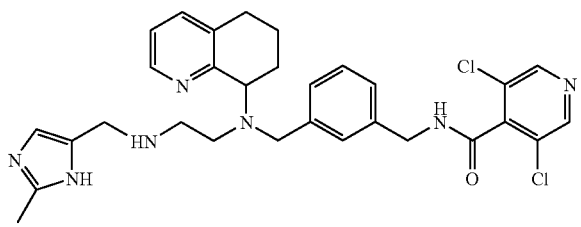

3,5-Dichloro-N-(3-{[{2-[(2-methyl-3H-imidazol-4-ylmethyl)-amino]-ethyl}-(5,6,7,8-tetrahydro-quinolin-8-yl)-amino]-methyl}-benzyl)-isonicotinamide

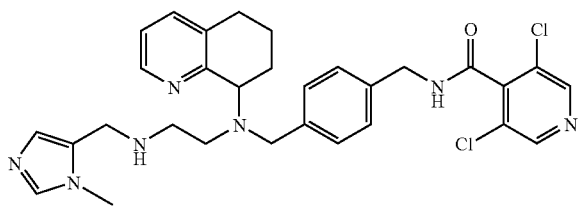

3,5-Dichloro-N-(4-{[{2-[(3-methyl-3H-imidazol-4-ylmethyl)-amino]-ethyl}-(5,6,7,8-tetrahydro-quinolin-8-yl)-amino]-methyl}-benzyl)-isonicotinamide

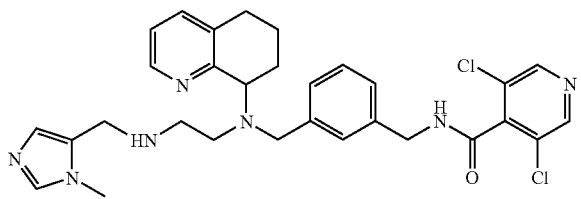

3,5-Dichloro-N-(3-{[{2-[(3-methyl-3H-imidazol-4-ylmethyl)-amino]-ethyl}-(5,6,7,8-tetrahydro-quinolin-8-yl)-amino]-methyl}-benzyl)-isonicotinamide

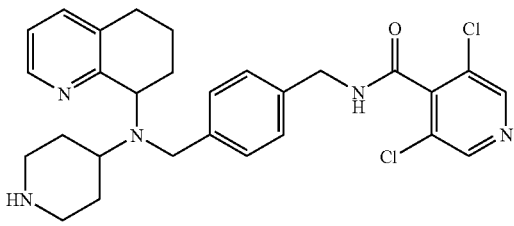

3,5-Dichloro-N-(4-{[piperidin-4-yl-(5,6,7,8-tetrahydro-quinolin-8-yl)-amino]-methyl}-benzyl)-isonicotinamide

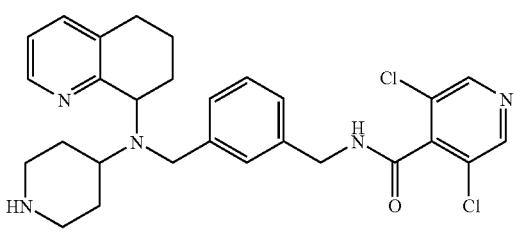

3,5-Dichloro-N-(3-{[piperidin-4-yl-(5,6,7,8-tetrahydro-quinolin-8-yl)-amino]-methyl}-benzyl)-isonicotinamide

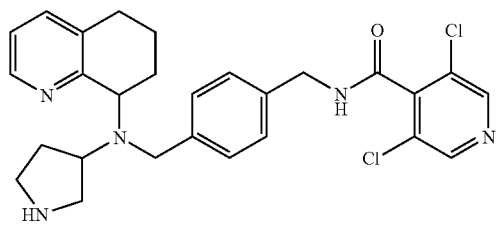

3,5-Dichloro-N-(4-{[pyrrolidin-3-yl-(5,6,7,8-tetrahydro-quinolin-8-yl)-amino]-methyl}-benzyl)-isonicotinamide

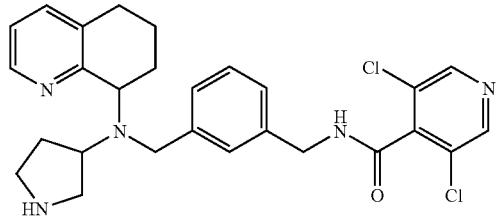

3,5-Dichloro-N-(3-{[pyrrolidin-3-yl-(5,6,7,8-tetrahydro-quinolin-8-yl-amino]-methyl}-benzyl)-isonicotinamide

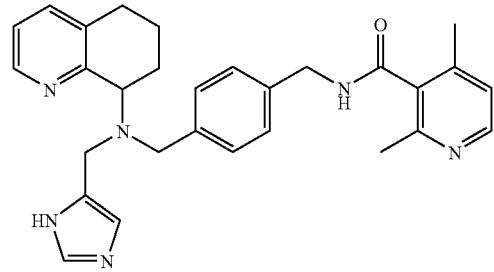

N-(4-{[(3H-Imidazol-4-ylmethyl)(5,6,7,8-tetrahydro-quinolin-8-yl)-amino]-methyl}-benzyl)-2,4-dimethyl-nicotinamide

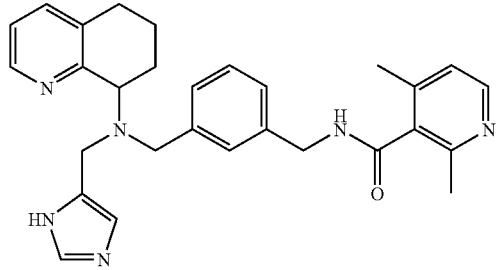

N-(3-{[(3H-Imidazol-4-ylmethyl)-(5,6,7,8-tetrahydro-quinolin-8-yl)-amino]-methyl}-benzyl)-2,4-dimethyl-nicotinamide

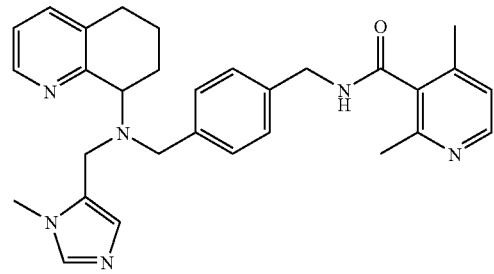

2,4-Dimethyl-N-(4-{[(3-methyl-3H-imidazol-4-ylmethyl)-(5,6,7,8-tetrahydro-quinolin-8-yl)-amino]-methyl}-benzyl)-nicotinamide

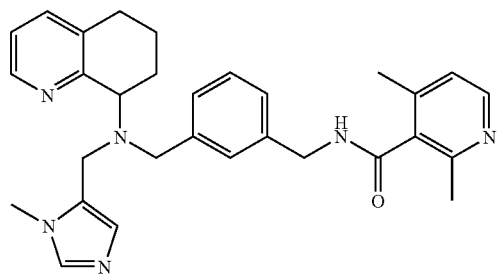

2,4-Dimethyl-N-(3-{[(3-methyl-3H-imidazol-4-ylmethyl)-(5,6,7,8-tetrahydro-quinolin-8-yl)-amino]-methyl}-benzyl)-nicotinamide

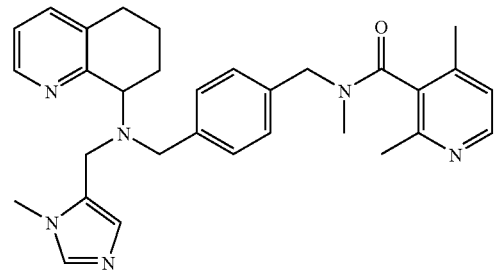

2,4,N-Trimethyl-N-(4-{[(3-methyl-3H-imidazol-4-ylmethyl)-(5,6,7,8-tetrahydro-quinolin-8-yl)-amino]-methyl}-benzyl)-nicotinamide

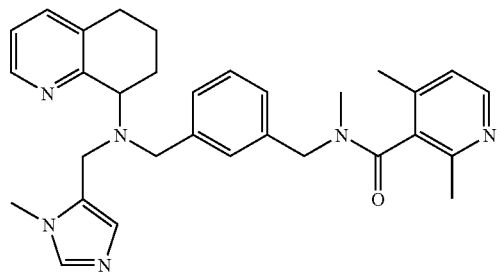

2,4,N-Trimethyl-N-(3-{[(3-methyl-3H-imidazol-4-ylmethyl)-(5,6,7,8-tetrahydro-quinolin-8-yl)-amino]-methyl}-benzyl)-nicotinamide

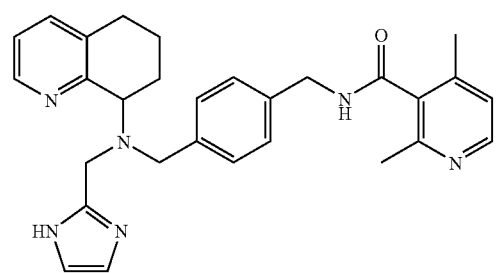

N-(4-{[(1H-Imidazol-2-ylmethyl)-(5,6,7,8-tetrahydro-quinolin-8-yl)-amino]-methyl}-benzyl)-2,4-dimethyl-nicotinamide

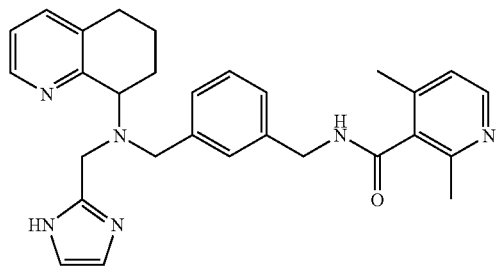

N-(3-{[(1H-Imidazol-2-ylmethyl)-(5,6,7,8-tetrahydro-quinolin-8-yl)-amino]-methyl}-benzyl)-2,4-dimethyl-nicotinamide

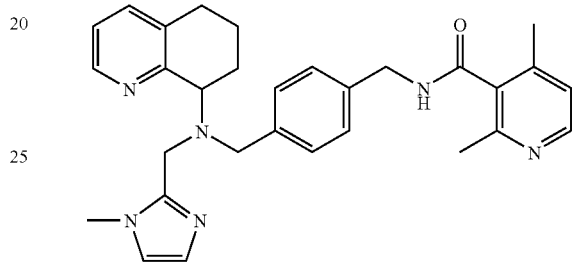

2,4-Dimethyl-N-(4-{[(1-methyl-1H-imidazol-2-ylmethyl)-(5,6,7,8-tetrahydro-quinolin-8-yl)-amino]-methyl}-benzyl)-nicotinamide

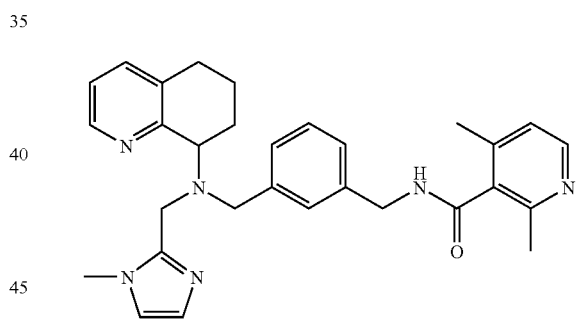

2,4-Dimethyl-N-(3-{[(1-methyl-1H-imidazol-2-ylmethyl)-(5,6,7,8-tetrahydro-quinolin-8-yl)-amino]-methyl}-benzyl)-nicotinamide

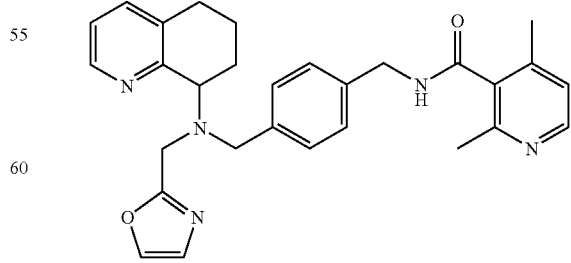

2,4-Dimethyl-N-(4-{[oxazol-2-ylmethyl-(5,6,7,8-tetrahydro-quinolin-8-yl)-amino]-methyl}-benzyl)-nicotinamide

101

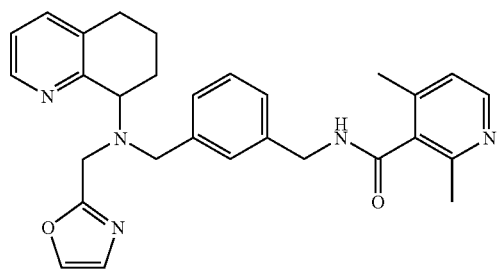

2,4-Dimethyl-N-(3-{[oxazol-2-ylmethyl-(5,6,7,8-tetrahydro-quinolin-8-yl)-amino]-methyl}-benzyl)-nicotinamide

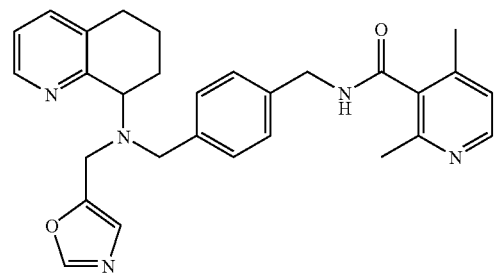

2,4-Dimethyl-N-(4-{[oxazol-5-ylmethyl-(5,6,7,8-tetrahydro-quinolin-8-yl)-amino]-methyl}-benzyl)-nicotinamide

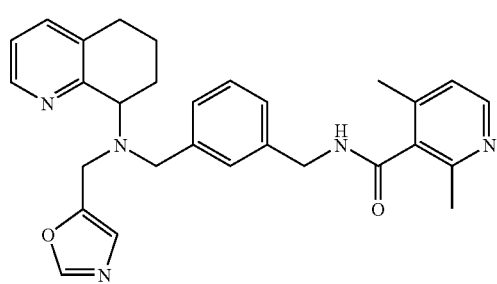

2,4-Dimethyl-N-(3-{[oxazol-5-ylmethyl-(5,6,7,8-tetrahydro-quinolin-8-yl)-amino]-methyl}-benzyl)-nicotinamide

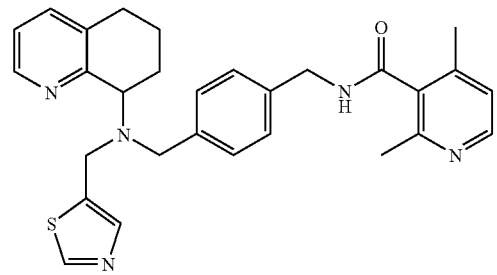

2,4-Dimethyl-N-(4-{[(5,6,7,8-tetrahydro-quinolin-8-yl)-thiazol-5-ylmethyl-amino]-methyl}-benzyl)-nicotinamide

102

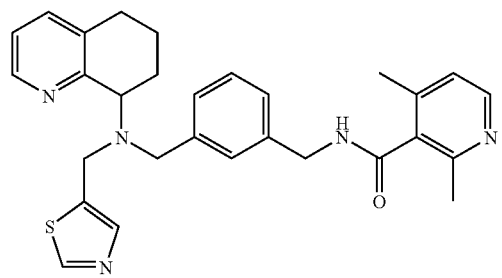

2,4-Dimethyl-N-(3-{[(5,6,7,8-tetrahydro-quinolin-8-yl)-thiazol-5-ylmethyl-amino]-methyl}-benzyl)-nicotinamide

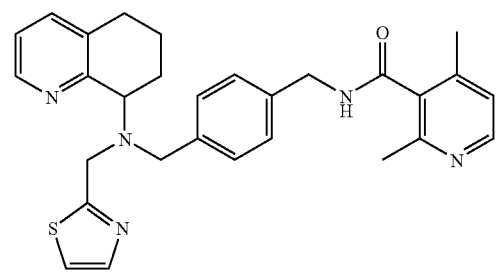

2,4-Dimethyl-N-(4-{[(5,6,7,8-tetrahydro-quinolin-8-yl)-thiazol-2-ylmethyl-amino]-methyl}-benzyl)-nicotinamide

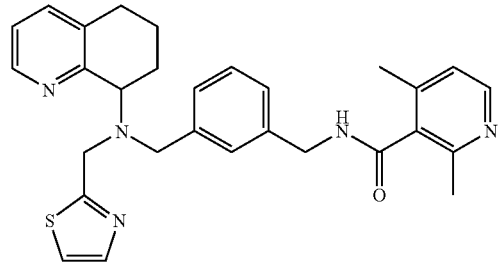

2,4-Dimethyl-N-(3-{[(5,6,7,8-tetrahydro-quinolin-8-yl)-thiazol-2-ylmethyl-amino]-methyl}-benzyl)-nicotinamide

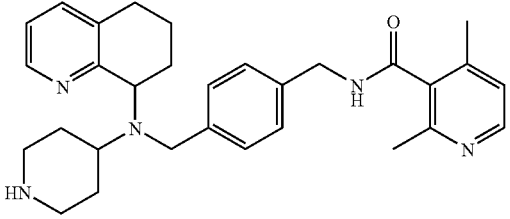

2,4-Dimethyl-N-(4-{[piperidin-4-yl-(5,6,7,8-tetrahydro-quinolin-8-yl)-amino]-methyl}-benzyl)-nicotinamide

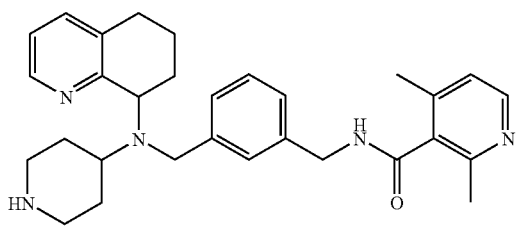

2,4-Dimethyl-N-(3-{[piperidin-4-yl-(5,6,7,8-tetrahydro-quinolin-8-yl)-amino]-methyl}-benzyl)-nicotinamide

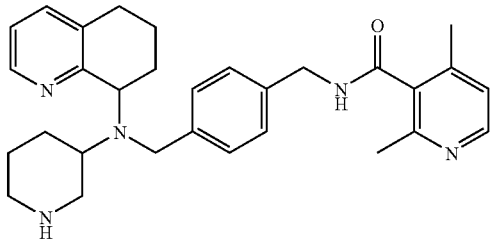

2,4-Dimethyl-N-(4-{[piperidin-3-yl-(5,6,7,8-tetrahydro-quinolin-8-yl)-amino]-methyl}-benzyl)-nicotinamide

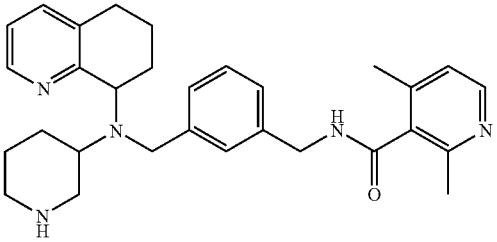

2,4-Dimethyl-N-(3-{[piperidin-3-yl-(5,6,7,8-tetrahydro-quinolin-8-yl)-amino]-methyl}-benzyl)-nicotinamide

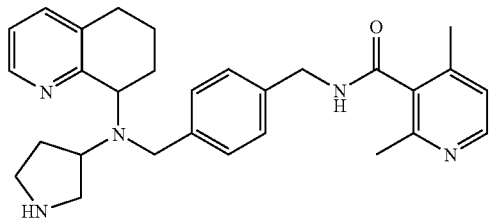

2,4-Dimethyl-N-(4-{[pyrrolidin-3-yl-(5,6,7,8-tetrahydro-quinolin-8-yl)-amino]-methyl}-benzyl)-nicotinamide

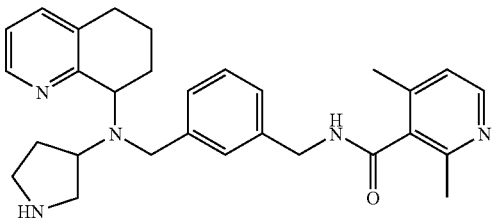

2,4-Dimethyl-N-(3-{[pyrrolidin-3-yl-(5,6,7,8-tetrahydro-quinolin-8-yl)-amino]-methyl}-benzyl)-nicotinamide

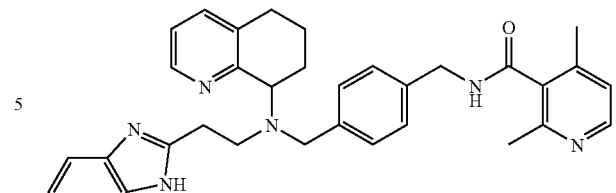

N-(4-{[[2-(1H-Benzoimidazol-2-yl)-ethyl]-(5,6,7,8-tetrahydro-quinolin-8-yl)-amino]-methyl}-benzyl)-2,4-dimethyl-nicotinamide

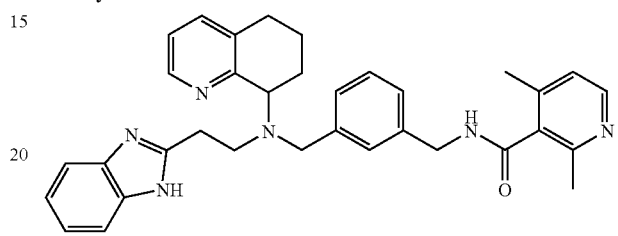

N-(3-{[[2-(1H-Benzoimidazol-2-yl)-ethyl]-(5,6,7,8-tetrahydro-quinolin-8-yl)-amino]-methyl}-benzyl)-2,4-dimethyl-nicotinamide

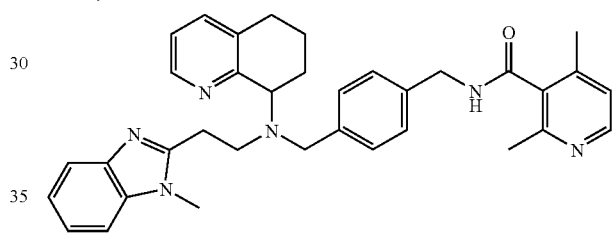

2,4-Dimethyl-N-(4-{[[2-(1-methyl-1H-benzoimidazol-2-yl)-ethyl]-(5,6,7,8-tetrahydro-quinolin-8-yl)-amino]-methyl}-benzyl)-nicotinamide

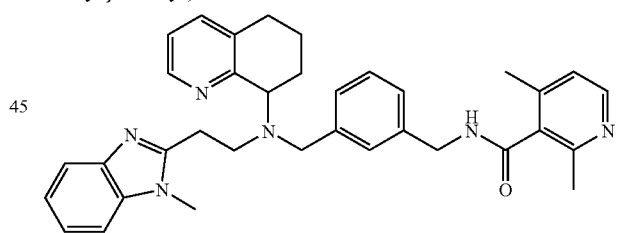

2,4-Dimethyl-N-(3-{[[2-(1-methyl-1H-benzoimidazol-2-yl)-ethyl]-(5,6,7,8-tetrahydro-quinolin-8-yl)-amino]-methyl}-benzyl)-nicotinamide

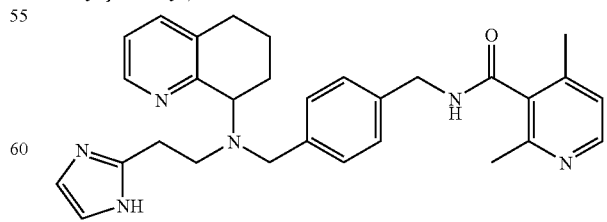

N-(4-{[[2-(1H-Imidazol-2-y)-ethyl]-(5,6,7,8-tetrahydro-quinolin-8-yl)-amino]-methyl}-benzyl)-2,4-dimethyl-nicotinamide

105

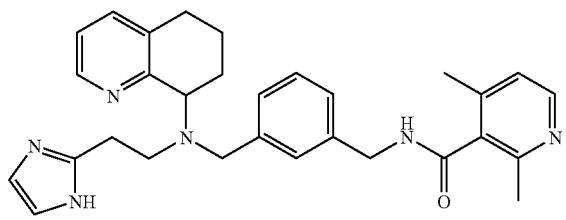

N-(3-{[[2-(1H-Imidazol-2-yl)-ethyl]-(5,6,7,8-tetrahydro-quinolin-8-yl)-amino]-methyl}-benzyl)-2,4-dimethyl-nicotinamide

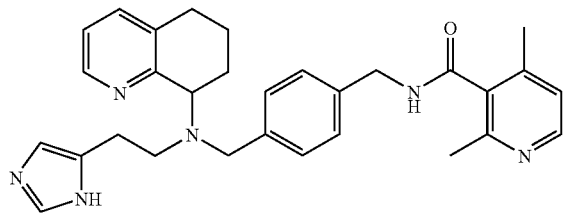

N-(4-{[[2-(3H-Imidazol-4-yl)-ethyl]-(5,6,7,8-tetrahydro-quinolin-8-yl)-amino]-methyl}-benzyl)-2,4-dimethyl-nicotinamide

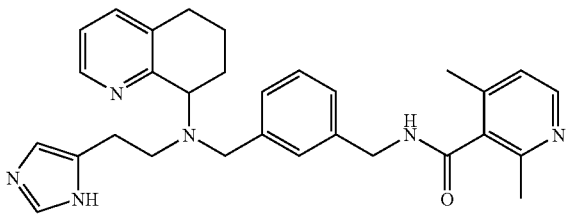

N-(3-{[[2-(3H-Imidazol-4-yl)-ethyl]-(5,6,7,8-tetrahydro-quinolin-8-yl)-amino]-methyl}-benzyl)-2,4-dimethyl-nicotinamide

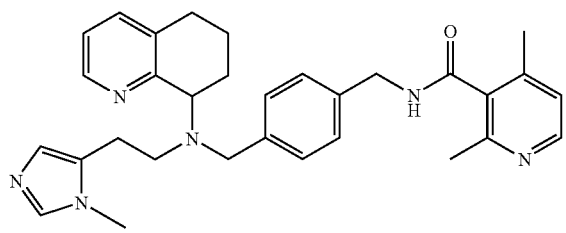

2,4-Dimethyl-N-(4-{[[2-(3-methyl-3H-imidazol-4-yl)-ethyl]-(5,6,7,8-tetrahydro-quinolin-8-yl)-amino]-methyl}-benzyl)-nicotinamide

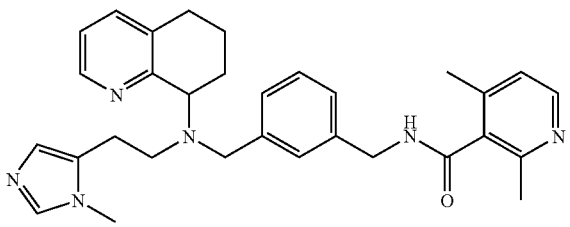

2,4-Dimethyl-N-(3-{[[2-(3-methyl-3H-imidazol-4-yl)-ethyl]-(5,6,7,8-tetrahydro-quinolin-8-yl)-amino]-methyl}-benzyl)-nicotinamide

106

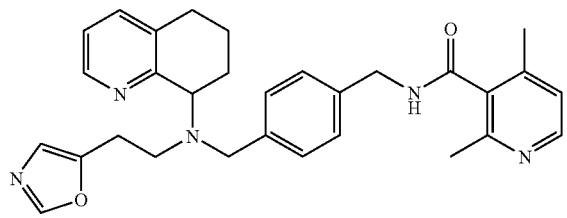

2,4-Dimethyl-N-(4-{[(2-oxazol-5-yl-ethyl)-(5,6,7,8-tetrahydro-quinolin-8-yl)-amino]-methyl}-benzyl)-nicotinamide

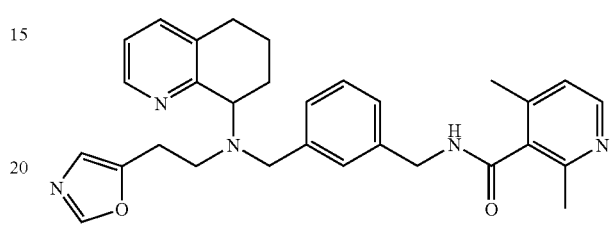

2,4-Dimethyl-N-(3-{[(2-oxazol-5-yl-ethyl)-(5,6,7,8-tetrahydro-quinolin-8-yl)-amino]-methyl}-benzyl)-nicotinamide

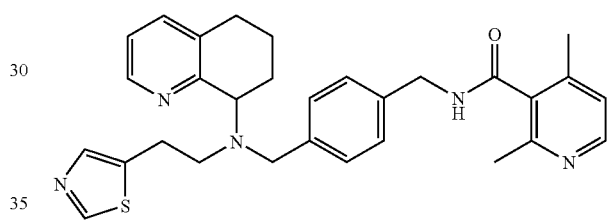

2,4-Dimethyl-N-(4-{[(5,6,7,8-tetrahydro-quinolin-8-yl)-(2-thiazol-5-yl-ethyl)-amino]-methyl}-benzyl)-nicotinamide

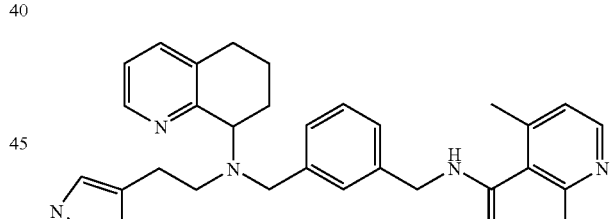

2,4-Dimethyl-N-(3-{[(5,6,7,8-tetrahydro-quinolin-8-yl)-(2-thiazol-5-yl-ethyl)-amino]-methyl}-benzyl)-nicotinamide

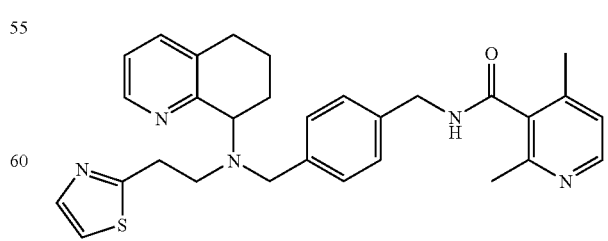

2,4-Dimethyl-N-(4-{[(5,6,7,8-tetrahydro-quinolin-8-yl)-(2-thiazol-2-yl-ethyl)-amino]-methyl}-benzyl)-nicotinamide 2,4-Dimethyl-N-(3-{[(5,6,7,8-tetrahydro-quinolin-8-yl)-(2-thiazol-2-yl-ethyl)-amino]-methyl}-benzyl)-nicotinamide

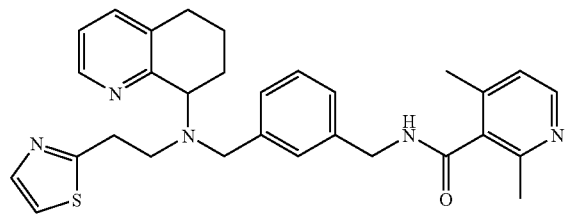

2,4-Dimethyl-N-(3-{[(5,6,7,8-tetrahydro-quinolin-8-yl)-(2-thiazol-2-yl-ethyl)-amino]-methyl}-benzyl)-nicotinamide

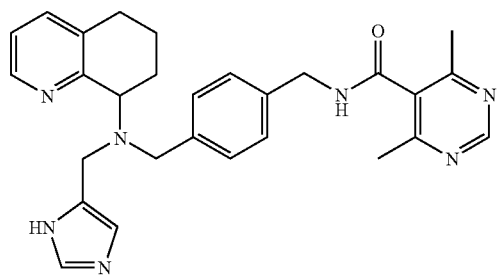

4,6-Dimethyl-pyrimidine-5-carboxylic acid 4-{[(3H-imidazol-4-ylmethyl)-(5,6,7,8-tetrahydro-quinolin-8-yl)-amino]-methyl}-benzylamide

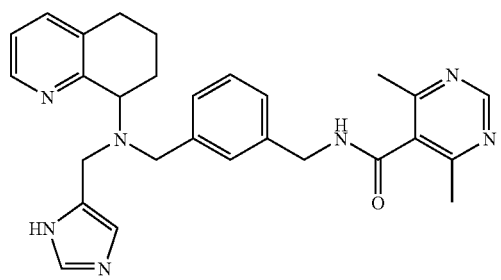

4,6-Dimethyl-pyrimidine-5-carboxylic acid 3-{[(3H-imidazol-4-ylmethyl)-(5,6,7,8-tetrahydro-quinolin-8-yl)-amino]-methyl}-benzylamide

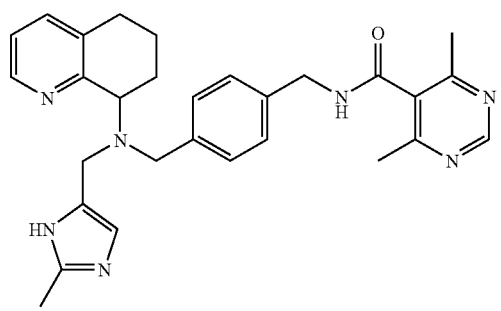

4,6-Dimethyl-pyrimidine-5-carboxylic acid 4-{[(2-methyl-3H-imidazol-4-ylmethyl)-(5,6,7,8-tetrahydro-quinolin-8-yl)-amino]-methyl}-benzylamide

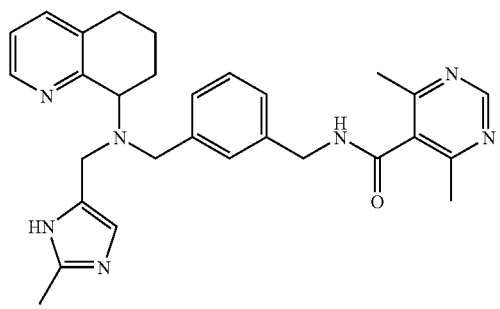

4,6-Dimethyl-pyrimidine-5-carboxylic acid 3-{[(2-methyl-3H-imidazol-4-ylmethyl)-(5,6,7,8-tetrahydro-quinolin-8-yl)-amino]-methyl}-benzylamide

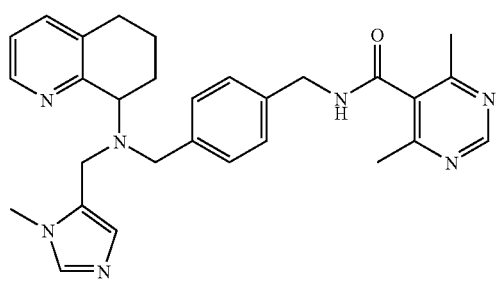

4,6-Dimethyl-pyrimidine-5-carboxylic acid 4-{[(3-methyl-3H-imidazol-4-ylmethyl)-(5,6,7,8-tetrahydro-quinolin-8-yl)-amino]-methyl}-benzylamide

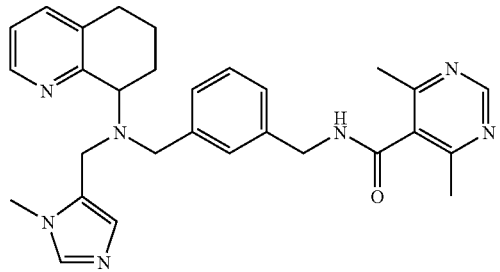

4,6-Dimethyl-pyrimidine-5-carboxylic acid 3-{[(3-methyl-3H-imidazol-4-ylmethyl)-(5,6,7,8-tetrahydro-quinolin-8-yl)-amino]-methyl}-benzylamide

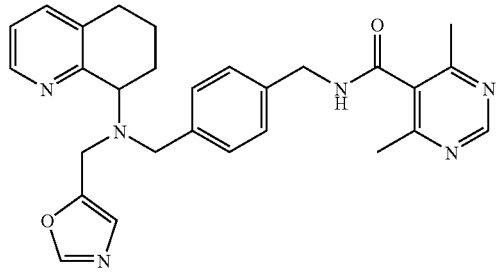

4,6-Dimethyl-pyrimidine-5-carboxylic acid 4-{[oxazol-5-ylmethyl-(5,6,7,8-tetrahydro-quinolin-8-yl)-amino]-methyl}-benzylamide

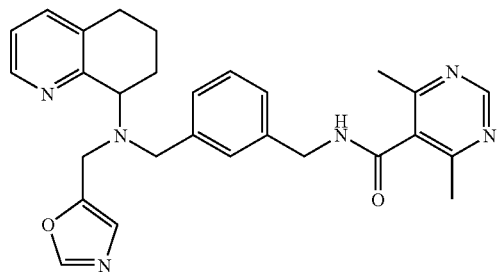

4,6-Dimethyl-pyrimidine-5-carboxylic acid 3-{[oxazol-5-ylmethyl-(5,6,7,8-tetrahydro-quinolin-8-yl)-amino]-methyl}-benzylamide

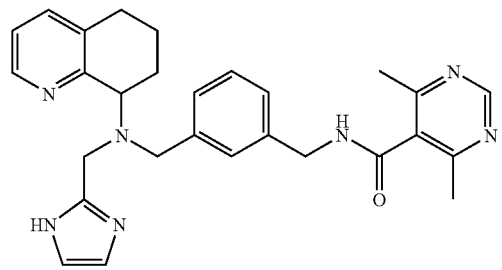

4,6-Dimethyl-pyrimidine-5-carboxylic acid 3-{[(1H-imidazol-2-ylmethyl)-(5,6,7,8-tetrahydro-quinolin-8-yl)-amino]-methyl}-benzylamide

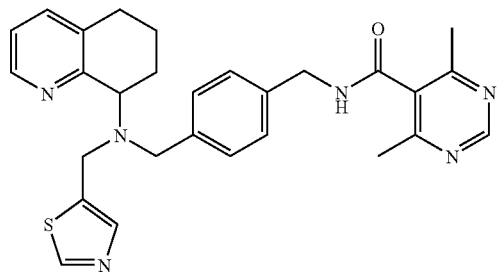

4,6-Dimethyl-pyrimidine-5-carboxylic acid 4-{[(5,6,7,8-tetrahydro-quinolin-8-yl)-thiazol-5-ylmethyl-amino]-methyl}-benzylamide

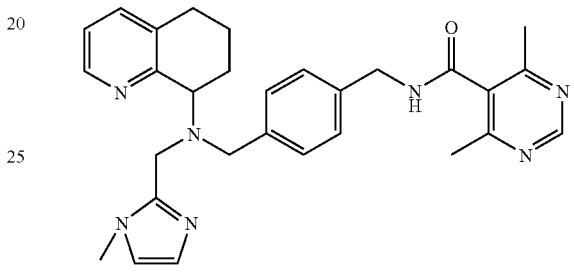

4,6-Dimethyl-pyrimidine-5-carboxylic acid 4-{[(1-methyl-1H-imidazol-2-ylmethyl)-(5,6,7,8-tetrahydro-quinolin-8-yl)-amino]-methyl}-benzylamide

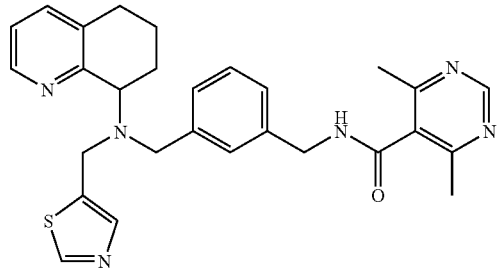

4,6-Dimethyl-pyrimidine-5-carboxylic acid 3-{[(5,6,7,8-tetrahydro-quinolin-8-yl)-thiazol-5-ylmethyl-amino]-methyl}-benzylamide

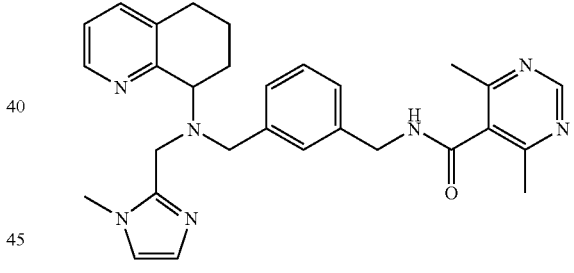

4,6-Dimethyl-pyrimidine-5-carboxylic acid 3-{[(1-methyl-1H-imidazol-2-ylmethyl)-(5,6,7,8-tetrahydro-quinolin-8-yl)-amino]-methyl}-benzylamide

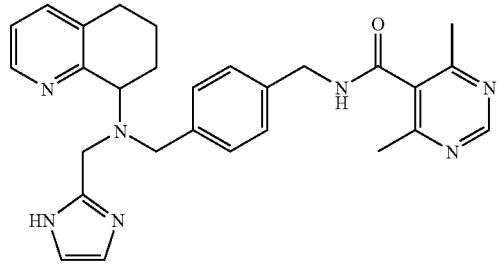

4,6-Dimethyl-pyrimidine-5-carboxylic acid 4-{[(1H-imidazol-2-ylmethyl)-(5,6,7,8-tetrahydro-quinolin-8-yl)-amino]-methyl}-benzylamide

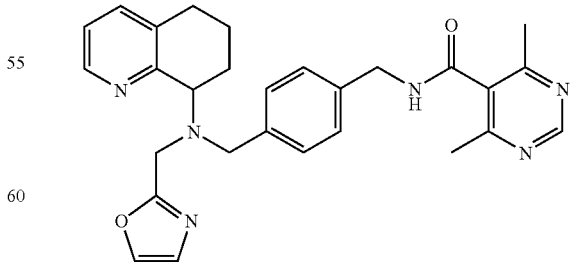

4,6-Dimethyl-pyrimidine-5-carboxylic acid 4-{[oxazol-2-ylmethyl-(5,6,7,8-tetrahydro-quinolin-8-yl)-amino]-methyl}-benzylamide

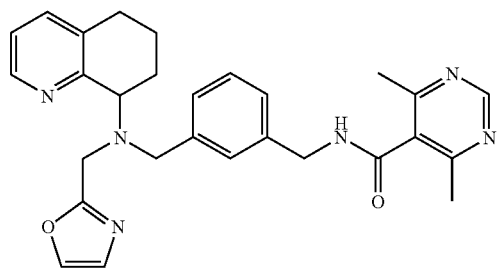

4,6-Dimethyl-pyrimidine-5-carboxylic acid 3-{[oxazol-2-ylmethyl-(5,6,7,8-tetrahydro-quinolin-8-yl)-amino]-methyl}-benzylamide

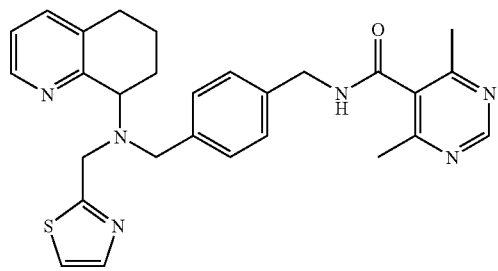

4,6-Dimethyl-pyrimidine-5-carboxylic acid 4-{[(5,6,7,8-tetrahydro-quinolin-8-yl)-thiazol-2-ylmethyl-amino]-methyl}-benzylamide

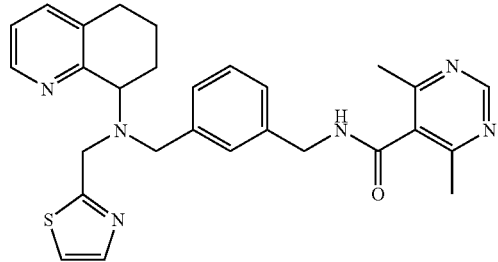

4,6-Dimethyl-pyrimidine-5-carboxylic acid 3-{[(5,6,7,8-tetrahydro-quinolin-8-yl)-thiazol-2-ylmethyl-amino]-methyl}-benzylamide

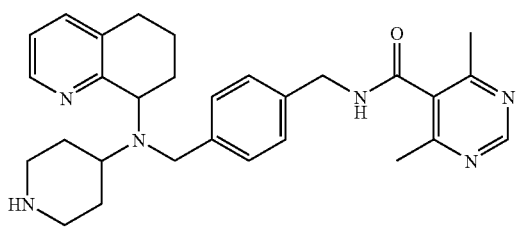

4,6-Dimethyl-pyrimidine-5-carboxylic acid 4-{[piperidin-4-yl-(5,6,7,8-tetrahydro-quinolin-8-yl)-amino]-methyl}-benzylamide

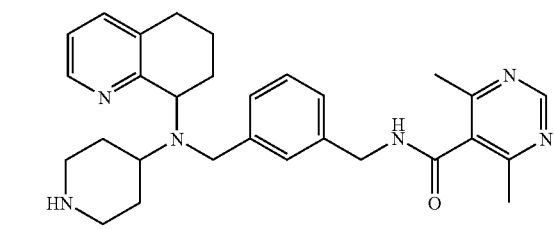

4,6-Dimethyl-pyrimidine-5-carboxylic acid 3-{[piperidin-4-yl-(5,6,7,8-tetrahydro-quinolin-8-yl)-amino]-methyl}-benzylamide

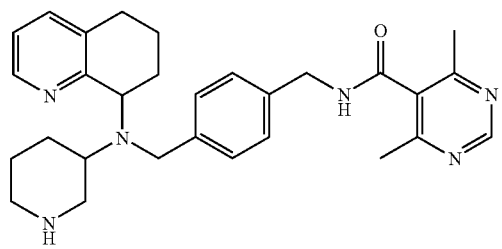

4,6-Dimethyl-pyrimidine-5-carboxylic acid 4-{[piperidin-3-yl-(5,6,7,8-tetrahydro-quinolin-8-yl)-amino]-methyl}-benzylamide

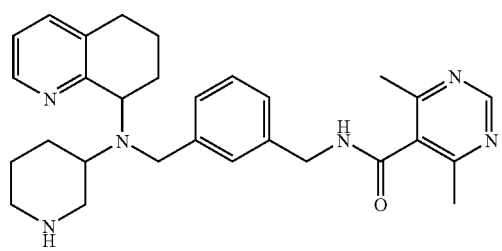

4,6-Dimethyl-pyrimidine-5-carboxylic acid 3-{[piperidin-3-yl-(5,6,7,8-tetrahydro-quinolin-8-yl)-amino]-methyl}-benzylamide

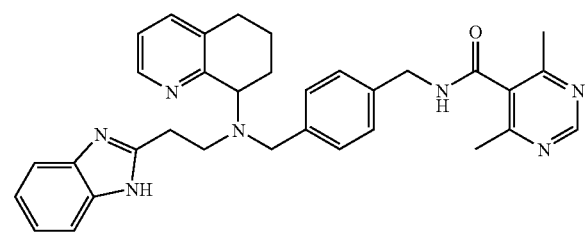

4,6-Dimethyl-pyrimidine-5-carboxylic acid 4-{[[2-(1H-benzoimidazol-2-yl)-ethyl]-(5,6,7,8-tetrahydro-quinolin-8-yl)-amino]-methyl}-benzylamide

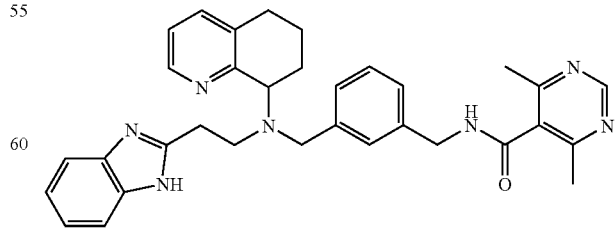

4,6-Dimethyl-pyrimidine-5-carboxylic acid 3-{[[2-(1H-benzoimidazol-2-yl)-ethyl]-(5,6,7,8-tetrahydro-quinolin-8-yl)-amino]-methyl}-benzylamide

113

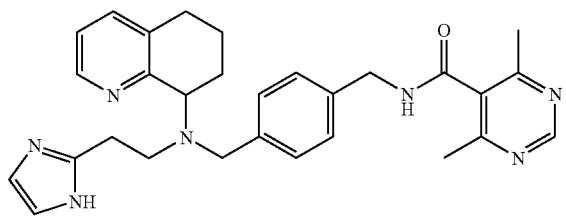

4,6-Dimethyl-pyrimidine-5-carboxylic acid 4-{[[2-(1H-imidazol-2-yl)-ethyl]-(5,6,7,8-tetrahydro-quinolin-8-yl)-amino]-methyl}-benzylamide

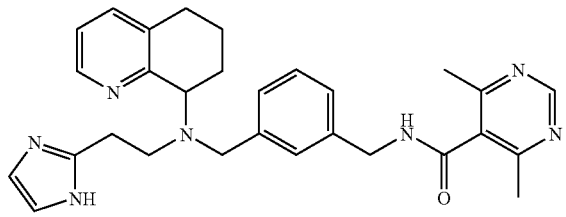

4,6-Dimethyl-pyrimidine-5-carboxylic acid 3-{[[2-(1H-imidazol-2-yl)-ethyl]-(5,6,7,8-tetrahydro-quinolin-8-yl)-amino]-methyl}-benzylamide

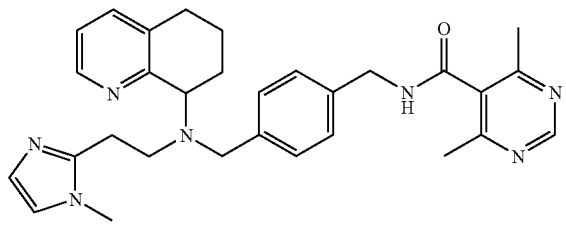

4,6-Dimethyl-pyrimidine-5-carboxylic acid 4-{[[2-(1-methyl-1H-imidazol-2-yl)-ethyl]-(5,6,7,8-tetrahydro-quinolin-8-yl)-amino]-methyl}-benzylamide

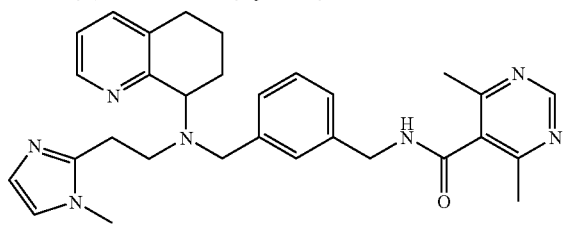

4,6-Dimethyl-pyrimidine-5-carboxylic acid 3-{[[2-(1-methyl-1H-imidazol-2-yl)-ethyl]-(5,6,7,8-tetrahydro-quinolin-8-yl)-amino]-methyl}-benzylamide

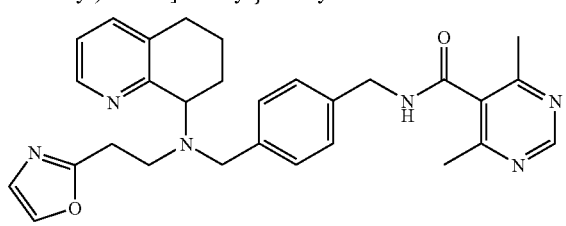

4,6-Dimethyl-pyrimidine-5-carboxylic acid 4-{[(2-oxazol-2-yl-ethyl)-(5,6,7,8-tetrahydro-quinolin-8-yl)-amino]-methyl}-benzylamide

114

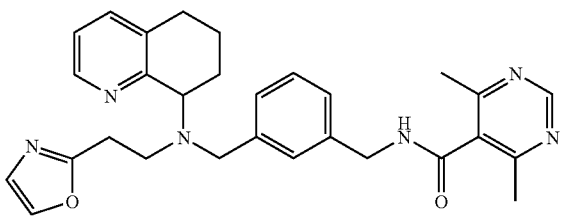

4,6-Dimethyl-pyrimidine-5-carboxylic acid 3-{[(2-oxazol-2-yl-ethyl)-(5,6,7,8-tetrahydro-quinolin-8-yl)-amino]-methyl}-benzylamide

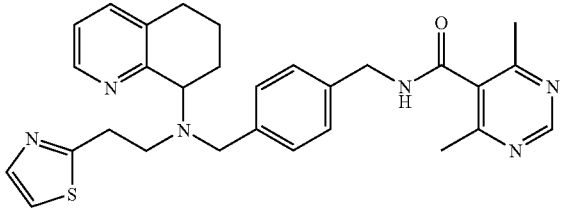

4,6-Dimethyl-pyrimidine-5-carboxylic acid 4-{[(5,6,7,8-tetrahydro-quinolin-8-yl)-(2-thiazol-2-yl-ethyl)-amino]-methyl}-benzylamide

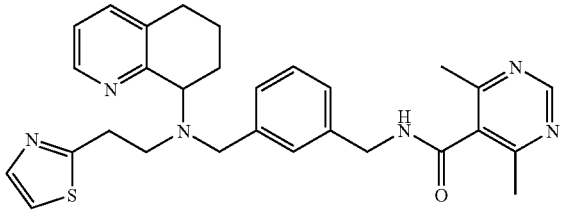

4,6-Dimethyl-pyrimidine-5-carboxylic acid 3-{[(5,6,7,8-tetrahydro-quinolin-8-yl)-(2-thiazol-2-yl-ethyl)-amino]-methyl}-benzylamide

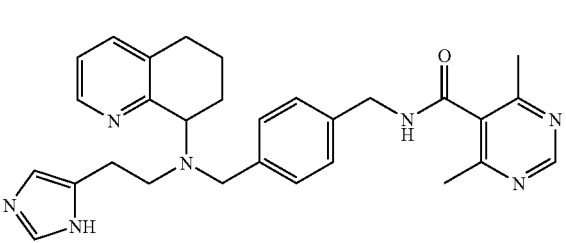

4,6-Dimethyl-pyrimidine-5-carboxylic acid 4-{[[2-(3H-imidazol-4-yl)-ethyl]-(5,6,7,8-tetrahydro-quinolin-8-yl)-amino]-methyl}-benzylamide

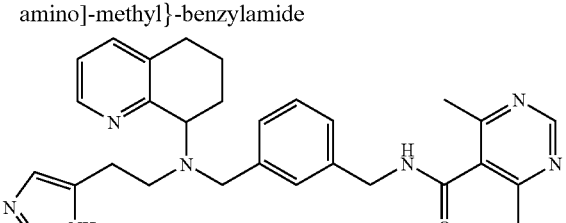

4,6-Dimethyl-pyrimidine-5-carboxylic acid 3-{[[2-(3H-imidazol-4-yl)-ethyl]-(5,6,7,8-tetrahydro-quinolin-8-yl)-amino]-methyl}-benzylamide

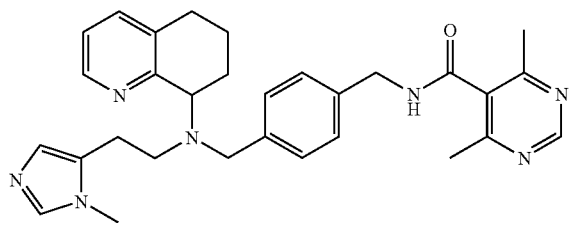

4,6-Dimethyl-pyrimidine-5-carboxylic acid 4-{[[2-(3-methyl-3H-imidazol-4-yl)-ethyl]-(5,6,7,8-tetrahydro-quinolin-8-yl)-amino]-methyl}-benzylamide

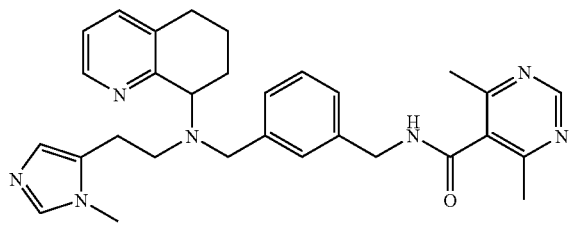

4,6-Dimethyl-pyrimidine-5-carboxylic acid 3-{[[2-(3-methyl-3H-imidazol-4-yl)-ethyl]-(5,6,7,8-tetrahydro-quinolin-8-yl)-amino]-methyl}-benzylamide

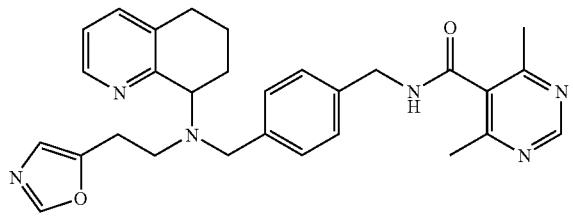

4,6-Dimethyl-pyrimidine-5-carboxylic acid 4-{[(2-oxazol-5-yl-ethyl)-(5,6,7,8-tetrahydro-quinolin-8-yl)-amino]-methyl}-benzylamide

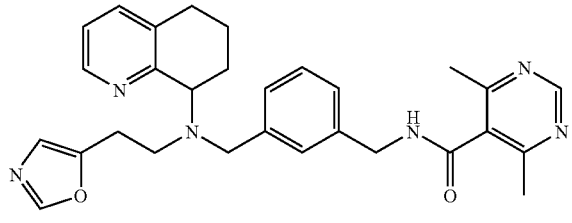

4,6-Dimethyl-pyrimidine-5-carboxylic acid 3-{[(2-oxazol-5-yl-ethyl)-(5,6,7,8-tetrahydro-quinolin-8-yl)-amino]-methyl}-benzylamide

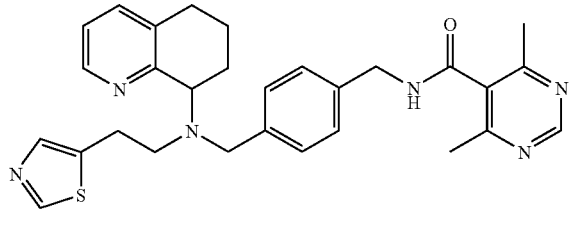

4,6-Dimethyl-pyrimidine-5-carboxylic acid 4-{[(5,6,7,8-tetrahydro-quinolin-8-yl)-(2-thiazol-5-yl-ethyl)-amino]-methyl}-benzylamide

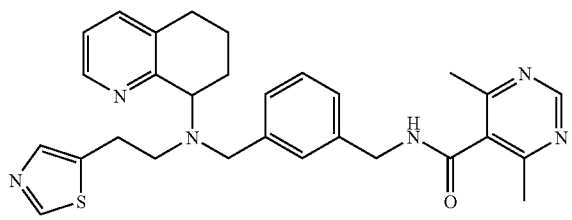

4,6-Dimethyl-pyrimidine-5-carboxylic acid 3-{[(5,6,7,8-tetrahydro-quinolin-8-yl)(2-thiazol-5-yl-ethyl)-amino]-methyl}-benzylamide

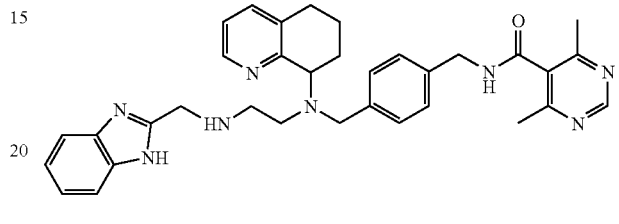

4,6-Dimethyl-pyrimidine-5-carboxylic acid 4-{[{2-[(1H-benzoimidazol-2-ylmethyl)-amino]-ethyl}-(5,6,7,8-tetrahydro-quinolin-8-yl)amino]-methyl}-benzylamide

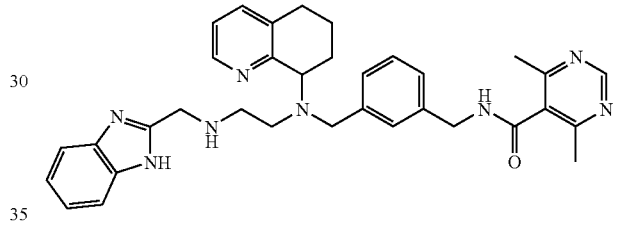

4,6-Dimethyl-pyrimidine-5-carboxylic acid 3-{[{2-[(1H-benzoimidazol-2-ylmethyl)-amino]-ethyl}-(5,6,7,8-tetrahydro-quinolin-8-yl)-amino]-methyl}-benzylamide

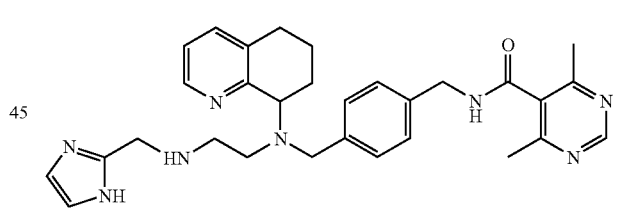

4,6-Dimethyl-pyrimidine-5-carboxylic acid 4-{[{2-[(1H-imidazol-2-ylmethyl)-amino]-ethyl}-(5,6,7,8-tetrahydro-quinolin-8-yl)amino]-methyl}-benzylamide

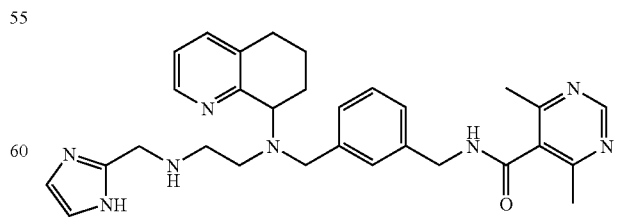

4,6-Dimethyl-pyrimidine-5-carboxylic acid 3-{[{2-[(1H-imidazol-2-ylmethyl)-amino]-ethyl}-(5,6,7,8-tetrahydro-quinolin-8-yl)-amino]-methyl}-benzylamide

117

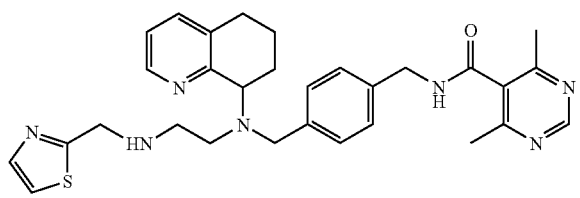

4,6-Dimethyl-pyrimidine-5-carboxylic acid 4-[((5,6,7,8-tetrahydro-quinolin-8-yl)-{2-[(thiazol-2-ylmethyl)-amino]-ethyl}-amino)-methyl]-benzylamide

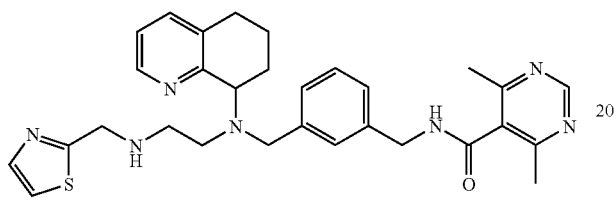

4,6-Dimethyl-pyrimidine-5-carboxylic acid 3-[((5,6,7,8-tetrahydro-quinolin-8-yl)-{2-[(thiazol-2-ylmethyl)-amino]-ethyl}-amino)-methyl]-benzylamide

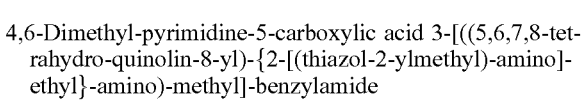

4,6-Dimethyl-pyrimidine-5-carboxylic acid 4-{[{2-[(oxazol-2-ylmethyl)-amino]-ethyl}-(5,6,7,8-tetrahydro-quinolin-8-yl)-amino]-methyl}-benzylamide

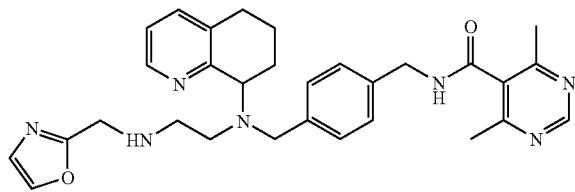

4,6-Dimethyl-pyrimidine-5-carboxylic acid 3-{[{2-[(oxazol-2-ylmethyl)-amino]-ethyl}-(5,6,7,8-tetrahydro-quinolin-8-yl)-amino]-methyl}-benzylamide

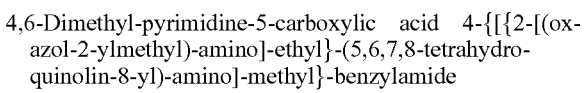

3,5-Dichloro-N-{4-[(3,4-dihydro-2H-pyrano[3,2-b]pyridin-4-ylamino)-methyl]-benzyl}-isonicotinamide

118

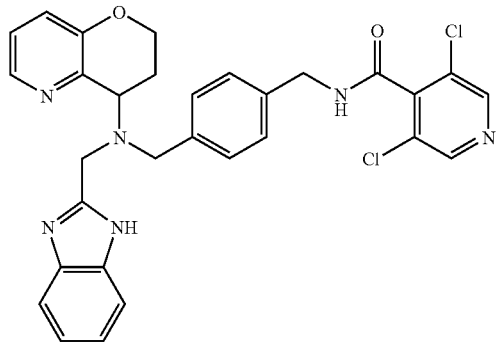

3,5-Dichloro-N-{3-[(3,4-dihydro-2H-pyrano[3,2-b]pyridin-4-ylamino)-methyl]-benzyl}-isonicotinamide

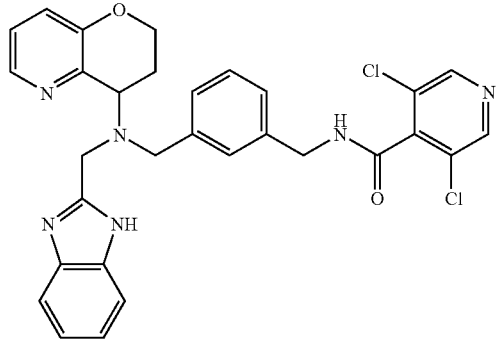

N-(4-{[(1H-Benzoimidazol-2-ylmethyl)-(3,4-dihydro-2H-pyrano[3,2-b]pyridin-4-yl)-amino]-methyl}-benzyl)-3,5-dichloro-isonicotinamide

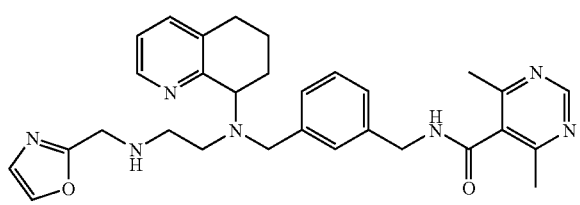

N-(3-{[(1H-Benzoimidazol-2-ylmethyl)-(3,4-dihydro-2H-pyrano[3,2-b]pyridin-4-yl)-amino]-methyl}-benzyl)-3,5-dichloro-isonicotinamide

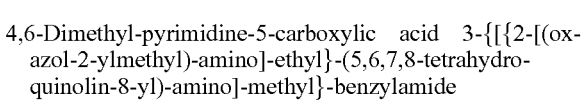
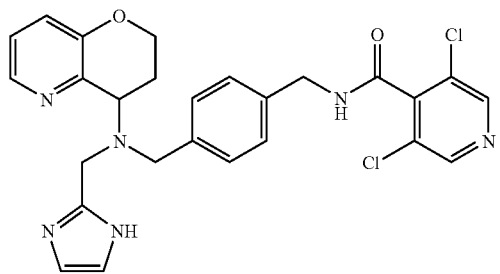
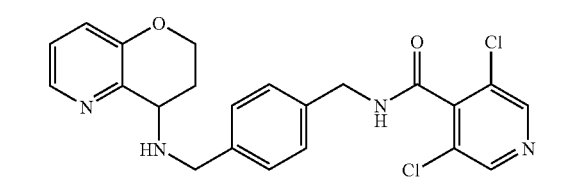

3,5-Dichloro-N-(4-{[(3,4-dihydro-2H-pyrano[3,2-b]pyridin-4-yl)-(1H-imidazol-2-ylmethyl)-amino]-methyl}-benzyl)-isonicotinamide

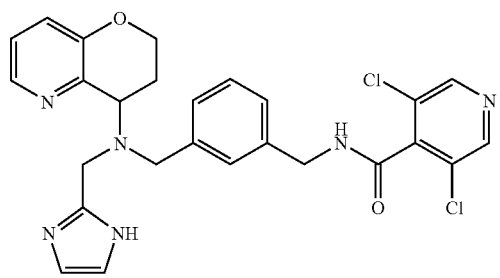

3,5-Dichloro-N-(3-{[(3,4-dihydro-2H-pyrano[3,2-b]pyridin-4-yl)-(1H-imidazol-2-ylmethyl)-amino]-methyl}-benzyl)-isonicotinamide

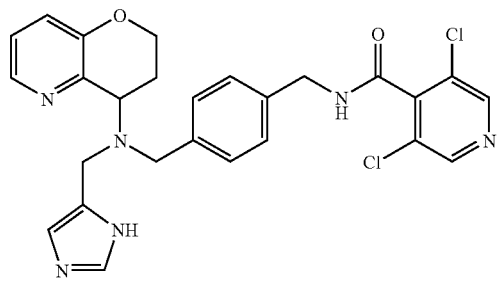

3,5-Dichloro-N-(4-{[(3,4-dihydro-2H-pyrano[3,2-b]pyridin-4-yl)-(3H-imidazol-4-ylmethyl)-amino]-methyl}-benzyl)-isonicotinamide

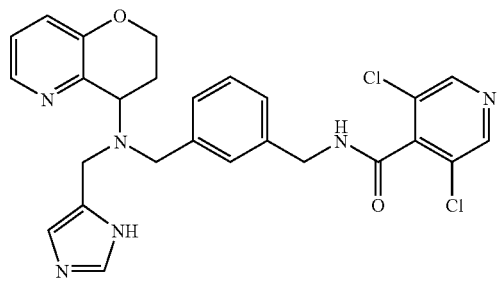

3,5-Dichloro-N-(3-{[(3,4-dihydro-2H-pyrano[3,2-b]pyridin-4-yl)-(3H-imidazol-4-ylmethyl)-amino]-methyl}-benzyl)-isonicotinamide

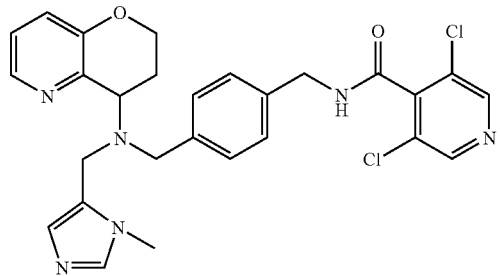

3,5-Dichloro-N-(4-{[(3,4-dihydro-2H-pyrano[3,2-b]pyridin-4-yl)-(3-methyl-3H-imidazol-4-ylmethyl)-amino]-methyl}-benzyl)-isonicotinamide

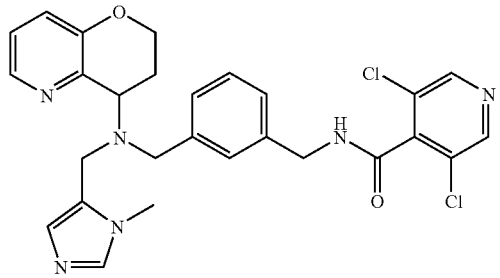

3,5-Dichloro-N-(3-{[(3,4-dihydro-2H-pyrano[3,2-b]pyridin-4-yl)-(3-methyl-3H-imidazol-4-ylmethyl)-amino]-methyl}-benzyl)-isonicotinamide

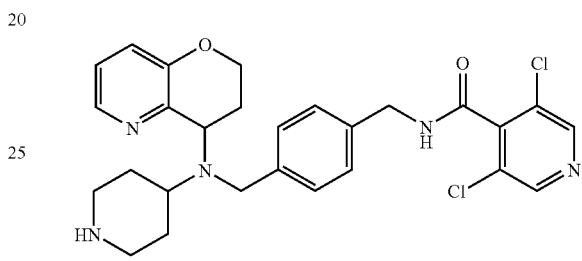

3,5-Dichloro-N-(4-{[(3,4-dihydro-2H-pyrano[3,2-b]pyridin-4-yl)-piperidin-4-yl-amino]-methyl}-benzyl)-isonicotinamide

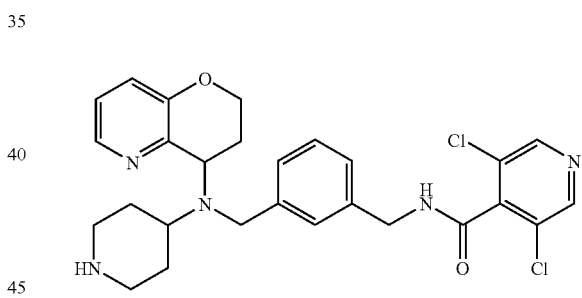

3,5-Dichloro-N-(3-{[(3,4-dihydro-2H-pyrano[3,2-b]pyridin-4-yl)-piperidin-4-yl-amino]-methyl}-benzyl)-isonicotinamide

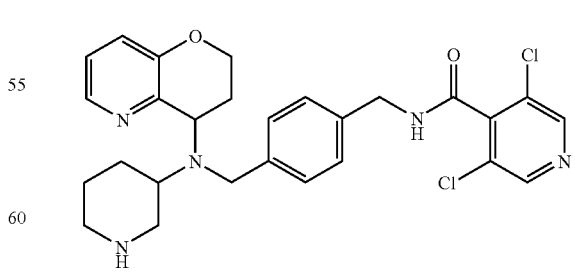

3,5-Dichloro-N-(4-{[(3,4-dihydro-2H-pyrano[3,2-b]pyridin-4-yl)-piperidin-3-yl-amino]-methyl}-benzyl)-isonicotinamide

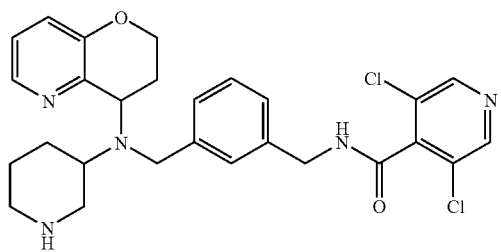

3,5-Dichloro-N-(3-{[(3,4-dihydro-2H-pyrano[3,2-b]pyridin-4-yl)-piperidin-3-yl-amino]-methyl}-benzyl)-isonicotinamide

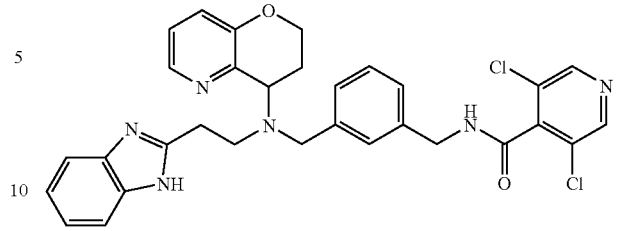

N-(3-{[[2-(1H-Benzoimidazol-2-yl)-ethyl]-(3,4-dihydro-2H-pyrano[3,2-b]pyridin-4-yl)-amino]-methyl}-benzyl)-3,5-dichloro-isonicotinamide

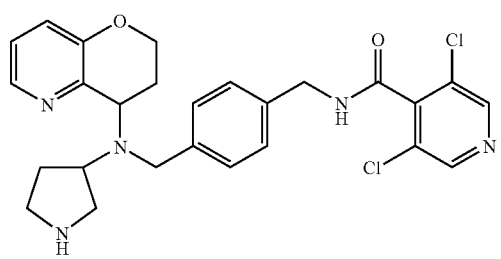

3,5-Dichloro-N-(4-{[(3,4-dihydro-2H-pyrano[3,2-b]pyridin-4-yl)-pyrrolidin-3-yl-amino]-methyl}-benzyl)-isonicotinamide

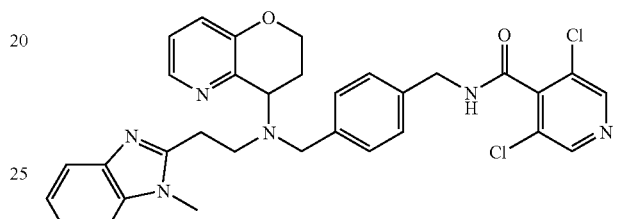

3,5-Dichloro-N-[4-({(3,4-dihydro-2H-pyrano[3,2-b]pyridin-4-yl)-[2-(1-methyl-1H-benzoimidazol-2-yl)-ethyl]-amino}-methyl)-benzyl]-isonicotinamide

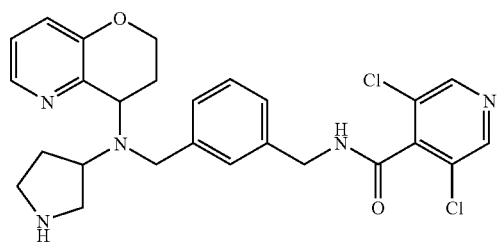

3,5-Dichloro-N-(3-{[(3,4-dihydro-2H-pyrano[3,2-b]pyridin-4-yl)-pyrrolidin-3-yl-amino]-methyl}-benzyl)-isonicotinamide

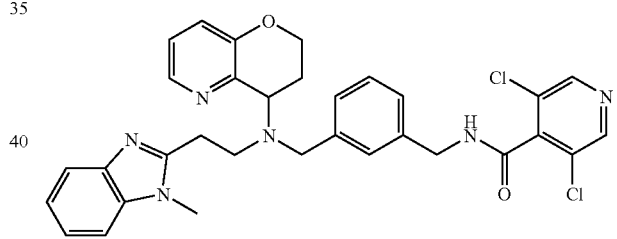

3,5-Dichloro-N-[3-({(3,4-dihydro-2H-pyrano[3,2-b]pyridin-4-yl)-[2-(1-methyl-1H-benzoimidazol-2-yl)-ethyl]-amino}-methyl)-benzyl]-isonicotinamide

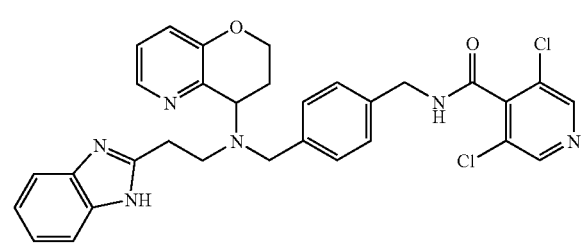

N-(4-{[[2-(1H-Benzoimidazol-2-yl)-ethyl]-(3,4-dihydro-2H-pyrano[3,2-b]pyridin-4-yl)-amino]-methyl}-benzyl)-3,5-dichloro-isonicotinamide

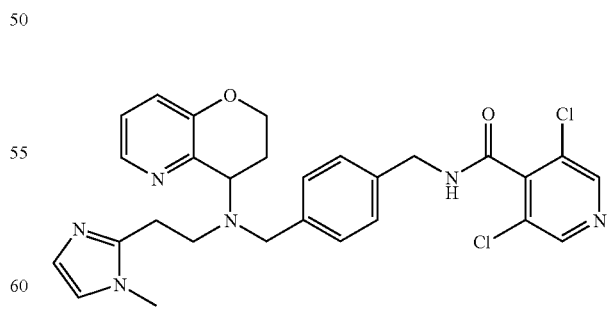

3,5-Dichloro-N-[4-({(3,4-dihydro-2H-pyrano[3,2-b]pyridin-4-yl)-[2-(1-methyl-1H-imidazol-2-yl)-ethyl]-amino}-methyl)-benzyl]-isonicotinamide

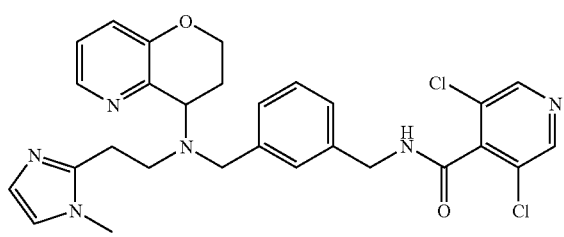

3,5-Dichloro-N-[3-({(3,4-dihydro-2H-pyrano[3,2-b]pyridin-4-yl)-[2-(1-methyl-1H-imidazol-2-yl)-ethyl]-amino}-methyl)-benzyl]-isonicotinamide

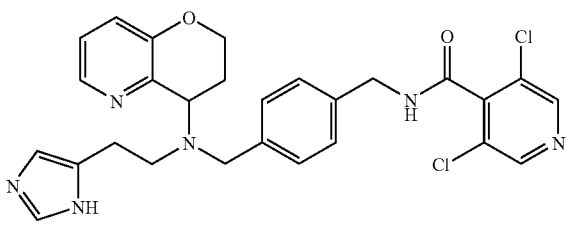

3,5-Dichloro-N-[4-({(3,4-dihydro-2H-pyrano[3,2-b]pyridin-4-yl)-[2-(3H-imidazol-4-yl)-ethyl]-amino}-methyl)-benzyl]-isonicotinamide

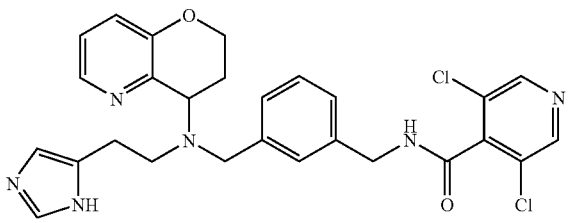

3,5-Dichloro-N-[3-({(3,4-dihydro-2H-pyrano[3,2-b]pyridin-4-yl)-[2-(3H-imidazol-4-yl)-ethyl]-amino}-methyl)-benzyl]-isonicotinamide

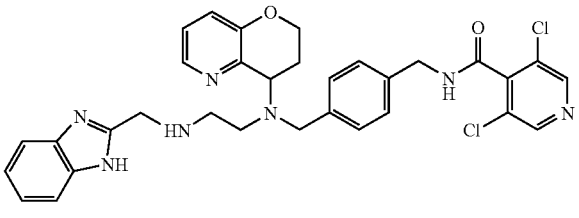

N-(4-{[{2-[(1H-Benzoimidazol-2-ylmethyl)-amino]-ethyl}-(3,4-dihydro-2H-pyrano[3,2-b]pyridin-4-yl)-amino]-methyl}-benzyl)-3,5-dichloro-isonicotinamide

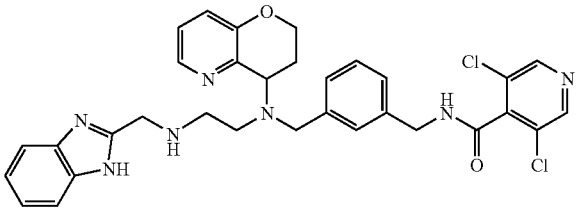

N-(3-{[{2-[(1H-Benzoimidazol-2-ylmethyl)-amino]-ethyl}-(3,4-dihydro-2H-pyrano[3,2-b]pyridin-4-yl)-amino]-methyl}-benzyl)-3,5-dichloro-isonicotinamide

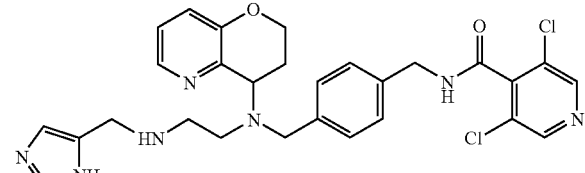

3,5-Dichloro-N-{4-[((3,4-dihydro-2H-pyrano[3,2-b]pyridin-4-yl)-{2-[(3H-imidazol-4-ylmethyl)-amino]-ethyl}-amino)-methyl]-benzyl}-isonicotinamide

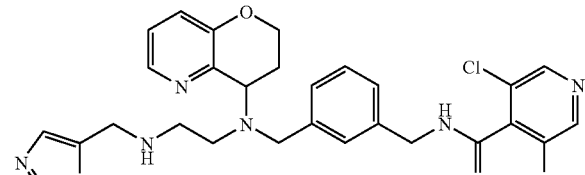

3,5-Dichloro-N-{3-[((3,4-dihydro-2H-pyrano[3,2-b]pyridin-4-yl)-{2-[(3H-imidazol-4-ylmethyl)-amino]-ethyl}-amino)-methyl]-benzyl}-isonicotinamide

What is claimed is:

1. A compound of the Formula

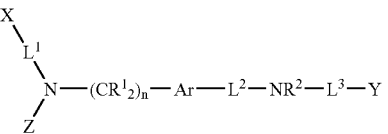

(1)

or a pharmaceutically acceptable salt thereof,
wherein:
X is a monocyclic (5-6 membered) ring system containing at least one heteroatom selected from N, O and S, wherein said ring system may be optionally substituted with 1-2 substituents selected from the group consisting of halogen, $C_{1-4}$ alkyl, $C_{1-4}$ alkoxy, and optionally substituted phenyl, wherein said phenyl may be optionally substituted by halogen, $C_{1-4}$ alkyl, or $C_{1-4}$ alkoxy;
$L^1$ is $CH_2$;
Z is a tetrahydroquinoline or dihydroquinoline ring system;
Ar is an optionally substituted aromatic or heteroaromatic ring;
$L^2$ is $CH_2$;
$L^3$ is CO;
n is 0, 1 or 2;
each $R^1$ and $R^2$ is independently H or straight or branched chain or cyclic alkyl (1-6C) which may optionally be substituted, and wherein $R^2$ may be alkylene coupled to Y; and
Y is a pyridinyl ring, wherein the ring nitrogen may optionally be oxidized, and wherein said ring may be optionally substituted with 1-3 substituents selected from the group consisting of halogen, cyano, alkyl, —OR, —SR, —$NR_2$, —NRCOR, —OOCR, —COR, -$CONR_2$, —COOR, —$NO_2$, and —$CF_3$, where R is H or alkyl (1-6C).

2. The compound of claim 1, wherein X is an optionally substituted imidazolyl, oxazolyl, thiazolyl, or pyrrolyl ring.

3. The compound of claim 1 which is a compound selected from the group consisting of
3,5-Dichloro-N-(4-{[(1H-imidazol-4-ylmethyl)-(5,6,7,8-tetrahydro-quinolin-8-yl)-amino]-methyl}-benzyl)-isonicotinamide;

3,5-Dichloro-N-(3-{[(1H-imidazol-4-ylmethyl)-(5,6,7,8-tetrahydro-quinolin-8-yl)-amino]-methyl}-benzyl)-isonicotinamide;

3,5-Dichloro-N-(4-{[(2-methyl-1H-imidazol-4-ylmethyl)-(5,6,7,8-tetrahydro-quinolin-8-yl)-amino]-methyl}-benzyl)-isonicotinamide;

3,5-Dichloro-N-(3-{[(2-methyl-1H-imidazol-4-ylmethyl)-(5,6,7,8-tetrahydro-quinolin-8-yl)-amino]-methyl}-benzyl)-isonicotinamide;

3,5-Dichloro-N-(4-{[(5-methyl-1H-imidazol-4-ylmethyl)-(5,6,7,8-tetrahydro-quinolin-8-yl)-amino]-methyl}-benzyl)-isonicotinamide;

3,5-Dichloro-N-(3-{[(5-methyl-1H-imidazol-4-ylmethyl)-(5,6,7,8-tetrahydro-quinolin-8-yl)-amino]-methyl}-benzyl)-isonicotinamide;

3,5-Dichloro-N-(4-{[(2,5-dimethyl-1H-imidazol-4-ylmethyl)-(5,6,7,8-tetrahydro-quinolin-8-yl)-amino]-methyl}-benzyl)-isonicotinamide;

3,5-Dichloro-N-(3-{[(2,5-dimethyl-1H-imidazol-4-ylmethyl)-(5,6,7,8-tetrahydro-quinolin-8-yl)-amino]-methyl}-benzyl)-isonicotinamide;

3,5-Dichloro-N-(4-{[(1-methyl-1H-imidazol-4-ylmethyl)-(5,6,7,8-tetrahydro-quinolin-8-yl)-amino]-methyl}-benzyl)-isonicotinamide;

3,5-Dichloro-N-(3-{[(1-methyl-1H-imidazol-4-ylmethyl)-(5,6,7,8-tetrahydro-quinolin-8-yl)-amino]-methyl}-benzyl)-isomcotinamide;

3,5-Dichloro-N-(4-[(1,2-dimethyl-1H-imidazol-4-ylmethyl)-(5,6,7,8-tetrahydro-quinolin-8-yl)-amino]-methyl -benzyl)-isonicotinamide;

3,5-Dichloro-N-(3-{[(1,2-dimethyl-1H-imidazol-4-ylmethyl)-(5,6,7,8-tetrahydro-quinolin-8-yl)-amino]-methyl}-benzyl)-isonicotinamide;

3,5-Dichloro-N-(4-{[(1,5-dimethyl-1H-imidazol-4-ylmethyl)-(5,6,7,8-tetrahydro-quinolin-8-yl)-amino]-methyl}-benzyl)-isonicotinamide;

3,5-Dichloro-N-(3-{[(1,5-dimethyl-1H-imidazol-4-ylmethyl)-(5,6,7,8-tetrahydro-quinolin-8-yl)-amino]-methyl}-benzyl)-isonicotinamide;

3,5-Dichloro-N-(4-{[(1H-imidazol-2-ylmethyl)-(5,6,7,8-tetrahydro-quinolin-8-yl)-amino]-methyl}-benzyl)-isonicotinamide;

3,5-Dichloro-N-(3-{[(1H-imidazol-2-ylmethyl)-(5,6,7,8-tetrahydro-quinolin-8-yl)-amino]-methyl}-benzyl)-isonicotinamide;

3,5-Dichloro-N-(4-{[(4-methyl-1H-imidazol-2-ylmethyl)-(5,6,7,8-tetrahydro-quinolin-8-yl)-amino]-methyl}-benzyl)-isonicotinamide;

3,5-Dichloro-N-(3-{[(4-methyl-1H-imidazol-2-ylmethyl)-(5,6,7,8-tetrahydro-quinolin-8-yl)-amino]-methyl}-benzyl)-isonicotinamide;

3,5-Dichloro-N-(4-{[[4-(2-fluoro-phenyl)-1H-imidazol-2-ylmethyl]-(5,6,7,8-tetrahydro-quinolin-8-yl)-amino]-methyl}-benzyl)-isonicotinamide;

3,5-Dichloro-N-(4-{[[4-(3-fluoro-phenyl)-1H-imidazol-2-ylmethyl]-(5,6,7,8-tetrahydro-quinolin-8-yl)-amino]-methyl}-benzyl)-isonicotinamide;

3,5-Dichloro-N-(4-{[[4-(4-fluoro-phenyl)-1H-imidazol-2-ylmethyl]-(5,6,7,8-tetrahydro-quinolin-8-yl)-amino]-methyl}-benzyl)-isonicotinamide;

3,5-Dichloro-N-(3-{[[4-(2-fluoro-phenyl)-1H-imidazol-2-ylmethyl]-(5,6,7,8-tetrahydro-quinolin-8-yl)-amino]-methyl}-benzyl)-isonicotinamide;

3,5-Dichloro-N-(3-{[[4-(3-fluoro-phenyl)-1H-imidazol-2-ylmethyl]-(5,6,7,8-tetrahydro-quinolin-8-yl)-amino]-methyl}-benzyl)-isonicotinamide;

3,5-Dichloro-N-(3-{[[4-(4-fluoro-phenyl)-1H-imidazol-2-ylmethyl]-(5,6,7,8-tetrahydro-quinolin-8-yl)-amino]-methyl}benzyl)-isonicotinamide;

3,5-Dichloro-N-(4-{[(4-phenyl-1H-imidazol-2-ylmethyl)-(5,6,7,8-tetrahydro-quinolin-8-yl)-amino]-methyl}benzyl)-isonicotinamide;

3,5-Dichloro-N-(3-{[(4-phenyl-1H-imidazol-2-ylmethyl)-(5,6,7,8-tetrahydro-quinolin-8-yl)-amino]-methyl}benzyl)-isonicotinamide;

3,5-Dichloro-N-(4-{[(2-phenyl-3H-imidazol-4-ylmethyl)-(5,6,7,8-tetrahydro-quinolin-8-yl)-amino]-methyl}benzyl)-isonicotinamide;

3,5-Dichloro-N-(4-{[[2-(2-methoxy-phenyl)-3H-imidazol-4-ylmethyl]-(5,6,7,8-tetrahydro-quinolin-8-yl)-amino]-methyl}benzyl)-isonicotinamide;

3,5-Dichloro-N-(4-{[[2-(3-methoxy-phenyl)-3H-imidazol-4-ylmethyl]-(5,6,7,8-tetrahydro-quinolin-8-yl)-amino]-methyl}benzyl)-isonicotinamide;

3,5-Dichloro-N-(4-{[[2-(4-methoxy-phenyl)-3H-imidazol-4-ylmethyl]-(5,6,7,8-tetrahydro-quinolin-8-yl)-amino]-methyl}benzyl)-isonicotinamide;

3,5-Dichloro-N-(3-{[[2-(2-methoxy-phenyl)-3H-imidazol-4-ylmethyl]-(5,6,7,8-tetrahydro-quinolin-8-yl)-amino]-methyl}benzyl)-isonicotinamide;

3,5-Dichloro-N-(3-{[[2-(3-methoxy-phenyl)-3H-imidazol-4-ylmethyl]-(5,6,7,8-tetrahydro-quinolin-8-yl)-amino]-methyl}benzyl)-isonicotinamide;

3,5-Dichloro-N-(3-{[[2-(4-methoxy-phenyl)-3H-imidazol-4-ylmethyl]-(5,6,7,8-tetrahydro-quinolin-8-yl)-amino]-methyl}benzyl)-isonicotinamide;

3,5-Dichloro-N-(4-{[[4-(2-methoxy-phenyl)-1H-imidazol-2-ylmethyl]-(5,6,7,8-tetrahydro-quinolin-8-yl)-amino]-methyl}benzyl)-isonicotinamide;

3,5-Dichloro-N-(4-{[[4-(3-methoxy-phenyl)-1H-imidazol-2-ylmethyl]-(5,6,7,8-tetrahydro-quinolin-8-yl)-amino]-methyl}benzyl)-isonicotinamide;

3,5-Dichloro-N-(4-{[[4-(4-methoxy-phenyl)-1H-imidazol-2-ylmethyl]-(5,6,7,8-tetrahydro-quinolin-8-yl)-amino]-methyl}benzyl)-isonicotinamide;

3,5-Dichloro-N-(3-{[[4-(2-methoxy-phenyl)-1H-imidazol-2-ylmethyl]-(5,6,7,8-tetrahydro-quinolin-8-yl)-amino]-methyl}benzyl)-isonicotinamide;

3,5-Dichloro-N-(3-{[[4-(3-methoxy-phenyl)-1H-imidazol-2-ylmethyl]-(5,6,7,8-tetrahydro-quinolin-8-yl)-amino]-methyl}benzyl)-isonicotinamide;

3,5-Dichloro-N-(3-{[[4-(4-methoxy-phenyl)-1H-imidazol-2-ylmethyl]-(5,6,7,8-tetrahydro-quinolin-8-yl)-amino]-methyl}benzyl)-isonicotinamide;

3,5-Dichloro-N-(4-{[(3H-pyrrol-2-ylmethyl)-(5,6,7,8-tetrahydro-quinolin-8-yl)-amino]-methyl}-benzyl)-isonicotinamide;

3,5-Dichloro-N-(3-{[(3H-pyrrol-2-ylmethyl)-(5,6,7,8-tetrahydro-quinolin-8-yl)-amino]-methyl}-benzyl)-isonicotinamide;

3,5-Dichloro-N-(4-{[(5-methyl-3H-pyrrol-2-ylmethyl)-(5,6,7,8-tetrahydro-quinolin-8-yl)-amino]-methyl}-benzyl)-isonicotinamide;

3,5-Dichloro-N-(4-{[(4-methyl-3H-pyrrol-2-ylmethyl)-(5,6,7,8-tetrahydro-quinolin-8-yl)-amino]-methyl}-benzyl)-isonicotinamide;

3,5-Dichloro-N-(3-{[(5-methyl-3H-pyrrol-2-ylmethyl)-(5,6,7,8-tetrahydro-quinolin-8-yl)-amino]-methyl}-benzyl)-isonicotinamide;

3,5-Dichloro-N-(3-{[(4-methyl-3H-pyrrol-2-ylmethyl)-(5,6,7,8-tetrahydro-quinolin-8-yl)-amino]-methyl}-benzyl)-isonicotinamide;

3,5-Dichloro-N-(4-{[oxazol-2-ylmethyl-(5,6,7,8-tetrahydro-quinolin-8-yl)-amino]-methyl}-benzyl)-isonicotinamide;

3,5-Dichloro-N-(4-{[(4-methyl-oxazol-2-ylmethyl)-(5,6,7,8-tetrahydro-quinolin-8-yl)-amino]-methyl}-benzyl)-isonicotinamide;

3,5-Dichloro-N-(4-{[(5-methyl-oxazol-2-ylmethyl)-(5,6,7,8-tetrahydro-quinolin-8-yl)-amino]-methyl}-benzyl)-isonicotinamide;
3,5-Dichloro-N-(4-{[oxazol-4-ylmethyl-(5,6,7,8-tetrahydro-quinolin-8-yl)-amino]-methyl}-benzyl)-isonicotinamide;
3,5-Dichloro-N-(4-{[(2-methyl-oxazol-4-ylmethyl)-(5,6,7,8-tetrahydro-quinolin-8-yl)-amino]-methyl}-benzyl)-isonicotinamide;
3,5-Dichloro-N-(3-{[oxazol-2-ylmethyl-(5,6,7,8-tetrahydro-quinolin-8-yl)-amino]-methyl}-benzyl)-isonicotinamide;
3,5-Dichloro-N-(3-{[(4-methyl-oxazol-2-ylmethyl)-(5,6,7,8-tetrahydro-quinolin-8-yl)-amino]-methyl}-benzyl)-isonicotinamide;
3,5-Dichloro-N-(3-{[(5-methyl-oxazol-2-ylmethyl)-(5,6,7,8-tetrahydro-quinolin-8-yl)-amino]-methyl}-benzyl)-isonicotinamide;
3,5-Dichloro-N-(3-{[oxazol-4-ylmethyl-(5,6,7,8-tetrahydro-quinolin-8-yl)-amino]-methyl}-benzyl)-isonicotinamide;
3,5-Dichloro-N-(3-{[(2-methyl-oxazol-4-ylmethyl)-(5,6,7,8-tetrahydro-quinolin-8-yl)-amino]-methyl}-benzyl)-isonicotinamide;
3,5-Dichloro-N-(4-{[(5,6,7,8-tetrahydro-quinolin-8-yl)-thiazol-2-ylmethyl-amino]-methyl}-benzyl)-isonicotinamide;
3,5-Dichloro-N-(4-{[(4-methyl-thiazol-2-ylmethyl)-(5,6,7,8-tetrahydro-quinolin-8-yl)-amino]-methyl}-benzyl)-isonicotinamide;
3,5-Dichloro-N-(4-{[(5-methyl-thiazol-2-ylmethyl)-(5,6,7,8-tetrahydro-quinolin-8-yl)-amino]-methyl}-benzyl)-isonicotinamide;
3,5-Dichloro-N-(4-{[(5,6,7,8-tetrahydro-quinolin-8-yl)-thiazol-4-ylmethyl-amino]-methyl}benzyl)-isonicotinamide;
3,5-Dichloro-N-(4-{[(2-methyl-thiazol-4-ylmethyl)-(5,6,7,8-tetrahydro-quinolin-8-yl)-amino]-methyl}benzyl)-isonicotinamide;
3,5-Dichloro-N-(3-{[(5,6,7,8-tetrahydro-quinolin-8-yl)-thiazol-2-ylmethyl-amino]-methyl}-benzyl)-isonicotinamide;
3,5-Dichloro-N-(3-{[(4-methyl-thiazol-2-ylmethyl)-(5,6,7,8-tetrahydro-quinolin-8-yl)-amino]-methyl}benzyl)-isonicotinamide;
3,5-Dichloro-N-(3-{[(5-methyl-thiazol-2-ylmethyl)-(5,6,7,8-tetrahydro-quinolin-8-yl)-amino]-methyl}benzyl)-isonicotinamide;
3,5-Dichloro-N-(3-{[(5,6,7,8-tetrahydro-quinolin-8-yl)-thiazol-4-ylmethyl-amino]-methyl}-benzyl)-isonicotinamide;
3,5-Dichloro-N-(3-{[(2-methyl-thiazol-4-ylmethyl)-(5,6,7,8-tetrahydro-quinolin-8-yl)-amino]-methyl}benzyl)-isonicotinamide;
N-(4-{[(3H-Imidazol-4-ylmethyl)-(5,6,7,8-tetrahydro-quinolin-8-yl)-amino]-methyl}-benzyl)-2,4-dimethyl-nicotinamide;
N-(3-{[(3H-Imidazol-4-ylmethyl)-(5,6,7,8-tetrahydro-quinolin-8-yl)-amino]-methyl}-benzyl)-2,4-dimethyl-nicotinamide;
2,4-Dimethyl-N-(4-{[(3-methyl-3H-imidazol-4-ylmethyl)-(5,6,7,8-tetrahydro-quinolin-8-yl)-amino]-methyl}-benzyl)-nicotinamide;
2,4-Dimethyl-N-(3-{[(3-methyl-3H-imidazol-4-ylmethyl)-(5,6,7,8-tetrahydro-quinolin-8-yl)-amino]-methyl}-benzyl)-nicotinamide;
2,4,N-Trimethyl-N-(4-{[(3-methyl-3H-imidazol-4-ylmethyl)-(5,6,7,8-tetrahydro-quinolin-8-yl)-amino]-methyl}-benzyl)-nicotinamide;
2,4,N-Trimethyl-N-(3-{[(3-methyl-3H-imidazol-4-ylmethyl)-(5,6,7,8-tetrahydro-quinolin-8-yl)-amino]-methyl}-benzyl)-nicotinamide;
N-(4-{[(1H-Imidazol-2-ylmethyl)-(5,6,7,8-tetrahydro-quinolin-8-yl)-amino]-methyl}-benzyl)-2,4-dimethyl-nicotinamide;
N-(3-{[(1H-Imidazol-2-ylmethyl)-(5,6,7,8-tetrahydro-quinolin-8-yl)-amino]-methyl}-benzyl)-2,4-dimethyl-nicotinamide;
2,4-Dimethyl-N-(4-{[(1-methyl-1H-imidazol-2-ylmethyl)-(5,6,7,8-tetrahydro-quinolin-8-yl)-amino]-methyl}-benzyl)-nicotinamide;
2,4-Dimethyl-N-(3-{[(1-methyl-1H-imidazol-2-ylmethyl)-(5,6,7,8-tetrahydro-quinolin-8-yl)-amino]-methyl}-benzyl)-nicotinamide;
2,4-Dimethyl-N-(4-{[oxazol-2-ylmethyl-(5,6,7,8-tetrahydro-quinolin-8-yl)-amino]-methyl}-benzyl)-nicotinamide;
2,4-Dimethyl-N-(3-{[oxazol-2-ylmethyl-(5,6,7,8-tetrahydro-quinolin-8-yl)-amino]-methyl}-benzyl)-nicotinamide;
2,4-Dimethyl-N-(4-{[oxazol-5-ylmethyl-(5,6,7,8-tetrahydro-quinolin-8-yl)-amino]-methyl}-benzyl)-nicotinamide;
2,4-Dimethyl-N-(3-{[oxazol-5-ylmethyl-(5,6,7,8-tetrahydro-quinolin-8-yl)-amino]-methyl}-benzyl)-nicotinamide;
2,4-Dimethyl-N-(4-{[(5,6,7,8-tetrahydro-quinolin-8-yl)-thiazol-5-ylmethyl-amino]-methyl}-benzyl)-nicotinamide;
2,4-Dimethyl-N-(3-{[(5,6,7,8-tetrahydro-quinolin-8-yl)-thiazol-5-ylmethyl-amino]-methyl}-benzyl)-nicotinamide;
2,4-Dimethyl-N-(4-{[(5,6,7,8-tetrahydro-quinolin-8-yl)-thiazol-2-ylmethyl-amino]-methyl}-benzyl)-nicotinamide; and
2,4-Dimethyl-N-(3-{[(5,6,7,8-tetrahydro-quinolin-8-yl)-thiazol-2-ylmethyl-amino]-methyl}-benzyl)-nicotinamide.

4. A pharmaceutical composition comprising the compound of claim 1 and a pharmaceutically acceptable carrier.

5. A compound of claim the formula

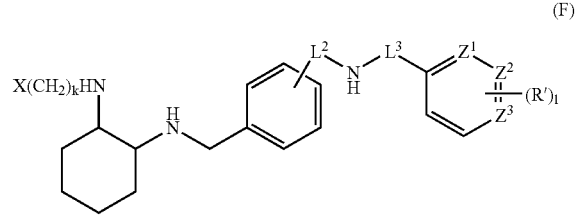

(F)

wherein l s 0-3, and R' is OH, MeO, SH, SMe, CN, $CO_2Me$, F, Cl, Br, $NO_2$, $CH_3CO$, $NH_2$, $NHCH_3$, $N(CH_3)_2$, $CH_3CONH$, $CH_3SO_2NH$, $CONH_2$, $SO_2NH_2$, $CF_3$, or Me; k is 0-2;

each of $Z^1$ and $Z^2$ is independently CH or CR';

$Z^3$ is N;

X is a tetrahydroquinoline or dihydroquinoline ring system;

$L^2$ is $CH_2$; and $L^3$ is CO.

6. A pharmaceutical composition comprising the compound of claim 5 and a pharmaceutically acceptable carrier.

* * * * *